US008815567B2

(12) United States Patent
Ye

(10) Patent No.: US 8,815,567 B2
(45) Date of Patent: Aug. 26, 2014

(54) COENZYME $Q_{10}$ PRODUCTION IN A RECOMBINANT OLEAGINOUS YEAST

(75) Inventor: Rick W. Ye, Hockessin, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 25 days.

(21) Appl. No.: 12/277,856

(22) Filed: Nov. 25, 2008

(65) Prior Publication Data

US 2009/0142322 A1 Jun. 4, 2009

Related U.S. Application Data

(60) Provisional application No. 60/991,266, filed on Nov. 30, 2007.

(51) Int. Cl.

| | |
|---|---|
| ***C12N 1/00*** | (2006.01) |
| ***C12N 9/00*** | (2006.01) |
| ***C12N 15/00*** | (2006.01) |
| ***C12P 23/00*** | (2006.01) |
| ***C07H 21/04*** | (2006.01) |

(52) U.S. Cl.
USPC ....... 435/254.2; 435/67; 435/320.1; 435/183; 536/23.2

(58) Field of Classification Search
None
See application file for complete search history.

(56) References Cited

U.S. PATENT DOCUMENTS

| | | | | |
|---|---|---|---|---|
| 6,461,842 | B1 | 10/2002 | Matsuda et al. | |
| 2005/0226858 | A1 | 10/2005 | Kitamura et al. | |
| 2006/0010519 | A1 | 1/2006 | Kadowaki et al. | |
| 2006/0057690 | A1 * | 3/2006 | Xue et al. | 435/134 |

FOREIGN PATENT DOCUMENTS

| | | |
|---|---|---|
| JP | 10057072 | 3/1998 |
| JP | 2005211020 | 1/2004 |
| JP | 2006204215 | 1/2005 |
| WO | 0047746 | 8/2000 |
| WO | 0226933 | 4/2002 |
| WO | 2005097091 | 10/2005 |
| WO | 2007120423 | 10/2007 |
| WO | 2008023264 | 2/2008 |

OTHER PUBLICATIONS

Whisstock et al. Quaterly Reviews of Biophysics, 2003, “Prediction of protein function from protein sequence and structure”, 36(3): 307-340.*

Chica et al. Semi-rational approaches to engineering enzyme activity: combining the benefits of directed evolution and rational design, Curr Opin Biotechnol. Aug. 2005;16(4):378-84. Review.*

Witkowski et al. Conversion of a beta-ketoacyl synthase to a malonyl decarboxylase by replacement of the active-site cysteine with glutamine, Biochemistry. Sep. 7, 1999;38(36):11643-50.*

Yoshida et al., Gen. Appl. Microbiol., 44:19-26 (1998).

Zahiri et al., Metabol. Engineering, 8:406-416 (2006).

* cited by examiner

*Primary Examiner* — Iqbal H Chowdhury

(57) ABSTRACT

Engineered strains of the oleaginous yeast *Yarrowia lipolytica* capable of co-producing coenzyme $Q_{10}$ and at least one ω-3/ω-6 polyunsaturated fatty acid are provided. The strains may also be engineered to co-produce at least one $C_{40}$ carotenoid. Methods of using the antioxidant products obtained (e.g., biomass and/or pigmented oils) in food and feed applications are also provided.

10 Claims, 9 Drawing Sheets

E. coli & Yeast
Eukaryotes
COO⁻
OH
chorismate
COO
Yeast
COO⁻
H
NH3+
OH
tyrosine
coQ?
ubiC
COO⁻
OH
4-hydroxybenzoate
ubiA
coQ2
E.coli
ubiD
ubiX
COO⁻
coQ?
Yeast
2-polyprenylphenol
R
OH
3-polyprenyl-4
hydroxybenzoate
COO⁻
3,4-dihydroxy-5-
polyprenylbenzoate
HO
R
OH
ubiB
Continued on Fig. 1B
R =
nH
coQ 3
Continued on Fig. 1B β-Carotene β-Cryptoxanthin Echinenone 3-Hydroxyechinenone Zeaxanthin Canthaxanthin FPP
CrtE
GGPP
CrtB
Phytoene
CrtI
Lycopene
CrtY
β-Carotene
CrtZ
CrtW
HO
CrtW
CrtZ
Echinenone
O
CrtZ
HO
O
CrtW
Zeaxanthin
HO
HO
CrtW
Continued on Fig. 3B
O
O
CrtZ
Continued on Fig. 3B Canthaxanthin
Zeaxanthin
3'-Hydroxyechinenone
Adonirubin
Adonixanthin
Astaxanthin ATCC
#20362
~20%LA
FOA
Y2224
Ura-,
Chr.E
pZKLeuN-29E3
Y4001
17% EDA,
Leu-, Chr.C
pY116
Y4001U1
Leu-, Ura-
pKO2UF8289
Y4036
18% DGLA,
Leu-
pY116
Y4036U
Leu-, Ura-
pZKSL-555R
Y4069
12% ARA,
Ura-
pZP3-Pa777U
Y4084
14% EPA
pY117
Y4084U1
Ura-
pZP2-2988
Y4127
18% EPA
pZKUE3S
Y4127U2
Ura-
pZKL1-2SP98C
Y4158
25% EPA
pZKUE3S
Y4158U1
Ura-
pZKL2-5U89GC
Y4184
30.7% EPA
pZKUE3S
Y4184U
Ura-

SEQUENCE LISTING

```
<160> NUMBER OF SEQ ID NOS: 54

<210> SEQ ID NO 1
<211> LENGTH: 2987
<212> TYPE: DNA
<213> ORGANISM: Yarrowia lipolytica
<220> FEATURE:
<221> NAME/KEY: misc_feature
<223> OTHER INFORMATION: mutant acetohydroxyacid synthase (AHAS) with
      W497L mutation
<300> PUBLICATION INFORMATION:
<302> TITLE: HIGH EICOSAPENTAENOIC ACID PRODUCING STRAINS OF YARROWIA
      LIPOLYTICA
<310> PATENT DOCUMENT NUMBER: US 2006-0115881-A1
<311> PATENT FILING DATE: 2005-11-02
<312> PUBLICATION DATE: 2006-06-01
<313> RELEVANT RESIDUES IN SEQ ID NO: (1)..(2987)
<300> PUBLICATION INFORMATION:
<302> TITLE: HIGH EICOSAPENTAENOIC ACID PRODUCING STRAINS OF YARROWIA
      LIPOLYTICA
<310> PATENT DOCUMENT NUMBER: WO 2006/052870
<311> PATENT FILING DATE: 2005-11-03
<312> PUBLICATION DATE: 2006-05-18
<313> RELEVANT RESIDUES IN SEQ ID NO: (1)..(2987)

<400> SEQUENCE: 1

ttccctagtc ccagtgtaca cccgccgata tcgcttaccc tgcagccgga ttaaggttgg      60

caatttttca cgtccttgtc tccgcaatta ctcaccgggt ggtttataag attgcaagcg     120

tcttgatttg tctctgtata ctaacatgca atcgcgactc gcccgacggg ccactaacct     180

ggccagaatc tccagatcca agtattctct tggtctgcga tatgtttcca acacaaaagc     240

ccctgctgcc cagccggcaa ctgctgagtg agtattcctt gccataaacg acccagaacc     300

actgtatagt gtttggaagc actagtcaga agaccagcga aaacaggtgg aaaaaactga     360

gacgaaaagc aacgaccaga aatgtaatgt gtggaaaagc gacacacaca gagcagataa     420

agaggtgaca aataacgaca aatgaaatat cagtatcttc ccacaatcac tacctctcag     480

ctgtctgaag gtgcggctga tatatccatc ccacgtctaa cgtatggagt gtgatagaat     540

atgacgacac aagcatgaga actcgctctc tatccaacca ccgaaacact gtcactacag     600

ccgttcttgt tgctccattc gcttttgtga ttccatgcct tctctggtga ctgacaacat     660

tccttccttt tctccagccc tgttgttatc tgctcatgac ctacggccac tctctatcgc     720

atactaacat agacgatccc agcccgctcc ccacttccag ggcaccgttg gcaagcctcc     780

tatcctcaag aaggctgagg ctgccaacgc tgacatggac gagtccttca tcggaatgtc     840

tggaggagag atcttccacg agatgatgct gcgacacaac gtcgacactg tcttcggtta     900

ccccggtgga gccattctcc ccgtctttga cgccattcac aactctgagt acttcaactt     960

tgtgctccct cgacacgagc agggtgccgg ccacatggcc gagggctacg ctcgagcctc    1020

tggtaagccc ggtgtcgttc tcgtcacctc tggccccggt gccaccaacg tcatcacccc    1080

catgcaggac gctctttccg atggtacccc catggttgtc ttcaccggtc aggtcctgac    1140

ctccgttatc ggcactgacg ccttccagga ggccgatgtt gtcggcatct cccgatcttg    1200

caccaagtgg aacgtcatgg tcaagaacgt tgctgagctc ccccgacgaa tcaacgaggc    1260

ctttgagatt gctacttccg gccgacccgg tcccgttctc gtcgatctgc ccaaggatgt    1320

tactgctgcc atcctgcgag agcccatccc caccaagtcc accattccct cgcattctct    1380

gaccaacctc acctctgccg ccgccaccga gttccagaag caggctatcc agcgagccgc    1440
```

caacctcatc aaccagtcca agaagcccgt cctttacgtc ggacagggta tccttggctc 1500
cgaggagggt cctaagctgc ttaaggagct ggctgagaag gccgagattc ccgtcaccac 1560
tactctgcag ggtcttggtg cctttgacga gcgagacccc aagtctctgc acatgctcgg 1620
tatgcacggt tccggctacg ccaacatggc catgcagaac gctgactgta tcattgctct 1680
cggcgcccga tttgatgacc gagttaccgg ctccatcccc aagtttgccc ccgaggctcg 1740
agccgctgcc cttgagggtc gaggtggtat tgttcacttt gagatccagg ccaagaacat 1800
caacaaggtt gttcaggcca ccgaagccgt tgagggagac gttaccgagt ctgtccgaca 1860
gctcatcccc ctcatcaaca aggtctctgc cgctgagcga gctccctgga ctgagactat 1920
ccagtcctgg aagcagcagt tccccttcct cttcgaggct gaaggtgagg atggtgttat 1980
caagccccag tccgtcattg ctctgctctc tgacctgaca gagaacaaca aggacaagac 2040
catcatcacc accggtgttg gtcagcatca gatgtggact gcccagcatt tccgatggcg 2100
acaccctcga accatgatca cttctggtgg tcttggaact atgggttacg gcctgcccgc 2160
cgctatcggc gccaaggttg cccgacctga ctgcgacgtc attgacatcg atggtgacgc 2220
ttctttcaac atgactctga ccgagctgtc caccgccgtt cagttcaaca ttggcgtcaa 2280
ggctattgtc ctcaacaacg aggaacaggg tatggtcacc cagctgcagt ctctcttcta 2340
cgagaaccga tactgccaca ctcatcagaa gaaccccgac ttcatgaagc tggccgagtc 2400
catgggcatg aagggtatcc gaatcactca cattgaccag ctggaggccg gtctcaagga 2460
gatgctcgca tacaagggcc ctgtgctcgt tgaggttgtt gtcgacaaga agatccccgt 2520
tcttcccatg gttcccgctg gtaaggcttt gcatgagttc cttgtctacg acgctgacgc 2580
cgaggctgct tctcgacccg atcgactgaa gaatgccccc gcccctcacg tccaccagac 2640
cacctttgag aactaagtgg aaaggaacac aagcaatccg aaccaaaaat aattggggtc 2700
ccgtgcccac agagtctagt gcagacctaa aatgaccaca gtaaattata gctgttatta 2760
aacatgagat tttgaccaac aagagcgtag gaatgttatt agctactact tgtacataca 2820
cagcatttgt tttaaataat gttgcctcca ggggcagtga gatcaggacc cagatccgtg 2880
gccagctctc tgacttcaga ccgcttgtac ttaagcagct cgcaacactg ttgtcgagga 2940
ttgaacttgc catattcgat tttgtggtca tgaatccagc acacctc 2987

<210> SEQ ID NO 2
<211> LENGTH: 13066
<212> TYPE: DNA
<213> ORGANISM: Artificial Sequence
<220> FEATURE:
<223> OTHER INFORMATION: Plasmid pZP3-Pa777U

<400> SEQUENCE: 2
tctcggtcta ttcttttgat ttataaggga ttttgccgat ttcggcctat tggttaaaaa 60
atgagctgat ttaacaaaaa tttaacgcga attttaacaa aatattaacg cttacaattt 120
cctgatgcgg tattttctcc ttacgcatct gtgcggtatt tcacaccgca tcaggtggca 180
cttttcgggg aaatgtgcgc ggaaccccta tttgtttatt tttctaaata cattcaaata 240
tgtatccgct catgagacaa taaccctgat aaatgcttca ataatattga aaaaggaaga 300
gtatgagtat tcaacatttc cgtgtcgccc ttattccctt ttttgcggca ttttgccttc 360
ctgtttttgc tcacccagaa acgctggtga aagtaaaaga tgctgaagat cagttgggtg 420
cacgagtggg ttacatcgaa ctggatctca acagcggtaa gatccttgag agttttcgcc 480
ccgaagaacg ttttccaatg atgagcactt ttaaagttct gctatgtggc gcggtattat 540

-continued

```
cccgtattga cgccgggcaa gagcaactcg gtcgccgcat acactattct cagaatgact    600
tggttgagta ctcaccagtc acagaaaagc atcttacgga tggcatgaca gtaagagaat    660
tatgcagtgc tgccataacc atgagtgata acactgcggc caacttactt ctgacaacga    720
tcggaggacc gaaggagcta accgcttttt tgcacaacat gggggatcat gtaactcgcc    780
ttgatcgttg ggaaccggag ctgaatgaag ccataccaaa cgacgagcgt gacaccacga    840
tgcctgtagc aatggcaaca acgttgcgca aactattaac tggcgaacta cttactctag    900
cttcccggca acaattaata gactggatgg aggcggataa agttgcagga ccacttctgc    960
gctcggccct tccggctggc tggtttattg ctgataaatc tggagccggt gagcgtgggt   1020
ctcgcggtat cattgcagca ctggggccag atggtaagcc ctcccgtatc gtagttatct   1080
acacgacggg gagtcaggca actatggatg aacgaaatag acagatcgct gagataggtg   1140
cctcactgat taagcattgg taactgtcag accaagttta ctcatatata ctttagattg   1200
atttaaaact tcatttttaa tttaaaagga tctaggtgaa gatccttttt gataatctca   1260
tgaccaaaat cccttaacgt gagttttcgt tccactgagc gtcagacccc gtagaaaaga   1320
tcaaaggatc ttcttgagat cctttttttc tgcgcgtaat ctgctgcttg caaacaaaaa   1380
aaccaccgct accagcggtg gtttgtttgc cggatcaaga gctaccaact ctttttccga   1440
aggtaactgg cttcagcaga gcgcagatac caaatactgt tcttctagtg tagccgtagt   1500
taggccacca cttcaagaac tctgtagcac cgcctacata cctcgctctg ctaatcctgt   1560
taccagtggc tgctgccagt ggcgataagt cgtgtcttac cgggttggac tcaagacgat   1620
agttaccgga taaggcgcag cggtcgggct gaacgggggg ttcgtgcaca cagcccagct   1680
tggagcgaac gacctacacc gaactgagat acctacagcg tgagctatga gaaagcgcca   1740
cgcttcccga agggagaaag gcggacaggt atccggtaag cggcagggtc ggaacaggag   1800
agcgcacgag ggagcttcca gggggaaacg cctggtatct ttatagtcct gtcgggtttc   1860
gccacctctg acttgagcgt cgatttttgt gatgctcgtc aggggggcgg agcctatgga   1920
aaaacgccag caacgcggcc tttttacggt tcctggcctt ttgctggcct tttgctcaca   1980
tgttctttcc tgcgttatcc cctgattctg tggataaccg tattaccgcc tttgagtgag   2040
ctgataccgc tcgccgcagc cgaacgaccg agcgcagcga gtcagtgagc gaggaagcgg   2100
aagagcgccc aatacgcaaa ccgcctctcc ccgcgcgttg gccgattcat taatgcagct   2160
ggcgcgccac caatcacaat tctgaaaagc acatcttgat ctcctcattg cggggagtcc   2220
aacggtggtc ttattccccc gaatttcccg ctcaatctcg ttccagaccg acccggacac   2280
agtgcttaac gccgttccga aactctaccg cagatatgct ccaacggact gggctgcata   2340
gatgtgatcc tcggcttgga gaaatggata aaagccggcc aaaaaaaaag cggaaaaaag   2400
cggaaaaaaa gagaaaaaaa atcgcaaaat ttgaaaaata gggggaaaag acgcaaaaac   2460
gcaaggaggg gggagtatat gacactgata agcaagctca caacggttcc tcttattttt   2520
ttcctcatct tctgcctagg ttcccaaaat cccagatgct tctctccagt gccaaaagta   2580
agtaccccac aggttttcgg ccgaaaattc cacgtgcagc aacgtcgtgt ggggtgttaa   2640
aatgtggggg gggggaacca ggacaagagg ctcttgtggg agccgaatga gagcacaaag   2700
cgggcgggtg tgataagggc atttttgccc attttccctt ctcctgtctc tccgacggtg   2760
atggcgttgt gcgtcctcta tttcttttta tttcttttg ttttatttct ctgactaccg    2820
atttggtttg atttcctcaa ccccacacaa ataagctcgg gccgaggaat atatatatac   2880
```

-continued

```
acggacacag tcgccctgtg gacaacacgt cactacctct acgatacaca ccgtacgttg   2940
tgtggaagct tgtgagcgga taacaatttc acacaggaaa cagctatgac catgattacg   3000
ccaagctcga aattaaccct cactaaaggg aacaaaagct ggagctccac cgcggacaca   3060
atatctggtc aaatttcagt ttcgttacat ttaaattcct tcacttcaag ttcattcttc   3120
atctgcttct gttttacttt gacaggcaaa tgaagacatg gtacgacttg atggaggcca   3180
agaacgccat ttcaccccga gacaccgaag tgcctgaaat cctggctgcc cccattgata   3240
acatcggaaa ctacggtatt ccggaaagtg tatatagaac ctttccccag cttgtgtctg   3300
tggatatgga tggtgtaatc ccctttgagt actcgtcttg gcttctctcc gagcagtatg   3360
aggctctcta atctagcgca tttaatatct caatgtattt atatatttat cttctcatgc   3420
ggccgcttag ttggctttgg tcttggcagc cttggcctcc ttgagggtaa acatcttggc   3480
atccttgtcg accacgccgt acttggcgta cataagacca attcggatga aggtgggaat   3540
gatgggagaa gccgactttc gcaccagttc gggaaaggcc tgagcgaagg cagcagtggc   3600
ctcgttgagc ttgtagtgag gaatgatggg aaacagatgg tggatctgat gtgtaccaat   3660
gttgtgggac aggttgtcga tgagggctcc gtagcttcgg tccacagagg acaagttgcc   3720
cttgacatag gtccactccg aatcggcgta ccagggagtt tcctcgtcgt tgtgatggag   3780
gaaggtagtg acaaccagca tggtggcgaa tccaaagaga ggtgcgaagt aatacagagc   3840
catggtcttg aggccgtaga cgtaggtaag gtaggcgtac agaccagcaa aggccacgag   3900
agagccgagg gaaatgatga cggcagacat tcttcgcagg tagagaggct cccagggatt   3960
gaagtggttg acctttcggg gaggaaatcc agcaacgagg taggcaaacc aagccgaacc   4020
aagggagatg accatgtgtc gggacagggg atgagagtcg gcttctcgct gagggtagaa   4080
gatctcatcc ttgtcgatgt tgccggtgtt cttgtgatgg tgtcgatggc tgatcttcca   4140
cgactcgtag ggagtcagaa tgatggagtg aatgagtgtg ccaacagaga agttgagcag   4200
gtgggatcgc gagaaggcac catgtccaca gtcgtgaccg atggtaaaga atccccagaa   4260
cacgataccc tggagcagaa tgtagccagt gcaaaggacg gcatcgagca gtgcaaactc   4320
ctgcacgata gcaagggctc gagcatagta cagtccgaga gcaagggaac cggcaatgcc   4380
cagagctcgc acggtatagt agagggacca gggaacagag gcttcgaagc agtgggcagg   4440
cagggatcgc ttgatctcgg tgagagtagg gaactcgtag ggagcggcaa cggtagagga   4500
agccatggtt gtgaattagg gtggtgagaa tggttggttg tagggaagaa tcaaaggccg   4560
gtctcgggat ccgtgggtat atatatatat atatatatat acgatccttc gttacctccc   4620
tgttctcaaa actgtggttt ttcgtttttc gtttttttgct ttttttgatt tttttagggc   4680
caactaagct tccagatttc gctaatcacc tttgtactaa ttacaagaaa ggaagaagct   4740
gattagagtt gggcttttta tgcaactgtg ctactcctta tctctgatat gaaagtgtag   4800
acccaatcac atcatgtcat ttagagttgg taatactggg aggatagata aggcacgaaa   4860
acgagccata gcagacatgc tgggtgtagc caagcagaag aaagtagatg ggagccaatt   4920
gacgagcgag ggagctacgc caatccgaca tacgacacgc tgagatcgtc ttggccgggg   4980
ggtacctaca gatgtccaag ggtaagtgct tgactgtaat tgtatgtctg aggacaaata   5040
tgtagtcagc cgtataaagt cataccaggc accagtgcca tcatcgaacc actaactctc   5100
tatgatacat gcctccggta ttattgtacc atgcgtcgct ttgttacata cgtatcttgc   5160
ctttttctct cagaaactcc agactttggc tattggtcga gataagcccg gaccatagtg   5220
agtctttcac actctacatt tctcccttgc tccaactatc gattgttgtc tactaactat   5280
```

```
cgtacgataa cttcgtatag catacattat acgaagttat cgcgtcgacg agtatctgtc   5340
tgactcgtca ttgccgcctt tggagtacga ctccaactat gagtgtgctt ggatcacttt   5400
gacgatacat tcttcgttgg aggctgtggg tctgacagct gcgttttcgg cgcggttggc   5460
cgacaacaat atcagctgca acgtcattgc tggctttcat catgatcaca tttttgtcgg   5520
caaaggcgac gcccagagag ccattgacgt tctttctaat ttggaccgat agccgtatag   5580
tccagtctat ctataagttc aactaactcg taactattac cataacatat acttcactgc   5640
cccagataag gttccgataa aaagttctgc agactaaatt tatttcagtc tcctcttcac   5700
caccaaaatg ccctcctacg aagctcgagc taacgtccac aagtccgcct ttgccgctcg   5760
agtgctcaag ctcgtggcag ccaagaaaac caacctgtgt gcttctctgg atgttaccac   5820
caccaaggag ctcattgagc ttgccgataa ggtcggacct tatgtgtgca tgatcaaaac   5880
ccatatcgac atcattgacg acttcaccta cgccggcact gtgctccccc tcaaggaact   5940
tgctcttaag cacggtttct tcctgttcga ggacagaaag ttcgcagata ttggcaacac   6000
tgtcaagcac cagtaccggt gtcaccgaat cgccgagtgg tccgatatca ccaacgccca   6060
cggtgtaccc ggaaccggaa tcattgctgg cctgcgagct ggtgccgagg aaactgtctc   6120
tgaacagaag aaggaggacg tctctgacta cgagaactcc cagtacaagg agttcctagt   6180
cccctctccc aacgagaagc tggccagagg tctgctcatg ctggccgagc tgtcttgcaa   6240
gggctctctg gccactggcg agtactccaa gcagaccatt gagcttgccc gatccgaccc   6300
cgagtttgtg gttggcttca ttgcccagaa ccgacctaag ggcgactctg aggactggct   6360
tattctgacc cccggggtgg gtcttgacga caagggagac gctctcggac agcagtaccg   6420
aactgttgag gatgtcatgt ctaccggaac ggatatcata attgtcggcc gaggtctgta   6480
cggccagaac cgagatccta ttgaggaggc caagcgatac cagaaggctg gctgggaggc   6540
ttaccagaag attaactgtt agaggttaga ctatggatat gtaatttaac tgtgtatata   6600
gagagcgtgc aagtatggag cgcttgttca gcttgtatga tggtcagacg acctgtctga   6660
tcgagtatgt atgatactgc acaacctgtg tatccgcatg atctgtccaa tggggcatgt   6720
tgttgtgttt ctcgatacgg agatgctggg tacagtgcta atacgttgaa ctacttatac   6780
ttatatgagg ctcgaagaaa gctgacttgt gtatgactta ttctcaacta catccccagt   6840
cacaatacca ccactgcact accactacac caaaaccatg atcaaaccac ccatggactt   6900
cctggaggca gaagaacttg ttatggaaaa gctcaagaga gagatcataa cttcgtatag   6960
catacattat acgaagttat cctgcaggta aaggaattca tgctgttcat cgtggttaat   7020
gctgctgtgt gctgtgtgtg tgtgttgttt ggcgctcatt gttgcgttat gcagcgtaca   7080
ccacaatatt ggaagcttat tagcctttct atttttttcgt ttgcaaggct taacaacatt   7140
gctgtggaga gggatgggga tatggaggcc gctggaggga gtcggagagg cgttttggag   7200
cggcttggcc tggcgcccag ctcgcgaaac gcacctagga ccctttggca cgccgaaatg   7260
tgccactttt cagtctagta acgccttacc tacgtcattc catgcgtgca tgtttgcgcc   7320
ttttttccct tgcccttgat cgccacacag tacagtgcac tgtacagtgg aggttttggg   7380
ggggtcttag atgggagcta aaagcggcct agcggtacac tagtgggatt gtatggagtg   7440
gcatggagcc taggtggagc ctgacaggac gcacgaccgg ctagcccgtg acagacgatg   7500
ggtggctcct gttgtccacc gcgtacaaat gtttgggcca aagtcttgtc agccttgctt   7560
gcgaacctaa ttcccaattt tgtcacttcg cacccccatt gatcgagccc taacccctgc   7620
```

-continued

```
ccatcaggca atccaattaa gctcgcattg tctgccttgt ttagtttggc tcctgcccgt   7680
ttcggcgtcc acttgcacaa acacaaacaa gcattatata taaggctcgt ctctccctcc   7740
caaccacact cacttttttg cccgtcttcc cttgctaaca caaaagtcaa gaacacaaac   7800
aaccacccca accccttac acacaagaca tatctacagc aatggccatg gcttcttcca   7860
ctgttgctgc gccgtacgag ttcccgacgc tgacggagat caagcgctcg ctgccagcgc   7920
actgctttga ggcctcggtc ccgtggtcgc tctactacac cgtgcgcgcg ctgggcatcg   7980
ccggctcgct cgcgctcggc ctctactacg cgcgcgcgct cgcgatcgtg caggagtttg   8040
ccctgctgga tgcggtgctc tgcacggggt acattctgct gcagggcatc gtattctggg   8100
ggttcttcac catcggccat gactgcggcc acggcgcgtt ctcgcgttcg cacctgctca   8160
acttcagcgt cggcacgctc attcactcga tcatcctcac gccgtacgag tcatggaaga   8220
tctcgcaccg ccaccaccac aagaacacgg gcaacatcga caaggacgag attttctacc   8280
cgcagcgcga ggccgactcg cacccactgt cccgacacat ggtgatctcg ctcggctcgg   8340
cctggttcgc gtacctcgtt gcgggcttcc ctcctcgcaa ggtgaaccac ttcaaccctt   8400
gggaaccgtt gtacctgcgc cgcatgtctg ccgtcatcat ctcactcggc tcgctcgtgg   8460
cgttcgcggg cttgtatgcg tatctcacct acgtctatgg ccttaagacc atggcgctgt   8520
actacttcgc ccctctcttt gggttcgcca cgatgctcgt ggtcactacc tttttgcacc   8580
acaatgacga ggaaacgcca tggtacgccg actcggagtg gacgtacgtc aagggcaacc   8640
tctcgtccgt ggaccgctcg tacggcgcgc tcatcgacaa cctgagccac aacatcggca   8700
cgcaccagat ccaccacctg tttccgatca tcccgcacta caagctgaac gaggcgacgg   8760
cagcgttcgc gcaggcgttc ccggagctcg tgcgcaagag cgcgtcgccg atcatcccga   8820
cgttcatccg catcgggctc atgtacgcca agtacggcgt cgtggacaag gacgccaaga   8880
tgtttacgct caaggaggcc aaggccgcca agaccaaggc caactaggcg gccgcattga   8940
tgattggaaa cacacacatg ggttatatct aggtgagagt tagttggaca gttatatatt   9000
aaatcagcta tgccaacggt aacttcattc atgtcaacga ggaaccagtg actgcaagta   9060
atatagaatt tgaccacctt gccattctct tgcactcctt tactatatct catttatttc   9120
ttatatacaa atcacttctt cttcccagca tcgagctcgg aaacctcatg agcaataaca   9180
tcgtggatct cgtcaataga gggctttttg gactccttgc tgttggccac cttgtccttg   9240
ctgtttaaac agtgtacgca gatctactat agaggaacat ttaaattgcc ccggagaaga   9300
cggccaggcc gcctagatga caaattcaac aactcacagc tgactttctg ccattgccac   9360
tagggggggg cctttttata tggccaagcc aagctctcca cgtcggttgg gctgcaccca   9420
acaataaatg ggtagggttg caccaacaaa gggatgggat ggggggtaga agatacgagg   9480
ataacggggc tcaatggcac aaataagaac gaatactgcc attaagactc gtgatccagc   9540
gactgacacc attgcatcat ctaagggcct caaaactacc tcggaactgc tgcgctgatc   9600
tggacaccac agaggttccg agcactttag gttgcaccaa atgtcccacc aggtgcaggc   9660
agaaaacgct ggaacagcgt gtacagtttg tcttaacaaa aagtgagggc gctgaggtcg   9720
agcagggtgg tgtgacttgt tatagccttt agagctgcga aagcgcgtat ggatttggct   9780
catcaggcca gattgagggt ctgtggacac atgtcatgtt agtgtacttc aatcgccccc   9840
tggatatagc cccgacaata ggccgtggcc tcattttttt gccttccgca catttccatt   9900
gctcggtacc cacaccttgc ttctcctgca cttgccaacc ttaatactgg tttacattga   9960
ccaacatctt acaagcgggg ggcttgtcta gggtatatat aaacagtggc tctcccaatc  10020
```

-continued ggttgccagt ctctttttc ctttctttcc ccacagattc gaaatctaaa ctacacatca 10080
cagaattccg agccgtgagt atccacgaca agatcagtgt cgagacgacg cgttttgtgt 10140
aatgacacaa tccgaaagtc gctagcaaca cacactctct acacaaacta acccagctct 10200
ggtaccatgg cttcttccac tgttgctgcg ccgtacgagt tcccgacgct gacggagatc 10260
aagcgctcgc tgccagcgca ctgctttgag gcctcggtcc cgtggtcgct ctactacacc 10320
gtgcgcgcgc tgggcatcgc cggctcgctc gcgctcggcc tctactacgc gcgcgcgctc 10380
gcgatcgtgc aggagtttgc cctgctggat gcggtgctct gcacggggta cattctgctg 10440
cagggcatcg tattctgggg gttcttcacc atcggccatg actgcggcca cggcgcgttc 10500
tcgcgttcgc acctgctcaa cttcagcgtc ggcacgctca ttcactcgat catcctcacg 10560
ccgtacgagt catggaagat ctcgcaccgc caccaccaca agaacacggg caacatcgac 10620
aaggacgaga ttttctaccc gcagcgcgag gccgactcgc acccactgtc ccgacacatg 10680
gtgatctcgc tcggctcggc ctggttcgcg tacctcgttg cgggcttccc tcctcgcaag 10740
gtgaaccact tcaacccttg ggaaccgttg tacctgcgcc gcatgtctgc cgtcatcatc 10800
tcactcggct cgctcgtggc gttcgcgggc ttgtatgcgt atctcaccta cgtctatggc 10860
cttaagacca tggcgctgta ctacttcgcc cctctctttg ggttcgccac gatgctcgtg 10920
gtcactacct ttttgcacca caatgacgag gaaacgccat ggtacgccga ctcggagtgg 10980
acgtacgtca agggcaacct ctcgtccgtg gaccgctcgt acggcgcgct catcgacaac 11040
ctgagccaca acatcggcac gcaccagatc caccacctgt ttccgatcat cccgcactac 11100
aagctgaacg aggcgacggc agcgttcgcg caggcgttcc cggagctcgt gcgcaagagc 11160
gcgtcgccga tcatcccgac gttcatccgc atcgggctca tgtacgccaa gtacggcgtc 11220
gtggacaagg acgccaagat gtttacgctc aaggaggcca aggccgccaa gaccaaggcc 11280
aactaggcgg ccgcatggag cgtgtgttct gagtcgatgt tttctatgga gttgtgagtg 11340
ttagtagaca tgatgggttt atatatgatg aatgaataga tgtgattttg atttgcacga 11400
tggaattgag aactttgtaa acgtacatgg gaatgtatga atgtgggggt tttgtgactg 11460
gataactgac ggtcagtgga cgccgttgtt caaatatcca agagatgcga gaaactttgg 11520
gtcaagtgaa catgtcctct ctgttcaagt aaaccatcaa ctatgggtag tatatttagt 11580
aaggacaaga gttgagattc tttggagtcc tagaaacgta ttttcgcgtt ccaagatcaa 11640
attagtagag taatacgggc acgggaatcc attcatagtc tcaatcctgc aggtgagtta 11700
attaagatga cgacatttgc gagctggacg aggaatagat ggagcgtgtg ttctgagtcg 11760
atgttttcta tggagttgtg agtgttagta gacatgatgg gtttatatat gatgaatgaa 11820
tagatgtgat tttgatttgc acgatggaat tgagaacttt gtaaacgtac atgggaatgt 11880
atgaatgtgg gggttttgtg actggataac tgacggtcag tggacgccgt tgttcaaata 11940
tccaagagat gcgagaaact ttgggtcaag tgaacatgtc ctctctgttc aagtaaacca 12000
tcaactatgg gtagtatatt tagtaaggac aagagttgag attctttgga gtcctagaaa 12060
cgtattttcg cgttccaaga tcaaattagt agagtaatac gggcacggga atccattcat 12120
agtctcaatt ttcccatagg tgtgctacaa ggtgttgaga tgtggtacag taccaccatg 12180
attcgaggta aagagcccag aagtcattga tgaggtcaag aaatacacag atctacagct 12240
caatacaatg aatatcttct ttcatattct tcaggtgaca ccaagggtgt ctattttccc 12300
cagaaatgcg tgaaaaggcg cgtgtgtagc gtggagtatg ggttcggttg gcgtatcctt 12360

-continued

```
catatatcga cgaaatagta gggcaagaga tgacaaaaag tatctatatg tagacagcgt  12420

agaatatgga tttgattggt ataaattcat ttattgcgtg tctcacaaat actctcgata  12480

agttggggtt aaactggaga tggaacaatg tcgatatctc gacgcatgcg acgtcgggcc  12540

caattcgccc tatagtgagt cgtattacaa ttcactggcc gtcgttttac aacgtcgtga  12600

ctgggaaaac cctggcgtta cccaacttaa tcgccttgca gcacatcccc ctttcgccag  12660

ctggcgtaat agcgaagagg cccgcaccga tcgcccttcc caacagttgc gcagcctgaa  12720

tggcgaatgg acgcgccctg tagcggcgca ttaagcgcgg cgggtgtggt ggttacgcgc  12780

agcgtgaccg ctacacttgc cagcgcccta gcgcccgctc ctttcgcttt cttcccttcc  12840

tttctcgcca cgttcgccgg ctttccccgt caagctctaa atcgggggct ccctttaggg  12900

ttccgattta gtgctttacg gcacctcgac cccaaaaaac ttgattaggg tgatggttca  12960

cgtagtgggc catcgccctg atagacggtt tttcgccctt tgacgttgga gtccacgttc  13020

tttaatagtg gactcttgtt ccaaactgga acaacactca acccta                13066


<210> SEQ ID NO 3
<211> LENGTH: 777
<212> TYPE: DNA
<213> ORGANISM: Euglena gracilis
<220> FEATURE:
<221> NAME/KEY: CDS
<222> LOCATION: (1)..(777)
<223> OTHER INFORMATION: delta-9 elongase
<300> PUBLICATION INFORMATION:
<302> TITLE: DELTA-9 ELONGASES AND THEIR USE IN MAKING POLYUNSATURATED
      FATTY ACIDS
<310> PATENT DOCUMENT NUMBER: WO 2007/061742
<311> PATENT FILING DATE: 2006-11-16
<312> PUBLICATION DATE: 2007-05-31
<313> RELEVANT RESIDUES IN SEQ ID NO: (1)..(777)
<300> PUBLICATION INFORMATION:
<302> TITLE: DELTA-9 ELONGASES AND THEIR USE IN MAKING POLYUNSATURATED
      FATTY ACIDS
<310> PATENT DOCUMENT NUMBER: US 2007-0117190-A1
<311> PATENT FILING DATE: 2006-11-16
<312> PUBLICATION DATE: 2007-05-24
<313> RELEVANT RESIDUES IN SEQ ID NO: (1)..(777)

<400> SEQUENCE: 3

atg gag gtg gtg aat gaa ata gtc tca att ggg cag gaa gtt tta ccc       48
Met Glu Val Val Asn Glu Ile Val Ser Ile Gly Gln Glu Val Leu Pro
1               5                   10                  15

aaa gtt gat tat gcc caa ctc tgg agt gat gcc agt cac tgt gag gtg       96
Lys Val Asp Tyr Ala Gln Leu Trp Ser Asp Ala Ser His Cys Glu Val
            20                  25                  30

ctt tac ttg tcc atc gca ttt gtc atc ttg aag ttc act ctt ggc ccc      144
Leu Tyr Leu Ser Ile Ala Phe Val Ile Leu Lys Phe Thr Leu Gly Pro
        35                  40                  45

ctt ggt cca aaa ggt cag tct cgt atg aag ttt gtt ttc acc aat tac      192
Leu Gly Pro Lys Gly Gln Ser Arg Met Lys Phe Val Phe Thr Asn Tyr
    50                  55                  60

aac ctt ctc atg tcc att tat tcg ttg gga tca ttc ctc tca atg gca      240
Asn Leu Leu Met Ser Ile Tyr Ser Leu Gly Ser Phe Leu Ser Met Ala
65                  70                  75                  80

tat gcc atg tac acc atc ggt gtt atg tct gac aac tgc gag aag gct      288
Tyr Ala Met Tyr Thr Ile Gly Val Met Ser Asp Asn Cys Glu Lys Ala
                85                  90                  95

ttt gac aac aac gtc ttc agg atc acc acg cag ttg ttc tat ttg agc      336
Phe Asp Asn Asn Val Phe Arg Ile Thr Thr Gln Leu Phe Tyr Leu Ser
            100                 105                 110

aag ttc ctg gag tat att gac tcc ttc tat ttg cca ctg atg ggc aag      384
```

```
Lys Phe Leu Glu Tyr Ile Asp Ser Phe Tyr Leu Pro Leu Met Gly Lys
        115                 120                 125

cct ctg acc tgg ttg caa ttc ttc cat cat ttg ggg gca ccg atg gat      432
Pro Leu Thr Trp Leu Gln Phe Phe His His Leu Gly Ala Pro Met Asp
    130                 135                 140

atg tgg ctg ttc tat aat tac cga aat gaa gct gtt tgg att ttt gtg      480
Met Trp Leu Phe Tyr Asn Tyr Arg Asn Glu Ala Val Trp Ile Phe Val
145                 150                 155                 160

ctg ttg aat ggt ttc atc cac tgg atc atg tac ggt tat tat tgg acc      528
Leu Leu Asn Gly Phe Ile His Trp Ile Met Tyr Gly Tyr Tyr Trp Thr
                165                 170                 175

aga ttg atc aag ctg aag ttc ccc atg cca aaa tcc ctg att aca tca      576
Arg Leu Ile Lys Leu Lys Phe Pro Met Pro Lys Ser Leu Ile Thr Ser
            180                 185                 190

atg cag atc att caa ttc aat gtt ggt ttc tac att gtc tgg aag tac      624
Met Gln Ile Ile Gln Phe Asn Val Gly Phe Tyr Ile Val Trp Lys Tyr
        195                 200                 205

agg aac att ccc tgt tat cgc caa gat ggg atg agg atg ttt ggc tgg      672
Arg Asn Ile Pro Cys Tyr Arg Gln Asp Gly Met Arg Met Phe Gly Trp
    210                 215                 220

ttc ttc aat tac ttt tat gtt ggc aca gtc ttg tgt ttg ttc ttg aat      720
Phe Phe Asn Tyr Phe Tyr Val Gly Thr Val Leu Cys Leu Phe Leu Asn
225                 230                 235                 240

ttc tat gtg caa acg tat atc gtc agg aag cac aag gga gcc aaa aag      768
Phe Tyr Val Gln Thr Tyr Ile Val Arg Lys His Lys Gly Ala Lys Lys
                245                 250                 255

att cag tga                                                          777
Ile Gln


<210> SEQ ID NO 4
<211> LENGTH: 258
<212> TYPE: PRT
<213> ORGANISM: Euglena gracilis

<400> SEQUENCE: 4

Met Glu Val Val Asn Glu Ile Val Ser Ile Gly Gln Glu Val Leu Pro
1               5                   10                  15

Lys Val Asp Tyr Ala Gln Leu Trp Ser Asp Ala Ser His Cys Glu Val
            20                  25                  30

Leu Tyr Leu Ser Ile Ala Phe Val Ile Leu Lys Phe Thr Leu Gly Pro
        35                  40                  45

Leu Gly Pro Lys Gly Gln Ser Arg Met Lys Phe Val Phe Thr Asn Tyr
    50                  55                  60

Asn Leu Leu Met Ser Ile Tyr Ser Leu Gly Ser Phe Leu Ser Met Ala
65                  70                  75                  80

Tyr Ala Met Tyr Thr Ile Gly Val Met Ser Asp Asn Cys Glu Lys Ala
                85                  90                  95

Phe Asp Asn Asn Val Phe Arg Ile Thr Thr Gln Leu Phe Tyr Leu Ser
            100                 105                 110

Lys Phe Leu Glu Tyr Ile Asp Ser Phe Tyr Leu Pro Leu Met Gly Lys
        115                 120                 125

Pro Leu Thr Trp Leu Gln Phe Phe His His Leu Gly Ala Pro Met Asp
    130                 135                 140

Met Trp Leu Phe Tyr Asn Tyr Arg Asn Glu Ala Val Trp Ile Phe Val
145                 150                 155                 160

Leu Leu Asn Gly Phe Ile His Trp Ile Met Tyr Gly Tyr Tyr Trp Thr
                165                 170                 175
```

-continued

```
Arg Leu Ile Lys Leu Lys Phe Pro Met Pro Lys Ser Leu Ile Thr Ser
            180                 185                 190

Met Gln Ile Ile Gln Phe Asn Val Gly Phe Tyr Ile Val Trp Lys Tyr
        195                 200                 205

Arg Asn Ile Pro Cys Tyr Arg Gln Asp Gly Met Arg Met Phe Gly Trp
    210                 215                 220

Phe Phe Asn Tyr Phe Tyr Val Gly Thr Val Leu Cys Leu Phe Leu Asn
225                 230                 235                 240

Phe Tyr Val Gln Thr Tyr Ile Val Arg Lys His Lys Gly Ala Lys Lys
                245                 250                 255

Ile Gln


<210> SEQ ID NO 5
<211> LENGTH: 8165
<212> TYPE: DNA
<213> ORGANISM: Artificial Sequence
<220> FEATURE:
<223> OTHER INFORMATION: Plasmid pZUF17

<400> SEQUENCE: 5

gtacgagccg gaagcataaa gtgtaaagcc tggggtgcct aatgagtgag ctaactcaca      60

ttaattgcgt tgcgctcact gcccgctttc cagtcgggaa acctgtcgtg ccagctgcat     120

taatgaatcg gccaacgcgc ggggagaggc ggtttgcgta ttgggcgctc ttccgcttcc     180

tcgctcactg actcgctgcg ctcggtcgtt cggctgcggc gagcggtatc agctcactca     240

aaggcggtaa tacggttatc cacagaatca ggggataacg caggaaagaa catgtgagca     300

aaaggccagc aaaaggccag gaaccgtaaa aaggccgcgt tgctggcgtt tttccatagg     360

ctccgccccc ctgacgagca tcacaaaaat cgacgctcaa gtcagaggtg gcgaaacccg     420

acaggactat aaagatacca ggcgtttccc cctggaagct ccctcgtgcg ctctcctgtt     480

ccgaccctgc cgcttaccgg atacctgtcc gcctttctcc cttcgggaag cgtggcgctt     540

tctcatagct cacgctgtag gtatctcagt tcggtgtagg tcgttcgctc caagctgggc     600

tgtgtgcacg aaccccccgt tcagcccgac cgctgcgcct tatccggtaa ctatcgtctt     660

gagtccaacc cggtaagaca cgacttatcg ccactggcag cagccactgg taacaggatt     720

agcagagcga ggtatgtagg cggtgctaca gagttcttga agtggtggcc taactacggc     780

tacactagaa ggacagtatt tggtatctgc gctctgctga agccagttac cttcggaaaa     840

agagttggta gctcttgatc cggcaaacaa accaccgctg gtagcggtgg tttttttgtt     900

tgcaagcagc agattacgcg cagaaaaaaa ggatctcaag aagatccttt gatcttttct     960

acggggtctg acgctcagtg gaacgaaaac tcacgttaag ggattttggt catgagatta    1020

tcaaaaagga tcttcaccta gatcctttta aattaaaaat gaagttttaa atcaatctaa    1080

agtatatatg agtaaacttg gtctgacagt taccaatgct taatcagtga ggcacctatc    1140

tcagcgatct gtctatttcg ttcatccata gttgcctgac tccccgtcgt gtagataact    1200

acgatacggg agggcttacc atctggcccc agtgctgcaa tgataccgcg agacccacgc    1260

tcaccggctc cagatttatc agcaataaac cagccagccg gaagggccga gcgcagaagt    1320

ggtcctgcaa ctttatccgc ctccatccag tctattaatt gttgccggga agctagagta    1380

agtagttcgc cagttaatag tttgcgcaac gttgttgcca ttgctacagg catcgtggtg    1440

tcacgctcgt cgtttggtat ggcttcattc agctccggtt cccaacgatc aaggcgagtt    1500

acatgatccc ccatgttgtg caaaaaagcg gttagctcct tcggtcctcc gatcgttgtc    1560
```

```
agaagtaagt tggccgcagt gttatcactc atggttatgg cagcactgca taattctctt   1620
actgtcatgc catccgtaag atgcttttct gtgactggtg agtactcaac caagtcattc   1680
tgagaatagt gtatgcggcg accgagttgc tcttgcccgg cgtcaatacg ggataatacc   1740
gcgccacata gcagaacttt aaaagtgctc atcattggaa aacgttcttc ggggcgaaaa   1800
ctctcaagga tcttaccgct gttgagatcc agttcgatgt aacccactcg tgcacccaac   1860
tgatcttcag catcttttac tttcaccagc gtttctgggt gagcaaaaac aggaaggcaa   1920
aatgccgcaa aaaagggaat aagggcgaca cggaaatgtt gaatactcat actcttcctt   1980
tttcaatatt attgaagcat ttatcagggt tattgtctca tgagcggata catatttgaa   2040
tgtatttaga aaaataaaca aataggggtt ccgcgcacat ttccccgaaa agtgccacct   2100
gacgcgccct gtagcggcgc attaagcgcg gcgggtgtgg tggttacgcg cagcgtgacc   2160
gctacacttg ccagcgccct agcgcccgct cctttcgctt tcttcccttc ctttctcgcc   2220
acgttcgccg gctttccccg tcaagctcta aatcgggggc tccctttagg gttccgattt   2280
agtgctttac ggcacctcga ccccaaaaaa cttgattagg gtgatggttc acgtagtggg   2340
ccatcgccct gatagacggt ttttcgccct ttgacgttgg agtccacgtt ctttaatagt   2400
ggactcttgt tccaaactgg aacaacactc aaccctatct cggtctattc ttttgattta   2460
taagggattt tgccgatttc ggcctattgg ttaaaaaatg agctgattta acaaaaattt   2520
aacgcgaatt ttaacaaaat attaacgctt acaatttcca ttcgccattc aggctgcgca   2580
actgttggga agggcgatcg gtgcgggcct cttcgctatt acgccagctg gcgaaagggg   2640
gatgtgctgc aaggcgatta agttgggtaa cgccagggtt ttcccagtca cgacgttgta   2700
aaacgacggc cagtgaattg taatacgact cactataggg cgaattgggt accgggcccc   2760
ccctcgaggt cgatggtgtc gataagcttg atatcgaatt catgtcacac aaaccgatct   2820
tcgcctcaag gaaacctaat tctacatccg agagactgcc gagatccagt ctacactgat   2880
taattttcgg gccaataatt taaaaaaatc gtgttatata atattatatg tattatatat   2940
atacatcatg atgatactga cagtcatgtc ccattgctaa atagacagac tccatctgcc   3000
gcctccaact gatgttctca atatttaagg ggtcatctcg cattgtttaa taataaacag   3060
actccatcta ccgcctccaa atgatgttct caaaatatat tgtatgaact tatttttatt   3120
acttagtatt attagacaac ttacttgctt tatgaaaaac acttcctatt taggaaacaa   3180
tttataatgg cagttcgttc atttaacaat ttatgtagaa taaatgttat aaatgcgtat   3240
gggaaatctt aaatatggat agcataaatg atatctgcat tgcctaattc gaaatcaaca   3300
gcaacgaaaa aaatcccttg tacaacataa atagtcatcg agaaatatca actatcaaag   3360
aacagctatt cacacgttac tattgagatt attattggac gagaatcaca cactcaactg   3420
tctttctctc ttctagaaat acaggtacaa gtatgtacta ttctcattgt tcatacttct   3480
agtcatttca tcccacatat tccttggatt tctctccaat gaatgacatt ctatcttgca   3540
aattcaacaa ttataataag atataccaaa gtagcggtat agtggcaatc aaaaagcttc   3600
tctggtgtgc ttctcgtatt tatttttatt ctaatgatcc attaaaggta tatatttatt   3660
tcttgttata taatcctttt gtttattaca tgggctggat acataaaggt attttgattt   3720
aattttttgc ttaaattcaa tcccccctcg ttcagtgtca actgtaatgg taggaaatta   3780
ccatactttt gaagaagcaa aaaaaatgaa agaaaaaaaa aatcgtattt ccaggttaga   3840
cgttccgcag aatctagaat gcggtatgcg gtacattgtt cttcgaacgt aaaagttgcg   3900
ctccctgaga tattgtacat tttgctttt acaagtacaa gtacatcgta caactatgta   3960
```

-continued

```
ctactgttga tgcatccaca acagtttgtt ttgttttttt ttgttttttt tttttctaat   4020

gattcattac cgctatgtat acctacttgt acttgtagta agccgggtta ttggcgttca   4080

attaatcata gacttatgaa tctgcacggt gtgcgctgcg agttactttt agcttatgca   4140

tgctacttgg gtgtaatatt gggatctgtt cggaaatcaa cggatgctca atcgatttcg   4200

acagtaatta attaagtcat acacaagtca gctttcttcg agcctcatat aagtataagt   4260

agttcaacgt attagcactg tacccagcat ctccgtatcg agaaacacaa caacatgccc   4320

cattggacag atcatgcgga tacacaggtt gtgcagtatc atacatactc gatcagacag   4380

gtcgtctgac catcatacaa gctgaacaag cgctccatac ttgcacgctc tctatataca   4440

cagttaaatt acatatccat agtctaacct ctaacagtta atcttctggt aagcctccca   4500

gccagccttc tggtatcgct tggcctcctc aataggatct cggttctggc cgtacagacc   4560

tcggccgaca attatgatat ccgttccggt agacatgaca tcctcaacag ttcggtactg   4620

ctgtccgaga gcgtctccct tgtcgtcaag acccaccccg ggggtcagaa taagccagtc   4680

ctcagagtcg cccttaggtc ggttctgggc aatgaagcca accacaaact cggggtcgga   4740

tcgggcaagc tcaatggtct gcttggagta ctcgccagtg gccagagagc ccttgcaaga   4800

cagctcggcc agcatgagca gacctctggc cagcttctcg ttgggagagg ggactaggaa   4860

ctccttgtac tgggagttct cgtagtcaga gacgtcctcc ttcttctgtt cagagacagt   4920

ttcctcggca ccagctcgca ggccagcaat gattccggtt ccgggtacac cgtgggcgtt   4980

ggtgatatcg gaccactcgg cgattcggtg acaccggtac tggtgcttga cagtgttgcc   5040

aatatctgcg aactttctgt cctcgaacag gaagaaaccg tgcttaagag caagttcctt   5100

gagggggagc acagtgccgg cgtaggtgaa gtcgtcaatg atgtcgatat gggttttgat   5160

catgcacaca taaggtccga ccttatcggc aagctcaatg agctccttgg tggtggtaac   5220

atccagagaa gcacacaggt tggttttctt ggctgccacg agcttgagca ctcgagcggc   5280

aaaggcggac ttgtggacgt tagctcgagc ttcgtaggag ggcattttgg tggtgaagag   5340

gagactgaaa taaatttagt ctgcagaact ttttatcgga accttatctg gggcagtgaa   5400

gtatatgtta tggtaatagt tacgagttag ttgaacttat agatagactg gactatacgg   5460

ctatcggtcc aaattagaaa gaacgtcaat ggctctctgg gcgtcgcctt tgccgacaaa   5520

aatgtgatca tgatgaaagc cagcaatgac gttgcagctg atattgttgt cggccaaccg   5580

cgccgaaaac gcagctgtca gacccacagc ctccaacgaa gaatgtatcg tcaaagtgat   5640

ccaagcacac tcatagttgg agtcgtactc caaaggcggc aatgacgagt cagacagata   5700

ctcgtcgact caggcgacga cggaattcct gcagcccatc tgcagaattc aggagagacc   5760

gggttggcgg cgtatttgtg tcccaaaaaa cagccccaat tgccccggag aagacggcca   5820

ggccgcctag atgacaaatt caacaactca cagctgactt tctgccattg ccactagggg   5880

ggggcctttt tatatggcca agccaagctc tccacgtcgg ttgggctgca cccaacaata   5940

aatgggtagg gttgcaccaa caaagggatg ggatgggggg tagaagatac gaggataacg   6000

gggctcaatg gcacaaataa gaacgaatac tgccattaag actcgtgatc cagcgactga   6060

caccattgca tcatctaagg gcctcaaaac tacctcggaa ctgctgcgct gatctggaca   6120

ccacagaggt tccgagcact ttaggttgca ccaaatgtcc caccaggtgc aggcagaaaa   6180

cgctggaaca gcgtgtacag tttgtcttaa caaaaagtga gggcgctgag gtcgagcagg   6240

gtggtgtgac ttgttatagc ctttagagct gcgaaagcgc gtatggattt ggctcatcag   6300
```

-continued

```
gccagattga gggtctgtgg acacatgtca tgttagtgta cttcaatcgc cccctggata   6360

tagccccgac aataggccgt ggcctcattt ttttgccttc cgcacatttc cattgctcgg   6420

tacccacacc ttgcttctcc tgcacttgcc aaccttaata ctggtttaca ttgaccaaca   6480

tcttacaagc ggggggcttg tctagggtat atataaacag tggctctccc aatcggttgc   6540

cagtctcttt tttcctttct ttccccacag attcgaaatc taaactacac atcacacaat   6600

gcctgttact gacgtcctta agcgaaagtc cggtgtcatc gtcggcgacg atgtccgagc   6660

cgtgagtatc cacgacaaga tcagtgtcga gacgacgcgt tttgtgtaat gacacaatcc   6720

gaaagtcgct agcaacacac actctctaca caaactaacc cagctctcca tggctgagga   6780

taagaccaag gtcgagttcc ctaccctgac tgagctgaag cactctatcc ctaacgcttg   6840

ctttgagtcc aacctcggac tctcgctcta ctacactgcc cgagcgatct tcaacgcatc   6900

tgcctctgct gctctgctct acgctgcccg atctactccc ttcattgccg ataacgttct   6960

gctccacgct ctggtttgcg ccacctacat ctacgtgcag ggtgtcatct tctggggttt   7020

ctttaccgtc ggtcacgact gtggtcactc tgccttctcc cgataccact ccgtcaactt   7080

catcattggc tgcatcatgc actctgccat tctgactccc ttcgagtcct ggcgagtgac   7140

ccaccgacac catcacaaga acactggcaa cattgataag gacgagatct tctaccctca   7200

tcggtccgtc aaggacctcc aggacgtgcg acaatgggtc tacaccctcg gaggtgcttg   7260

gtttgtctac ctgaaggtcg gatatgctcc tcgaaccatg tcccactttg accccctgga   7320

ccctctcctg cttcgacgag cctccgctgt catcgtgtcc ctcggagtct gggctgcctt   7380

cttcgctgcc tacgcctacc tcacatactc gctcggcttt gccgtcatgg gcctctacta   7440

ctatgctcct ctctttgtct ttgcttcgtt cctcgtcatt actaccttct tgcatcacaa   7500

cgacgaagct actccctggt acggtgactc ggagtggacc tacgtcaagg gcaacctgag   7560

ctccgtcgac cgatcgtacg gagctttcgt ggacaacctg tctcaccaca ttggcaccca   7620

ccaggtccat cacttgttcc ctatcattcc ccactacaag ctcaacgaag ccaccaagca   7680

ctttgctgcc gcttaccctc acctcgtgag acgtaacgac gagcccatca ttactgcctt   7740

cttcaagacc gctcacctct ttgtcaacta cggagctgtg cccgagactg ctcagatttt   7800

caccctcaaa gagtctgccg ctgcagccaa ggccaagagc gactaagcgg ccgcaagtgt   7860

ggatggggaa gtgagtgccc ggttctgtgt gcacaattgg caatccaaga tggatggatt   7920

caacacaggg atatagcgag ctacgtggtg gtgcgaggat atagcaacgg atatttatgt   7980

ttgacacttg agaatgtacg atacaagcac tgtccaagta caatactaaa catactgtac   8040

atactcatac tcgtacccgg gcaacggttt cacttgagtg cagtggctag tgctcttact   8100

cgtacagtgt gcaatactgc gtatcatagt ctttgatgta tatcgtattc attcatgtta   8160

gttgc                                                               8165
```

<210> SEQ ID NO 6
<211> LENGTH: 7865
<212> TYPE: DNA
<213> ORGANISM: Artificial Sequence
<220> FEATURE:
<223> OTHER INFORMATION: Plasmid pDMW359

<400> SEQUENCE: 6

```
catggaggtg gtgaatgaaa tagtctcaat tgggcaggaa gttttaccca aagttgatta     60

tgcccaactc tggagtgatg ccagtcactg tgaggtgctt tacttgtcca tcgcatttgt    120

catcttgaag ttcactcttg gcccccttgg tccaaaaggt cagtctcgta tgaagtttgt    180
```

```
tttcaccaat tacaaccttc tcatgtccat ttattcgttg ggatcattcc tctcaatggc    240
atatgccatg tacaccatcg gtgttatgtc tgacaactgc gagaaggctt ttgacaacaa    300
cgtcttcagg atcaccacgc agttgttcta tttgagcaag ttcctggagt atattgactc    360
cttctatttg ccactgatgg gcaagcctct gacctggttg caattcttcc atcatttggg    420
ggcaccgatg gatatgtggc tgttctataa ttaccgaaat gaagctgttt ggatttttgt    480
gctgttgaat ggtttcatcc actggatcat gtacggttat tattggacca gattgatcaa    540
gctgaagttc cccatgccaa aatccctgat tacatcaatg cagatcattc aattcaatgt    600
tggtttctac attgtctgga agtacaggaa cattccctgt tatcgccaag atgggatgag    660
gatgtttggc tggttcttca attactttta tgttggcaca gtcttgtgtt tgttcttgaa    720
tttctatgtg caaacgtata tcgtcaggaa gcacaaggga gccaaaaaga ttcagtgagc    780
ggccgcaagt gtggatgggg aagtgagtgc ccggttctgt gtgcacaatt ggcaatccaa    840
gatggatgga ttcaacacag ggatatagcg agctacgtgg tggtgcgagg atatagcaac    900
ggatatttat gtttgacact tgagaatgta cgatacaagc actgtccaag tacaatacta    960
aacatactgt acatactcat actcgtaccc gggcaacggt ttcacttgag tgcagtggct   1020
agtgctctta ctcgtacagt gtgcaatact gcgtatcata gtctttgatg tatatcgtat   1080
tcattcatgt tagttgcgta cgagccggaa gcataaagtg taaagcctgg ggtgcctaat   1140
gagtgagcta actcacatta attgcgttgc gctcactgcc cgctttccag tcgggaaacc   1200
tgtcgtgcca gctgcattaa tgaatcggcc aacgcgcggg gagaggcggt ttgcgtattg   1260
ggcgctcttc cgcttcctcg ctcactgact cgctgcgctc ggtcgttcgg ctgcggcgag   1320
cggtatcagc tcactcaaag gcggtaatac ggttatccac agaatcaggg gataacgcag   1380
gaaagaacat gtgagcaaaa ggccagcaaa aggccaggaa ccgtaaaaag gccgcgttgc   1440
tggcgttttt ccataggctc cgcccccctg acgagcatca caaaaatcga cgctcaagtc   1500
agaggtggcg aaacccgaca ggactataaa gataccaggc gtttccccct ggaagctccc   1560
tcgtgcgctc tcctgttccg accctgccgc ttaccggata cctgtccgcc tttctccctt   1620
cgggaagcgt ggcgctttct catagctcac gctgtaggta tctcagttcg gtgtaggtcg   1680
ttcgctccaa gctgggctgt gtgcacgaac cccccgttca gcccgaccgc tgcgccttat   1740
ccggtaacta tcgtcttgag tccaacccgg taagacacga cttatcgcca ctggcagcag   1800
ccactggtaa caggattagc agagcgaggt atgtaggcgg tgctacagag ttcttgaagt   1860
ggtggcctaa ctacggctac actagaagga cagtatttgg tatctgcgct ctgctgaagc   1920
cagttacctt cggaaaaaga gttggtagct cttgatccgg caaacaaacc accgctggta   1980
gcggtggttt ttttgtttgc aagcagcaga ttacgcgcag aaaaaaagga tctcaagaag   2040
atcctttgat cttttctacg gggtctgacg ctcagtggaa cgaaaactca cgttaaggga   2100
ttttggtcat gagattatca aaaaggatct tcacctagat ccttttaaat taaaaatgaa   2160
gttttaaatc aatctaaagt atatatgagt aaacttggtc tgacagttac caatgcttaa   2220
tcagtgaggc acctatctca gcgatctgtc tatttcgttc atccatagtt gcctgactcc   2280
ccgtcgtgta gataactacg atacgggagg gcttaccatc tggccccagt gctgcaatga   2340
taccgcgaga cccacgctca ccggctccag atttatcagc aataaaccag ccagccggaa   2400
gggccgagcg cagaagtggt cctgcaactt tatccgcctc catccagtct attaattgtt   2460
gccgggaagc tagagtaagt agttcgccag ttaatagttt gcgcaacgtt gttgccattg   2520
```

-continued

```
ctacaggcat cgtggtgtca cgctcgtcgt ttggtatggc ttcattcagc tccggttccc   2580
aacgatcaag gcgagttaca tgatccccca tgttgtgcaa aaaagcggtt agctccttcg   2640
gtcctccgat cgttgtcaga agtaagttgg ccgcagtgtt atcactcatg gttatggcag   2700
cactgcataa ttctcttact gtcatgccat ccgtaagatg cttttctgtg actggtgagt   2760
actcaaccaa gtcattctga gaatagtgta tgcggcgacc gagttgctct tgcccggcgt   2820
caatacggga taataccgcg ccacatagca gaactttaaa agtgctcatc attggaaaac   2880
gttcttcggg gcgaaaactc tcaaggatct taccgctgtt gagatccagt tcgatgtaac   2940
ccactcgtgc acccaactga tcttcagcat cttttacttt caccagcgtt tctgggtgag   3000
caaaaacagg aaggcaaaat gccgcaaaaa agggaataag ggcgacacgg aaatgttgaa   3060
tactcatact cttccttttt caatattatt gaagcattta tcagggttat tgtctcatga   3120
gcggatacat atttgaatgt atttagaaaa ataaacaaat aggggttccg cgcacatttc   3180
cccgaaaagt gccacctgac gcgccctgta gcggcgcatt aagcgcggcg ggtgtggtgg   3240
ttacgcgcag cgtgaccgct acacttgcca gcgccctagc gcccgctcct ttcgctttct   3300
tcccttcctt tctcgccacg ttcgccggct ttccccgtca agctctaaat cgggggctcc   3360
ctttagggtt ccgatttagt gctttacggc acctcgaccc caaaaaactt gattagggtg   3420
atggttcacg tagtgggcca tcgccctgat agacggtttt tcgccctttg acgttggagt   3480
ccacgttctt taatagtgga ctcttgttcc aaactggaac aacactcaac cctatctcgg   3540
tctattcttt tgatttataa gggattttgc cgatttcggc ctattggtta aaaaatgagc   3600
tgatttaaca aaaatttaac gcgaatttta acaaaatatt aacgcttaca atttccattc   3660
gccattcagg ctgcgcaact gttgggaagg gcgatcggtg cgggcctctt cgctattacg   3720
ccagctggcg aaagggggat gtgctgcaag gcgattaagt tgggtaacgc cagggttttc   3780
ccagtcacga cgttgtaaaa cgacggccag tgaattgtaa tacgactcac tatagggcga   3840
attgggtacc gggccccccc tcgaggtcga tggtgtcgat aagcttgata tcgaattcat   3900
gtcacacaaa ccgatcttcg cctcaaggaa acctaattct acatccgaga gactgccgag   3960
atccagtcta cactgattaa ttttcgggcc aataatttaa aaaaatcgtg ttatataata   4020
ttatatgtat tatatatata catcatgatg atactgacag tcatgtccca ttgctaaata   4080
gacagactcc atctgccgcc tccaactgat gttctcaata tttaaggggt catctcgcat   4140
tgtttaataa taaacagact ccatctaccg cctccaaatg atgttctcaa aatatattgt   4200
atgaacttat ttttattact tagtattatt agacaactta cttgctttat gaaaaacact   4260
tcctatttag gaaacaattt ataatggcag ttcgttcatt taacaattta tgtagaataa   4320
atgttataaa tgcgtatggg aaatcttaaa tatggatagc ataaatgata tctgcattgc   4380
ctaattcgaa atcaacagca acgaaaaaaa tcccttgtac aacataaata gtcatcgaga   4440
aatatcaact atcaaagaac agctattcac acgttactat tgagattatt attggacgag   4500
aatcacacac tcaactgtct ttctctcttc tagaaataca ggtacaagta tgtactattc   4560
tcattgttca tacttctagt catttcatcc cacatattcc ttggatttct ctccaatgaa   4620
tgacattcta tcttgcaaat tcaacaatta taataagata taccaaagta gcggtatagt   4680
ggcaatcaaa aagcttctct ggtgtgcttc tcgtatttat ttttattcta atgatccatt   4740
aaaggtatat atttatttct tgttatataa tccttttgtt tattacatgg gctggataca   4800
taaaggtatt ttgatttaat tttttgctta aattcaatcc cccctcgttc agtgtcaact   4860
gtaatggtag gaaattacca tacttttgaa gaagcaaaaa aaatgaaaga aaaaaaaaat   4920
```

```
cgtatttcca ggttagacgt tccgcagaat ctagaatgcg gtatgcggta cattgttctt   4980
cgaacgtaaa agttgcgctc cctgagatat tgtacatttt tgcttttaca agtacaagta   5040
catcgtacaa ctatgtacta ctgttgatgc atccacaaca gtttgttttg ttttttttg   5100
ttttttttt ttctaatgat tcattaccgc tatgtatacc tacttgtact tgtagtaagc   5160
cgggttattg gcgttcaatt aatcatagac ttatgaatct gcacggtgtg cgctgcgagt   5220
tacttttagc ttatgcatgc tacttgggtg taatattggg atctgttcgg aaatcaacgg   5280
atgctcaatc gatttcgaca gtaattaatt aagtcataca caagtcagct ttcttcgagc   5340
ctcatataag tataagtagt tcaacgtatt agcactgtac ccagcatctc cgtatcgaga   5400
aacacaacaa catgccccat tggacagatc atgcggatac acaggttgtg cagtatcata   5460
catactcgat cagacaggtc gtctgaccat catacaagct gaacaagcgc tccatacttg   5520
cacgctctct atatacacag ttaaattaca tatccatagt ctaacctcta acagttaatc   5580
ttctggtaag cctcccagcc agccttctgg tatcgcttgg cctcctcaat aggatctcgg   5640
ttctggccgt acagacctcg gccgacaatt atgatatccg ttccggtaga catgacatcc   5700
tcaacagttc ggtactgctg tccgagagcg tctcccttgt cgtcaagacc caccccgggg   5760
gtcagaataa gccagtcctc agagtcgccc ttaggtcggt tctgggcaat gaagccaacc   5820
acaaactcgg ggtcggatcg ggcaagctca atggtctgct tggagtactc gccagtggcc   5880
agagagccct tgcaagacag ctcggccagc atgagcagac ctctggccag cttctcgttg   5940
ggagagggga ctaggaactc cttgtactgg gagttctcgt agtcagagac gtcctccttc   6000
ttctgttcag agacagtttc ctcggcacca gctcgcaggc cagcaatgat tccggttccg   6060
ggtacaccgt gggcgttggt gatatcggac cactcggcga ttcggtgaca ccggtactgg   6120
tgcttgacag tgttgccaat atctgcgaac tttctgtcct cgaacaggaa gaaaccgtgc   6180
ttaagagcaa gttccttgag ggggagcaca gtgccggcgt aggtgaagtc gtcaatgatg   6240
tcgatatggg ttttgatcat gcacacataa ggtccgacct tatcggcaag ctcaatgagc   6300
tccttggtgg tggtaacatc cagagaagca cacaggttgg ttttcttggc tgccacgagc   6360
ttgagcactc gagcggcaaa ggcggacttg tggacgttag ctcgagcttc gtaggagggc   6420
attttggtgg tgaagaggag actgaaataa atttagtctg cagaactttt tatcggaacc   6480
ttatctgggg cagtgaagta tatgttatgg taatagttac gagttagttg aacttataga   6540
tagactggac tatacggcta tcggtccaaa ttagaaagaa cgtcaatggc tctctgggcg   6600
tcgcctttgc cgacaaaaat gtgatcatga tgaaagccag caatgacgtt gcagctgata   6660
ttgttgtcgg ccaaccgcgc cgaaaacgca gctgtcagac ccacagcctc caacgaagaa   6720
tgtatcgtca aagtgatcca agcacactca tagttggagt cgtactccaa aggcggcaat   6780
gacgagtcag acagatactc gtcgactcag gcgacgacgg aattcctgca gcccatctgc   6840
agaattcagg agagaccggg ttggcggcgt atttgtgtcc caaaaaacag ccccaattgc   6900
cccggagaag acggccaggc cgcctagatg acaaattcaa caactcacag ctgactttct   6960
gccattgcca ctaggggggg gcctttttat atggccaagc caagctctcc acgtcggttg   7020
ggctgcaccc aacaataaat gggtagggtt gcaccaacaa agggatggga tggggggtag   7080
aagatacgag gataacgggg ctcaatggca caaataagaa cgaatactgc cattaagact   7140
cgtgatccag cgactgacac cattgcatca tctaagggcc tcaaaactac ctcggaactg   7200
ctgcgctgat ctggacacca cagaggttcc gagcacttta ggttgcacca aatgtcccac   7260
```

-continued

```
caggtgcagg cagaaaacgc tggaacagcg tgtacagttt gtcttaacaa aaagtgaggg   7320

cgctgaggtc gagcagggtg gtgtgacttg ttatagcctt tagagctgcg aaagcgcgta   7380

tggatttggc tcatcaggcc agattgaggg tctgtggaca catgtcatgt tagtgtactt   7440

caatcgcccc ctggatatag ccccgacaat aggccgtggc ctcatttttt tgccttccgc   7500

acatttccat tgctcggtac ccacaccttg cttctcctgc acttgccaac cttaatactg   7560

gtttacattg accaacatct tacaagcggg gggcttgtct agggtatata taaacagtgg   7620

ctctcccaat cggttgccag tctctttttt cctttctttc cccacagatt cgaaatctaa   7680

actacacatc acacaatgcc tgttactgac gtccttaagc gaaagtccgg tgtcatcgtc   7740

ggcgacgatg tccgagccgt gagtatccac gacaagatca gtgtcgagac gacgcgtttt   7800

gtgtaatgac acaatccgaa agtcgctagc aacacacact ctctacacaa actaacccag   7860

ctctc                                                               7865
```

```
<210> SEQ ID NO 7
<211> LENGTH: 315
<212> TYPE: PRT
<213> ORGANISM: Gluconobacter oxydans

<400> SEQUENCE: 7

Met Leu Ala Cys Asn Arg Ala Ile Ile Ala Arg Met Glu Ser Pro Val
1               5                   10                  15

Pro Leu Ile Pro Gln Leu Gly Ala His Leu Val Ala Ala Gly Gly Lys
            20                  25                  30

Arg Leu Arg Pro Leu Leu Thr Leu Ala Ser Ala Arg Leu Cys Gly Tyr
        35                  40                  45

Gln Pro Gly Pro Asp His Gln Arg His Val Gly Leu Ala Ala Cys Val
    50                  55                  60

Glu Phe Ile His Thr Ala Thr Leu Leu His Asp Asp Val Val Asp Glu
65                  70                  75                  80

Ser Thr Leu Arg Arg Gly Leu Ala Ser Ala Asn Ala Val Phe Gly Asn
                85                  90                  95

Lys Ala Ser Val Leu Val Gly Asp Phe Leu Phe Ala Arg Ser Phe Gln
            100                 105                 110

Leu Met Thr Ala Asp Gly Ser Leu Lys Val Met Ala Ile Leu Ser Asp
        115                 120                 125

Ala Ser Ala Thr Ile Ala Glu Gly Glu Val Leu Gln Met Val Val Gln
    130                 135                 140

Asn Asp Leu Thr Thr Pro Val Glu Arg Tyr Leu Glu Val Ile His Gly
145                 150                 155                 160

Lys Thr Ala Ala Leu Phe Ala Ala Ala Cys Arg Val Gly Ala Val Val
                165                 170                 175

Ala Glu Arg Pro Glu Ala Glu Glu Glu Ala Leu Glu Arg Phe Gly Thr
            180                 185                 190

Asn Leu Gly Met Ala Phe Gln Leu Val Asp Asp Ala Leu Asp Tyr Ala
        195                 200                 205

Ala Asp Gln Gln Val Leu Gly Lys Thr Val Gly Asp Asp Met Arg Glu
    210                 215                 220

Gly Lys Ile Thr Leu Pro Val Leu Ala Ala Tyr Glu Ala Gly Ser Pro
225                 230                 235                 240

Glu Asp Arg Ile Phe Trp Glu Arg Val Ile Gly Glu Gly Glu Gln Thr
                245                 250                 255

Glu Asp Asp Leu Pro His Ala Leu Asn Leu Ile Ala Lys Thr Gly Ala
```

```
            260                 265                 270

Ile Asn Thr Thr Ile Ala Arg Ala Gln Val Tyr Ala Asp Ala Ala Val
        275                 280                 285

Glu Ala Leu Ser Ile Phe Pro Asp Ser Glu Leu Arg Arg Leu Leu Ile
    290                 295                 300

Glu Thr Val Gln Phe Thr Val Asn Arg Ala Arg
305                 310                 315


<210> SEQ ID NO 8
<211> LENGTH: 332
<212> TYPE: PRT
<213> ORGANISM: Sulfitobacter sp. NAS-14.1

<400> SEQUENCE: 8

Met Thr Ser Glu Asn Thr Gln Lys Pro His Asp Arg Met Ala Ala Tyr
1               5                   10                  15

Leu Asn Ala Asp Met Thr Ala Val Asn Asp Leu Ile Arg Asp Arg Met
            20                  25                  30

Ala Ser Glu His Ala Pro Arg Ile Pro Glu Val Thr Ala His Leu Val
        35                  40                  45

Glu Ala Gly Gly Lys Arg Leu Arg Pro Met Leu Thr Leu Ala Ala Ala
    50                  55                  60

Arg Leu Cys Gly Tyr Asp Gly Pro Tyr His Val His Leu Ala Ala Thr
65                  70                  75                  80

Val Glu Phe Ile His Thr Ala Thr Leu Leu His Asp Asp Val Val Asp
                85                  90                  95

Glu Ser Ala Gln Arg Arg Gly Arg Pro Thr Ala Asn Leu Leu Trp Asp
            100                 105                 110

Asn Lys Ser Ser Val Leu Val Gly Asp Tyr Leu Phe Ala Arg Ser Phe
        115                 120                 125

Gln Leu Met Thr Glu Thr Asn Asn Met Arg Val Leu Ala Ile Leu Ala
    130                 135                 140

Asn Ala Ser Ala Thr Ile Ala Glu Gly Glu Val Leu Gln Leu Thr Ala
145                 150                 155                 160

Ala Gln Asn Leu Ala Thr Asp Glu Gly Ile Tyr Leu Gln Val Val Arg
                165                 170                 175

Gly Lys Thr Ala Ala Leu Phe Ser Ala Ala Thr Gln Val Gly Gly Val
            180                 185                 190

Ile Ala Ala Ala Pro Asp Ala Gln Val Gln Ala Leu Phe Asp Tyr Gly
        195                 200                 205

Asp Ala Leu Gly Ile Ala Phe Gln Ile Val Asp Asp Leu Leu Asp Tyr
    210                 215                 220

Gln Gly Asp Pro Asn Ala Thr Gly Lys Asn Ile Gly Asp Asp Phe Arg
225                 230                 235                 240

Glu Arg Lys Leu Thr Leu Pro Val Ile Lys Ala Ile Ala Lys Gly Asp
                245                 250                 255

Ala Thr Glu Arg Ala Phe Trp Thr Arg Thr Ile Glu Lys Gly Lys Gln
            260                 265                 270

Glu Asp Gly Asp Leu Glu His Ala Leu Ser Leu Leu Asn Ala His Gly
        275                 280                 285

Thr Leu Asp Glu Thr Lys Ala Glu Ala Leu Ala Trp Ala Glu Gln Ala
    290                 295                 300

Lys Thr Ala Leu Asn Thr Leu Pro Asp His Glu Leu Thr Gln Met Leu
305                 310                 315                 320
```

```
Arg Asp Leu Ala Asp Tyr Val Val Ala Arg Ile Ser
                325                 330


<210> SEQ ID NO 9
<211> LENGTH: 332
<212> TYPE: PRT
<213> ORGANISM: Silicibacter pomeroyi

<400> SEQUENCE: 9

Met Asp Ala Lys Val Ser Thr Lys Pro His Glu Met Leu Ala Ala Thr
1               5                   10                  15

Leu Ser Gln Glu Met Ala Ala Val Asn Ala Leu Ile Arg Thr Arg Met
            20                  25                  30

Ala Ser Glu His Ala Pro Arg Ile Pro Glu Val Thr Ala His Leu Val
        35                  40                  45

Glu Ala Gly Gly Lys Arg Leu Arg Pro Met Leu Thr Leu Ala Ala Ala
    50                  55                  60

Arg Leu Cys Gly Tyr Gln Gly Glu Asp His Val Lys Leu Ala Ala Thr
65                  70                  75                  80

Val Glu Phe Ile His Thr Ala Thr Leu Leu His Asp Asp Val Val Asp
                85                  90                  95

Glu Ser Gly Gln Arg Arg Gly Arg Pro Thr Ala Asn Leu Leu Trp Asp
            100                 105                 110

Asn Lys Ser Ser Val Leu Val Gly Asp Tyr Leu Phe Ala Arg Ser Phe
        115                 120                 125

Gln Leu Met Val Glu Thr Gly Ser Leu Arg Val Leu Asp Ile Leu Ala
    130                 135                 140

Asn Ala Ala Ala Thr Ile Ala Glu Gly Glu Val Leu Gln Met Thr Ala
145                 150                 155                 160

Ala Ser Asp Leu Arg Thr Asp Glu Ser Val Tyr Leu Gln Val Val Arg
                165                 170                 175

Gly Lys Thr Ala Ala Leu Phe Ser Ala Ala Thr Glu Val Gly Gly Val
            180                 185                 190

Ile Ala Gly Val Pro Glu Ala Gln Val Arg Ala Leu Phe Glu Tyr Gly
        195                 200                 205

Asp Ala Leu Gly Ile Ala Phe Gln Ile Ala Asp Asp Leu Leu Asp Tyr
    210                 215                 220

Gln Gly Asp Ala Lys Ala Thr Gly Lys Asn Val Gly Asp Asp Phe Arg
225                 230                 235                 240

Glu Arg Lys Leu Thr Leu Pro Val Ile Lys Ala Val Ala Gln Ala Thr
                245                 250                 255

Asp Glu Glu Arg Ala Phe Trp Val Arg Thr Ile Glu Lys Gly Lys Gln
            260                 265                 270

Ala Glu Gly Asp Leu Glu Gln Ala Leu Ala Leu Met Glu Lys Tyr Gly
        275                 280                 285

Thr Leu Ala Ala Thr Arg Ala Asp Ala His Ala Trp Ala Glu Lys Ala
    290                 295                 300

Arg Thr Ala Leu Glu Leu Leu Pro Asn His Glu Ile Arg Thr Met Leu
305                 310                 315                 320

Ser Asp Leu Ala Asp Tyr Val Val Ala Arg Leu Ser
                325                 330


<210> SEQ ID NO 10
<211> LENGTH: 331
<212> TYPE: PRT
<213> ORGANISM: Oceanicola batsensis
```

<400> SEQUENCE: 10

Met Asp Lys Pro Val Glu Lys Pro His Glu Ala Ile Ala Ala Leu Leu
1 5 10 15

Ala Asp Asp Leu Gly Ala Val Asn Ala Leu Ile Arg Glu Arg Met Ala
20 25 30

Ser Arg His Ala Pro Arg Ile Pro Glu Val Thr Ala His Leu Val Glu
35 40 45

Ala Gly Gly Lys Arg Ile Arg Pro Met Leu Thr Leu Ala Ala Ala Arg
50 55 60

Leu Cys Gly Tyr Asp Gly Pro Tyr His Ile His Leu Ala Ala Thr Val
65 70 75 80

Glu Phe Ile His Thr Ala Thr Leu Leu His Asp Asp Val Val Asp Glu
85 90 95

Ser Ala Gln Arg Arg Gly Arg Pro Thr Ala Asn Leu Leu Trp Asp Asn
100 105 110

Lys Ser Ser Val Leu Val Gly Asp Tyr Leu Phe Ala Arg Ala Phe Gln
115 120 125

Leu Met Val Glu Pro Gly Asn Leu Arg Val Leu Ser Ile Leu Ser Asp
130 135 140

Ala Ala Ala Thr Ile Ala Glu Gly Glu Val Leu Gln Leu Ser Ala Ala
145 150 155 160

Gln Asp Leu Lys Thr Thr Glu Glu Thr Tyr Leu Gln Val Ile Arg Gly
165 170 175

Lys Thr Ala Ala Leu Phe Ser Ala Ala Thr Glu Ala Gly Gly Glu Ile
180 185 190

Ala Gly Ala Ser Pro Ala Gln Val Arg Ala Leu Phe Asp Tyr Gly Asp
195 200 205

Ala Leu Gly Ile Ala Phe Gln Met Ala Asp Asp Leu Leu Asp Trp Thr
210 215 220

Gly Lys Thr Asp Ser Thr Gly Lys Asn Val Gly Asp Asp Phe Arg Glu
225 230 235 240

Arg Lys Leu Thr Leu Pro Leu Ile Arg Ala Val Ala Ala Ala Asp Asp
245 250 255

Glu Glu Arg Ala Phe Trp Thr Arg Thr Ile Glu Lys Gly Arg Gln Asn
260 265 270

Asp Glu Asp Leu Ala Thr Ala Arg Glu Leu Leu Asp Arg His Gly Ala
275 280 285

Leu Gly Ser Thr Arg Glu Thr Ala Leu Asp Trp Ala Asp Arg Ala Lys
290 295 300

Ser Ala Leu Thr His Leu Pro Asp His Asp Leu Thr Ala His Leu Ser
305 310 315 320

Asp Leu Ala Asp Tyr Val Val Glu Arg Leu Arg
325 330

<210> SEQ ID NO 11
<211> LENGTH: 338
<212> TYPE: PRT
<213> ORGANISM: Rhizobium leguminosarum bv. viciae

<400> SEQUENCE: 11

Met Gly Val Val Ile Pro Leu Glu Glu Ser Lys Asn Lys Leu Ala Ser
1 5 10 15

Ile Lys Pro Leu Val Asp Leu Thr Arg Ala Asp Met Glu Arg Val Asn
20 25 30

```
Gln Leu Ile Leu Ser Lys Ala Gly Ser Asp Val Gln Met Ile Pro Glu
        35                  40                  45

Val Ala Asn His Leu Ile Ser Ser Gly Gly Lys Arg Leu Arg Pro Met
    50                  55                  60

Leu Thr Leu Ala Ser Ala Ser Leu Phe Asp Tyr Arg Gly Glu Asn His
65                  70                  75                  80

Ile Lys Leu Ala Thr Ser Val Glu Phe Met His Thr Ala Thr Leu Leu
                85                  90                  95

His Asp Asp Val Val Asp Glu Ser Asp Leu Arg Arg Gly Lys Ser Thr
            100                 105                 110

Ala Arg Met Ile Trp Gly Asn Gln Ala Ser Val Leu Val Gly Asp Phe
        115                 120                 125

Leu Leu Gly Gln Ala Phe Arg Met Met Val Asp Val Gly Ser Leu Asp
    130                 135                 140

Ala Leu Asp Val Leu Ser Ser Ala Ala Cys Val Ile Ala Glu Gly Glu
145                 150                 155                 160

Val Leu Gln Leu Ser Val Ala Lys Asn Met Glu Thr Thr Glu Asp Asp
                165                 170                 175

Tyr Leu Ser Val Ile Arg Ala Lys Thr Ala Ala Leu Phe Ala Ala Ala
            180                 185                 190

Ala Glu Val Gly Pro Ile Val Ala Glu Val Gly Arg Ser Gly Arg Asn
        195                 200                 205

Ala Leu Lys Ser Tyr Gly Met Asn Leu Gly Leu Ala Phe Gln Leu Val
    210                 215                 220

Asp Asp Ala Leu Asp Tyr Gly Gly Lys Ala Ala Asp Leu Gly Lys Asn
225                 230                 235                 240

Val Gly Asp Asp Phe Arg Glu Gly Lys Ile Thr Leu Pro Val Ile Leu
                245                 250                 255

Ala Tyr Arg Arg Gly Thr Glu Asp Glu Arg Ala Phe Trp Arg Asp Ala
            260                 265                 270

Ile Glu Ala Gly Asn Ser Thr Asp Ala Asn Leu Glu Lys Ala Leu Gly
        275                 280                 285

Leu Ile Thr Lys Tyr Gly Thr Leu Ser Asp Thr Ile Gly Arg Ala Ile
    290                 295                 300

His Tyr Gly Thr Ile Ala Arg Asp Ala Leu Ala Pro Leu Pro Asp Thr
305                 310                 315                 320

Val Trp Lys Ser Ala Leu Met Glu Val Ile Asp Phe Cys Ile Glu Arg
                325                 330                 335

Val Asn


<210> SEQ ID NO 12
<211> LENGTH: 338
<212> TYPE: PRT
<213> ORGANISM: Mesorhizobium loti

<400> SEQUENCE: 12

Met Gly Val Val Leu Asn Ile Glu Asn Gly Lys Arg Glu Pro Ala Ser
1               5                   10                  15

Ile Lys Asp Leu Ile Asp Leu Thr Ala Ala Asp Met Gly Arg Val Asn
            20                  25                  30

Glu Leu Ile Leu Ser Lys Ala Gly Ser Asp Val Glu Met Ile Pro Glu
        35                  40                  45

Val Ala Asn His Leu Ile Ser Ser Gly Gly Lys Arg Leu Arg Pro Met
    50                  55                  60
```

```
Leu Thr Leu Ala Ala Ala Gln Met Phe Gly Tyr Ala Gly Glu Gly His
65                  70                  75                  80

Val Lys Leu Ala Thr Ser Val Glu Phe Met His Thr Ala Thr Leu Leu
                85                  90                  95

His Asp Asp Val Val Asp Glu Ser Gly Met Arg Arg Gly Lys Lys Thr
            100                 105                 110

Ala Arg Met Ile Trp Gly Asn Gln Ala Ser Val Leu Val Gly Asp Phe
        115                 120                 125

Leu Leu Gly Gln Ala Phe Arg Met Met Val Asp Val Gly Ser Leu Glu
    130                 135                 140

Ala Leu Asp Ile Leu Ser Ser Ala Ala Ser Ile Ile Ala Glu Gly Glu
145                 150                 155                 160

Val Met Gln Leu Ala Ala Ala Lys Asn Leu Glu Thr Thr Glu Asp Glu
                165                 170                 175

His Phe Ala Val Ile Lys Ala Lys Thr Ala Ala Leu Phe Ser Ala Ala
            180                 185                 190

Ala Glu Val Gly Pro Val Ile Ala Gln Ala Thr Arg Asn Asp Arg Ala
        195                 200                 205

Ala Leu Arg Ser Tyr Gly Met Asn Leu Gly Leu Ala Phe Gln Leu Ile
    210                 215                 220

Asp Asp Ala Leu Asp Tyr Gly Gly Thr Ser Lys Asp Leu Gly Lys Asn
225                 230                 235                 240

Val Gly Asp Asp Phe Arg Glu Gly Lys Val Thr Leu Pro Val Ile Leu
                245                 250                 255

Ala Tyr Arg Arg Gly Thr Lys Ala Glu Arg Thr Phe Trp Lys Arg Ala
            260                 265                 270

Ile Glu Asp Asn Val Val Asp Asp Ala Gly Leu Glu Lys Ala Ile Gly
        275                 280                 285

Leu Met Thr Arg His Gly Ala Ile Ala Asp Thr Ile Gly Arg Ala Arg
    290                 295                 300

His Phe Gly Glu Ile Ala Arg Asp Ala Leu Ala Pro Leu Glu Glu Thr
305                 310                 315                 320

Arg Gln Lys Ser Ala Leu Ile Asp Val Ile Asp Phe Cys Ile Ser Arg
                325                 330                 335

Val Asn


<210> SEQ ID NO 13
<211> LENGTH: 338
<212> TYPE: PRT
<213> ORGANISM: Agrobacterium tumefaciens str. C58

<400> SEQUENCE: 13

Met Gly Val Val Ile Pro Leu Glu Glu Ser Lys Asn Lys Leu Ala Ser
1               5                   10                  15

Val Lys Pro Leu Val Asp Leu Thr Arg Pro Asp Met Glu Arg Val Asn
            20                  25                  30

Gln Leu Ile Leu Ser Arg Ala Gly Ser Asp Val Gln Met Ile Pro Glu
        35                  40                  45

Val Ala Asn His Leu Ile Ser Ser Gly Gly Lys Arg Leu Arg Pro Met
    50                  55                  60

Leu Thr Leu Ala Ser Ala Ser Met Phe Gly Tyr Glu Gly Asp Asn His
65                  70                  75                  80

Ile Lys Leu Ala Thr Ser Val Glu Phe Met His Thr Ala Thr Leu Leu
                85                  90                  95
```

```
His Asp Asp Val Val Asp Glu Ser Asp Leu Arg Arg Gly Lys Ser Thr
            100                 105                 110

Ala Arg Thr Ile Trp Gly Asn Gln Ala Ser Val Leu Val Gly Asp Phe
        115                 120                 125

Leu Leu Gly Gln Ala Phe Arg Met Met Val Asp Val Gly Ser Leu Asp
    130                 135                 140

Ala Leu Asp Val Leu Ser Thr Ala Ala Ser Val Ile Ala Glu Gly Glu
145                 150                 155                 160

Val Leu Gln Leu Ser Val Ala Lys Asn Met Glu Thr Thr Glu Asp Asp
                165                 170                 175

Tyr Leu Gln Val Ile Arg Ala Lys Thr Ala Ala Leu Phe Ala Ala Ala
            180                 185                 190

Ala Glu Val Gly Pro Ile Val Ala Lys Thr Asp Lys Ala Ser Arg Ser
        195                 200                 205

Ala Leu Lys Ser Tyr Gly Met Asn Leu Gly Leu Ala Phe Gln Leu Val
    210                 215                 220

Asp Asp Val Leu Asp Tyr Gly Gly Lys Ser Ala Asp Leu Gly Lys Asn
225                 230                 235                 240

Thr Gly Asp Asp Phe Arg Glu Gly Lys Ile Thr Leu Pro Val Ile Leu
                245                 250                 255

Ser Tyr Arg Arg Gly Thr Gln Asp Glu Arg Ala Phe Trp Arg Asn Ala
            260                 265                 270

Ile Glu Lys Gly Glu Ser Ser Asp Glu Asn Leu Glu Lys Ala Leu Gly
        275                 280                 285

Leu Ile Thr Lys Tyr Asn Gly Leu Gly Asp Thr Ile Gly Arg Ala Thr
    290                 295                 300

His Tyr Gly Thr Ile Ala Arg Asp Ala Leu Ala Pro Leu Pro Gln Ser
305                 310                 315                 320

Pro Trp Lys Asn Ala Leu Leu Glu Val Ile Asp Phe Cys Ile Glu Arg
                325                 330                 335

Leu Asn


<210> SEQ ID NO 14
<211> LENGTH: 333
<212> TYPE: PRT
<213> ORGANISM: Roseovarius sp. 217

<400> SEQUENCE: 14

Met Gly Leu Asp Glu Ile Ala Thr Lys Pro His Glu Gln Leu Ala Ala
1               5                   10                  15

His Leu Ala Thr Lys Met Glu Ala Val Asn Val Leu Ile Arg Glu Arg
            20                  25                  30

Met Ala Ser Arg His Ala Pro Arg Ile Pro Gln Val Thr Ala His Leu
        35                  40                  45

Val Glu Ala Gly Gly Lys Arg Leu Arg Pro Met Leu Val Leu Ala Thr
    50                  55                  60

Ala Asp Leu Cys Gly Tyr Asp Gly Pro Phe Asp Val His Leu Ala Ala
65                  70                  75                  80

Thr Val Glu Phe Ile His Thr Ala Thr Leu Leu His Asp Asp Val Val
                85                  90                  95

Asp Glu Ser Ala Gln Arg Arg Gly Arg Pro Thr Ala Asn Leu Leu Trp
            100                 105                 110

Asp Asn Lys Ser Ser Val Leu Val Gly Asp Tyr Leu Phe Ala Arg Ala
        115                 120                 125
```

```
Phe Gln Leu Met Val Glu Pro Gly Ser Leu Arg Val Leu Asp Ile Leu
    130                 135                 140

Ser Asn Ala Ser Ala Thr Ile Ala Glu Gly Glu Val Leu Gln Leu Ser
145                 150                 155                 160

Ala Ala Gln Asp Leu Ala Thr Thr Glu Asp Ile Tyr Leu Gln Val Val
                165                 170                 175

Arg Gly Lys Thr Ala Ala Leu Phe Ser Ala Ala Thr Glu Val Gly Gly
            180                 185                 190

Val Ile Ala Gly Ala Pro Glu Asp His Val Lys Ala Leu Phe Glu Tyr
        195                 200                 205

Gly Asp Ala Leu Gly Ile Ala Phe Gln Ile Val Asp Asp Leu Leu Asp
    210                 215                 220

Tyr Gln Gly Asp Val Lys Ser Thr Gly Lys Asn Val Gly Asp Asp Phe
225                 230                 235                 240

Arg Glu Arg Lys Leu Thr Leu Pro Val Ile Lys Ala Val Ala Ala Ala
                245                 250                 255

Ser Ala Glu Glu Arg Ala Phe Trp Lys Arg Thr Ile Glu Lys Gly Asp
            260                 265                 270

Gln Arg Asp Gly Asp Leu Glu His Ala Leu Thr Leu Met Gln Ala His
        275                 280                 285

Gly Ala Leu Glu Gln Thr Arg Ala Glu Ala Leu Asp Trp Ala Ala Arg
    290                 295                 300

Ala Arg Ala Ala Ile Ala Val Leu Pro Asp His Pro Val Gln Arg Met
305                 310                 315                 320

Leu Asp Asn Leu Ala Gly Tyr Val Val Ala Arg Ile Ser
                325                 330


<210> SEQ ID NO 15
<211> LENGTH: 336
<212> TYPE: PRT
<213> ORGANISM: Rhodopseudomonas palustris

<400> SEQUENCE: 15

Met Ala Val Ile Val Pro Phe Glu Gly Pro Pro Thr Ala Ser Ile Asp
1               5                   10                  15

Gln Leu Val Glu Leu Val Ala Ala Asp Met Glu Arg Val Asn Ala Val
            20                  25                  30

Ile Leu Ser Arg Thr Gly Ser Glu Val Thr Met Ile Pro Glu Val Ala
        35                  40                  45

Asn His Leu Ile Ser Ser Gly Gly Lys Arg Leu Arg Pro Asn Leu Thr
    50                  55                  60

Leu Ala Met Ala Gln Leu Thr Gly Tyr Ser Gly Glu Gly His Ile Lys
65                  70                  75                  80

Leu Ala Ala Ala Val Glu Phe Met His Thr Ala Thr Leu Leu His Asp
                85                  90                  95

Asp Val Val Asp Glu Ser Glu Met Arg Arg Gly Lys Lys Ser Ala Arg
            100                 105                 110

Met Leu Trp Gly Asn Glu Ala Ser Val Leu Val Gly Asp Phe Leu Leu
        115                 120                 125

Gly Gln Ala Phe Arg Met Met Val Glu Val Gly Ser Leu Arg Ala Leu
    130                 135                 140

Asp Ile Leu Ser Ser Ala Ala Ala Thr Ile Ala Glu Gly Glu Val Met
145                 150                 155                 160

Gln Leu Ala Ala Ala Lys Asn Thr Ala Thr Thr Glu Asp Glu Tyr Leu
```

```
                165                 170                 175

Ala Val Ile Arg Gly Lys Thr Ala Glu Leu Phe Ala Ala Ala Cys Glu
            180                 185                 190

Val Gly Pro Ala Ile Ala Gly Arg Pro Lys Ala Glu Gln Ser Ala Cys
        195                 200                 205

Arg Ser Phe Gly Met Asn Leu Gly Ile Ala Phe Gln Leu Val Asp Asp
    210                 215                 220

Val Leu Asp Tyr Gly Gly Lys Ala Ala Lys Leu Gly Lys Asn Val Gly
225                 230                 235                 240

Asp Asp Phe Arg Glu Gly Lys Ile Thr Leu Pro Val Val Leu Ala Phe
                245                 250                 255

Arg Arg Gly Asn Asp Ala Glu Arg Ala Phe Trp Ile Lys Ala Leu Glu
            260                 265                 270

Arg Gly Glu Ile Thr Glu Pro Asp Leu Asp Gln Ala Ile Gly Leu Met
        275                 280                 285

Thr Lys His Arg Ala Leu Glu Asp Thr Ile Gln Arg Ala His His Tyr
    290                 295                 300

Gly Ala Met Ala Val Asp Ala Leu Ala Leu Phe Pro Thr Ser Pro Met
305                 310                 315                 320

Lys Ala Ala Leu Glu Gln Val Val Ala Phe Cys Leu Ala Arg Ser His
                325                 330                 335


<210> SEQ ID NO 16
<211> LENGTH: 397
<212> TYPE: PRT
<213> ORGANISM: Yarrowia lipolytica

<400> SEQUENCE: 16

Met Leu Ala Leu Arg Leu Ala Arg Val Val Arg Pro Thr Gly Ala Ser
1               5                   10                  15

Ile Arg His Leu Thr Trp Ser His Pro Ala Arg Leu Tyr Ser Ser Val
            20                  25                  30

Asp Lys Val Asn Leu Pro Lys Ala Pro Ser Lys Glu Glu Leu Lys Thr
        35                  40                  45

Pro Val Pro Asp Glu Leu Leu Glu Glu Val Lys Val Leu Glu Asn Thr
    50                  55                  60

Pro Leu Glu Pro Val Asp Pro Glu Lys Ala Thr Ile Asp Leu Lys Thr
65                  70                  75                  80

Gln Phe Gln Ala Ala Arg Glu Ala Glu Leu Ala Ala Met Thr Leu Pro
                85                  90                  95

Glu Arg Phe Val Tyr Ser Leu Pro Lys Ser Met Ile Pro Tyr Ala Arg
            100                 105                 110

Leu Met Arg Met Glu Lys Pro Val Gly Thr Trp Leu Leu Phe Asn Pro
        115                 120                 125

Gly Val Trp Ser Ile Gly Met Ala Ala Tyr Met Ser His Ala Ala Val
    130                 135                 140

Ala Pro Thr Leu Tyr Thr Leu Ser Leu Phe Gly Ile Gly Ala Phe Ile
145                 150                 155                 160

Met Arg Ser Ala Gly Cys Thr Ile Asn Asp Ile Leu Asp Arg Lys Leu
                165                 170                 175

Asp Ala Gln Val Ala Arg Thr Phe Asp Arg Pro Ile Ala Ala Gly Asp
            180                 185                 190

Val Ser Val Lys Gln Ala Val Ala Phe Leu Gly Ala Gln Cys Ala Ala
        195                 200                 205
```

```
Gly Leu Gly Ile Leu Met Leu Leu Pro Met Asn Cys Trp Trp Leu Gly
    210                 215                 220

Ala Leu Ser Met Pro Phe Val Met Thr Tyr Pro Leu Phe Lys Arg Phe
225                 230                 235                 240

Thr Tyr Tyr Pro Gln Ala Ile Leu Ser Leu Cys Phe Thr Trp Ala Ala
                245                 250                 255

Leu Leu Gly Pro Pro Ala Met Gly Val Trp Cys Trp Pro Val Met Leu
            260                 265                 270

Ser Leu Trp Gly Ser Asn Phe Leu Trp Cys Met Val Tyr Asp Thr Ile
        275                 280                 285

Tyr Ala His Gln Asp Lys Val Phe Asp Val Glu Ala Gly Ile Lys Ser
    290                 295                 300

Thr Ala Leu Ala Trp Gly Asp Asn Ser Lys Ser Ile Met Thr Val Leu
305                 310                 315                 320

Thr Leu Gly Gln Leu Gly Leu Leu Phe Gly Ala Gly Val Tyr Ala Asp
                325                 330                 335

Met Gly Pro Gly Phe Tyr Ser Ala Phe Thr Trp Val Ser Tyr Arg Leu
            340                 345                 350

Gly Lys Met Ile Lys Thr Val Asp Leu Asp Asp Pro Val Asp Cys Gly
        355                 360                 365

Lys His Phe Arg Ser Asn Ile Asn Thr Gly His Ile Met Ser Ala Gly
    370                 375                 380

Ile Leu Ala Asp Trp Gly Met Arg Leu Ala Gly Phe Tyr
385                 390                 395


<210> SEQ ID NO 17
<211> LENGTH: 1168
<212> TYPE: DNA
<213> ORGANISM: Artificial Sequence
<220> FEATURE:
<223> OTHER INFORMATION: Fusion of GenBank Accession No. XP_505040
      (N-terminus of Yarrowia lipolytica ppt1 gene encoding
      p-hydroxybenzoate:polyprenyl transferase) and GenBank Accession
      No. BAA32241 (Gluconobacter oxydans ddsA)

<400> SEQUENCE: 17

ccatggtagc gttgagactg gctcgagtcg tgcgaccgac aggagcctcg atccgtcact      60

tgacatggtc ccaccctgct cgactctatt cgtccgtcga caaggtgaat ctgcccaagg     120

ctccctccaa ggaggagctc aagactcccg tggttcaggg tgcaggaggt gagtctgctc     180

tctccgctct ctctacctac cttgaggaag acatgcttgc ctgtaatcga gccatcattg     240

ctcgaatgga gtctcctgtt cccctcatcc ctcagctggg tgctcacctt gtcgctgctg     300

gtggtaagcg actccgacct ctccttacac tcgcatctgc ccgactctgt ggctaccagc     360

caggtcctga tcatcagcga catgtcggtc tcgctgcctg tgttgagttc atccacacgg     420

ccaccctcct ccatgacgac gttgtggatg agtctactct gcgacgagga ctggcctctg     480

ccaacgctgt cttcggcaac aaagcctctg ttctcgttgg tgactttctc ttcgctcgat     540

ctttccagct gatgactgcc gacggaagcc tcaaggttat ggccatcctc tcggatgcct     600

ccgctaccat agctgagggt gaagtccttc agatggtcgt tcagaacgac cttaccacac     660

cagtcgagcg atacctcgag gttatccacg gcaagacagc tgcactcttc gcagctgctt     720

gccgagttgg agcagtcgtt gccgaacgac ctgaggctga ggaagaggct cttgagcgat     780

tcggaaccaa cctgggaatg gccttccagc tggttgatga cgctctggat tacgctgccg     840

accaacaggt gctcggaaag accgtcggtg acgacatgcg agagggaaag atcactctgc     900
```

-continued

```
cagtgctggc tgcctacgag gctggatctc cagaggaccg gatcttctgg gagcgagtga    960

taggtgaagg agagcagact gaggacgatc tccctcacgc tcttaacctc atcgccaaga   1020

ctggtgccat caacacaacg attgctcgag cccaggtcta cgccgacgca gctgtcgagg   1080

ctctctctat cttccctgac tccgagctcc gacgactgct gatcgagaca gttcagttca   1140

ccgtcaaccg agctcgatag cggccgca                                      1168


<210> SEQ ID NO 18
<211> LENGTH: 385
<212> TYPE: PRT
<213> ORGANISM: Artificial Sequence
<220> FEATURE:
<223> OTHER INFORMATION: Fusion of GenBank Accession No. XP_505040
      (N-terminus of Yarrowia lipolytica ppt1 gene encoding
      p-hydroxybenzoate:polyprenyl transferase) and GenBank Accession
      No. BAA32241 (Gluconobacter oxydans ddsA)

<400> SEQUENCE: 18

Met Val Ala Leu Arg Leu Ala Arg Val Val Arg Pro Thr Gly Ala Ser
1               5                   10                  15

Ile Arg His Leu Thr Trp Ser His Pro Ala Arg Leu Tyr Ser Ser Val
            20                  25                  30

Asp Lys Val Asn Leu Pro Lys Ala Pro Ser Lys Glu Glu Leu Lys Thr
        35                  40                  45

Pro Val Val Gln Gly Ala Gly Gly Glu Ser Ala Leu Ser Ala Leu Ser
    50                  55                  60

Thr Tyr Leu Glu Glu Asp Met Leu Ala Cys Asn Arg Ala Ile Ile Ala
65                  70                  75                  80

Arg Met Glu Ser Pro Val Pro Leu Ile Pro Gln Leu Gly Ala His Leu
                85                  90                  95

Val Ala Ala Gly Gly Lys Arg Leu Arg Pro Leu Leu Thr Leu Ala Ser
            100                 105                 110

Ala Arg Leu Cys Gly Tyr Gln Pro Gly Pro Asp His Gln Arg His Val
        115                 120                 125

Gly Leu Ala Ala Cys Val Glu Phe Ile His Thr Ala Thr Leu Leu His
    130                 135                 140

Asp Asp Val Val Asp Glu Ser Thr Leu Arg Arg Gly Leu Ala Ser Ala
145                 150                 155                 160

Asn Ala Val Phe Gly Asn Lys Ala Ser Val Leu Val Gly Asp Phe Leu
                165                 170                 175

Phe Ala Arg Ser Phe Gln Leu Met Thr Ala Asp Gly Ser Leu Lys Val
            180                 185                 190

Met Ala Ile Leu Ser Asp Ala Ser Ala Thr Ile Ala Glu Gly Glu Val
        195                 200                 205

Leu Gln Met Val Val Gln Asn Asp Leu Thr Thr Pro Val Glu Arg Tyr
    210                 215                 220

Leu Glu Val Ile His Gly Lys Thr Ala Ala Leu Phe Ala Ala Ala Cys
225                 230                 235                 240

Arg Val Gly Ala Val Val Ala Glu Arg Pro Glu Ala Glu Glu Glu Ala
                245                 250                 255

Leu Glu Arg Phe Gly Thr Asn Leu Gly Met Ala Phe Gln Leu Val Asp
            260                 265                 270

Asp Ala Leu Asp Tyr Ala Ala Asp Gln Gln Val Leu Gly Lys Thr Val
        275                 280                 285

Gly Asp Asp Met Arg Glu Gly Lys Ile Thr Leu Pro Val Leu Ala Ala
    290                 295                 300
```

```
Tyr Glu Ala Gly Ser Pro Glu Asp Arg Ile Phe Trp Glu Arg Val Ile
305                 310                 315                 320

Gly Glu Gly Glu Gln Thr Glu Asp Asp Leu Pro His Ala Leu Asn Leu
                325                 330                 335

Ile Ala Lys Thr Gly Ala Ile Asn Thr Thr Ile Ala Arg Ala Gln Val
            340                 345                 350

Tyr Ala Asp Ala Ala Val Glu Ala Leu Ser Ile Phe Pro Asp Ser Glu
        355                 360                 365

Leu Arg Arg Leu Leu Ile Glu Thr Val Gln Phe Thr Val Asn Arg Ala
    370                 375                 380

Arg
385
```

```
<210> SEQ ID NO 19
<211> LENGTH: 8231
<212> TYPE: DNA
<213> ORGANISM: Artificial Sequence
<220> FEATURE:
<223> OTHER INFORMATION: Plasmid pDMW359-Ss_ddsA

<400> SEQUENCE: 19

catggtagcg ttgagactgg ctcgagtcgt gcgaccgaca ggagcctcga tccgtcactt     60

gacatggtcc caccctgctc gactctattc gtccgtcgac aaggtgaatc tgcccaaggc    120

tccctccaag gaggagctca agactatgac ttctgagaac acccagaagc ctcacgaccg    180

aatggctgcc tacctgaacg ccgacatgac tgctgtcaac gacctcatcc gagatcgaat    240

ggcctctgag cacgctcctc gaatccctga ggtcaccgct catctggttg aagcaggtgg    300

taagcgactc cgacccatgc tgactctggc tgcagcccga ctgtgtggct acgatggtcc    360

ctaccatgtg cacctcgctg ccacagtcga gttcatccat actgccacac tccttcacga    420

cgatgttgtc gacgagtctg cccagagacg aggccgaccc acagccaacc ttctctggga    480

caacaagtcg tccgtcctgg ttggtgacta cctcttcgct cgatctttcc agctcatgac    540

cgagaccaac aacatgcgag tcctcgctat cctggctaac gcttctgcca ccatcgccga    600

aggtgaggtg cttcagctca ctgctgccca gaacctggcc actgatgaag gcatctacct    660

ccaggtcgtt cgaggcaaga ctgctgccct gttctctgca gccactcagg tcggaggcgt    720

catagctgct gcacccgacg cccaggtcca ggctctcttc gattacggtg atgcccttgg    780

tatcgctttc cagatcgtcg acgatctgct cgactaccag ggagacccta acgccactgg    840

caagaacatc ggagatgact tccgagagcg aaagctgact ctccctgtga tcaaggccat    900

cgctaaggga gatgctacag agcgagcctt ctggactcga accatcgaga agggcaagca    960

ggaggatggt gacctcgaac atgccctgtc tctgctcaac gctcatggca ctctcgacga   1020

gaccaaggct gaagccctcg cttgggctga acaggccaag acagccctga ataccettcc   1080

cgatcacgaa ctgacccaga tgctgcgaga ccttgctgac tacgtcgttg ctcgaatctc   1140

ctaagcggcc gcaagtgtgg atggggaagt gagtgcccgg ttctgtgtgc acaattggca   1200

atccaagatg gatggattca acacagggat atagcgagct acgtggtggt gcgaggatat   1260

agcaacggat atttatgttt gacacttgag aatgtacgat acaagcactg tccaagtaca   1320

atactaaaca tactgtacat actcatactc gtacccgggc aacggtttca cttgagtgca   1380

gtggctagtg ctcttactcg tacagtgtgc aatactgcgt atcatagtct ttgatgtata   1440

tcgtattcat tcatgttagt tgcgtacgag ccggaagcat aaagtgtaaa gcctggggtg   1500
```

-continued

```
cctaatgagt gagctaactc acattaattg cgttgcgctc actgcccgct ttccagtcgg   1560
gaaacctgtc gtgccagctg cattaatgaa tcggccaacg cgcggggaga ggcggtttgc   1620
gtattgggcg ctcttccgct tcctcgctca ctgactcgct gcgctcggtc gttcggctgc   1680
ggcgagcggt atcagctcac tcaaaggcgg taatacggtt atccacagaa tcaggggata   1740
acgcaggaaa gaacatgtga gcaaaaggcc agcaaaaggc caggaaccgt aaaaaggccg   1800
cgttgctggc gtttttccat aggctccgcc cccctgacga gcatcacaaa aatcgacgct   1860
caagtcagag gtggcgaaac ccgacaggac tataaagata ccaggcgttt ccccctggaa   1920
gctccctcgt gcgctctcct gttccgaccc tgccgcttac cggatacctg tccgcctttc   1980
tcccttcggg aagcgtggcg ctttctcata gctcacgctg taggtatctc agttcggtgt   2040
aggtcgttcg ctccaagctg ggctgtgtgc acgaaccccc cgttcagccc gaccgctgcg   2100
ccttatccgg taactatcgt cttgagtcca acccggtaag acacgactta tcgccactgg   2160
cagcagccac tggtaacagg attagcagag cgaggtatgt aggcggtgct acagagttct   2220
tgaagtggtg gcctaactac ggctacacta gaaggacagt atttggtatc tgcgctctgc   2280
tgaagccagt taccttcgga aaaagagttg gtagctcttg atccggcaaa caaaccaccg   2340
ctggtagcgg tggttttttt gtttgcaagc agcagattac gcgcagaaaa aaaggatctc   2400
aagaagatcc tttgatcttt tctacggggt ctgacgctca gtggaacgaa aactcacgtt   2460
aagggatttt ggtcatgaga ttatcaaaaa ggatcttcac ctagatcctt ttaaattaaa   2520
aatgaagttt taaatcaatc taaagtatat atgagtaaac ttggtctgac agttaccaat   2580
gcttaatcag tgaggcacct atctcagcga tctgtctatt tcgttcatcc atagttgcct   2640
gactccccgt cgtgtagata actacgatac gggagggctt accatctggc cccagtgctg   2700
caatgatacc gcgagaccca cgctcaccgg ctccagattt atcagcaata aaccagccag   2760
ccggaagggc cgagcgcaga agtggtcctg caactttatc cgcctccatc cagtctatta   2820
attgttgccg ggaagctaga gtaagtagtt cgccagttaa tagtttgcgc aacgttgttg   2880
ccattgctac aggcatcgtg gtgtcacgct cgtcgtttgg tatggcttca ttcagctccg   2940
gttcccaacg atcaaggcga gttacatgat cccccatgtt gtgcaaaaaa gcggttagct   3000
ccttcggtcc tccgatcgtt gtcagaagta agttggccgc agtgttatca ctcatggtta   3060
tggcagcact gcataattct cttactgtca tgccatccgt aagatgcttt tctgtgactg   3120
gtgagtactc aaccaagtca ttctgagaat agtgtatgcg gcgaccgagt tgctcttgcc   3180
cggcgtcaat acgggataat accgcgccac atagcagaac tttaaaagtg ctcatcattg   3240
gaaaacgttc ttcggggcga aaactctcaa ggatcttacc gctgttgaga tccagttcga   3300
tgtaacccac tcgtgcaccc aactgatctt cagcatcttt tactttcacc agcgtttctg   3360
ggtgagcaaa aacaggaagg caaaatgccg caaaaaaggg aataagggcg acacggaaat   3420
gttgaatact catactcttc ctttttcaat attattgaag catttatcag ggttattgtc   3480
tcatgagcgg atacatattt gaatgtattt agaaaaataa acaaataggg gttccgcgca   3540
catttccccg aaaagtgcca cctgacgcgc cctgtagcgg cgcattaagc gcggcgggtg   3600
tggtggttac gcgcagcgtg accgctacac ttgccagcgc cctagcgccc gctcctttcg   3660
ctttcttccc ttcctttctc gccacgttcg ccggctttcc ccgtcaagct ctaaatcggg   3720
ggctcccttt agggttccga tttagtgctt tacggcacct cgaccccaaa aaacttgatt   3780
agggtgatgg ttcacgtagt gggccatcgc cctgatagac ggtttttcgc cctttgacgt   3840
tggagtccac gttctttaat agtggactct tgttccaaac tggaacaaca ctcaacccta   3900
```

```
tctcggtcta ttcttttgat ttataaggga ttttgccgat ttcggcctat tggttaaaaa   3960
atgagctgat ttaacaaaaa tttaacgcga attttaacaa aatattaacg cttacaattt   4020
ccattcgcca ttcaggctgc gcaactgttg ggaagggcga tcggtgcggg cctcttcgct   4080
attacgccag ctggcgaaag ggggatgtgc tgcaaggcga ttaagttggg taacgccagg   4140
gttttcccag tcacgacgtt gtaaaacgac ggccagtgaa ttgtaatacg actcactata   4200
gggcgaattg ggtaccgggc ccccctcga ggtcgatggt gtcgataagc ttgatatcga    4260
attcatgtca cacaaaccga tcttcgcctc aaggaaacct aattctacat ccgagagact   4320
gccgagatcc agtctacact gattaatttt cgggccaata atttaaaaaa atcgtgttat   4380
ataatattat atgtattata tatatacatc atgatgatac tgacagtcat gtcccattgc   4440
taaatagaca gactccatct gccgcctcca actgatgttc tcaatattta aggggtcatc   4500
tcgcattgtt taataataaa cagactccat ctaccgcctc caaatgatgt tctcaaaata   4560
tattgtatga acttattttt attacttagt attattagac aacttacttg ctttatgaaa   4620
aacacttcct atttaggaaa caatttataa tggcagttcg ttcatttaac aatttatgta   4680
gaataaatgt tataaatgcg tatgggaaat cttaaatatg gatagcataa atgatatctg   4740
cattgcctaa ttcgaaatca acagcaacga aaaaaatccc ttgtacaaca taaatagtca   4800
tcgagaaata tcaactatca aagaacagct attcacacgt tactattgag attattattg   4860
gacgagaatc acacactcaa ctgtctttct ctcttctaga aatacaggta caagtatgta   4920
ctattctcat tgttcatact tctagtcatt tcatcccaca tattccttgg atttctctcc   4980
aatgaatgac attctatctt gcaaattcaa caattataat aagatatacc aaagtagcgg   5040
tatagtggca atcaaaaagc ttctctggtg tgcttctcgt atttattttt attctaatga   5100
tccattaaag gtatatattt atttcttgtt atataatcct tttgtttatt acatgggctg   5160
gatacataaa ggtattttga tttaattttt tgcttaaatt caatcccccc tcgttcagtg   5220
tcaactgtaa tggtaggaaa ttaccatact tttgaagaag caaaaaaaat gaaagaaaaa   5280
aaaaatcgta tttccaggtt agacgttccg cagaatctag aatgcggtat gcggtacatt   5340
gttcttcgaa cgtaaaagtt gcgctccctg agatattgta catttttgct tttacaagta   5400
caagtacatc gtacaactat gtactactgt tgatgcatcc acaacagttt gttttgtttt   5460
tttttgtttt ttttttttct aatgattcat taccgctatg tatacctact tgtacttgta   5520
gtaagccggg ttattggcgt tcaattaatc atagacttat gaatctgcac ggtgtgcgct   5580
gcgagttact tttagcttat gcatgctact tgggtgtaat attgggatct gttcggaaat   5640
caacggatgc tcaatcgatt tcgacagtaa ttaattaagt catacacaag tcagctttct   5700
tcgagcctca tataagtata agtagttcaa cgtattagca ctgtacccag catctccgta   5760
tcgagaaaca caacaacatg ccccattgga cagatcatgc ggatacacag gttgtgcagt   5820
atcatacata ctcgatcaga caggtcgtct gaccatcata caagctgaac aagcgctcca   5880
tacttgcacg ctctctatat acacagttaa attacatatc catagtctaa cctctaacag   5940
ttaatcttct ggtaagcctc ccagccagcc ttctggtatc gcttggcctc ctcaatagga   6000
tctcggttct ggccgtacag acctcggccg acaattatga tatccgttcc ggtagacatg   6060
acatcctcaa cagttcggta ctgctgtccg agagcgtctc ccttgtcgtc aagacccacc   6120
ccgggggtca gaataagcca gtcctcagag tcgcccttag gtcggttctg ggcaatgaag   6180
ccaaccacaa actcggggtc ggatcgggca agctcaatgg tctgcttgga gtactcgcca   6240
```

-continued

```
gtggccagag agcccttgca agacagctcg gccagcatga gcagacctct ggccagcttc   6300

tcgttgggag aggggactag gaactccttg tactgggagt tctcgtagtc agagacgtcc   6360

tccttcttct gttcagagac agtttcctcg gcaccagctc gcaggccagc aatgattccg   6420

gttccgggta caccgtgggc gttggtgata tcggaccact cggcgattcg gtgacaccgg   6480

tactggtgct tgacagtgtt gccaatatct gcgaactttc tgtcctcgaa caggaagaaa   6540

ccgtgcttaa gagcaagttc cttgaggggg agcacagtgc cggcgtaggt gaagtcgtca   6600

atgatgtcga tatgggtttt gatcatgcac acataaggtc cgaccttatc ggcaagctca   6660

atgagctcct tggtggtggt aacatccaga gaagcacaca ggttggtttt cttggctgcc   6720

acgagcttga gcactcgagc ggcaaaggcg gacttgtgga cgttagctcg agcttcgtag   6780

gagggcattt tggtggtgaa gaggagactg aaataaattt agtctgcaga actttttatc   6840

ggaaccttat ctggggcagt gaagtatatg ttatggtaat agttacgagt tagttgaact   6900

tatagataga ctggactata cggctatcgg tccaaattag aaagaacgtc aatggctctc   6960

tgggcgtcgc ctttgccgac aaaaatgtga tcatgatgaa agccagcaat gacgttgcag   7020

ctgatattgt tgtcggccaa ccgcgccgaa aacgcagctg tcagacccac agcctccaac   7080

gaagaatgta tcgtcaaagt gatccaagca cactcatagt tggagtcgta ctccaaaggc   7140

ggcaatgacg agtcagacag atactcgtcg actcaggcga cgacggaatt cctgcagccc   7200

atctgcagaa ttcaggagag accgggttgg cggcgtattt gtgtcccaaa aaacagcccc   7260

aattgccccg gagaagacgg ccaggccgcc tagatgacaa attcaacaac tcacagctga   7320

ctttctgcca ttgccactag gggggggcct tttatatggc caagccaag ctctccacgt    7380

cggttgggct gcacccaaca ataaatgggt agggttgcac caacaaaggg atgggatggg   7440

gggtagaaga tacgaggata acggggctca atggcacaaa taagaacgaa tactgccatt   7500

aagactcgtg atccagcgac tgacaccatt gcatcatcta agggcctcaa aactacctcg   7560

gaactgctgc gctgatctgg acaccacaga ggttccgagc actttaggtt gcaccaaatg   7620

tcccaccagg tgcaggcaga aaacgctgga acagcgtgta cagtttgtct taacaaaaag   7680

tgagggcgct gaggtcgagc agggtggtgt gacttgttat agcctttaga gctgcgaaag   7740

cgcgtatgga tttggctcat caggccagat tgagggtctg tggacacatg tcatgttagt   7800

gtacttcaat cgccccctgg atatagcccc gacaataggc cgtggcctca tttttttgcc   7860

ttccgcacat ttccattgct cggtacccac accttgcttc tcctgcactt gccaacctta   7920

atactggttt acattgacca acatcttaca agcggggggc ttgtctaggg tatatataaa   7980

cagtggctct cccaatcggt tgccagtctc ttttttcctt tctttcccca cagattcgaa   8040

atctaaacta cacatcacac aatgcctgtt actgacgtcc ttaagcgaaa gtccggtgtc   8100

atcgtcggcg acgatgtccg agccgtgagt atccacgaca agatcagtgt cgagacgacg   8160

cgttttgtgt aatgacacaa tccgaaagtc gctagcaaca cacactctct acacaaacta   8220

acccagctct c                                                        8231
```

<210> SEQ ID NO 20
<211> LENGTH: 1153
<212> TYPE: DNA
<213> ORGANISM: Artificial Sequence
<220> FEATURE:
<223> OTHER INFORMATION: Fusion of GenBank Accession No. XP_505040
(N-terminus of Yarrowia lipolytica ppt1 gene encoding
p-hydroxybenzoate:polyprenyl transferase) and GenBank Accession
No. EAP81866 (Sulfitobacter sp. NAS-14.1 ddsA)

<400> SEQUENCE: 20

```
ccatggtagc gttgagactg gctcgagtcg tgcgaccgac aggagcctcg atccgtcact     60
tgacatggtc ccaccctgct cgactctatt cgtccgtcga caaggtgaat ctgcccaagg    120
ctccctccaa ggaggagctc aagactatga cttctgagaa cacccagaag cctcacgacc    180
gaatggctgc ctacctgaac gccgacatga ctgctgtcaa cgacctcatc cgagatcgaa    240
tggcctctga gcacgctcct cgaatccctg aggtcaccgc tcatctggtt gaagcaggtg    300
gtaagcgact ccgacccatg ctgactctgg ctgcagcccg actgtgtggc tacgatggtc    360
cctaccatgt gcacctcgct gccacagtcg agttcatcca tactgccaca ctccttcacg    420
acgatgttgt cgacgagtct gcccagagac gaggccgacc cacagccaac cttctctggg    480
acaacaagtc gtccgtcctg gttggtgact acctcttcgc tcgatctttc cagctcatga    540
ccgagaccaa caacatgcga gtcctcgcta tcctggctaa cgcttctgcc accatcgccg    600
aaggtgaggt gcttcagctc actgctgccc agaacctggc cactgatgaa ggcatctacc    660
tccaggtcgt tcgaggcaag actgctgccc tgttctctgc agccactcag gtcggaggcg    720
tcatagctgc tgcacccgac gcccaggtcc aggctctctt cgattacggt gatgcccttg    780
gtatcgcttt ccagatcgtc gacgatctgc tcgactacca gggagaccct aacgccactg    840
gcaagaacat cggagatgac ttccgagagc gaaagctgac tctccctgtg atcaaggcca    900
tcgctaaggg agatgctaca gagcgagcct tctggactcg aaccatcgag aagggcaagc    960
aggaggatgg tgacctcgaa catgccctgt ctctgctcaa cgctcatggc actctcgacg   1020
agaccaaggc tgaagccctc gcttgggctg aacaggccaa gacagccctg aatacccttc   1080
ccgatcacga actgacccag atgctgcgag accttgctga ctacgtcgtt gctcgaatct   1140
cctaagcggc cgc                                                      1153
```

<210> SEQ ID NO 21
<211> LENGTH: 380
<212> TYPE: PRT
<213> ORGANISM: Artificial Sequence
<220> FEATURE:
<223> OTHER INFORMATION: Fusion of GenBank Accession No. XP_505040 (N-terminus of Yarrowia lipolytica ppt1 gene encoding p-hydroxybenzoate:polyprenyl transferase) and GenBank Accession No. EAP81866 (Sulfitobacter sp. NAS-14.1 ddsA)

<400> SEQUENCE: 21

```
Met Val Ala Leu Arg Leu Ala Arg Val Val Arg Pro Thr Gly Ala Ser
1               5                   10                  15

Ile Arg His Leu Thr Trp Ser His Pro Ala Arg Leu Tyr Ser Ser Val
            20                  25                  30

Asp Lys Val Asn Leu Pro Lys Ala Pro Ser Lys Glu Glu Leu Lys Thr
        35                  40                  45

Met Thr Ser Glu Asn Thr Gln Lys Pro His Asp Arg Met Ala Ala Tyr
    50                  55                  60

Leu Asn Ala Asp Met Thr Ala Val Asn Asp Leu Ile Arg Asp Arg Met
65                  70                  75                  80

Ala Ser Glu His Ala Pro Arg Ile Pro Glu Val Thr Ala His Leu Val
                85                  90                  95

Glu Ala Gly Gly Lys Arg Leu Arg Pro Met Leu Thr Leu Ala Ala Ala
            100                 105                 110

Arg Leu Cys Gly Tyr Asp Gly Pro Tyr His Val His Leu Ala Ala Thr
        115                 120                 125
```

```
Val Glu Phe Ile His Thr Ala Thr Leu Leu His Asp Asp Val Val Asp
    130                 135                 140

Glu Ser Ala Gln Arg Arg Gly Arg Pro Thr Ala Asn Leu Leu Trp Asp
145                 150                 155                 160

Asn Lys Ser Ser Val Leu Val Gly Asp Tyr Leu Phe Ala Arg Ser Phe
                165                 170                 175

Gln Leu Met Thr Glu Thr Asn Asn Met Arg Val Leu Ala Ile Leu Ala
            180                 185                 190

Asn Ala Ser Ala Thr Ile Ala Glu Gly Glu Val Leu Gln Leu Thr Ala
        195                 200                 205

Ala Gln Asn Leu Ala Thr Asp Glu Gly Ile Tyr Leu Gln Val Val Arg
    210                 215                 220

Gly Lys Thr Ala Ala Leu Phe Ser Ala Ala Thr Gln Val Gly Gly Val
225                 230                 235                 240

Ile Ala Ala Ala Pro Asp Ala Gln Val Gln Ala Leu Phe Asp Tyr Gly
                245                 250                 255

Asp Ala Leu Gly Ile Ala Phe Gln Ile Val Asp Asp Leu Leu Asp Tyr
            260                 265                 270

Gln Gly Asp Pro Asn Ala Thr Gly Lys Asn Ile Gly Asp Asp Phe Arg
        275                 280                 285

Glu Arg Lys Leu Thr Leu Pro Val Ile Lys Ala Ile Ala Lys Gly Asp
    290                 295                 300

Ala Thr Glu Arg Ala Phe Trp Thr Arg Thr Ile Glu Lys Gly Lys Gln
305                 310                 315                 320

Glu Asp Gly Asp Leu Glu His Ala Leu Ser Leu Leu Asn Ala His Gly
                325                 330                 335

Thr Leu Asp Glu Thr Lys Ala Glu Ala Leu Ala Trp Ala Glu Gln Ala
            340                 345                 350

Lys Thr Ala Leu Asn Thr Leu Pro Asp His Glu Leu Thr Gln Met Leu
        355                 360                 365

Arg Asp Leu Ala Asp Tyr Val Val Ala Arg Ile Ser
    370                 375                 380
```

<210> SEQ ID NO 22
<211> LENGTH: 8231
<212> TYPE: DNA
<213> ORGANISM: Artificial Sequence
<220> FEATURE:
<223> OTHER INFORMATION: Plasmid pDMW359-Sp_ddsA

<400> SEQUENCE: 22

```
catggtagcg ttgagactgg ctcgagtcgt gcgaccgaca ggagcctcga tccgtcactt     60

gacatggtcc caccctgctc gactctattc gtccgtcgac aaggtgaatc tgcccaaggc    120

tccctccaag gaggagctca agactatgga cgccaaggtg tccaccaagc ctcatgagat    180

gctggctgcc actctgtctc aggagatggc tgccgtcaac gctctcatcc gaacccgaat    240

ggcctctgag cacgctcctc gaatccctga ggttactgcc catcttgtgg aggctggtgg    300

caagcgactt cgacccatgc tgacccttgc tgcagctcga ctctgtggat accagggtga    360

ggaccacgtc aagctggctg ccacagtcga gttcatccat accgctacac tgctccatga    420

tgacgtcgtt gacgagtctg gtcagagacg aggccgacct actgccaacc tcctgtggga    480

caacaagtct tccgtccttg tgggcgacta cctgttcgct cgatccttcc agctcatggt    540

cgagactgga tctctccgag ttctcgacat cctcgccaat gctgcagcta ccatcgctga    600

aggtgaggtt ctgcagatga ctgctgcctc tgacctccga actgacgagt ccgtgtacct    660
```

-continued

```
ccaggtcgtt cgaggcaaga cagctgccct gttctctgct gccaccgagg ttggaggtgt    720
catcgctgga gttcccgagg ctcaggtccg agctctgttc gagtacggag acgctctggg    780
tatcgccttc cagatcgctg atgacctgct cgactaccag ggtgatgcca aggctactgg    840
caagaacgtc ggtgacgact tccgagagcg aaagctgact ctgcctgtca tcaaggctgt    900
cgcacaggcc accgacgagg aacgagcctt ctgggtccga acaatcgaga agggtaagca    960
ggctgaggga gacctggagc aggctctcgc actcatggag aagtacggaa ccctcgcagc   1020
cactcgagct gatgctcatg cctgggctga gaaggctcga accgctctcg agctgctgcc   1080
caaccatgag atccgaacca tgctgtccga ccttgccgac tacgttgtcg ctcgactgtc   1140
ttaggcggcc gcaagtgtgg atggggaagt gagtgcccgg ttctgtgtgc acaattggca   1200
atccaagatg gatggattca acacagggat atagcgagct acgtggtggt gcgaggatat   1260
agcaacggat atttatgttt gacacttgag aatgtacgat acaagcactg tccaagtaca   1320
atactaaaca tactgtacat actcatactc gtacccgggc aacggtttca cttgagtgca   1380
gtggctagtg ctcttactcg tacagtgtgc aatactgcgt atcatagtct ttgatgtata   1440
tcgtattcat tcatgttagt tgcgtacgag ccggaagcat aaagtgtaaa gcctggggtg   1500
cctaatgagt gagctaactc acattaattg cgttgcgctc actgcccgct ttccagtcgg   1560
gaaacctgtc gtgccagctg cattaatgaa tcggccaacg cgcggggaga ggcggtttgc   1620
gtattgggcg ctcttccgct tcctcgctca ctgactcgct gcgctcggtc gttcggctgc   1680
ggcgagcggt atcagctcac tcaaaggcgg taatacggtt atccacagaa tcaggggata   1740
acgcaggaaa gaacatgtga gcaaaaggcc agcaaaaggc caggaaccgt aaaaaggccg   1800
cgttgctggc gtttttccat aggctccgcc cccctgacga gcatcacaaa aatcgacgct   1860
caagtcagag gtggcgaaac ccgacaggac tataaagata ccaggcgttt ccccctggaa   1920
gctccctcgt gcgctctcct gttccgaccc tgccgcttac cggatacctg tccgcctttc   1980
tcccttcggg aagcgtggcg ctttctcata gctcacgctg taggtatctc agttcggtgt   2040
aggtcgttcg ctccaagctg ggctgtgtgc acgaaccccc cgttcagccc gaccgctgcg   2100
ccttatccgg taactatcgt cttgagtcca acccggtaag acacgactta tcgccactgg   2160
cagcagccac tggtaacagg attagcagag cgaggtatgt aggcggtgct acagagttct   2220
tgaagtggtg gcctaactac ggctacacta gaaggacagt atttggtatc tgcgctctgc   2280
tgaagccagt taccttcgga aaaagagttg gtagctcttg atccggcaaa caaaccaccg   2340
ctggtagcgg tggttttttt gtttgcaagc agcagattac gcgcagaaaa aaaggatctc   2400
aagaagatcc tttgatcttt tctacggggt ctgacgctca gtggaacgaa aactcacgtt   2460
aagggatttt ggtcatgaga ttatcaaaaa ggatcttcac ctagatcctt ttaaattaaa   2520
aatgaagttt taaatcaatc taaagtatat atgagtaaac ttggtctgac agttaccaat   2580
gcttaatcag tgaggcacct atctcagcga tctgtctatt tcgttcatcc atagttgcct   2640
gactccccgt cgtgtagata actacgatac gggagggctt accatctggc cccagtgctg   2700
caatgatacc gcgagaccca cgctcaccgg ctccagattt atcagcaata aaccagccag   2760
ccggaagggc cgagcgcaga agtggtcctg caactttatc cgcctccatc cagtctatta   2820
attgttgccg ggaagctaga gtaagtagtt cgccagttaa tagtttgcgc aacgttgttg   2880
ccattgctac aggcatcgtg gtgtcacgct cgtcgtttgg tatggcttca ttcagctccg   2940
gttcccaacg atcaaggcga gttacatgat cccccatgtt gtgcaaaaaa gcggttagct   3000
```

-continued

```
ccttcggtcc tccgatcgtt gtcagaagta agttggccgc agtgttatca ctcatggtta   3060
tggcagcact gcataattct cttactgtca tgccatccgt aagatgcttt tctgtgactg   3120
gtgagtactc aaccaagtca ttctgagaat agtgtatgcg gcgaccgagt tgctcttgcc   3180
cggcgtcaat acgggataat accgcgccac atagcagaac tttaaaagtg ctcatcattg   3240
gaaaacgttc ttcggggcga aaactctcaa ggatcttacc gctgttgaga tccagttcga   3300
tgtaacccac tcgtgcaccc aactgatctt cagcatcttt tactttcacc agcgtttctg   3360
ggtgagcaaa aacaggaagg caaaatgccg caaaaaaggg aataagggcg acacggaaat   3420
gttgaatact catactcttc ctttttcaat attattgaag catttatcag ggttattgtc   3480
tcatgagcgg atacatattt gaatgtattt agaaaaataa acaaataggg gttccgcgca   3540
catttccccg aaaagtgcca cctgacgcgc cctgtagcgg cgcattaagc gcggcgggtg   3600
tggtggttac gcgcagcgtg accgctacac ttgccagcgc cctagcgccc gctcctttcg   3660
ctttcttccc ttcctttctc gccacgttcg ccggctttcc ccgtcaagct ctaaatcggg   3720
ggctcccttt agggttccga tttagtgctt tacggcacct cgaccccaaa aaacttgatt   3780
agggtgatgg ttcacgtagt gggccatcgc cctgatagac ggtttttcgc cctttgacgt   3840
tggagtccac gttctttaat agtggactct tgttccaaac tggaacaaca ctcaacccta   3900
tctcggtcta ttcttttgat ttataaggga ttttgccgat ttcggcctat tggttaaaaa   3960
atgagctgat ttaacaaaaa tttaacgcga attttaacaa aatattaacg cttacaattt   4020
ccattcgcca ttcaggctgc gcaactgttg ggaagggcga tcggtgcggg cctcttcgct   4080
attacgccag ctggcgaaag ggggatgtgc tgcaaggcga ttaagttggg taacgccagg   4140
gttttcccag tcacgacgtt gtaaaacgac ggccagtgaa ttgtaatacg actcactata   4200
gggcgaattg ggtaccgggc ccccccctcga ggtcgatggt gtcgataagc ttgatatcga   4260
attcatgtca cacaaaccga tcttcgcctc aaggaaacct aattctacat ccgagagact   4320
gccgagatcc agtctacact gattaatttt cgggccaata atttaaaaaa atcgtgttat   4380
ataatattat atgtattata tatatacatc atgatgatac tgacagtcat gtcccattgc   4440
taaatagaca gactccatct gccgcctcca actgatgttc tcaatattta aggggtcatc   4500
tcgcattgtt taataataaa cagactccat ctaccgcctc caaatgatgt tctcaaaata   4560
tattgtatga acttattttt attacttagt attattagac aacttacttg ctttatgaaa   4620
aacacttcct atttaggaaa caatttataa tggcagttcg ttcatttaac aatttatgta   4680
gaataaatgt tataaatgcg tatgggaaat cttaaatatg gatagcataa atgatatctg   4740
cattgcctaa ttcgaaatca acagcaacga aaaaaatccc ttgtacaaca taaatagtca   4800
tcgagaaata tcaactatca aagaacagct attcacacgt tactattgag attattattg   4860
gacgagaatc acacactcaa ctgtctttct ctcttctaga aatacaggta caagtatgta   4920
ctattctcat tgttcatact tctagtcatt tcatcccaca tattccttgg atttctctcc   4980
aatgaatgac attctatctt gcaaattcaa caattataat aagatatacc aaagtagcgg   5040
tatagtggca atcaaaaagc ttctctggtg tgcttctcgt atttattttt attctaatga   5100
tccattaaag gtatatattt atttcttgtt atataatcct tttgtttatt acatgggctg   5160
gatacataaa ggtattttga tttaattttt tgcttaaatt caatcccccc tcgttcagtg   5220
tcaactgtaa tggtaggaaa ttaccatact tttgaagaag caaaaaaaat gaaagaaaaa   5280
aaaaatcgta tttccaggtt agacgttccg cagaatctag aatgcggtat gcggtacatt   5340
gttcttcgaa cgtaaaagtt gcgctccctg agatattgta catttttgct tttacaagta   5400
```

-continued caagtacatc gtacaactat gtactactgt tgatgcatcc acaacagttt gttttgtttt 5460
tttttgtttt ttttttttct aatgattcat taccgctatg tatacctact tgtacttgta 5520
gtaagccggg ttattggcgt tcaattaatc atagacttat gaatctgcac ggtgtgcgct 5580
gcgagttact tttagcttat gcatgctact tgggtgtaat attgggatct gttcggaaat 5640
caacggatgc tcaatcgatt tcgacagtaa ttaattaagt catacacaag tcagctttct 5700
tcgagcctca tataagtata agtagttcaa cgtattagca ctgtacccag catctccgta 5760
tcgagaaaca caacaacatg ccccattgga cagatcatgc ggatacacag gttgtgcagt 5820
atcatacata ctcgatcaga caggtcgtct gaccatcata caagctgaac aagcgctcca 5880
tacttgcacg ctctctatat acacagttaa attacatatc catagtctaa cctctaacag 5940
ttaatcttct ggtaagcctc ccagccagcc ttctggtatc gcttggcctc ctcaatagga 6000
tctcggttct ggccgtacag acctcggccg acaattatga tatccgttcc ggtagacatg 6060
acatcctcaa cagttcggta ctgctgtccg agagcgtctc ccttgtcgtc aagacccacc 6120
ccgggggtca gaataagcca gtcctcagag tcgcccttag gtcggttctg ggcaatgaag 6180
ccaaccacaa actcggggtc ggatcgggca agctcaatgg tctgcttgga gtactcgcca 6240
gtggccagag agcccttgca agacagctcg gccagcatga gcagacctct ggccagcttc 6300
tcgttgggag aggggactag gaactccttg tactgggagt tctcgtagtc agagacgtcc 6360
tccttcttct gttcagagac agtttcctcg gcaccagctc gcaggccagc aatgattccg 6420
gttccgggta caccgtgggc gttggtgata tcggaccact cggcgattcg gtgacaccgg 6480
tactggtgct tgacagtgtt gccaatatct gcgaactttc tgtcctcgaa caggaagaaa 6540
ccgtgcttaa gagcaagttc cttgaggggg agcacagtgc cggcgtaggt gaagtcgtca 6600
atgatgtcga tatgggtttt gatcatgcac acataaggtc cgaccttatc ggcaagctca 6660
atgagctcct tggtggtggt aacatccaga gaagcacaca ggttggtttt cttggctgcc 6720
acgagcttga gcactcgagc ggcaaaggcg gacttgtgga cgttagctcg agcttcgtag 6780
gagggcattt tggtggtgaa gaggagactg aaataaattt agtctgcaga actttttatc 6840
ggaaccttat ctggggcagt gaagtatatg ttatggtaat agttacgagt tagttgaact 6900
tatagataga ctggactata cggctatcgg tccaaattag aaagaacgtc aatggctctc 6960
tgggcgtcgc ctttgccgac aaaaatgtga tcatgatgaa agccagcaat gacgttgcag 7020
ctgatattgt tgtcggccaa ccgcgccgaa aacgcagctg tcagacccac agcctccaac 7080
gaagaatgta tcgtcaaagt gatccaagca cactcatagt tggagtcgta ctccaaaggc 7140
ggcaatgacg agtcagacag atactcgtcg actcaggcga cgacggaatt cctgcagccc 7200
atctgcagaa ttcaggagag accgggttgg cggcgtattt gtgtcccaaa aaacagcccc 7260
aattgccccg gagaagacgg ccaggccgcc tagatgacaa attcaacaac tcacagctga 7320
ctttctgcca ttgccactag gggggggcct ttttatatgg ccaagccaag ctctccacgt 7380
cggttgggct gcacccaaca ataaatgggt agggttgcac caacaaaggg atgggatggg 7440
gggtagaaga tacgaggata acggggctca atggcacaaa taagaacgaa tactgccatt 7500
aagactcgtg atccagcgac tgacaccatt gcatcatcta agggcctcaa aactacctcg 7560
gaactgctgc gctgatctgg acaccacaga ggttccgagc actttaggtt gcaccaaatg 7620
tcccaccagg tgcaggcaga aaacgctgga acagcgtgta cagtttgtct taacaaaaag 7680
tgagggcgct gaggtcgagc agggtggtgt gacttgttat agcctttaga gctgcgaaag 7740

```
cgcgtatgga tttggctcat caggccagat tgagggtctg tggacacatg tcatgttagt   7800
gtacttcaat cgccccctgg atatagcccc gacaataggc cgtggcctca tttttttgcc   7860
ttccgcacat ttccattgct cggtacccac accttgcttc tcctgcactt gccaacctta   7920
atactggttt acattgacca acatcttaca agcggggggc ttgtctaggg tatatataaa   7980
cagtggctct cccaatcggt tgccagtctc ttttttcctt tctttcccca cagattcgaa   8040
atctaaacta cacatcacac aatgcctgtt actgacgtcc ttaagcgaaa gtccggtgtc   8100
atcgtcggcg acgatgtccg agccgtgagt atccacgaca agatcagtgt cgagacgacg   8160
cgttttgtgt aatgacacaa tccgaaagtc gctagcaaca cacactctct acacaaacta   8220
acccagctct c                                                        8231
```

<210> SEQ ID NO 23
<211> LENGTH: 1153
<212> TYPE: DNA
<213> ORGANISM: Artificial Sequence
<220> FEATURE:
<223> OTHER INFORMATION: Fusion of GenBank Accession No. XP_505040 (N-terminus of Yarrowia lipolytica ppt1 gene encoding p-hydroxybenzoate:polyprenyl transferase) and GenBank Accession No. AAV93637 (Silicibacter pomeroyi DSS-3 ddsA)

<400> SEQUENCE: 23

```
ccatggtagc gttgagactg gctcgagtcg tgcgaccgac aggagcctcg atccgtcact     60
tgacatggtc ccaccctgct cgactctatt cgtccgtcga caaggtgaat ctgcccaagg    120
ctccctccaa ggaggagctc aagactatgg acgccaaggt gtccaccaag cctcatgaga    180
tgctggctgc cactctgtct caggagatgg ctgccgtcaa cgctctcatc cgaacccgaa    240
tggcctctga gcacgctcct cgaatccctg aggttactgc ccatcttgtg gaggctggtg    300
gcaagcgact tcgacccatg ctgacccttg ctgcagctcg actctgtgga taccagggtg    360
aggaccacgt caagctggct gccacagtcg agttcatcca taccgctaca ctgctccatg    420
atgacgtcgt tgacgagtct ggtcagagac gaggccgacc tactgccaac ctcctgtggg    480
acaacaagtc ttccgtcctt gtgggcgact acctgttcgc tcgatccttc cagctcatgg    540
tcgagactgg atctctccga gttctcgaca tcctcgccaa tgctgcagct accatcgctg    600
aaggtgaggt tctgcagatg actgctgcct ctgacctccg aactgacgag tccgtgtacc    660
tccaggtcgt tcgaggcaag acagctgccc tgttctctgc tgccaccgag gttggaggtg    720
tcatcgctgg agttcccgag gctcaggtcc gagctctgtt cgagtacgga gacgctctgg    780
gtatcgcctt ccagatcgct gatgacctgc tcgactacca gggtgatgcc aaggctactg    840
gcaagaacgt cggtgacgac ttccgagagc gaaagctgac tctgcctgtc atcaaggctg    900
tcgcacaggc caccgacgag gaacgagcct tctgggtccg aacaatcgag aagggtaagc    960
aggctgaggg agacctggag caggctctcg cactcatgga gaagtacgga accctcgcag   1020
ccactcgagc tgatgctcat gcctgggctg agaaggctcg aaccgctctc gagctgctgc   1080
ccaaccatga gatccgaacc atgctgtccg accttgccga ctacgttgtc gctcgactgt   1140
cttaggcggc cgc                                                      1153
```

<210> SEQ ID NO 24
<211> LENGTH: 380
<212> TYPE: PRT
<213> ORGANISM: Artificial Sequence
<220> FEATURE:
<223> OTHER INFORMATION: Fusion of GenBank Accession No. XP_505040 (N-terminus of Yarrowia lipolytica ppt1 gene encoding p-hydroxybenzoate:polyprenyl transferase) and GenBank Accession No. AAV93637 (Silicibacter pomeroyi DSS-3 ddsA)

<400> SEQUENCE: 24

```
Met Val Ala Leu Arg Leu Ala Arg Val Val Arg Pro Thr Gly Ala Ser
1               5                   10                  15

Ile Arg His Leu Thr Trp Ser His Pro Ala Arg Leu Tyr Ser Ser Val
            20                  25                  30

Asp Lys Val Asn Leu Pro Lys Ala Pro Ser Lys Glu Glu Leu Lys Thr
        35                  40                  45

Met Asp Ala Lys Val Ser Thr Lys Pro His Glu Met Leu Ala Ala Thr
    50                  55                  60

Leu Ser Gln Glu Met Ala Ala Val Asn Ala Leu Ile Arg Thr Arg Met
65                  70                  75                  80

Ala Ser Glu His Ala Pro Arg Ile Pro Glu Val Thr Ala His Leu Val
                85                  90                  95

Glu Ala Gly Gly Lys Arg Leu Arg Pro Met Leu Thr Leu Ala Ala Ala
            100                 105                 110

Arg Leu Cys Gly Tyr Gln Gly Glu Asp His Val Lys Leu Ala Ala Thr
        115                 120                 125

Val Glu Phe Ile His Thr Ala Thr Leu Leu His Asp Asp Val Val Asp
    130                 135                 140

Glu Ser Gly Gln Arg Arg Gly Arg Pro Thr Ala Asn Leu Leu Trp Asp
145                 150                 155                 160

Asn Lys Ser Ser Val Leu Val Gly Asp Tyr Leu Phe Ala Arg Ser Phe
                165                 170                 175

Gln Leu Met Val Glu Thr Gly Ser Leu Arg Val Leu Asp Ile Leu Ala
            180                 185                 190

Asn Ala Ala Ala Thr Ile Ala Glu Gly Glu Val Leu Gln Met Thr Ala
        195                 200                 205

Ala Ser Asp Leu Arg Thr Asp Glu Ser Val Tyr Leu Gln Val Val Arg
    210                 215                 220

Gly Lys Thr Ala Ala Leu Phe Ser Ala Ala Thr Glu Val Gly Gly Val
225                 230                 235                 240

Ile Ala Gly Val Pro Glu Ala Gln Val Arg Ala Leu Phe Glu Tyr Gly
                245                 250                 255

Asp Ala Leu Gly Ile Ala Phe Gln Ile Ala Asp Asp Leu Leu Asp Tyr
            260                 265                 270

Gln Gly Asp Ala Lys Ala Thr Gly Lys Asn Val Gly Asp Asp Phe Arg
        275                 280                 285

Glu Arg Lys Leu Thr Leu Pro Val Ile Lys Ala Val Ala Gln Ala Thr
    290                 295                 300

Asp Glu Glu Arg Ala Phe Trp Val Arg Thr Ile Glu Lys Gly Lys Gln
305                 310                 315                 320

Ala Glu Gly Asp Leu Glu Gln Ala Leu Ala Leu Met Glu Lys Tyr Gly
                325                 330                 335

Thr Leu Ala Ala Thr Arg Ala Asp Ala His Ala Trp Ala Glu Lys Ala
            340                 345                 350

Arg Thr Ala Leu Glu Leu Leu Pro Asn His Glu Ile Arg Thr Met Leu
        355                 360                 365

Ser Asp Leu Ala Asp Tyr Val Val Ala Arg Leu Ser
    370                 375                 380
```

<210> SEQ ID NO 25

-continued

<211> LENGTH: 8228
<212> TYPE: DNA
<213> ORGANISM: Artificial Sequence
<220> FEATURE:
<223> OTHER INFORMATION: Plasmid pDMW359-Ob_ddsA

<400> SEQUENCE: 25
catggtagcg ttgagactgg ctcgagtcgt gcgaccgaca ggagcctcga tccgtcactt 60
gacatggtcc caccctgctc gactctattc gtccgtcgac aaggtgaatc tgcccaaggc 120
tccctccaag gaggagctca agactatgga caagcctgtt gagaagcccc atgaggccat 180
cgctgcactg cttgccgacg atctcggagc cgtcaacgct ctgatccgag agcgaatggc 240
ctctcgacat gctcctcgaa tcccagaggt gactgcccat ctggttgagg ctggaggcaa 300
gcgaatccga cccatgctca ctcttgctgc agcccgactg tgtggatacg acggtcctta 360
ccacatccac cttgcagcca cagtggagtt catccacaca gccacactcc tgcatgacga 420
tgtcgttgac gagtctgctc agcgacgagg cagacccact gccaatctgc tctgggacaa 480
caagtcgtcc gtcctcgttg gagactacct gttcgctcga gccttccagc tcatggtcga 540
gcctggcaac cttcgagtcc tctccatcct ctctgacgct gcagccacta tcgctgaggg 600
tgaggtcctg cagctgtctg ctgcacagga cctcaagact accgaggaga cctaccttca 660
ggtcatccga ggcaagaccg ctgccctgtt ctctgcagct actgaagctg gaggtgagat 720
cgcaggagcc tctcctgctc aggttcgagc cctcttcgac tacggagatg cacttggcat 780
cgccttccag atggctgatg acctccttga ctggactggc aagactgatt ccactggcaa 840
gaacgtcggt gatgacttcc gagagcgaaa gctcactctg cctctcatcc gagctgttgc 900
tgcagccgat gacgaggaac gagctttctg gactcgaacc atcgagaagg gtcgacagaa 960
cgacgaggat ctggccacag ctcgagagct gcttgaccga cacggtgctc tcggatccac 1020
ccgagagact gctctggact gggcagatcg agccaagtct gctctgactc accttcctga 1080
tcacgacctg acagcccacc tctctgatct cgctgactac gttgtcgagc gactccgata 1140
ggcggccgca agtgtggatg gggaagtgag tgcccggttc tgtgtgcaca attggcaatc 1200
caagatggat ggattcaaca cagggatata gcgagctacg tggtggtgcg aggatatagc 1260
aacggatatt tatgtttgac acttgagaat gtacgataca agcactgtcc aagtacaata 1320
ctaaacatac tgtacatact catactcgta cccgggcaac ggtttcactt gagtgcagtg 1380
gctagtgctc ttactcgtac agtgtgcaat actgcgtatc atagtctttg atgtatatcg 1440
tattcattca tgttagttgc gtacgagccg gaagcataaa gtgtaaagcc tggggtgcct 1500
aatgagtgag ctaactcaca ttaattgcgt tgcgctcact gcccgctttc cagtcgggaa 1560
acctgtcgtg ccagctgcat taatgaatcg gccaacgcgc ggggagaggc ggtttgcgta 1620
ttgggcgctc ttccgcttcc tcgctcactg actcgctgcg ctcggtcgtt cggctgcggc 1680
gagcggtatc agctcactca aaggcggtaa tacggttatc cacagaatca ggggataacg 1740
caggaaagaa catgtgagca aaaggccagc aaaaggccag gaaccgtaaa aaggccgcgt 1800
tgctggcgtt tttccatagg ctccgccccc ctgacgagca tcacaaaaat cgacgctcaa 1860
gtcagaggtg gcgaaacccg acaggactat aaagatacca ggcgtttccc cctggaagct 1920
ccctcgtgcg ctctcctgtt ccgaccctgc cgcttaccgg atacctgtcc gcctttctcc 1980
cttcgggaag cgtggcgctt tctcatagct cacgctgtag gtatctcagt tcggtgtagg 2040
tcgttcgctc caagctgggc tgtgtgcacg aaccccccgt tcagcccgac cgctgcgcct 2100
tatccggtaa ctatcgtctt gagtccaacc cggtaagaca cgacttatcg ccactggcag 2160

-continued

```
cagccactgg taacaggatt agcagagcga ggtatgtagg cggtgctaca gagttcttga   2220
agtggtggcc taactacggc tacactagaa ggacagtatt tggtatctgc gctctgctga   2280
agccagttac cttcggaaaa agagttggta gctcttgatc cggcaaacaa accaccgctg   2340
gtagcggtgg tttttttgtt tgcaagcagc agattacgcg cagaaaaaaa ggatctcaag   2400
aagatccttt gatcttttct acggggtctg acgctcagtg gaacgaaaac tcacgttaag   2460
ggattttggt catgagatta tcaaaaagga tcttcaccta gatcctttta aattaaaaat   2520
gaagttttaa atcaatctaa agtatatatg agtaaacttg gtctgacagt taccaatgct   2580
taatcagtga ggcacctatc tcagcgatct gtctatttcg ttcatccata gttgcctgac   2640
tccccgtcgt gtagataact acgatacggg agggcttacc atctggcccc agtgctgcaa   2700
tgataccgcg agacccacgc tcaccggctc cagatttatc agcaataaac cagccagccg   2760
gaagggccga gcgcagaagt ggtcctgcaa ctttatccgc ctccatccag tctattaatt   2820
gttgccggga agctagagta agtagttcgc cagttaatag tttgcgcaac gttgttgcca   2880
ttgctacagg catcgtggtg tcacgctcgt cgtttggtat ggcttcattc agctccggtt   2940
cccaacgatc aaggcgagtt acatgatccc ccatgttgtg caaaaaagcg gttagctcct   3000
tcggtcctcc gatcgttgtc agaagtaagt tggccgcagt gttatcactc atggttatgg   3060
cagcactgca taattctctt actgtcatgc catccgtaag atgcttttct gtgactggtg   3120
agtactcaac caagtcattc tgagaatagt gtatgcggcg accgagttgc tcttgcccgg   3180
cgtcaatacg ggataatacc gcgccacata gcagaacttt aaaagtgctc atcattggaa   3240
aacgttcttc ggggcgaaaa ctctcaagga tcttaccgct gttgagatcc agttcgatgt   3300
aacccactcg tgcacccaac tgatcttcag catcttttac tttcaccagc gtttctgggt   3360
gagcaaaaac aggaaggcaa aatgccgcaa aaaagggaat aagggcgaca cggaaatgtt   3420
gaatactcat actcttcctt tttcaatatt attgaagcat ttatcagggt tattgtctca   3480
tgagcggata catatttgaa tgtatttaga aaaataaaca aataggggtt ccgcgcacat   3540
ttccccgaaa agtgccacct gacgcgccct gtagcggcgc attaagcgcg gcgggtgtgg   3600
tggttacgcg cagcgtgacc gctacacttg ccagcgccct agcgcccgct cctttcgctt   3660
tcttcccttc ctttctcgcc acgttcgccg gctttccccg tcaagctcta aatcgggggc   3720
tccctttagg gttccgattt agtgctttac ggcacctcga ccccaaaaaa cttgattagg   3780
gtgatggttc acgtagtggg ccatcgccct gatagacggt ttttcgccct ttgacgttgg   3840
agtccacgtt ctttaatagt ggactcttgt tccaaactgg aacaacactc aaccctatct   3900
cggtctattc ttttgattta taagggattt tgccgatttc ggcctattgg ttaaaaaatg   3960
agctgattta acaaaaattt aacgcgaatt ttaacaaaat attaacgctt acaatttcca   4020
ttcgccattc aggctgcgca actgttggga agggcgatcg gtgcgggcct cttcgctatt   4080
acgccagctg gcgaaagggg gatgtgctgc aaggcgatta agttgggtaa cgccagggtt   4140
ttcccagtca cgacgttgta aaacgacggc cagtgaattg taatacgact cactataggg   4200
cgaattgggt accgggcccc ccctcgaggt cgatggtgtc gataagcttg atatcgaatt   4260
catgtcacac aaaccgatct tcgcctcaag gaaacctaat tctacatccg agagactgcc   4320
gagatccagt ctacactgat taattttcgg gccaataatt taaaaaaatc gtgttatata   4380
atattatatg tattatatat atacatcatg atgatactga cagtcatgtc ccattgctaa   4440
atagacagac tccatctgcc gcctccaact gatgttctca atatttaagg ggtcatctcg   4500
```

-continued

```
cattgtttaa taataaacag actccatcta ccgcctccaa atgatgttct caaaatatat   4560
tgtatgaact tatttttatt acttagtatt attagacaac ttacttgctt tatgaaaaac   4620
acttcctatt taggaaacaa tttataatgg cagttcgttc atttaacaat ttatgtagaa   4680
taaatgttat aaatgcgtat gggaaatctt aaatatggat agcataaatg atatctgcat   4740
tgcctaattc gaaatcaaca gcaacgaaaa aaatcccttg tacaacataa atagtcatcg   4800
agaaatatca actatcaaag aacagctatt cacacgttac tattgagatt attattggac   4860
gagaatcaca cactcaactg tctttctctc ttctagaaat acaggtacaa gtatgtacta   4920
ttctcattgt tcatacttct agtcatttca tcccacatat tccttggatt tctctccaat   4980
gaatgacatt ctatcttgca aattcaacaa ttataataag atataccaaa gtagcggtat   5040
agtggcaatc aaaaagcttc tctggtgtgc ttctcgtatt tatttttatt ctaatgatcc   5100
attaaaggta tatatttatt tcttgttata taatcctttt gtttattaca tgggctggat   5160
acataaaggt attttgattt aatttttttgc ttaaattcaa tccccccctcg ttcagtgtca   5220
actgtaatgg taggaaatta ccatactttt gaagaagcaa aaaaaatgaa agaaaaaaaa   5280
aatcgtattt ccaggttaga cgttccgcag aatctagaat gcggtatgcg gtacattgtt   5340
cttcgaacgt aaaagttgcg ctccctgaga tattgtacat ttttgctttt acaagtacaa   5400
gtacatcgta caactatgta ctactgttga tgcatccaca acagtttgtt ttgttttttt   5460
ttgttttttt tttttctaat gattcattac cgctatgtat acctacttgt acttgtagta   5520
agccgggtta ttggcgttca attaatcata gacttatgaa tctgcacggt gtgcgctgcg   5580
agttactttt agcttatgca tgctacttgg gtgtaatatt gggatctgtt cggaaatcaa   5640
cggatgctca atcgatttcg acagtaatta attaagtcat acacaagtca gctttcttcg   5700
agcctcatat aagtataagt agttcaacgt attagcactg tacccagcat ctccgtatcg   5760
agaaacacaa caacatgccc cattggacag atcatgcgga tacacaggtt gtgcagtatc   5820
atacatactc gatcagacag gtcgtctgac catcatacaa gctgaacaag cgctccatac   5880
ttgcacgctc tctatataca cagttaaatt acatatccat agtctaacct ctaacagtta   5940
atcttctggt aagcctccca gccagccttc tggtatcgct tggcctcctc aataggatct   6000
cggttctggc cgtacagacc tcggccgaca attatgatat ccgttccggt agacatgaca   6060
tcctcaacag ttcggtactg ctgtccgaga gcgtctccct tgtcgtcaag acccaccccg   6120
ggggtcagaa taagccagtc ctcagagtcg ccccttaggtc ggttctgggc aatgaagcca   6180
accacaaact cggggtcgga tcgggcaagc tcaatggtct gcttggagta ctcgccagtg   6240
gccagagagc ccttgcaaga cagctcggcc agcatgagca gacctctggc cagcttctcg   6300
ttgggagagg ggactaggaa ctccttgtac tgggagttct cgtagtcaga gacgtcctcc   6360
ttcttctgtt cagagacagt ttcctcggca ccagctcgca ggccagcaat gattccggtt   6420
ccgggtacac cgtgggcgtt ggtgatatcg gaccactcgg cgattcggtg acaccggtac   6480
tggtgcttga cagtgttgcc aatatctgcg aactttctgt cctcgaacag gaagaaaccg   6540
tgcttaagag caagttcctt gagggggagc acagtgccgg cgtaggtgaa gtcgtcaatg   6600
atgtcgatat gggttttgat catgcacaca taaggtccga ccttatcggc aagctcaatg   6660
agctccttgg tggtggtaac atccagagaa gcacacaggt tggttttctt ggctgccacg   6720
agcttgagca ctcgagcggc aaaggcggac ttgtggacgt tagctcgagc ttcgtaggag   6780
ggcattttgg tggtgaagag gagactgaaa taaatttagt ctgcagaact ttttatcgga   6840
accttatctg ggcagtgaa gtatatgtta tggtaatagt tacgagttag ttgaacttat   6900
```

-continued agatagactg gactatacgg ctatcggtcc aaattagaaa gaacgtcaat ggctctctgg 6960
gcgtcgcctt tgccgacaaa aatgtgatca tgatgaaagc cagcaatgac gttgcagctg 7020
atattgttgt cggccaaccg cgccgaaaac gcagctgtca gacccacagc ctccaacgaa 7080
gaatgtatcg tcaaagtgat ccaagcacac tcatagttgg agtcgtactc caaaggcggc 7140
aatgacgagt cagacagata ctcgtcgact caggcgacga cggaattcct gcagcccatc 7200
tgcagaattc aggagagacc gggttggcgg cgtatttgtg tcccaaaaaa cagccccaat 7260
tgccccggag aagacggcca ggccgcctag atgacaaatt caacaactca cagctgactt 7320
tctgccattg ccactagggg ggggcctttt tatatggcca agccaagctc tccacgtcgg 7380
ttgggctgca cccaacaata aatgggtagg gttgcaccaa caaagggatg ggatgggggg 7440
tagaagatac gaggataacg gggctcaatg gcacaaataa gaacgaatac tgccattaag 7500
actcgtgatc cagcgactga caccattgca tcatctaagg gcctcaaaac tacctcggaa 7560
ctgctgcgct gatctggaca ccacagaggt tccgagcact ttaggttgca ccaaatgtcc 7620
caccaggtgc aggcagaaaa cgctggaaca gcgtgtacag tttgtcttaa caaaaagtga 7680
gggcgctgag gtcgagcagg gtggtgtgac ttgttatagc ctttagagct gcgaaagcgc 7740
gtatggattt ggctcatcag gccagattga gggtctgtgg acacatgtca tgttagtgta 7800
cttcaatcgc cccctggata tagccccgac aataggccgt ggcctcattt ttttgccttc 7860
cgcacatttc cattgctcgg tacccacacc ttgcttctcc tgcacttgcc aaccttaata 7920
ctggtttaca ttgaccaaca tcttacaagc ggggggcttg tctagggtat atataaacag 7980
tggctctccc aatcggttgc cagtctcttt tttcctttct ttccccacag attcgaaatc 8040
taaactacac atcacacaat gcctgttact gacgtcctta agcgaaagtc cggtgtcatc 8100
gtcggcgacg atgtccgagc cgtgagtatc cacgacaaga tcagtgtcga gacgacgcgt 8160
tttgtgtaat gacacaatcc gaaagtcgct agcaacacac actctctaca caaactaacc 8220
cagctctc 8228

<210> SEQ ID NO 26
<211> LENGTH: 1150
<212> TYPE: DNA
<213> ORGANISM: Artificial Sequence
<220> FEATURE:
<223> OTHER INFORMATION: Fusion of GenBank Accession No. XP_505040
(N-terminus of Yarrowia lipolytica ppt1 gene encoding
p-hydroxybenzoate:polyprenyl transferase) and GenBank Accession
No. EAQ04419 (Oceanicola batsensis HTCC2597 ddsA)

<400> SEQUENCE: 26
ccatggtagc gttgagactg gctcgagtcg tgcgaccgac aggagcctcg atccgtcact 60
tgacatggtc ccaccctgct cgactctatt cgtccgtcga caaggtgaat ctgcccaagg 120
ctccctccaa ggaggagctc aagactatgg acaagcctgt tgagaagccc catgaggcca 180
tcgctgcact gcttgccgac gatctcggag ccgtcaacgc tctgatccga gagcgaatgg 240
cctctcgaca tgctcctcga atcccagagg tgactgccca tctggttgag gctggaggca 300
agcgaatccg acccatgctc actcttgctg cagcccgact gtgtggatac gacggtcctt 360
accacatcca ccttgcagcc acagtggagt tcatccacac agccacactc ctgcatgacg 420
atgtcgttga cgagtctgct cagcgacgag gcagacccac tgccaatctg ctctgggaca 480
acaagtcgtc cgtcctcgtt ggagactacc tgttcgctcg agccttccag ctcatggtcg 540
agcctggcaa ccttcgagtc ctctccatcc tctctgacgc tgcagccact atcgctgagg 600

```
gtgaggtcct gcagctgtct gctgcacagg acctcaagac taccgaggag acctaccttc    660

aggtcatccg aggcaagacc gctgccctgt tctctgcagc tactgaagct ggaggtgaga    720

tcgcaggagc ctctcctgct caggttcgag ccctcttcga ctacggagat gcacttggca    780

tcgccttcca gatggctgat gacctccttg actggactgg caagactgat tccactggca    840

agaacgtcgg tgatgacttc cgagagcgaa agctcactct gcctctcatc cgagctgttg    900

ctgcagccga tgacgaggaa cgagctttct ggactcgaac catcgagaag ggtcgacaga    960

acgacgagga tctggccaca gctcgagagc tgcttgaccg acacggtgct ctcggatcca   1020

cccgagagac tgctctggac tgggcagatc gagccaagtc tgctctgact caccttcctg   1080

atcacgacct gacagcccac ctctctgatc tcgctgacta cgttgtcgag cgactccgat   1140

aggcggccgc                                                          1150
```

<210> SEQ ID NO 27
<211> LENGTH: 379
<212> TYPE: PRT
<213> ORGANISM: Artificial Sequence
<220> FEATURE:
<223> OTHER INFORMATION: Fusion of GenBank Accession No. XP_505040 (N-terminus of Yarrowia lipolytica ppt1 gene encoding p-hydroxybenzoate:polyprenyl transferase) and GenBank Accession No. EAQ04419 (Oceanicola batsensis HTCC2597 ddsA)

<400> SEQUENCE: 27

```
Met Val Ala Leu Arg Leu Ala Arg Val Val Arg Pro Thr Gly Ala Ser
1               5                   10                  15

Ile Arg His Leu Thr Trp Ser His Pro Ala Arg Leu Tyr Ser Ser Val
            20                  25                  30

Asp Lys Val Asn Leu Pro Lys Ala Pro Ser Lys Glu Glu Leu Lys Thr
        35                  40                  45

Met Asp Lys Pro Val Glu Lys Pro His Glu Ala Ile Ala Ala Leu Leu
    50                  55                  60

Ala Asp Asp Leu Gly Ala Val Asn Ala Leu Ile Arg Glu Arg Met Ala
65                  70                  75                  80

Ser Arg His Ala Pro Arg Ile Pro Glu Val Thr Ala His Leu Val Glu
                85                  90                  95

Ala Gly Gly Lys Arg Ile Arg Pro Met Leu Thr Leu Ala Ala Ala Arg
            100                 105                 110

Leu Cys Gly Tyr Asp Gly Pro Tyr His Ile His Leu Ala Ala Thr Val
        115                 120                 125

Glu Phe Ile His Thr Ala Thr Leu Leu His Asp Asp Val Val Asp Glu
    130                 135                 140

Ser Ala Gln Arg Arg Gly Arg Pro Thr Ala Asn Leu Leu Trp Asp Asn
145                 150                 155                 160

Lys Ser Ser Val Leu Val Gly Asp Tyr Leu Phe Ala Arg Ala Phe Gln
                165                 170                 175

Leu Met Val Glu Pro Gly Asn Leu Arg Val Leu Ser Ile Leu Ser Asp
            180                 185                 190

Ala Ala Ala Thr Ile Ala Glu Gly Glu Val Leu Gln Leu Ser Ala Ala
        195                 200                 205

Gln Asp Leu Lys Thr Thr Glu Glu Thr Tyr Leu Gln Val Ile Arg Gly
    210                 215                 220

Lys Thr Ala Ala Leu Phe Ser Ala Ala Thr Glu Ala Gly Gly Glu Ile
225                 230                 235                 240
```

```
Ala Gly Ala Ser Pro Ala Gln Val Arg Ala Leu Phe Asp Tyr Gly Asp
                245                 250                 255

Ala Leu Gly Ile Ala Phe Gln Met Ala Asp Asp Leu Leu Asp Trp Thr
            260                 265                 270

Gly Lys Thr Asp Ser Thr Gly Lys Asn Val Gly Asp Asp Phe Arg Glu
        275                 280                 285

Arg Lys Leu Thr Leu Pro Leu Ile Arg Ala Val Ala Ala Ala Asp Asp
    290                 295                 300

Glu Glu Arg Ala Phe Trp Thr Arg Thr Ile Glu Lys Gly Arg Gln Asn
305                 310                 315                 320

Asp Glu Asp Leu Ala Thr Ala Arg Glu Leu Leu Asp Arg His Gly Ala
                325                 330                 335

Leu Gly Ser Thr Arg Glu Thr Ala Leu Asp Trp Ala Asp Arg Ala Lys
            340                 345                 350

Ser Ala Leu Thr His Leu Pro Asp His Asp Leu Thr Ala His Leu Ser
        355                 360                 365

Asp Leu Ala Asp Tyr Val Val Glu Arg Leu Arg
    370                 375
```

<210> SEQ ID NO 28
<211> LENGTH: 8249
<212> TYPE: DNA
<213> ORGANISM: Artificial Sequence
<220> FEATURE:
<223> OTHER INFORMATION: Plasmid pDMW359-Rl_ddsA

<400> SEQUENCE: 28

```
catggtagcg ttgagactgg ctcgagtcgt gcgaccgaca ggagcctcga tccgtcactt      60

gacatggtcc caccctgctc gactctattc gtccgtcgac aaggtgaatc tgcccaaggc     120

tccctccaag gaggagctca agactatggg tgtggtcatc cctctggaag agtccaagaa     180

caaactggcc tcgatcaagc ctctggtcga cctcactcga gccgacatgg agcgagtcaa     240

ccagctcatc ctgtccaagg ctggctcgga cgttcagatg attcccgagg tcgccaacca     300

tctcatctcg tctggaggca agcgacttcg acccatgctc actcttgcct ctgcctcact     360

cttcgactac cgaggtgaga atcatatcaa gctcgctacc tctgtcgagt tcatgcacac     420

tgctactctc ctgcatgacg atgtggtcga cgagtccgac cttcgacgag gcaagtccac     480

cgctcgaatg atctggggta accaggcttc tgtgcttgtg ggtgacttcc tgctcggtca     540

ggccttccga atgatggtgg acgtcggttc gctcgacgct cttgacgttc tctcgtccgc     600

tgcctgcgtc atagcagagg gagaagtcct ccagctctcc gtcgctaaga acatggagac     660

cactgaggat gactacctct ctgtcatccg agccaagact gctgccctgt tcgctgcagc     720

tgccgaggtc ggtcccatcg ttgctgaggt cggacgatct ggacgaaacg ccctgaagtc     780

ctacggtatg aacctgggtc ttgcattcca gctggttgat gacgctctcg actacggtgg     840

aaaggctgcc gatctcggta agaacgttgg tgatgacttc cgagaaggca agatcaccct     900

gcctgtcatc cttgcctacc gacgaggaac cgaggacgag cgagccttct ggcgagatgc     960

cattgaagct ggcaactcca ctgacgccaa cctcgagaag gctctcggac tcatcactaa    1020

gtacggcact ctgtctgaca caatcggacg agccatccac tacggaacca tcgctcgaga    1080

tgctctggct cctcttcctg acactgtctg gaagtctgct ctgatggaag tgatcgactt    1140

ctgcatcgag cgagtgaact aggcggccgc aagtgtggat ggggaagtga gtgcccggtt    1200

ctgtgtgcac aattggcaat ccaagatgga tggattcaac acagggatat agcgagctac    1260
```

-continued

```
gtggtggtgc gaggatatag caacggatat ttatgtttga cacttgagaa tgtacgatac   1320
aagcactgtc caagtacaat actaaacata ctgtacatac tcatactcgt acccgggcaa   1380
cggtttcact tgagtgcagt ggctagtgct cttactcgta cagtgtgcaa tactgcgtat   1440
catagtcttt gatgtatatc gtattcattc atgttagttg cgtacgagcc ggaagcataa   1500
agtgtaaagc ctggggtgcc taatgagtga gctaactcac attaattgcg ttgcgctcac   1560
tgcccgcttt ccagtcggga aacctgtcgt gccagctgca ttaatgaatc ggccaacgcg   1620
cggggagagg cggtttgcgt attgggcgct cttccgcttc ctcgctcact gactcgctgc   1680
gctcggtcgt tcggctgcgg cgagcggtat cagctcactc aaaggcggta atacggttat   1740
ccacagaatc aggggataac gcaggaaaga acatgtgagc aaaaggccag caaaaggcca   1800
ggaaccgtaa aaaggccgcg ttgctggcgt ttttccatag gctccgcccc cctgacgagc   1860
atcacaaaaa tcgacgctca agtcagaggt ggcgaaaccc gacaggacta taaagatacc   1920
aggcgtttcc ccctggaagc tccctcgtgc gctctcctgt tccgaccctg ccgcttaccg   1980
gatacctgtc cgcctttctc ccttcgggaa gcgtggcgct ttctcatagc tcacgctgta   2040
ggtatctcag ttcggtgtag gtcgttcgct ccaagctggg ctgtgtgcac gaaccccccg   2100
ttcagcccga ccgctgcgcc ttatccggta actatcgtct tgagtccaac ccggtaagac   2160
acgacttatc gccactggca gcagccactg gtaacaggat tagcagagcg aggtatgtag   2220
gcggtgctac agagttcttg aagtggtggc ctaactacgg ctacactaga aggacagtat   2280
ttggtatctg cgctctgctg aagccagtta ccttcggaaa aagagttggt agctcttgat   2340
ccggcaaaca aaccaccgct ggtagcggtg gtttttttgt ttgcaagcag cagattacgc   2400
gcagaaaaaa aggatctcaa gaagatcctt tgatcttttc tacggggtct gacgctcagt   2460
ggaacgaaaa ctcacgttaa gggattttgg tcatgagatt atcaaaaagg atcttcacct   2520
agatcctttt aaattaaaaa tgaagtttta aatcaatcta aagtatatat gagtaaactt   2580
ggtctgacag ttaccaatgc ttaatcagtg aggcacctat ctcagcgatc tgtctatttc   2640
gttcatccat agttgcctga ctccccgtcg tgtagataac tacgatacgg gagggcttac   2700
catctggccc cagtgctgca atgataccgc gagacccacg ctcaccggct ccagatttat   2760
cagcaataaa ccagccagcc ggaagggccg agcgcagaag tggtcctgca actttatccg   2820
cctccatcca gtctattaat tgttgccggg aagctagagt aagtagttcg ccagttaata   2880
gtttgcgcaa cgttgttgcc attgctacag gcatcgtggt gtcacgctcg tcgtttggta   2940
tggcttcatt cagctccggt tcccaacgat caaggcgagt tacatgatcc cccatgttgt   3000
gcaaaaaagc ggttagctcc ttcggtcctc cgatcgttgt cagaagtaag ttggccgcag   3060
tgttatcact catggttatg gcagcactgc ataattctct tactgtcatg ccatccgtaa   3120
gatgcttttc tgtgactggt gagtactcaa ccaagtcatt ctgagaatag tgtatgcggc   3180
gaccgagttg ctcttgcccg gcgtcaatac gggataatac cgcgccacat agcagaactt   3240
taaaagtgct catcattgga aaacgttctt cggggcgaaa actctcaagg atcttaccgc   3300
tgttgagatc cagttcgatg taacccactc gtgcacccaa ctgatcttca gcatctttta   3360
ctttcaccag cgtttctggg tgagcaaaaa caggaaggca aaatgccgca aaaaagggaa   3420
taagggcgac acggaaatgt tgaatactca tactcttcct ttttcaatat tattgaagca   3480
tttatcaggg ttattgtctc atgagcggat acatatttga atgtatttag aaaaataaac   3540
aaataggggt tccgcgcaca tttccccgaa aagtgccacc tgacgcgccc tgtagcggcg   3600
cattaagcgc ggcgggtgtg gtggttacgc gcagcgtgac cgctacactt gccagcgccc   3660
```

-continued

```
tagcgcccgc tcctttcgct ttcttccctt cctttctcgc cacgttcgcc ggctttcccc   3720
gtcaagctct aaatcggggg ctccctttag ggttccgatt tagtgcttta cggcacctcg   3780
accccaaaaa acttgattag ggtgatggtt cacgtagtgg gccatcgccc tgatagacgg   3840
tttttcgccc tttgacgttg gagtccacgt tctttaatag tggactcttg ttccaaactg   3900
gaacaacact caaccctatc tcggtctatt cttttgattt ataagggatt ttgccgattt   3960
cggcctattg gttaaaaaat gagctgattt aacaaaaatt taacgcgaat tttaacaaaa   4020
tattaacgct tacaatttcc attcgccatt caggctgcgc aactgttggg aagggcgatc   4080
ggtgcgggcc tcttcgctat tacgccagct ggcgaaaggg ggatgtgctg caaggcgatt   4140
aagttgggta acgccagggt tttcccagtc acgacgttgt aaaacgacgg ccagtgaatt   4200
gtaatacgac tcactatagg gcgaattggg taccgggccc cccctcgagg tcgatggtgt   4260
cgataagctt gatatcgaat tcatgtcaca caaaccgatc ttcgcctcaa ggaaacctaa   4320
ttctacatcc gagagactgc cgagatccag tctacactga ttaattttcg ggccaataat   4380
ttaaaaaaat cgtgttatat aatattatat gtattatata tatacatcat gatgatactg   4440
acagtcatgt cccattgcta aatagacaga ctccatctgc cgcctccaac tgatgttctc   4500
aatatttaag ggtcatctc gcattgttta ataataaaca gactccatct accgcctcca    4560
aatgatgttc tcaaaatata ttgtatgaac ttatttttat tacttagtat tattagacaa   4620
cttacttgct ttatgaaaaa cacttcctat ttaggaaaca atttataatg gcagttcgtt   4680
catttaacaa tttatgtaga ataaatgtta taaatgcgta tgggaaatct taaatatgga   4740
tagcataaat gatatctgca ttgcctaatt cgaaatcaac agcaacgaaa aaaatccctt   4800
gtacaacata aatagtcatc gagaaatatc aactatcaaa gaacagctat tcacacgtta   4860
ctattgagat tattattgga cgagaatcac acactcaact gtctttctct cttctagaaa   4920
tacaggtaca agtatgtact attctcattg ttcatacttc tagtcatttc atcccacata   4980
ttccttggat ttctctccaa tgaatgacat tctatcttgc aaattcaaca attataataa   5040
gatataccaa agtagcggta tagtggcaat caaaaagctt ctctggtgtg cttctcgtat   5100
ttatttttat tctaatgatc cattaaaggt atatatttat ttcttgttat ataatccttt   5160
tgtttattac atgggctgga tacataaagg tattttgatt taattttttg cttaaattca   5220
atcccccctc gttcagtgtc aactgtaatg gtaggaaatt accatacttt tgaagaagca   5280
aaaaaaatga aagaaaaaaa aaatcgtatt tccaggttag acgttccgca gaatctagaa   5340
tgcggtatgc ggtacattgt tcttcgaacg taaaagttgc gctccctgag atattgtaca   5400
tttttgcttt tacaagtaca agtacatcgt acaactatgt actactgttg atgcatccac   5460
aacagtttgt tttgtttttt tttgtttttt ttttttctaa tgattcatta ccgctatgta   5520
tacctacttg tacttgtagt aagccgggtt attggcgttc aattaatcat agacttatga   5580
atctgcacgg tgtgcgctgc gagttacttt tagcttatgc atgctacttg ggtgtaatat   5640
tgggatctgt tcggaaatca acggatgctc aatcgatttc gacagtaatt aattaagtca   5700
tacacaagtc agctttcttc gagcctcata taagtataag tagttcaacg tattagcact   5760
gtacccagca tctccgtatc gagaaacaca acaacatgcc ccattggaca gatcatgcgg   5820
atacacaggt tgtgcagtat catacatact cgatcagaca ggtcgtctga ccatcataca   5880
agctgaacaa gcgctccata cttgcacgct ctctatatac acagttaaat tacatatcca   5940
tagtctaacc tctaacagtt aatcttctgg taagcctccc agccagcctt ctggtatcgc   6000
```

-continued

```
ttggcctcct caataggatc tcggttctgg ccgtacagac ctcggccgac aattatgata   6060
tccgttccgg tagacatgac atcctcaaca gttcggtact gctgtccgag agcgtctccc   6120
ttgtcgtcaa gacccacccc gggggtcaga ataagccagt cctcagagtc gcccttaggt   6180
cggttctggg caatgaagcc aaccacaaac tcggggtcgg atcgggcaag ctcaatggtc   6240
tgcttggagt actcgccagt ggccagagag cccttgcaag acagctcggc cagcatgagc   6300
agacctctgg ccagcttctc gttgggagag gggactagga actccttgta ctgggagttc   6360
tcgtagtcag agacgtcctc cttcttctgt tcagagacag tttcctcggc accagctcgc   6420
aggccagcaa tgattccggt tccgggtaca ccgtgggcgt tggtgatatc ggaccactcg   6480
gcgattcggt gacaccggta ctggtgcttg acagtgttgc caatatctgc gaactttctg   6540
tcctcgaaca ggaagaaacc gtgcttaaga gcaagttcct tgagggggag cacagtgccg   6600
gcgtaggtga agtcgtcaat gatgtcgata tgggttttga tcatgcacac ataaggtccg   6660
accttatcgg caagctcaat gagctccttg gtggtggtaa catccagaga agcacacagg   6720
ttggttttct tggctgccac gagcttgagc actcgagcgg caaaggcgga cttgtggacg   6780
ttagctcgag cttcgtagga gggcattttg gtggtgaaga ggagactgaa ataaatttag   6840
tctgcagaac tttttatcgg aaccttatct ggggcagtga agtatatgtt atggtaatag   6900
ttacgagtta gttgaactta tagatagact ggactatacg gctatcggtc caaattagaa   6960
agaacgtcaa tggctctctg ggcgtcgcct ttgccgacaa aaatgtgatc atgatgaaag   7020
ccagcaatga cgttgcagct gatattgttg tcggccaacc gcgccgaaaa cgcagctgtc   7080
agacccacag cctccaacga agaatgtatc gtcaaagtga tccaagcaca ctcatagttg   7140
gagtcgtact ccaaaggcgg caatgacgag tcagacagat actcgtcgac tcaggcgacg   7200
acggaattcc tgcagcccat ctgcagaatt caggagagac cgggttggcg gcgtatttgt   7260
gtcccaaaaa acagccccaa ttgccccgga gaagacggcc aggccgccta gatgacaaat   7320
tcaacaactc acagctgact ttctgccatt gccactaggg gggggccttt ttatatggcc   7380
aagccaagct ctccacgtcg gttgggctgc acccaacaat aaatgggtag ggttgcacca   7440
acaaagggat gggatggggg gtagaagata cgaggataac ggggctcaat ggcacaaata   7500
agaacgaata ctgccattaa gactcgtgat ccagcgactg acaccattgc atcatctaag   7560
ggcctcaaaa ctacctcgga actgctgcgc tgatctggac accacagagg ttccgagcac   7620
tttaggttgc accaaatgtc ccaccaggtg caggcagaaa acgctggaac agcgtgtaca   7680
gtttgtctta acaaaaagtg agggcgctga ggtcgagcag ggtggtgtga cttgttatag   7740
cctttagagc tgcgaaagcg cgtatggatt tggctcatca ggccagattg agggtctgtg   7800
gacacatgtc atgttagtgt acttcaatcg ccccctggat atagccccga caataggccg   7860
tggcctcatt tttttgcctt ccgcacattt ccattgctcg gtacccacac cttgcttctc   7920
ctgcacttgc caaccttaat actggtttac attgaccaac atcttacaag cggggggctt   7980
gtctagggta tatataaaca gtggctctcc caatcggttg ccagtctctt ttttcctttc   8040
tttccccaca gattcgaaat ctaaactaca catcacacaa tgcctgttac tgacgtcctt   8100
aagcgaaagt ccggtgtcat cgtcggcgac gatgtccgag ccgtgagtat ccacgacaag   8160
atcagtgtcg agacgacgcg ttttgtgtaa tgacacaatc cgaaagtcgc tagcaacaca   8220
cactctctac acaaactaac ccagctctc                                     8249
```

<210> SEQ ID NO 29
<211> LENGTH: 1171

<212> TYPE: DNA
<213> ORGANISM: Artificial Sequence
<220> FEATURE:
<223> OTHER INFORMATION: Fusion of GenBank Accession No. XP_505040 (N-terminus of Yarrowia lipolytica ppt1 gene encoding p-hydroxybenzoate:polyprenyl transferase) and GenBank Accession No. CAK06434 (Rhizobium leguminosarum bv. viciae 3841 ddsA)

<400> SEQUENCE: 29

```
ccatggtagc gttgagactg gctcgagtcg tgcgaccgac aggagcctcg atccgtcact     60

tgacatggtc ccaccctgct cgactctatt cgtccgtcga caaggtgaat ctgcccaagg    120

ctccctccaa ggaggagctc aagactatgg gtgtggtcat ccctctggaa gagtccaaga    180

acaaactggc ctcgatcaag cctctggtcg acctcactcg agccgacatg gagcgagtca    240

accagctcat cctgtccaag gctggctcgg acgttcagat gattcccgag gtcgccaacc    300

atctcatctc gtctggaggc aagcgacttc gacccatgct cactcttgcc tctgcctcac    360

tcttcgacta ccgaggtgag aatcatatca agctcgctac ctctgtcgag ttcatgcaca    420

ctgctactct cctgcatgac gatgtggtcg acgagtccga ccttcgacga ggcaagtcca    480

ccgctcgaat gatctggggt aaccaggctt ctgtgcttgt gggtgacttc ctgctcggtc    540

aggccttccg aatgatggtg gacgtcggtt cgctcgacgc tcttgacgtt ctctcgtccg    600

ctgcctgcgt catagcagag ggagaagtcc tccagctctc cgtcgctaag aacatggaga    660

ccactgagga tgactacctc tctgtcatcc gagccaagac tgctgccctg ttcgctgcag    720

ctgccgaggt cggtcccatc gttgctgagg tcggacgatc tggacgaaac gccctgaagt    780

cctacggtat gaacctgggt cttgcattcc agctggttga tgacgctctc gactacggtg    840

gaaaggctgc cgatctcggt aagaacgttg gtgatgactt ccgagaaggc aagatcaccc    900

tgcctgtcat ccttgcctac cgacgaggaa ccgaggacga gcgagccttc tggcgagatg    960

ccattgaagc tggcaactcc actgacgcca acctcgagaa ggctctcgga ctcatcacta   1020

agtacggcac tctgtctgac acaatcggac gagccatcca ctacggaacc atcgctcgag   1080

atgctctggc tcctcttcct gacactgtct ggaagtctgc tctgatggaa gtgatcgact   1140

tctgcatcga gcgagtgaac taggcggccg c                                  1171
```

<210> SEQ ID NO 30
<211> LENGTH: 386
<212> TYPE: PRT
<213> ORGANISM: Artificial Sequence
<220> FEATURE:
<223> OTHER INFORMATION: Fusion of GenBank Accession No. XP_505040 (N-terminus of Yarrowia lipolytica ppt1 gene encoding p-hydroxybenzoate:polyprenyl transferase) and GenBank Accession No. CAK06434 (Rhizobium leguminosarum bv. viciae 3841 ddsA)

<400> SEQUENCE: 30

```
Met Val Ala Leu Arg Leu Ala Arg Val Val Arg Pro Thr Gly Ala Ser
1               5                   10                  15

Ile Arg His Leu Thr Trp Ser His Pro Ala Arg Leu Tyr Ser Ser Val
            20                  25                  30

Asp Lys Val Asn Leu Pro Lys Ala Pro Ser Lys Glu Glu Leu Lys Thr
        35                  40                  45

Met Gly Val Val Ile Pro Leu Glu Glu Ser Lys Asn Lys Leu Ala Ser
    50                  55                  60

Ile Lys Pro Leu Val Asp Leu Thr Arg Ala Asp Met Glu Arg Val Asn
65                  70                  75                  80

Gln Leu Ile Leu Ser Lys Ala Gly Ser Asp Val Gln Met Ile Pro Glu
```

-continued

```
                85                  90                  95

Val Ala Asn His Leu Ile Ser Ser Gly Gly Lys Arg Leu Arg Pro Met
            100                 105                 110

Leu Thr Leu Ala Ser Ala Ser Leu Phe Asp Tyr Arg Gly Glu Asn His
        115                 120                 125

Ile Lys Leu Ala Thr Ser Val Glu Phe Met His Thr Ala Thr Leu Leu
    130                 135                 140

His Asp Asp Val Val Asp Glu Ser Asp Leu Arg Arg Gly Lys Ser Thr
145                 150                 155                 160

Ala Arg Met Ile Trp Gly Asn Gln Ala Ser Val Leu Val Gly Asp Phe
                165                 170                 175

Leu Leu Gly Gln Ala Phe Arg Met Met Val Asp Val Gly Ser Leu Asp
            180                 185                 190

Ala Leu Asp Val Leu Ser Ser Ala Ala Cys Val Ile Ala Glu Gly Glu
        195                 200                 205

Val Leu Gln Leu Ser Val Ala Lys Asn Met Glu Thr Thr Glu Asp Asp
    210                 215                 220

Tyr Leu Ser Val Ile Arg Ala Lys Thr Ala Ala Leu Phe Ala Ala Ala
225                 230                 235                 240

Ala Glu Val Gly Pro Ile Val Ala Glu Val Gly Arg Ser Gly Arg Asn
                245                 250                 255

Ala Leu Lys Ser Tyr Gly Met Asn Leu Gly Leu Ala Phe Gln Leu Val
            260                 265                 270

Asp Asp Ala Leu Asp Tyr Gly Gly Lys Ala Ala Asp Leu Gly Lys Asn
        275                 280                 285

Val Gly Asp Asp Phe Arg Glu Gly Lys Ile Thr Leu Pro Val Ile Leu
    290                 295                 300

Ala Tyr Arg Arg Gly Thr Glu Asp Glu Arg Ala Phe Trp Arg Asp Ala
305                 310                 315                 320

Ile Glu Ala Gly Asn Ser Thr Asp Ala Asn Leu Glu Lys Ala Leu Gly
                325                 330                 335

Leu Ile Thr Lys Tyr Gly Thr Leu Ser Asp Thr Ile Gly Arg Ala Ile
            340                 345                 350

His Tyr Gly Thr Ile Ala Arg Asp Ala Leu Ala Pro Leu Pro Asp Thr
        355                 360                 365

Val Trp Lys Ser Ala Leu Met Glu Val Ile Asp Phe Cys Ile Glu Arg
    370                 375                 380

Val Asn
385
```

<210> SEQ ID NO 31
<211> LENGTH: 8249
<212> TYPE: DNA
<213> ORGANISM: Artificial Sequence
<220> FEATURE:
<223> OTHER INFORMATION: Plasmid pDMW359-Ml_ddsA

<400> SEQUENCE: 31

```
catggtagcg ttgagactgg ctcgagtcgt gcgaccgaca ggagcctcga tccgtcactt      60

gacatggtcc caccctgctc gactctattc gtccgtcgac aaggtgaatc tgcccaaggc     120

tccctccaag gaggagctca agactatggg agtcgtgctc aacatcgaga atggcaagcg     180

agaacctgcc tccatcaagg acctgatcga tctcactgct gcagacatgg gtcgagtcaa     240

cgaactcatc ctgtccaagg ctggttcgga cgtcgagatg attcccgaag ttgccaacca     300
```

-continued

```
tctgatctcc tctggaggta agcgacttcg acccatgctg acactcgctg cagcccagat    360
gttcggatat gctggtgaag gacatgtcaa gcttgccacc tctgttgagt tcatgcacac    420
tgccacactc ctgcatgatg acgtcgtgga tgagtctggc atgagacgag gcaagaagac    480
tgctcgaatg atctggggta accaggcttc tgtcctggtt ggagacttcc tccttggaca    540
agcctttcga atgatggtcg atgttggatc tctggaagct ctcgacatcc tgtcctctgc    600
tgcctctatc attgctgaag gtgaggtcat gcagcttgct gcagccaaga acctcgagac    660
cacagaagat gagcacttcg ctgtcatcaa ggctaagact gctgcactgt tctctgctgc    720
agccgaggtt ggacccgtca ttgctcaggc tactcgaaac gatcgagctg cactgcgatc    780
ctacggaatg aacctcggac ttgccttcca gctgatcgac gatgctctgg actacggtgg    840
cacctccaag gaccttggca agaacgttgg agatgacttc cgagaaggta aggtcactct    900
ccctgtcatc ctggcttacc gacgaggtac taaggctgaa cgaaccttct ggaagcgagc    960
catcgaggat aacgtggtcg acgatgctgg tctggagaag gccatcggtc tcatgactcg   1020
acatggagcc atcgctgaca ccatcggacg agctcgacac ttcggtgaga tcgcacgaga   1080
cgcccttgct cctctcgaag agacccgaca gaagtctgct ctgatcgatg tcatcgactt   1140
ctgcatctct cgagtgaact aggcggccgc aagtgtggat ggggaagtga gtgcccggtt   1200
ctgtgtgcac aattggcaat ccaagatgga tggattcaac acagggatat agcgagctac   1260
gtggtggtgc gaggatatag caacggatat ttatgtttga cacttgagaa tgtacgatac   1320
aagcactgtc caagtacaat actaaacata ctgtacatac tcatactcgt acccgggcaa   1380
cggtttcact tgagtgcagt ggctagtgct cttactcgta cagtgtgcaa tactgcgtat   1440
catagtcttt gatgtatatc gtattcattc atgttagttg cgtacgagcc ggaagcataa   1500
agtgtaaagc ctggggtgcc taatgagtga gctaactcac attaattgcg ttgcgctcac   1560
tgcccgcttt ccagtcggga aacctgtcgt gccagctgca ttaatgaatc ggccaacgcg   1620
cggggagagg cggtttgcgt attgggcgct cttccgcttc ctcgctcact gactcgctgc   1680
gctcggtcgt tcggctgcgg cgagcggtat cagctcactc aaaggcggta atacggttat   1740
ccacagaatc aggggataac gcaggaaaga acatgtgagc aaaaggccag caaaaggcca   1800
ggaaccgtaa aaaggccgcg ttgctggcgt ttttccatag gctccgcccc cctgacgagc   1860
atcacaaaaa tcgacgctca agtcagaggt ggcgaaaccc gacaggacta taaagatacc   1920
aggcgtttcc ccctggaagc tccctcgtgc gctctcctgt tccgaccctg ccgcttaccg   1980
gatacctgtc cgcctttctc ccttcgggaa gcgtggcgct ttctcatagc tcacgctgta   2040
ggtatctcag ttcggtgtag gtcgttcgct ccaagctggg ctgtgtgcac gaaccccccg   2100
ttcagcccga ccgctgcgcc ttatccggta actatcgtct tgagtccaac ccggtaagac   2160
acgacttatc gccactggca gcagccactg gtaacaggat tagcagagcg aggtatgtag   2220
gcggtgctac agagttcttg aagtggtggc ctaactacgg ctacactaga aggacagtat   2280
ttggtatctg cgctctgctg aagccagtta ccttcggaaa aagagttggt agctcttgat   2340
ccggcaaaca aaccaccgct ggtagcggtg gtttttttgt ttgcaagcag cagattacgc   2400
gcagaaaaaa aggatctcaa gaagatcctt tgatcttttc tacggggtct gacgctcagt   2460
ggaacgaaaa ctcacgttaa gggattttgg tcatgagatt atcaaaaagg atcttcacct   2520
agatcctttt aaattaaaaa tgaagtttta aatcaatcta aagtatatat gagtaaactt   2580
ggtctgacag ttaccaatgc ttaatcagtg aggcacctat ctcagcgatc tgtctatttc   2640
gttcatccat agttgcctga ctccccgtcg tgtagataac tacgatacgg gagggcttac   2700
```

-continued

```
catctggccc cagtgctgca atgataccgc gagacccacg ctcaccggct ccagatttat   2760
cagcaataaa ccagccagcc ggaagggccg agcgcagaag tggtcctgca actttatccg   2820
cctccatcca gtctattaat tgttgccggg aagctagagt aagtagttcg ccagttaata   2880
gtttgcgcaa cgttgttgcc attgctacag gcatcgtggt gtcacgctcg tcgtttggta   2940
tggcttcatt cagctccggt tcccaacgat caaggcgagt tacatgatcc cccatgttgt   3000
gcaaaaaagc ggttagctcc ttcggtcctc cgatcgttgt cagaagtaag ttggccgcag   3060
tgttatcact catggttatg gcagcactgc ataattctct tactgtcatg ccatccgtaa   3120
gatgcttttc tgtgactggt gagtactcaa ccaagtcatt ctgagaatag tgtatgcggc   3180
gaccgagttg ctcttgcccg gcgtcaatac gggataatac cgcgccacat agcagaactt   3240
taaaagtgct catcattgga aaacgttctt cggggcgaaa actctcaagg atcttaccgc   3300
tgttgagatc cagttcgatg taacccactc gtgcacccaa ctgatcttca gcatctttta   3360
ctttcaccag cgtttctggg tgagcaaaaa caggaaggca aaatgccgca aaaaagggaa   3420
taagggcgac acggaaatgt tgaatactca tactcttcct ttttcaatat tattgaagca   3480
tttatcaggg ttattgtctc atgagcggat acatatttga atgtatttag aaaaataaac   3540
aaataggggt tccgcgcaca tttccccgaa aagtgccacc tgacgcgccc tgtagcggcg   3600
cattaagcgc ggcgggtgtg gtggttacgc gcagcgtgac cgctacactt gccagcgccc   3660
tagcgcccgc tcctttcgct ttcttccctt cctttctcgc cacgttcgcc ggctttcccc   3720
gtcaagctct aaatcggggg ctccctttag ggttccgatt tagtgcttta cggcacctcg   3780
accccaaaaa acttgattag ggtgatggtt cacgtagtgg gccatcgccc tgatagacgg   3840
tttttcgccc tttgacgttg gagtccacgt tctttaatag tggactcttg ttccaaactg   3900
gaacaacact caaccctatc tcggtctatt cttttgattt ataagggatt ttgccgattt   3960
cggcctattg gttaaaaaat gagctgattt aacaaaaatt taacgcgaat tttaacaaaa   4020
tattaacgct tacaatttcc attcgccatt caggctgcgc aactgttggg aagggcgatc   4080
ggtgcgggcc tcttcgctat tacgccagct ggcgaaaggg ggatgtgctg caaggcgatt   4140
aagttgggta acgccagggt tttcccagtc acgacgttgt aaaacgacgg ccagtgaatt   4200
gtaatacgac tcactatagg gcgaattggg taccgggccc cccctcgagg tcgatggtgt   4260
cgataagctt gatatcgaat tcatgtcaca caaaccgatc ttcgcctcaa ggaaacctaa   4320
ttctacatcc gagagactgc cgagatccag tctacactga ttaattttcg ggccaataat   4380
ttaaaaaaat cgtgttatat aatattatat gtattatata tatacatcat gatgatactg   4440
acagtcatgt cccattgcta aatagacaga ctccatctgc cgcctccaac tgatgttctc   4500
aatatttaag gggtcatctc gcattgttta ataataaaca gactccatct accgcctcca   4560
aatgatgttc tcaaaatata ttgtatgaac ttatttttat tacttagtat tattagacaa   4620
cttacttgct ttatgaaaaa cacttcctat ttaggaaaca atttataatg gcagttcgtt   4680
catttaacaa tttatgtaga ataaatgtta taaatgcgta tgggaaatct taaatatgga   4740
tagcataaat gatatctgca ttgcctaatt cgaaatcaac agcaacgaaa aaaatccctt   4800
gtacaacata aatagtcatc gagaaatatc aactatcaaa gaacagctat tcacacgtta   4860
ctattgagat tattattgga cgagaatcac acactcaact gtctttctct cttctagaaa   4920
tacaggtaca agtatgtact attctcattg ttcatacttc tagtcatttc atcccacata   4980
ttccttggat ttctctccaa tgaatgacat tctatcttgc aaattcaaca attataataa   5040
```

-continued

```
gatataccaa agtagcggta tagtggcaat caaaaagctt ctctggtgtg cttctcgtat   5100
ttatttttat tctaatgatc cattaaaggt atatatttat ttcttgttat ataatccttt   5160
tgtttattac atgggctgga tacataaagg tattttgatt taattttttg cttaaattca   5220
atcccccctc gttcagtgtc aactgtaatg gtaggaaatt accatacttt tgaagaagca   5280
aaaaaaatga aagaaaaaaa aaatcgtatt tccaggttag acgttccgca gaatctagaa   5340
tgcggtatgc ggtacattgt tcttcgaacg taaaagttgc gctccctgag atattgtaca   5400
tttttgcttt tacaagtaca agtacatcgt acaactatgt actactgttg atgcatccac   5460
aacagtttgt tttgtttttt tttgtttttt ttttttctaa tgattcatta ccgctatgta   5520
tacctacttg tacttgtagt aagccgggtt attggcgttc aattaatcat agacttatga   5580
atctgcacgg tgtgcgctgc gagttacttt tagcttatgc atgctacttg ggtgtaatat   5640
tgggatctgt tcggaaatca acggatgctc aatcgatttc gacagtaatt aattaagtca   5700
tacacaagtc agctttcttc gagcctcata taagtataag tagttcaacg tattagcact   5760
gtacccagca tctccgtatc gagaaacaca acaacatgcc ccattggaca gatcatgcgg   5820
atacacaggt tgtgcagtat catacatact cgatcagaca ggtcgtctga ccatcataca   5880
agctgaacaa gcgctccata cttgcacgct ctctatatac acagttaaat tacatatcca   5940
tagtctaacc tctaacagtt aatcttctgg taagcctccc agccagcctt ctggtatcgc   6000
ttggcctcct caataggatc tcggttctgg ccgtacagac ctcggccgac aattatgata   6060
tccgttccgg tagacatgac atcctcaaca gttcggtact gctgtccgag agcgtctccc   6120
ttgtcgtcaa gacccacccc gggggtcaga ataagccagt cctcagagtc gcccttaggt   6180
cggttctggg caatgaagcc aaccacaaac tcggggtcgg atcgggcaag ctcaatggtc   6240
tgcttggagt actcgccagt ggccagagag cccttgcaag acagctcggc cagcatgagc   6300
agacctctgg ccagcttctc gttgggagag gggactagga actccttgta ctgggagttc   6360
tcgtagtcag agacgtcctc cttcttctgt tcagagacag tttcctcggc accagctcgc   6420
aggccagcaa tgattccggt tccgggtaca ccgtgggcgt tggtgatatc ggaccactcg   6480
gcgattcggt gacaccggta ctggtgcttg acagtgttgc caatatctgc gaactttctg   6540
tcctcgaaca ggaagaaacc gtgcttaaga gcaagttcct tgagggggag cacagtgccg   6600
gcgtaggtga agtcgtcaat gatgtcgata tgggttttga tcatgcacac ataaggtccg   6660
accttatcgg caagctcaat gagctccttg gtggtggtaa catccagaga agcacacagg   6720
ttggttttct tggctgccac gagcttgagc actcgagcgg caaaggcgga cttgtggacg   6780
ttagctcgag cttcgtagga gggcattttg gtggtgaaga ggagactgaa ataaatttag   6840
tctgcagaac tttttatcgg aaccttatct ggggcagtga agtatatgtt atggtaatag   6900
ttacgagtta gttgaactta tagatagact ggactatacg gctatcggtc caaattagaa   6960
agaacgtcaa tggctctctg ggcgtcgcct ttgccgacaa aaatgtgatc atgatgaaag   7020
ccagcaatga cgttgcagct gatattgttg tcggccaacc gcgccgaaaa cgcagctgtc   7080
agacccacag cctccaacga agaatgtatc gtcaaagtga tccaagcaca ctcatagttg   7140
gagtcgtact ccaaaggcgg caatgacgag tcagacagat actcgtcgac tcaggcgacg   7200
acggaattcc tgcagcccat ctgcagaatt caggagagac cgggttggcg gcgtatttgt   7260
gtcccaaaaa acagccccaa ttgccccgga gaagacggcc aggccgccta gatgacaaat   7320
tcaacaactc acagctgact ttctgccatt gccactaggg gggggccttt ttatatggcc   7380
aagccaagct ctccacgtcg gttgggctgc acccaacaat aaatgggtag ggttgcacca   7440
```

acaaagggat gggatggggg gtagaagata cgaggataac ggggctcaat ggcacaaata 7500
agaacgaata ctgccattaa gactcgtgat ccagcgactg acaccattgc atcatctaag 7560
ggcctcaaaa ctacctcgga actgctgcgc tgatctggac accacagagg ttccgagcac 7620
tttaggttgc accaaatgtc ccaccaggtg caggcagaaa acgctggaac agcgtgtaca 7680
gtttgtctta acaaaaagtg agggcgctga ggtcgagcag ggtggtgtga cttgttatag 7740
cctttagagc tgcgaaagcg cgtatggatt tggctcatca ggccagattg agggtctgtg 7800
gacacatgtc atgttagtgt acttcaatcg ccccctggat atagccccga caataggccg 7860
tggcctcatt tttttgcctt ccgcacattt ccattgctcg gtacccacac cttgcttctc 7920
ctgcacttgc caaccttaat actggtttac attgaccaac atcttacaag cggggggctt 7980
gtctagggta tatataaaca gtggctctcc caatcggttg ccagtctctt ttttcctttc 8040
tttccccaca gattcgaaat ctaaactaca catcacacaa tgcctgttac tgacgtcctt 8100
aagcgaaagt ccggtgtcat cgtcggcgac gatgtccgag ccgtgagtat ccacgacaag 8160
atcagtgtcg agacgacgcg ttttgtgtaa tgacacaatc cgaaagtcgc tagcaacaca 8220
cactctctac acaaactaac ccagctctc 8249

<210> SEQ ID NO 32
<211> LENGTH: 1171
<212> TYPE: DNA
<213> ORGANISM: Artificial Sequence
<220> FEATURE:
<223> OTHER INFORMATION: Fusion of GenBank Accession No. XP_505040
(N-terminus of Yarrowia lipolytica ppt1 gene encoding
p-hydroxybenzoate:polyprenyl transferase) and GenBank Accession
No. BAB53531 (Mesorhizobium loti MAFF303099 ddsA)

<400> SEQUENCE: 32
ccatggtagc gttgagactg gctcgagtcg tgcgaccgac aggagcctcg atccgtcact 60
tgacatggtc ccaccctgct cgactctatt cgtccgtcga caaggtgaat ctgcccaagg 120
ctccctccaa ggaggagctc aagactatgg gagtcgtgct caacatcgag aatggcaagc 180
gagaacctgc ctccatcaag gacctgatcg atctcactgc tgcagacatg ggtcgagtca 240
acgaactcat cctgtccaag gctggttcgg acgtcgagat gattcccgaa gttgccaacc 300
atctgatctc ctctggaggt aagcgacttc gacccatgct gacactcgct gcagcccaga 360
tgttcggata tgctggtgaa ggacatgtca agcttgccac ctctgttgag ttcatgcaca 420
ctgccacact cctgcatgat gacgtcgtgg atgagtctgg catgagacga ggcaagaaga 480
ctgctcgaat gatctggggt aaccaggctt ctgtcctggt tggagacttc ctccttggac 540
aagcctttcg aatgatggtc gatgttggat ctctggaagc tctcgacatc ctgtcctctg 600
ctgcctctat cattgctgaa ggtgaggtca tgcagcttgc tgcagccaag aacctcgaga 660
ccacagaaga tgagcacttc gctgtcatca aggctaagac tgctgcactg ttctctgctg 720
cagccgaggt tggacccgtc attgctcagg ctactcgaaa cgatcgagct gcactgcgat 780
cctacggaat gaacctcgga cttgccttcc agctgatcga cgatgctctg gactacggtg 840
gcacctccaa ggaccttggc aagaacgttg gagatgactt ccgagaaggt aaggtcactc 900
tccctgtcat cctggcttac cgacgaggta ctaaggctga acgaaccttc tggaagcgag 960
ccatcgagga taacgtggtc gacgatgctg gtctggagaa ggccatcggt ctcatgactc 1020
gacatggagc catcgctgac accatcggac gagctcgaca cttcggtgag atcgcacgag 1080
acgcccttgc tcctctcgaa gagacccgac agaagtctgc tctgatcgat gtcatcgact 1140

```
tctgcatctc tcgagtgaac taggcggccg c                                1171


<210> SEQ ID NO 33
<211> LENGTH: 386
<212> TYPE: PRT
<213> ORGANISM: Artificial Sequence
<220> FEATURE:
<223> OTHER INFORMATION: Fusion of GenBank Accession No. XP_505040
      (N-terminus of Yarrowia lipolytica ppt1 gene encoding
      p-hydroxybenzoate:polyprenyl transferase) and GenBank Accession
      No. BAB53531 (Mesorhizobium loti MAFF303099 ddsA)

<400> SEQUENCE: 33

Met Val Ala Leu Arg Leu Ala Arg Val Val Arg Pro Thr Gly Ala Ser
1               5                   10                  15

Ile Arg His Leu Thr Trp Ser His Pro Ala Arg Leu Tyr Ser Ser Val
            20                  25                  30

Asp Lys Val Asn Leu Pro Lys Ala Pro Ser Lys Glu Glu Leu Lys Thr
        35                  40                  45

Met Gly Val Val Leu Asn Ile Glu Asn Gly Lys Arg Glu Pro Ala Ser
    50                  55                  60

Ile Lys Asp Leu Ile Asp Leu Thr Ala Ala Asp Met Gly Arg Val Asn
65                  70                  75                  80

Glu Leu Ile Leu Ser Lys Ala Gly Ser Asp Val Glu Met Ile Pro Glu
                85                  90                  95

Val Ala Asn His Leu Ile Ser Ser Gly Gly Lys Arg Leu Arg Pro Met
            100                 105                 110

Leu Thr Leu Ala Ala Ala Gln Met Phe Gly Tyr Ala Gly Glu Gly His
        115                 120                 125

Val Lys Leu Ala Thr Ser Val Glu Phe Met His Thr Ala Thr Leu Leu
    130                 135                 140

His Asp Asp Val Val Asp Glu Ser Gly Met Arg Arg Gly Lys Lys Thr
145                 150                 155                 160

Ala Arg Met Ile Trp Gly Asn Gln Ala Ser Val Leu Val Gly Asp Phe
                165                 170                 175

Leu Leu Gly Gln Ala Phe Arg Met Met Val Asp Val Gly Ser Leu Glu
            180                 185                 190

Ala Leu Asp Ile Leu Ser Ser Ala Ala Ser Ile Ile Ala Glu Gly Glu
        195                 200                 205

Val Met Gln Leu Ala Ala Ala Lys Asn Leu Glu Thr Thr Glu Asp Glu
    210                 215                 220

His Phe Ala Val Ile Lys Ala Lys Thr Ala Ala Leu Phe Ser Ala Ala
225                 230                 235                 240

Ala Glu Val Gly Pro Val Ile Ala Gln Ala Thr Arg Asn Asp Arg Ala
                245                 250                 255

Ala Leu Arg Ser Tyr Gly Met Asn Leu Gly Leu Ala Phe Gln Leu Ile
            260                 265                 270

Asp Asp Ala Leu Asp Tyr Gly Gly Thr Ser Lys Asp Leu Gly Lys Asn
        275                 280                 285

Val Gly Asp Asp Phe Arg Glu Gly Lys Val Thr Leu Pro Val Ile Leu
    290                 295                 300

Ala Tyr Arg Arg Gly Thr Lys Ala Glu Arg Thr Phe Trp Lys Arg Ala
305                 310                 315                 320

Ile Glu Asp Asn Val Val Asp Asp Ala Gly Leu Glu Lys Ala Ile Gly
                325                 330                 335
```

-continued

```
Leu Met Thr Arg His Gly Ala Ile Ala Asp Thr Ile Gly Arg Ala Arg
            340                 345                 350

His Phe Gly Glu Ile Ala Arg Asp Ala Leu Ala Pro Leu Glu Glu Thr
        355                 360                 365

Arg Gln Lys Ser Ala Leu Ile Asp Val Ile Asp Phe Cys Ile Ser Arg
    370                 375                 380

Val Asn
385
```

<210> SEQ ID NO 34
<211> LENGTH: 8248
<212> TYPE: DNA
<213> ORGANISM: Artificial Sequence
<220> FEATURE:
<223> OTHER INFORMATION: Plasmid pDMW359-At_ddsA

<400> SEQUENCE: 34

```
catggtagcg ttgagactgg ctcgagtcgt gcgaccgaca ggagcctcga tccgtcactt     60

gacatggtcc caccctgctc gactctattc gtccgtcgac aaggtgaatc tgcccaaggc    120

tccctccaag gaggagctca agactatggg agttgtcatt cctcttgaag agtccaagaa    180

caagctggct tcggtcaagc ctctcgtcga cctgacacga cccgacatgg agcgagtcaa    240

tcaactcatc ctgtctcgag ctggttccga cgttcagatg atcccagagg ttgccaacca    300

tctgatctcc tctggaggca agcgacttcg acccatgctg accctggctt ctgcttctat    360

gtttggttac gagggtgaca accacatcaa gctggctacc tccgtcgagt tcatgcacac    420

tgccactctg ctccatgacg atgtggtgga cgagtctgac ctccgacgag gtaagtctac    480

ggctcgaact atctggggaa accaggcttc tgtcctcgtt ggtgacttcc tgctcggtca    540

ggccttccga atgatggtcg atgttggttc gcttgatgct ctcgacgtcc tgtccactgc    600

tgcctctgtc atcgctgaag gtgaggttct ccagctctct gttgccaaga acatggagac    660

cacggaggat gactacctcc aggtcattcg agccaagact gctgcactct tcgctgcagc    720

tgccgaggtc ggaccgatcg ttgccaagac tgacaaggcc agccgatctg ccctgaagtc    780

ttatggcatg aacctcggtc tcgctttcca gcttgtggac gatgttcttg actacggcgg    840

aaagtctgcc gacctcggta agaacactgg tgacgacttc cgagagggaa agatcactct    900

tccagtcatc ctcagctacc gacgaggcac tcaggatgag cgagccttct ggcgaaacgc    960

catcgagaag ggagagtctt ccgatgagaa cctcgagaag gctctcggac tgatcaccaa   1020

gtacaacggt cttggtgaca ccatcggtcg agccactcac tacggtacca tcgctcgaga   1080

cgctcttgct cctcttccgc agtcgccctg gaagaacgct ctcctggaag tcatcgactt   1140

ctgtatcgag cgactcaact agcggccgca agtgtggatg gggaagtgag tgcccggttc   1200

tgtgtgcaca attggcaatc caagatggat ggattcaaca cagggatata gcgagctacg   1260

tggtggtgcg aggatatagc aacggatatt tatgtttgac acttgagaat gtacgataca   1320

agcactgtcc aagtacaata ctaaacatac tgtacatact catactcgta cccgggcaac   1380

ggtttcactt gagtgcagtg gctagtgctc ttactcgtac agtgtgcaat actgcgtatc   1440

atagtctttg atgtatatcg tattcattca tgttagttgc gtacgagccg gaagcataaa   1500

gtgtaaagcc tggggtgcct aatgagtgag ctaactcaca ttaattgcgt tgcgctcact   1560

gcccgctttc cagtcgggaa acctgtcgtg ccagctgcat taatgaatcg gccaacgcgc   1620

ggggagaggc ggtttgcgta ttgggcgctc ttccgcttcc tcgctcactg actcgctgcg   1680

ctcggtcgtt cggctgcggc gagcggtatc agctcactca aaggcggtaa tacggttatc   1740
```

-continued

```
cacagaatca ggggataacg caggaaagaa catgtgagca aaaggccagc aaaaggccag   1800
gaaccgtaaa aaggccgcgt tgctggcgtt tttccatagg ctccgccccc ctgacgagca   1860
tcacaaaaat cgacgctcaa gtcagaggtg gcgaaacccg acaggactat aaagatacca   1920
ggcgtttccc cctggaagct ccctcgtgcg ctctcctgtt ccgaccctgc cgcttaccgg   1980
atacctgtcc gcctttctcc cttcgggaag cgtggcgctt tctcatagct cacgctgtag   2040
gtatctcagt tcggtgtagg tcgttcgctc caagctgggc tgtgtgcacg aaccccccgt   2100
tcagcccgac cgctgcgcct tatccggtaa ctatcgtctt gagtccaacc cggtaagaca   2160
cgacttatcg ccactggcag cagccactgg taacaggatt agcagagcga ggtatgtagg   2220
cggtgctaca gagttcttga agtggtggcc taactacggc tacactagaa ggacagtatt   2280
tggtatctgc gctctgctga agccagttac cttcggaaaa agagttggta gctcttgatc   2340
cggcaaacaa accaccgctg gtagcggtgg tttttttgtt tgcaagcagc agattacgcg   2400
cagaaaaaaa ggatctcaag aagatccttt gatcttttct acggggtctg acgctcagtg   2460
gaacgaaaac tcacgttaag ggattttggt catgagatta tcaaaaagga tcttcaccta   2520
gatcctttta aattaaaaat gaagttttaa atcaatctaa agtatatatg agtaaacttg   2580
gtctgacagt taccaatgct taatcagtga ggcacctatc tcagcgatct gtctatttcg   2640
ttcatccata gttgcctgac tccccgtcgt gtagataact acgatacggg agggcttacc   2700
atctggcccc agtgctgcaa tgataccgcg agacccacgc tcaccggctc cagatttatc   2760
agcaataaac cagccagccg gaagggccga gcgcagaagt ggtcctgcaa ctttatccgc   2820
ctccatccag tctattaatt gttgccggga agctagagta agtagttcgc cagttaatag   2880
tttgcgcaac gttgttgcca ttgctacagg catcgtggtg tcacgctcgt cgtttggtat   2940
ggcttcattc agctccggtt cccaacgatc aaggcgagtt acatgatccc ccatgttgtg   3000
caaaaaagcg gttagctcct tcggtcctcc gatcgttgtc agaagtaagt tggccgcagt   3060
gttatcactc atggttatgg cagcactgca taattctctt actgtcatgc catccgtaag   3120
atgcttttct gtgactggtg agtactcaac caagtcattc tgagaatagt gtatgcggcg   3180
accgagttgc tcttgcccgg cgtcaatacg ggataatacc gcgccacata gcagaacttt   3240
aaaagtgctc atcattggaa aacgttcttc ggggcgaaaa ctctcaagga tcttaccgct   3300
gttgagatcc agttcgatgt aacccactcg tgcacccaac tgatcttcag catcttttac   3360
tttcaccagc gtttctgggt gagcaaaaac aggaaggcaa aatgccgcaa aaaagggaat   3420
aagggcgaca cggaaatgtt gaatactcat actcttcctt tttcaatatt attgaagcat   3480
ttatcagggt tattgtctca tgagcggata catatttgaa tgtatttaga aaaataaaca   3540
aataggggtt ccgcgcacat ttccccgaaa agtgccacct gacgcgccct gtagcggcgc   3600
attaagcgcg gcgggtgtgg tggttacgcg cagcgtgacc gctacacttg ccagcgccct   3660
agcgcccgct cctttcgctt tcttcccttc ctttctcgcc acgttcgccg gctttccccg   3720
tcaagctcta aatcgggggc tccctttagg gttccgattt agtgctttac ggcacctcga   3780
ccccaaaaaa cttgattagg gtgatggttc acgtagtggg ccatcgccct gatagacggt   3840
ttttcgccct ttgacgttgg agtccacgtt ctttaatagt ggactcttgt tccaaactgg   3900
aacaacactc aaccctatct cggtctattc ttttgattta taagggattt tgccgatttc   3960
ggcctattgg ttaaaaaatg agctgattta acaaaaattt aacgcgaatt ttaacaaaat   4020
attaacgctt acaatttcca ttcgccattc aggctgcgca actgttggga agggcgatcg   4080
```

-continued

```
gtgcgggcct cttcgctatt acgccagctg gcgaaagggg gatgtgctgc aaggcgatta   4140
agttgggtaa cgccagggtt ttcccagtca cgacgttgta aaacgacggc cagtgaattg   4200
taatacgact cactataggg cgaattgggt accgggcccc ccctcgaggt cgatggtgtc   4260
gataagcttg atatcgaatt catgtcacac aaaccgatct tcgcctcaag gaaacctaat   4320
tctacatccg agagactgcc gagatccagt ctacactgat taattttcgg gccaataatt   4380
taaaaaaatc gtgttatata atattatatg tattatatat atacatcatg atgatactga   4440
cagtcatgtc ccattgctaa atagacagac tccatctgcc gcctccaact gatgttctca   4500
atatttaagg ggtcatctcg cattgtttaa taataaacag actccatcta ccgcctccaa   4560
atgatgttct caaaatatat tgtatgaact tatttttatt acttagtatt attagacaac   4620
ttacttgctt tatgaaaaac acttcctatt taggaaacaa tttataatgg cagttcgttc   4680
atttaacaat ttatgtagaa taaatgttat aaatgcgtat gggaaatctt aaatatggat   4740
agcataaatg atatctgcat tgcctaattc gaaatcaaca gcaacgaaaa aaatcccttg   4800
tacaacataa atagtcatcg agaaatatca actatcaaag aacagctatt cacacgttac   4860
tattgagatt attattggac gagaatcaca cactcaactg tctttctctc ttctagaaat   4920
acaggtacaa gtatgtacta ttctcattgt tcatacttct agtcatttca tcccacatat   4980
tccttggatt tctctccaat gaatgacatt ctatcttgca aattcaacaa ttataataag   5040
atataccaaa gtagcggtat agtggcaatc aaaaagcttc tctggtgtgc ttctcgtatt   5100
tatttttatt ctaatgatcc attaaaggta tatatttatt tcttgttata taatcctttt   5160
gtttattaca tgggctggat acataaaggt attttgattt aattttttgc ttaaattcaa   5220
tccccccctcg ttcagtgtca actgtaatgg taggaaatta ccatactttt gaagaagcaa   5280
aaaaaatgaa agaaaaaaaa aatcgtattt ccaggttaga cgttccgcag aatctagaat   5340
gcggtatgcg gtacattgtt cttcgaacgt aaaagttgcg ctccctgaga tattgtacat   5400
ttttgctttt acaagtacaa gtacatcgta caactatgta ctactgttga tgcatccaca   5460
acagtttgtt ttgttttttt ttgttttttt tttttctaat gattcattac cgctatgtat   5520
acctacttgt acttgtagta agccgggtta ttggcgttca attaatcata gacttatgaa   5580
tctgcacggt gtgcgctgcg agttactttt agcttatgca tgctacttgg gtgtaatatt   5640
gggatctgtt cggaaatcaa cggatgctca atcgatttcg acagtaatta attaagtcat   5700
acacaagtca gctttcttcg agcctcatat aagtataagt agttcaacgt attagcactg   5760
tacccagcat ctccgtatcg agaaacacaa caacatgccc cattggacag atcatgcgga   5820
tacacaggtt gtgcagtatc atacatactc gatcagacag gtcgtctgac catcatacaa   5880
gctgaacaag cgctccatac ttgcacgctc tctatataca cagttaaatt acatatccat   5940
agtctaacct ctaacagtta atcttctggt aagcctccca gccagccttc tggtatcgct   6000
tggcctcctc aataggatct cggttctggc cgtacagacc tcggccgaca attatgatat   6060
ccgttccggt agacatgaca tcctcaacag ttcggtactg ctgtccgaga gcgtctccct   6120
tgtcgtcaag acccaccccg ggggtcagaa taagccagtc ctcagagtcg cccttaggtc   6180
ggttctgggc aatgaagcca accacaaact cggggtcgga tcgggcaagc tcaatggtct   6240
gcttggagta ctcgccagtg gccagagagc ccttgcaaga cagctcggcc agcatgagca   6300
gacctctggc cagcttctcg ttgggagagg ggactaggaa ctccttgtac tgggagttct   6360
cgtagtcaga gacgtcctcc ttcttctgtt cagagacagt ttcctcggca ccagctcgca   6420
ggccagcaat gattccggtt ccgggtacac cgtgggcgtt ggtgatatcg gaccactcgg   6480
```

```
cgattcggtg acaccggtac tggtgcttga cagtgttgcc aatatctgcg aactttctgt   6540
cctcgaacag gaagaaaccg tgcttaagag caagttcctt gagggggagc acagtgccgg   6600
cgtaggtgaa gtcgtcaatg atgtcgatat gggttttgat catgcacaca taaggtccga   6660
ccttatcggc aagctcaatg agctccttgg tggtggtaac atccagagaa gcacacaggt   6720
tggttttctt ggctgccacg agcttgagca ctcgagcggc aaaggcggac ttgtggacgt   6780
tagctcgagc ttcgtaggag ggcattttgg tggtgaagag gagactgaaa taaatttagt   6840
ctgcagaact ttttatcgga accttatctg gggcagtgaa gtatatgtta tggtaatagt   6900
tacgagttag ttgaacttat agatagactg gactatacgg ctatcggtcc aaattagaaa   6960
gaacgtcaat ggctctctgg gcgtcgcctt tgccgacaaa aatgtgatca tgatgaaagc   7020
cagcaatgac gttgcagctg atattgttgt cggccaaccg cgccgaaaac gcagctgtca   7080
gacccacagc ctccaacgaa gaatgtatcg tcaaagtgat ccaagcacac tcatagttgg   7140
agtcgtactc caaaggcggc aatgacgagt cagacagata ctcgtcgact caggcgacga   7200
cggaattcct gcagcccatc tgcagaattc aggagagacc gggttggcgg cgtatttgtg   7260
tcccaaaaaa cagccccaat tgccccggag aagacggcca ggccgcctag atgacaaatt   7320
caacaactca cagctgactt tctgccattg ccactagggg ggggcctttt tatatggcca   7380
agccaagctc tccacgtcgg ttgggctgca cccaacaata aatgggtagg gttgcaccaa   7440
caaagggatg ggatgggggg tagaagatac gaggataacg gggctcaatg gcacaaataa   7500
gaacgaatac tgccattaag actcgtgatc cagcgactga caccattgca tcatctaagg   7560
gcctcaaaac tacctcggaa ctgctgcgct gatctggaca ccacagaggt tccgagcact   7620
ttaggttgca ccaaatgtcc caccaggtgc aggcagaaaa cgctggaaca gcgtgtacag   7680
tttgtcttaa caaaaagtga gggcgctgag gtcgagcagg gtggtgtgac ttgttatagc   7740
ctttagagct gcgaaagcgc gtatggattt ggctcatcag gccagattga gggtctgtgg   7800
acacatgtca tgttagtgta cttcaatcgc cccctggata tagccccgac aataggccgt   7860
ggcctcattt ttttgccttc cgcacatttc cattgctcgg tacccacacc ttgcttctcc   7920
tgcacttgcc aaccttaata ctggtttaca ttgaccaaca tcttacaagc ggggggcttg   7980
tctagggtat atataaacag tggctctccc aatcggttgc cagtctcttt tttcctttct   8040
ttccccacag attcgaaatc taaactacac atcacacaat gcctgttact gacgtcctta   8100
agcgaaagtc cggtgtcatc gtcggcgacg atgtccgagc cgtgagtatc cacgacaaga   8160
tcagtgtcga gacgacgcgt tttgtgtaat gacacaatcc gaaagtcgct agcaacacac   8220
actctctaca caaactaacc cagctctc                                      8248
```

<210> SEQ ID NO 35
<211> LENGTH: 1170
<212> TYPE: DNA
<213> ORGANISM: Artificial Sequence
<220> FEATURE:
<223> OTHER INFORMATION: Fusion of GenBank Accession No. XP_505040 (N-terminus of Yarrowia lipolytica ppt1 gene encoding p-hydroxybenzoate:polyprenyl transferase) and GenBank Accession No. AAL41650 (Agrobacterium tumefaciens str. C58 ddsA)

<400> SEQUENCE: 35

```
ccatggtagc gttgagactg gctcgagtcg tgcgaccgac aggagcctcg atccgtcact     60
tgacatggtc ccaccctgct cgactctatt cgtccgtcga caaggtgaat ctgcccaagg    120
ctccctccaa ggaggagctc aagactatgg gagttgtcat tcctcttgaa gagtccaaga    180
```

```
acaagctggc ttcggtcaag cctctcgtcg acctgacacg acccgacatg gagcgagtca    240

atcaactcat cctgtctcga gctggttccg acgttcagat gatcccagag gttgccaacc    300

atctgatctc ctctggaggc aagcgacttc gacccatgct gaccctggct tctgcttcta    360

tgtttggtta cgagggtgac aaccacatca agctggctac ctccgtcgag ttcatgcaca    420

ctgccactct gctccatgac gatgtggtgg acgagtctga cctccgacga ggtaagtcta    480

cggctcgaac tatctgggga aaccaggctt ctgtcctcgt tggtgacttc ctgctcggtc    540

aggccttccg aatgatggtc gatgttggtt cgcttgatgc tctcgacgtc ctgtccactg    600

ctgcctctgt catcgctgaa ggtgaggttc tccagctctc tgttgccaag aacatggaga    660

ccacggagga tgactacctc caggtcattc gagccaagac tgctgcactc ttcgctgcag    720

ctgccgaggt cggaccgatc gttgccaaga ctgacaaggc cagccgatct gccctgaagt    780

cttatggcat gaacctcggt ctcgctttcc agcttgtgga cgatgttctt gactacggcg    840

gaaagtctgc cgacctcggt aagaacactg gtgacgactt ccgagaggga aagatcactc    900

ttccagtcat cctcagctac cgacgaggca ctcaggatga gcgagccttc tggcgaaacg    960

ccatcgagaa gggagagtct tccgatgaga acctcgagaa ggctctcgga ctgatcacca   1020

agtacaacgg tcttggtgac accatcggtc gagccactca ctacggtacc atcgctcgag   1080

acgctcttgc tcctcttccg cagtcgccct ggaagaacgc tctcctggaa gtcatcgact   1140

tctgtatcga gcgactcaac tagcggccgc                                    1170
```

```
<210> SEQ ID NO 36
<211> LENGTH: 386
<212> TYPE: PRT
<213> ORGANISM: Artificial Sequence
<220> FEATURE:
<223> OTHER INFORMATION: Fusion of GenBank Accession No. XP_505040
      (N-terminus of Yarrowia lipolytica ppt1 gene encoding
      p-hydroxybenzoate:polyprenyl transferase) and GenBank Accession
      No. AAL41650 (Agrobacterium tumefaciens str. C58 ddsA)

<400> SEQUENCE: 36

Met Val Ala Leu Arg Leu Ala Arg Val Val Arg Pro Thr Gly Ala Ser
1               5                   10                  15

Ile Arg His Leu Thr Trp Ser His Pro Ala Arg Leu Tyr Ser Ser Val
            20                  25                  30

Asp Lys Val Asn Leu Pro Lys Ala Pro Ser Lys Glu Glu Leu Lys Thr
        35                  40                  45

Met Gly Val Val Ile Pro Leu Glu Glu Ser Lys Asn Lys Leu Ala Ser
    50                  55                  60

Val Lys Pro Leu Val Asp Leu Thr Arg Pro Asp Met Glu Arg Val Asn
65                  70                  75                  80

Gln Leu Ile Leu Ser Arg Ala Gly Ser Asp Val Gln Met Ile Pro Glu
                85                  90                  95

Val Ala Asn His Leu Ile Ser Ser Gly Gly Lys Arg Leu Arg Pro Met
            100                 105                 110

Leu Thr Leu Ala Ser Ala Ser Met Phe Gly Tyr Glu Gly Asp Asn His
        115                 120                 125

Ile Lys Leu Ala Thr Ser Val Glu Phe Met His Thr Ala Thr Leu Leu
    130                 135                 140

His Asp Asp Val Val Asp Glu Ser Asp Leu Arg Arg Gly Lys Ser Thr
145                 150                 155                 160

Ala Arg Thr Ile Trp Gly Asn Gln Ala Ser Val Leu Val Gly Asp Phe
```

```
                165                 170                 175

Leu Leu Gly Gln Ala Phe Arg Met Met Val Asp Val Gly Ser Leu Asp
            180                 185                 190

Ala Leu Asp Val Leu Ser Thr Ala Ala Ser Val Ile Ala Glu Gly Glu
        195                 200                 205

Val Leu Gln Leu Ser Val Ala Lys Asn Met Glu Thr Thr Glu Asp Asp
    210                 215                 220

Tyr Leu Gln Val Ile Arg Ala Lys Thr Ala Ala Leu Phe Ala Ala Ala
225                 230                 235                 240

Ala Glu Val Gly Pro Ile Val Ala Lys Thr Asp Lys Ala Ser Arg Ser
                245                 250                 255

Ala Leu Lys Ser Tyr Gly Met Asn Leu Gly Leu Ala Phe Gln Leu Val
            260                 265                 270

Asp Asp Val Leu Asp Tyr Gly Gly Lys Ser Ala Asp Leu Gly Lys Asn
        275                 280                 285

Thr Gly Asp Asp Phe Arg Glu Gly Lys Ile Thr Leu Pro Val Ile Leu
    290                 295                 300

Ser Tyr Arg Arg Gly Thr Gln Asp Glu Arg Ala Phe Trp Arg Asn Ala
305                 310                 315                 320

Ile Glu Lys Gly Glu Ser Ser Asp Glu Asn Leu Glu Lys Ala Leu Gly
                325                 330                 335

Leu Ile Thr Lys Tyr Asn Gly Leu Gly Asp Thr Ile Gly Arg Ala Thr
            340                 345                 350

His Tyr Gly Thr Ile Ala Arg Asp Ala Leu Ala Pro Leu Pro Gln Ser
        355                 360                 365

Pro Trp Lys Asn Ala Leu Leu Glu Val Ile Asp Phe Cys Ile Glu Arg
    370                 375                 380

Leu Asn
385
```

<210> SEQ ID NO 37
<211> LENGTH: 8234
<212> TYPE: DNA
<213> ORGANISM: Artificial Sequence
<220> FEATURE:
<223> OTHER INFORMATION: Plasmid pDMW359-Rs_ddsA

<400> SEQUENCE: 37

```
catggtagcg ttgagactgg ctcgagtcgt gcgaccgaca ggagcctcga tccgtcactt     60

gacatggtcc caccctgctc gactctattc gtccgtcgac aaggtgaatc tgcccaaggc    120

tccctccaag gaggagctca agactatggg tctcgacgag attgccacca agcctcacga    180

gcagctcgct gcccatcttg ccaccaagat ggaggccgtg aacgttctca tccgagaacg    240

aatggcctcc cgacacgcac ctcgaatccc tcaggtgact gctcaccttg ttgaagctgg    300

tggaaagcga cttcgaccca tgctcgttct cgccaccgct gacctctgcg gatacgatgg    360

tcccttcgac gtgcatcttg ctgccaccgt ggagttcatc cacactgcca ccctcctgca    420

tgacgatgtc gttgacgagt ctgctcagag acgaggacga cccactgcta atctgctttg    480

ggacaacaag tcgtctgtcc ttgtcggtga ctacctgttt gcacgagcct tccagctcat    540

ggtggaacct ggctctcttc gagtcctcga catcctgtcg aacgcatctg ctaccatcgc    600

tgaaggagag gttctgcagc tctctgctgc acaggacctg gctaccacag aggacatcta    660

cctccaggtc gtgcgaggta agacagcagc tctcttctct gctgccaccg aagtcggtgg    720

agtcatcgca ggagctcctg aggaccacgt caaggctctc ttcgagtacg gtgacgctct    780
```

-continued

```
cggtatagcc ttccagatcg tcgatgacct gcttgactac cagggtgacg tgaagtctac    840
tggcaagaac gtcggagacg acttccgaga acgaaagctc actcttcctg tcatcaaggc    900
agtcgcagct gcctctgctg aggaacgagc cttctggaag cgaaccatcg agaagggtga    960
ccagcgagat ggtgatctcg agcacgcact gaccctcatg caggctcacg gtgcacttga   1020
gcagacccga gctgaggcac ttgattgggc tgcacgagct cgagctgcca ttgccgtcct   1080
tcccgaccac cctgtccagc gaatgcttga caacctggct ggatacgtcg ttgctcgaat   1140
ctcttaggcg gccgcaagtg tggatgggga agtgagtgcc cggttctgtg tgcacaattg   1200
gcaatccaag atggatggat tcaacacagg gatatagcga gctacgtggt ggtgcgagga   1260
tatagcaacg gatatttatg tttgacactt gagaatgtac gatacaagca ctgtccaagt   1320
acaatactaa acatactgta catactcata ctcgtacccg ggcaacggtt tcacttgagt   1380
gcagtggcta gtgctcttac tcgtacagtg tgcaatactg cgtatcatag tctttgatgt   1440
atatcgtatt cattcatgtt agttgcgtac gagccggaag cataaagtgt aaagcctggg   1500
gtgcctaatg agtgagctaa ctcacattaa ttgcgttgcg ctcactgccc gctttccagt   1560
cgggaaacct gtcgtgccag ctgcattaat gaatcggcca acgcgcgggg agaggcggtt   1620
tgcgtattgg gcgctcttcc gcttcctcgc tcactgactc gctgcgctcg gtcgttcggc   1680
tgcggcgagc ggtatcagct cactcaaagg cggtaatacg gttatccaca gaatcagggg   1740
ataacgcagg aaagaacatg tgagcaaaag gccagcaaaa ggccaggaac cgtaaaaagg   1800
ccgcgttgct ggcgtttttc cataggctcc gcccccctga cgagcatcac aaaaatcgac   1860
gctcaagtca gaggtggcga aacccgacag gactataaag ataccaggcg tttccccctg   1920
gaagctccct cgtgcgctct cctgttccga ccctgccgct taccggatac ctgtccgcct   1980
ttctcccttc gggaagcgtg gcgctttctc atagctcacg ctgtaggtat ctcagttcgg   2040
tgtaggtcgt tcgctccaag ctgggctgtg tgcacgaacc ccccgttcag cccgaccgct   2100
gcgccttatc cggtaactat cgtcttgagt ccaacccggt aagacacgac ttatcgccac   2160
tggcagcagc cactggtaac aggattagca gagcgaggta tgtaggcggt gctacagagt   2220
tcttgaagtg gtggcctaac tacggctaca ctagaaggac agtatttggt atctgcgctc   2280
tgctgaagcc agttaccttc ggaaaaagag ttggtagctc ttgatccggc aaacaaacca   2340
ccgctggtag cggtggtttt tttgtttgca agcagcagat tacgcgcaga aaaaaaggat   2400
ctcaagaaga tcctttgatc ttttctacgg ggtctgacgc tcagtggaac gaaaactcac   2460
gttaagggat tttggtcatg agattatcaa aaaggatctt cacctagatc cttttaaatt   2520
aaaaatgaag ttttaaatca atctaaagta tatatgagta aacttggtct gacagttacc   2580
aatgcttaat cagtgaggca cctatctcag cgatctgtct atttcgttca tccatagttg   2640
cctgactccc cgtcgtgtag ataactacga tacgggaggg cttaccatct ggccccagtg   2700
ctgcaatgat accgcgagac ccacgctcac cggctccaga tttatcagca ataaaccagc   2760
cagccggaag ggccgagcgc agaagtggtc ctgcaacttt atccgcctcc atccagtcta   2820
ttaattgttg ccgggaagct agagtaagta gttcgccagt taatagtttg cgcaacgttg   2880
ttgccattgc tacaggcatc gtggtgtcac gctcgtcgtt tggtatggct tcattcagct   2940
ccggttccca acgatcaagg cgagttacat gatcccccat gttgtgcaaa aaagcggtta   3000
gctccttcgg tcctccgatc gttgtcagaa gtaagttggc cgcagtgtta tcactcatgg   3060
ttatggcagc actgcataat tctcttactg tcatgccatc cgtaagatgc ttttctgtga   3120
```

-continued

```
ctggtgagta ctcaaccaag tcattctgag aatagtgtat gcggcgaccg agttgctctt   3180
gcccggcgtc aatacgggat aataccgcgc cacatagcag aactttaaaa gtgctcatca   3240
ttggaaaacg ttcttcgggg cgaaaactct caaggatctt accgctgttg agatccagtt   3300
cgatgtaacc cactcgtgca cccaactgat cttcagcatc ttttactttc accagcgttt   3360
ctgggtgagc aaaaacagga aggcaaaatg ccgcaaaaaa gggaataagg gcgacacgga   3420
aatgttgaat actcatactc ttcctttttc aatattattg aagcatttat cagggttatt   3480
gtctcatgag cggatacata tttgaatgta tttagaaaaa taaacaaata ggggttccgc   3540
gcacatttcc ccgaaaagtg ccacctgacg cgccctgtag cggcgcatta agcgcggcgg   3600
gtgtggtggt tacgcgcagc gtgaccgcta cacttgccag cgccctagcg cccgctcctt   3660
tcgctttctt cccttccttt ctcgccacgt tcgccggctt tccccgtcaa gctctaaatc   3720
gggggctccc tttagggttc cgatttagtg ctttacggca cctcgacccc aaaaaacttg   3780
attagggtga tggttcacgt agtgggccat cgccctgata gacggttttt cgccctttga   3840
cgttggagtc cacgttcttt aatagtggac tcttgttcca aactggaaca acactcaacc   3900
ctatctcggt ctattctttt gatttataag ggattttgcc gatttcggcc tattggttaa   3960
aaaatgagct gatttaacaa aaatttaacg cgaattttaa caaaatatta acgcttacaa   4020
tttccattcg ccattcaggc tgcgcaactg ttgggaaggg cgatcggtgc gggcctcttc   4080
gctattacgc cagctggcga aagggggatg tgctgcaagg cgattaagtt gggtaacgcc   4140
agggttttcc cagtcacgac gttgtaaaac gacggccagt gaattgtaat acgactcact   4200
atagggcgaa ttgggtaccg ggccccccct cgaggtcgat ggtgtcgata agcttgatat   4260
cgaattcatg tcacacaaac cgatcttcgc ctcaaggaaa cctaattcta catccgagag   4320
actgccgaga tccagtctac actgattaat tttcgggcca ataatttaaa aaaatcgtgt   4380
tatataatat tatatgtatt atatatatac atcatgatga tactgacagt catgtcccat   4440
tgctaaatag acagactcca tctgccgcct ccaactgatg ttctcaatat ttaaggggtc   4500
atctcgcatt gtttaataat aaacagactc catctaccgc ctccaaatga tgttctcaaa   4560
atatattgta tgaacttatt tttattactt agtattatta gacaacttac ttgctttatg   4620
aaaaacactt cctatttagg aaacaattta taatggcagt tcgttcattt aacaatttat   4680
gtagaataaa tgttataaat gcgtatggga aatcttaaat atggatagca taaatgatat   4740
ctgcattgcc taattcgaaa tcaacagcaa cgaaaaaaat cccttgtaca acataaatag   4800
tcatcgagaa atatcaacta tcaaagaaca gctattcaca cgttactatt gagattatta   4860
ttggacgaga atcacacact caactgtctt tctctcttct agaaatacag gtacaagtat   4920
gtactattct cattgttcat acttctagtc atttcatccc acatattcct tggatttctc   4980
tccaatgaat gacattctat cttgcaaatt caacaattat aataagatat accaaagtag   5040
cggtatagtg gcaatcaaaa agcttctctg gtgtgcttct cgtatttatt tttattctaa   5100
tgatccatta aaggtatata tttatttctt gttatataat ccttttgttt attacatggg   5160
ctggatacat aaaggtattt tgatttaatt ttttgcttaa attcaatccc ccctcgttca   5220
gtgtcaactg taatggtagg aaattaccat acttttgaag aagcaaaaaa aatgaaagaa   5280
aaaaaaaatc gtatttccag gttagacgtt ccgcagaatc tagaatgcgg tatgcggtac   5340
attgttcttc gaacgtaaaa gttgcgctcc ctgagatatt gtacattttt gcttttacaa   5400
gtacaagtac atcgtacaac tatgtactac tgttgatgca tccacaacag tttgttttgt   5460
tttttttgt ttttttttt tctaatgatt cattaccgct atgtatacct acttgtactt   5520
```

-continued

```
gtagtaagcc gggttattgg cgttcaatta atcatagact tatgaatctg cacggtgtgc   5580
gctgcgagtt acttttagct tatgcatgct acttgggtgt aatattggga tctgttcgga   5640
aatcaacgga tgctcaatcg atttcgacag taattaatta agtcatacac aagtcagctt   5700
tcttcgagcc tcatataagt ataagtagtt caacgtatta gcactgtacc cagcatctcc   5760
gtatcgagaa acacaacaac atgccccatt ggacagatca tgcggataca caggttgtgc   5820
agtatcatac atactcgatc agacaggtcg tctgaccatc atacaagctg aacaagcgct   5880
ccatacttgc acgctctcta tatacacagt taaattacat atccatagtc taacctctaa   5940
cagttaatct tctggtaagc ctcccagcca gccttctggt atcgcttggc ctcctcaata   6000
ggatctcggt tctggccgta cagacctcgg ccgacaatta tgatatccgt tccggtagac   6060
atgacatcct caacagttcg gtactgctgt ccgagagcgt ctcccttgtc gtcaagaccc   6120
accccggggg tcagaataag ccagtcctca gagtcgccct taggtcggtt ctgggcaatg   6180
aagccaacca caaactcggg gtcggatcgg gcaagctcaa tggtctgctt ggagtactcg   6240
ccagtggcca gagagccctt gcaagacagc tcggccagca tgagcagacc tctggccagc   6300
ttctcgttgg gagaggggac taggaactcc ttgtactggg agttctcgta gtcagagacg   6360
tcctccttct tctgttcaga gacagtttcc tcggcaccag ctcgcaggcc agcaatgatt   6420
ccggttccgg gtacaccgtg ggcgttggtg atatcggacc actcggcgat tcggtgacac   6480
cggtactggt gcttgacagt gttgccaata tctgcgaact ttctgtcctc gaacaggaag   6540
aaaccgtgct taagagcaag ttccttgagg gggagcacag tgccggcgta ggtgaagtcg   6600
tcaatgatgt cgatatgggt tttgatcatg cacacataag gtccgacctt atcggcaagc   6660
tcaatgagct ccttggtggt ggtaacatcc agagaagcac acaggttggt tttcttggct   6720
gccacgagct tgagcactcg agcggcaaag gcggacttgt ggacgttagc tcgagcttcg   6780
taggagggca ttttggtggt gaagaggaga ctgaaataaa tttagtctgc agaacttttt   6840
atcggaacct tatctggggc agtgaagtat atgttatggt aatagttacg agttagttga   6900
acttatagat agactggact atacggctat cggtccaaat tagaaagaac gtcaatggct   6960
ctctgggcgt cgcctttgcc gacaaaaatg tgatcatgat gaaagccagc aatgacgttg   7020
cagctgatat tgttgtcggc caaccgcgcc gaaaacgcag ctgtcagacc cacagcctcc   7080
aacgaagaat gtatcgtcaa agtgatccaa gcacactcat agttggagtc gtactccaaa   7140
ggcggcaatg acgagtcaga cagatactcg tcgactcagg cgacgacgga attcctgcag   7200
cccatctgca gaattcagga gagaccgggt tggcggcgta tttgtgtccc aaaaaacagc   7260
cccaattgcc ccggagaaga cggccaggcc gcctagatga caaattcaac aactcacagc   7320
tgactttctg ccattgccac taggggggggg cctttttata tggccaagcc aagctctcca   7380
cgtcggttgg gctgcaccca acaataaatg ggtagggttg caccaacaaa gggatgggat   7440
ggggggtaga agatacgagg ataacggggc tcaatggcac aaataagaac gaatactgcc   7500
attaagactc gtgatccagc gactgacacc attgcatcat ctaagggcct caaaactacc   7560
tcggaactgc tgcgctgatc tggacaccac agaggttccg agcactttag gttgcaccaa   7620
atgtcccacc aggtgcaggc agaaaacgct ggaacagcgt gtacagtttg tcttaacaaa   7680
aagtgagggc gctgaggtcg agcagggtgg tgtgacttgt tatagccttt agagctgcga   7740
aagcgcgtat ggatttggct catcaggcca gattgagggt ctgtggacac atgtcatgtt   7800
agtgtacttc aatcgccccc tggatatagc cccgacaata ggccgtggcc tcattttttt   7860
```

```
gccttccgca catttccatt gctcggtacc cacaccttgc ttctcctgca cttgccaacc   7920

ttaatactgg tttacattga ccaacatctt acaagcgggg ggcttgtcta gggtatatat   7980

aaacagtggc tctcccaatc ggttgccagt ctcttttttc ctttctttcc ccacagattc   8040

gaaatctaaa ctacacatca cacaatgcct gttactgacg tccttaagcg aaagtccggt   8100

gtcatcgtcg gcgacgatgt ccgagccgtg agtatccacg acaagatcag tgtcgagacg   8160

acgcgttttg tgtaatgaca caatccgaaa gtcgctagca acacacactc tctacacaaa   8220

ctaacccagc tctc                                                     8234
```

<210> SEQ ID NO 38
<211> LENGTH: 1156
<212> TYPE: DNA
<213> ORGANISM: Artificial Sequence
<220> FEATURE:
<223> OTHER INFORMATION: Fusion of GenBank Accession No. XP_505040 (N-terminus of Yarrowia lipolytica ppt1 gene encoding p-hydroxybenzoate:polyprenyl transferase) and GenBank Accession No. EAQ24568 (Roseovarius sp. 217 ddsA)

<400> SEQUENCE: 38

```
ccatggtagc gttgagactg gctcgagtcg tgcgaccgac aggagcctcg atccgtcact     60

tgacatggtc ccaccctgct cgactctatt cgtccgtcga caaggtgaat ctgcccaagg    120

ctccctccaa ggaggagctc aagactatgg gtctcgacga gattgccacc aagcctcacg    180

agcagctcgc tgcccatctt gccaccaaga tggaggccgt gaacgttctc atccgagaac    240

gaatggcctc ccgacacgca cctcgaatcc ctcaggtgac tgctcacctt gttgaagctg    300

gtggaaagcg acttcgaccc atgctcgttc tcgccaccgc tgacctctgc ggatacgatg    360

gtcccttcga cgtgcatctt gctgccaccg tggagttcat ccacactgcc accctcctgc    420

atgacgatgt cgttgacgag tctgctcaga gacgaggacg acccactgct aatctgcttt    480

gggacaacaa gtcgtctgtc cttgtcggtg actacctgtt tgcacgagcc ttccagctca    540

tggtggaacc tggctctctt cgagtcctcg acatcctgtc gaacgcatct gctaccatcg    600

ctgaaggaga ggttctgcag ctctctgctg cacaggacct ggctaccaca gaggacatct    660

acctccaggt cgtgcgaggt aagacagcag ctctcttctc tgctgccacc gaagtcggtg    720

gagtcatcgc aggagctcct gaggaccacg tcaaggctct cttcgagtac ggtgacgctc    780

tcggtatagc cttccagatc gtcgatgacc tgcttgacta ccagggtgac gtgaagtcta    840

ctggcaagaa cgtcggagac gacttccgag aacgaaagct cactcttcct gtcatcaagg    900

cagtcgcagc tgcctctgct gaggaacgag ccttctggaa gcgaaccatc gagaagggtg    960

accagcgaga tggtgatctc gagcacgcac tgaccctcat gcaggctcac ggtgcacttg   1020

agcagacccg agctgaggca cttgattggg ctgcacgagc tcgagctgcc attgccgtcc   1080

ttcccgacca ccctgtccag cgaatgcttg acaacctggc tggatacgtc gttgctcgaa   1140

tctcttaggc ggccgc                                                   1156
```

<210> SEQ ID NO 39
<211> LENGTH: 381
<212> TYPE: PRT
<213> ORGANISM: Artificial Sequence
<220> FEATURE:
<223> OTHER INFORMATION: Fusion of GenBank Accession No. XP_505040 (N-terminus of Yarrowia lipolytica ppt1 gene encoding p-hydroxybenzoate:polyprenyl transferase) and GenBank Accession No. EAQ24568 (Roseovarius sp. 217 ddsA)

<400> SEQUENCE: 39

-continued

```
Met Val Ala Leu Arg Leu Ala Arg Val Val Arg Pro Thr Gly Ala Ser
1               5                   10                  15

Ile Arg His Leu Thr Trp Ser His Pro Ala Arg Leu Tyr Ser Ser Val
            20                  25                  30

Asp Lys Val Asn Leu Pro Lys Ala Pro Ser Lys Glu Glu Leu Lys Thr
        35                  40                  45

Met Gly Leu Asp Glu Ile Ala Thr Lys Pro His Glu Gln Leu Ala Ala
    50                  55                  60

His Leu Ala Thr Lys Met Glu Ala Val Asn Val Leu Ile Arg Glu Arg
65                  70                  75                  80

Met Ala Ser Arg His Ala Pro Arg Ile Pro Gln Val Thr Ala His Leu
                85                  90                  95

Val Glu Ala Gly Gly Lys Arg Leu Arg Pro Met Leu Val Leu Ala Thr
            100                 105                 110

Ala Asp Leu Cys Gly Tyr Asp Gly Pro Phe Asp Val His Leu Ala Ala
        115                 120                 125

Thr Val Glu Phe Ile His Thr Ala Thr Leu Leu His Asp Asp Val Val
    130                 135                 140

Asp Glu Ser Ala Gln Arg Arg Gly Arg Pro Thr Ala Asn Leu Leu Trp
145                 150                 155                 160

Asp Asn Lys Ser Ser Val Leu Val Gly Asp Tyr Leu Phe Ala Arg Ala
                165                 170                 175

Phe Gln Leu Met Val Glu Pro Gly Ser Leu Arg Val Leu Asp Ile Leu
            180                 185                 190

Ser Asn Ala Ser Ala Thr Ile Ala Glu Gly Glu Val Leu Gln Leu Ser
        195                 200                 205

Ala Ala Gln Asp Leu Ala Thr Thr Glu Asp Ile Tyr Leu Gln Val Val
    210                 215                 220

Arg Gly Lys Thr Ala Ala Leu Phe Ser Ala Ala Thr Glu Val Gly Gly
225                 230                 235                 240

Val Ile Ala Gly Ala Pro Glu Asp His Val Lys Ala Leu Phe Glu Tyr
                245                 250                 255

Gly Asp Ala Leu Gly Ile Ala Phe Gln Ile Val Asp Asp Leu Leu Asp
            260                 265                 270

Tyr Gln Gly Asp Val Lys Ser Thr Gly Lys Asn Val Gly Asp Asp Phe
        275                 280                 285

Arg Glu Arg Lys Leu Thr Leu Pro Val Ile Lys Ala Val Ala Ala Ala
    290                 295                 300

Ser Ala Glu Glu Arg Ala Phe Trp Lys Arg Thr Ile Glu Lys Gly Asp
305                 310                 315                 320

Gln Arg Asp Gly Asp Leu Glu His Ala Leu Thr Leu Met Gln Ala His
                325                 330                 335

Gly Ala Leu Glu Gln Thr Arg Ala Glu Ala Leu Asp Trp Ala Ala Arg
            340                 345                 350

Ala Arg Ala Ala Ile Ala Val Leu Pro Asp His Pro Val Gln Arg Met
        355                 360                 365

Leu Asp Asn Leu Ala Gly Tyr Val Val Ala Arg Ile Ser
    370                 375                 380
```

<210> SEQ ID NO 40
<211> LENGTH: 8243
<212> TYPE: DNA
<213> ORGANISM: Artificial Sequence
<220> FEATURE:

-continued

<223> OTHER INFORMATION: Plasmid pDMW359-Rp_ddsA

<400> SEQUENCE: 40

```
catggtagcg ttgagactgg ctcgagtcgt gcgaccgaca ggagcctcga tccgtcactt     60
gacatggtcc caccctgctc gactctattc gtccgtcgac aaggtgaatc tgcccaaggc    120
tccctccaag gaggagctca agactatggc tgtcatcgtt cccttcgagg gacctcccac    180
tgcatctatc gaccagctgg tcgagcttgt cgctgctgac atggaacgag tcaatgcagt    240
tatcctgtcg cgaactggtt ccgaggtgac catgataccc gaggttgcta accacctgat    300
ctcctctgga ggcaagcgac ttcgacccaa cctgactctt gcaatggctc agctcactgg    360
ttactctgga gaaggtcata tcaagctggc tgcagccgtc gagttcatgc acaccgccac    420
cctgctccat gatgacgtgg ttgacgagtc tgagatgcga cgaggtaaga agtctgctcg    480
aatgctttgg ggtaacgagg cttcggtcct ggttggtgac ttcctccttg gacaggcctt    540
ccgaatgatg gtggaggtcg gttctcttcg agccctggat atactctcct ctgctgcagc    600
caccattgct gagggtgagg tcatgcagct cgctgcagcc aagaacacag ccaccactga    660
agacgagtac ctggcagtca tccgaggcaa gactgccgag ctgtttgctg cagcctgcga    720
agtcggacct gccattgcag gtcgacccaa ggctgaacag tctgcctgcc gatcctttgg    780
catgaacctt ggcatcgctt tccagctggt tgacgatgtc ctggactacg gaggtaaggc    840
tgccaagctt ggtaagaacg tcggtgacga tttccgagaa ggcaagatca ctcttcctgt    900
cgtgctcgcc ttccgacgag gcaacgatgc tgagcgagcc ttctggatca aggctcttga    960
gcgaggagag atcaccgaac ctgaccttga ccaggccatt ggactcatga ccaagcaccg   1020
agctctggag gacactatcc agcgagccca tcactacggt gcaatggctg ttgacgcact   1080
cgctctcttc cctacctctc ccatgaaggc agctctcgag caggtcgtcg ctttctgtct   1140
ggctcgatct cattaggcgg ccgcaagtgt ggatggggaa gtgagtgccc ggttctgtgt   1200
gcacaattgg caatccaaga tggatggatt caacacaggg atatagcgag ctacgtggtg   1260
gtgcgaggat atagcaacgg atatttatgt ttgacacttg agaatgtacg atacaagcac   1320
tgtccaagta caatactaaa catactgtac atactcatac tcgtacccgg gcaacggttt   1380
cacttgagtg cagtggctag tgctcttact cgtacagtgt gcaatactgc gtatcatagt   1440
ctttgatgta tatcgtattc attcatgtta gttgcgtacg agccggaagc ataaagtgta   1500
aagcctgggg tgcctaatga gtgagctaac tcacattaat tgcgttgcgc tcactgcccg   1560
ctttccagtc gggaaacctg tcgtgccagc tgcattaatg aatcggccaa cgcgcgggga   1620
gaggcggttt gcgtattggg cgctcttccg cttcctcgct cactgactcg ctgcgctcgg   1680
tcgttcggct gcggcgagcg gtatcagctc actcaaaggc ggtaatacgg ttatccacag   1740
aatcagggga taacgcagga aagaacatgt gagcaaaagg ccagcaaaag gccaggaacc   1800
gtaaaaaggc cgcgttgctg gcgtttttcc ataggctccg cccccctgac gagcatcaca   1860
aaaatcgacg ctcaagtcag aggtggcgaa acccgacagg actataaaga taccaggcgt   1920
ttccccctgg aagctccctc gtgcgctctc ctgttccgac cctgccgctt accggatacc   1980
tgtccgcctt tctcccttcg ggaagcgtgg cgctttctca tagctcacgc tgtaggtatc   2040
tcagttcggt gtaggtcgtt cgctccaagc tgggctgtgt gcacgaaccc cccgttcagc   2100
ccgaccgctg cgccttatcc ggtaactatc gtcttgagtc caacccggta agacacgact   2160
tatcgccact ggcagcagcc actggtaaca ggattagcag agcgaggtat gtaggcggtg   2220
ctacagagtt cttgaagtgg tggcctaact acggctacac tagaaggaca gtatttggta   2280
```

```
tctgcgctct gctgaagcca gttaccttcg gaaaaagagt tggtagctct tgatccggca   2340

aacaaaccac cgctggtagc ggtggttttt ttgtttgcaa gcagcagatt acgcgcagaa   2400

aaaaaggatc tcaagaagat cctttgatct tttctacggg gtctgacgct cagtggaacg   2460

aaaactcacg ttaagggatt ttggtcatga gattatcaaa aaggatcttc acctagatcc   2520

ttttaaatta aaaatgaagt tttaaatcaa tctaaagtat atatgagtaa acttggtctg   2580

acagttacca atgcttaatc agtgaggcac ctatctcagc gatctgtcta tttcgttcat   2640

ccatagttgc ctgactcccc gtcgtgtaga taactacgat acgggagggc ttaccatctg   2700

gccccagtgc tgcaatgata ccgcgagacc cacgctcacc ggctccagat ttatcagcaa   2760

taaaccagcc agccggaagg gccgagcgca gaagtggtcc tgcaacttta tccgcctcca   2820

tccagtctat taattgttgc cgggaagcta gagtaagtag ttcgccagtt aatagtttgc   2880

gcaacgttgt tgccattgct acaggcatcg tggtgtcacg ctcgtcgttt ggtatggctt   2940

cattcagctc cggttcccaa cgatcaaggc gagttacatg atcccccatg ttgtgcaaaa   3000

aagcggttag ctccttcggt cctccgatcg ttgtcagaag taagttggcc gcagtgttat   3060

cactcatggt tatggcagca ctgcataatt ctcttactgt catgccatcc gtaagatgct   3120

tttctgtgac tggtgagtac tcaaccaagt cattctgaga atagtgtatg cggcgaccga   3180

gttgctcttg cccggcgtca atacgggata ataccgcgcc acatagcaga actttaaaag   3240

tgctcatcat tggaaaacgt tcttcggggc gaaaactctc aaggatctta ccgctgttga   3300

gatccagttc gatgtaaccc actcgtgcac ccaactgatc ttcagcatct tttactttca   3360

ccagcgtttc tgggtgagca aaaacaggaa ggcaaaatgc cgcaaaaaag ggaataaggg   3420

cgacacggaa atgttgaata ctcatactct tcctttttca atattattga agcatttatc   3480

agggttattg tctcatgagc ggatacatat ttgaatgtat ttagaaaaat aaacaaatag   3540

gggttccgcg cacatttccc cgaaaagtgc cacctgacgc gccctgtagc ggcgcattaa   3600

gcgcggcggg tgtggtggtt acgcgcagcg tgaccgctac acttgccagc gccctagcgc   3660

ccgctccttt cgctttcttc ccttcctttc tcgccacgtt cgccggcttt ccccgtcaag   3720

ctctaaatcg ggggctccct ttagggttcc gatttagtgc tttacggcac ctcgacccca   3780

aaaaacttga ttagggtgat ggttcacgta gtgggccatc gccctgatag acggtttttc   3840

gccctttgac gttggagtcc acgttcttta atagtggact cttgttccaa actggaacaa   3900

cactcaaccc tatctcggtc tattcttttg atttataagg gattttgccg atttcggcct   3960

attggttaaa aaatgagctg atttaacaaa aatttaacgc gaattttaac aaaatattaa   4020

cgcttacaat ttccattcgc cattcaggct gcgcaactgt tgggaagggc gatcggtgcg   4080

ggcctcttcg ctattacgcc agctggcgaa agggggatgt gctgcaaggc gattaagttg   4140

ggtaacgcca gggttttccc agtcacgacg ttgtaaaacg acggccagtg aattgtaata   4200

cgactcacta tagggcgaat tgggtaccgg gccccccctc gaggtcgatg gtgtcgataa   4260

gcttgatatc gaattcatgt cacacaaacc gatcttcgcc tcaaggaaac ctaattctac   4320

atccgagaga ctgccgagat ccagtctaca ctgattaatt ttcgggccaa taatttaaaa   4380

aaatcgtgtt atataatatt atatgtatta tatatataca tcatgatgat actgacagtc   4440

atgtcccatt gctaaataga cagactccat ctgccgcctc caactgatgt tctcaatatt   4500

taaggggtca tctcgcattg tttaataata aacagactcc atctaccgcc tccaaatgat   4560

gttctcaaaa tatattgtat gaacttattt ttattactta gtattattag acaacttact   4620
```

-continued

```
tgctttatga aaaacacttc ctatttagga aacaatttat aatggcagtt cgttcattta   4680

acaatttatg tagaataaat gttataaatg cgtatgggaa atcttaaata tggatagcat   4740

aaatgatatc tgcattgcct aattcgaaat caacagcaac gaaaaaaatc ccttgtacaa   4800

cataaatagt catcgagaaa tatcaactat caaagaacag ctattcacac gttactattg   4860

agattattat tggacgagaa tcacacactc aactgtcttt ctctcttcta gaaatacagg   4920

tacaagtatg tactattctc attgttcata cttctagtca tttcatccca catattcctt   4980

ggatttctct ccaatgaatg acattctatc ttgcaaattc aacaattata ataagatata   5040

ccaaagtagc ggtatagtgg caatcaaaaa gcttctctgg tgtgcttctc gtatttattt   5100

ttattctaat gatccattaa aggtatatat ttatttcttg ttatataatc cttttgttta   5160

ttacatgggc tggatacata aaggtatttt gatttaattt tttgcttaaa ttcaatcccc   5220

cctcgttcag tgtcaactgt aatggtagga aattaccata cttttgaaga agcaaaaaaa   5280

atgaaagaaa aaaaaaatcg tatttccagg ttagacgttc cgcagaatct agaatgcggt   5340

atgcggtaca ttgttcttcg aacgtaaaag ttgcgctccc tgagatattg tacatttttg   5400

cttttacaag tacaagtaca tcgtacaact atgtactact gttgatgcat ccacaacagt   5460

ttgttttgtt ttttttgtt ttttttttt ctaatgattc attaccgcta tgtataccta   5520

cttgtacttg tagtaagccg ggttattggc gttcaattaa tcatagactt atgaatctgc   5580

acggtgtgcg ctgcgagtta cttttagctt atgcatgcta cttgggtgta atattgggat   5640

ctgttcggaa atcaacggat gctcaatcga tttcgacagt aattaattaa gtcatacaca   5700

agtcagcttt cttcgagcct catataagta taagtagttc aacgtattag cactgtaccc   5760

agcatctccg tatcgagaaa cacaacaaca tgccccattg gacagatcat gcggatacac   5820

aggttgtgca gtatcataca tactcgatca gacaggtcgt ctgaccatca tacaagctga   5880

acaagcgctc catacttgca cgctctctat atacacagtt aaattacata tccatagtct   5940

aacctctaac agttaatctt ctggtaagcc tcccagccag ccttctggta tcgcttggcc   6000

tcctcaatag gatctcggtt ctggccgtac agacctcggc cgacaattat gatatccgtt   6060

ccggtagaca tgacatcctc aacagttcgg tactgctgtc cgagagcgtc tcccttgtcg   6120

tcaagaccca ccccgggggt cagaataagc cagtcctcag agtcgccctt aggtcggttc   6180

tgggcaatga agccaaccac aaactcgggg tcggatcggg caagctcaat ggtctgcttg   6240

gagtactcgc cagtggccag agagcccttg caagacagct cggccagcat gagcagacct   6300

ctggccagct tctcgttggg agaggggact aggaactcct tgtactggga gttctcgtag   6360

tcagagacgt cctccttctt ctgttcagag acagtttcct cggcaccagc tcgcaggcca   6420

gcaatgattc cggttccggg tacaccgtgg gcgttggtga tatcggacca ctcggcgatt   6480

cggtgacacc ggtactggtg cttgacagtg ttgccaatat ctgcgaactt tctgtcctcg   6540

aacaggaaga aaccgtgctt aagagcaagt tccttgaggg ggagcacagt gccggcgtag   6600

gtgaagtcgt caatgatgtc gatatgggtt ttgatcatgc acacataagg tccgacctta   6660

tcggcaagct caatgagctc cttggtggtg gtaacatcca gagaagcaca caggttggtt   6720

ttcttggctg ccacgagctt gagcactcga gcggcaaagg cggacttgtg gacgttagct   6780

cgagcttcgt aggagggcat tttggtggtg aagaggagac tgaaataaat ttagtctgca   6840

gaacttttta tcggaacctt atctggggca gtgaagtata tgttatggta atagttacga   6900

gttagttgaa cttatagata gactggacta tacggctatc ggtccaaatt agaaagaacg   6960

tcaatggctc tctgggcgtc gcctttgccg acaaaaatgt gatcatgatg aaagccagca   7020
```

```
atgacgttgc agctgatatt gttgtcggcc aaccgcgccg aaaacgcagc tgtcagaccc   7080

acagcctcca acgaagaatg tatcgtcaaa gtgatccaag cacactcata gttggagtcg   7140

tactccaaag gcggcaatga cgagtcagac agatactcgt cgactcaggc gacgacggaa   7200

ttcctgcagc ccatctgcag aattcaggag agaccgggtt ggcggcgtat ttgtgtccca   7260

aaaaacagcc ccaattgccc cggagaagac ggccaggccg cctagatgac aaattcaaca   7320

actcacagct gactttctgc cattgccact aggggggggc ctttttatat ggccaagcca   7380

agctctccac gtcggttggg ctgcacccaa caataaatgg gtagggttgc accaacaaag   7440

ggatgggatg gggggtagaa gatacgagga taacggggct caatggcaca aataagaacg   7500

aatactgcca ttaagactcg tgatccagcg actgacacca ttgcatcatc taagggcctc   7560

aaaactacct cggaactgct gcgctgatct ggacaccaca gaggttccga gcactttagg   7620

ttgcaccaaa tgtcccacca ggtgcaggca gaaaacgctg gaacagcgtg tacagtttgt   7680

cttaacaaaa agtgagggcg ctgaggtcga gcagggtggt gtgacttgtt atagccttta   7740

gagctgcgaa agcgcgtatg gatttggctc atcaggccag attgagggtc tgtggacaca   7800

tgtcatgtta gtgtacttca atcgccccct ggatatagcc ccgacaatag gccgtggcct   7860

catttttttg ccttccgcac atttccattg ctcggtaccc acaccttgct tctcctgcac   7920

ttgccaacct taatactggt ttacattgac caacatctta caagcggggg gcttgtctag   7980

ggtatatata aacagtggct ctcccaatcg gttgccagtc tctttttcc tttctttccc   8040

cacagattcg aaatctaaac tacacatcac acaatgcctg ttactgacgt ccttaagcga   8100

aagtccggtg tcatcgtcgg cgacgatgtc cgagccgtga gtatccacga caagatcagt   8160

gtcgagacga cgcgttttgt gtaatgacac aatccgaaag tcgctagcaa cacacactct   8220

ctacacaaac taacccagct ctc                                           8243
```

```
<210> SEQ ID NO 41
<211> LENGTH: 1165
<212> TYPE: DNA
<213> ORGANISM: Artificial Sequence
<220> FEATURE:
<223> OTHER INFORMATION: Fusion of GenBank Accession No. XP_505040
      (N-terminus of Yarrowia lipolytica ppt1 gene encoding
      p-hydroxybenzoate:polyprenyl transferase) and GenBank Accession
      No. ABD89877 (Rhodopseudomonas palustris BisB18 ddsA)

<400> SEQUENCE: 41

ccatggtagc gttgagactg gctcgagtcg tgcgaccgac aggagcctcg atccgtcact     60

tgacatggtc ccaccctgct cgactctatt cgtccgtcga caaggtgaat ctgcccaagg    120

ctccctccaa ggaggagctc aagactatgg ctgtcatcgt tcccttcgag ggacctccca    180

ctgcatctat cgaccagctg gtcgagcttg tcgctgctga catggaacga gtcaatgcag    240

ttatcctgtc gcgaactggt tccgaggtga ccatgatacc cgaggttgct aaccacctga    300

tctcctctgg aggcaagcga cttcgaccca acctgactct tgcaatggct cagctcactg    360

gttactctgg agaaggtcat atcaagctgg ctgcagccgt cgagttcatg cacaccgcca    420

ccctgctcca tgatgacgtg gttgacgagt ctgagatgcg acgaggtaag aagtctgctc    480

gaatgctttg gggtaacgag gcttcggtcc tggttggtga cttcctcctt ggacaggcct    540

tccgaatgat ggtggaggtc ggttctcttc gagccctgga tatactctcc tctgctgcag    600

ccaccattgc tgagggtgag gtcatgcagc tcgctgcagc caagaacaca gccaccactg    660

aagacgagta cctggcagtc atccgaggca agactgccga gctgtttgct gcagcctgcg    720
```

```
aagtcggacc tgccattgca ggtcgaccca aggctgaaca gtctgcctgc cgatcctttg    780

gcatgaacct tggcatcgct ttccagctgg ttgacgatgt cctggactac ggaggtaagg    840

ctgccaagct tggtaagaac gtcggtgacg atttccgaga aggcaagatc actcttcctg    900

tcgtgctcgc cttccgacga ggcaacgatg ctgagcgagc cttctggatc aaggctcttg    960

agcgaggaga gatcaccgaa cctgaccttg accaggccat tggactcatg accaagcacc   1020

gagctctgga ggacactatc cagcgagccc atcactacgg tgcaatggct gttgacgcac   1080

tcgctctctt ccctacctct cccatgaagg cagctctcga gcaggtcgtc gctttctgtc   1140

tggctcgatc tcattaggcg gccgc                                         1165


<210> SEQ ID NO 42
<211> LENGTH: 384
<212> TYPE: PRT
<213> ORGANISM: Artificial Sequence
<220> FEATURE:
<223> OTHER INFORMATION: Fusion of GenBank Accession No. XP_505040
      (N-terminus of Yarrowia lipolytica ppt1 gene encoding
      p-hydroxybenzoate:polyprenyl transferase) and GenBank Accession
      No. ABD89877 (Rhodopseudomonas palustris BisB18 ddsA)

<400> SEQUENCE: 42

Met Val Ala Leu Arg Leu Ala Arg Val Val Arg Pro Thr Gly Ala Ser
1               5                   10                  15

Ile Arg His Leu Thr Trp Ser His Pro Ala Arg Leu Tyr Ser Ser Val
            20                  25                  30

Asp Lys Val Asn Leu Pro Lys Ala Pro Ser Lys Glu Glu Leu Lys Thr
        35                  40                  45

Met Ala Val Ile Val Pro Phe Glu Gly Pro Pro Thr Ala Ser Ile Asp
    50                  55                  60

Gln Leu Val Glu Leu Val Ala Ala Asp Met Glu Arg Val Asn Ala Val
65                  70                  75                  80

Ile Leu Ser Arg Thr Gly Ser Glu Val Thr Met Ile Pro Glu Val Ala
                85                  90                  95

Asn His Leu Ile Ser Ser Gly Gly Lys Arg Leu Arg Pro Asn Leu Thr
            100                 105                 110

Leu Ala Met Ala Gln Leu Thr Gly Tyr Ser Gly Glu Gly His Ile Lys
        115                 120                 125

Leu Ala Ala Ala Val Glu Phe Met His Thr Ala Thr Leu Leu His Asp
    130                 135                 140

Asp Val Val Asp Glu Ser Glu Met Arg Arg Gly Lys Lys Ser Ala Arg
145                 150                 155                 160

Met Leu Trp Gly Asn Glu Ala Ser Val Leu Val Gly Asp Phe Leu Leu
                165                 170                 175

Gly Gln Ala Phe Arg Met Met Val Glu Val Gly Ser Leu Arg Ala Leu
            180                 185                 190

Asp Ile Leu Ser Ser Ala Ala Ala Thr Ile Ala Glu Gly Glu Val Met
        195                 200                 205

Gln Leu Ala Ala Ala Lys Asn Thr Ala Thr Thr Glu Asp Glu Tyr Leu
    210                 215                 220

Ala Val Ile Arg Gly Lys Thr Ala Glu Leu Phe Ala Ala Ala Cys Glu
225                 230                 235                 240

Val Gly Pro Ala Ile Ala Gly Arg Pro Lys Ala Glu Gln Ser Ala Cys
                245                 250                 255

Arg Ser Phe Gly Met Asn Leu Gly Ile Ala Phe Gln Leu Val Asp Asp
```

```
            260                 265                 270

Val Leu Asp Tyr Gly Gly Lys Ala Ala Lys Leu Gly Lys Asn Val Gly
        275                 280                 285

Asp Asp Phe Arg Glu Gly Lys Ile Thr Leu Pro Val Val Leu Ala Phe
    290                 295                 300

Arg Arg Gly Asn Asp Ala Glu Arg Ala Phe Trp Ile Lys Ala Leu Glu
305                 310                 315                 320

Arg Gly Glu Ile Thr Glu Pro Asp Leu Asp Gln Ala Ile Gly Leu Met
                325                 330                 335

Thr Lys His Arg Ala Leu Glu Asp Thr Ile Gln Arg Ala His His Tyr
            340                 345                 350

Gly Ala Met Ala Val Asp Ala Leu Ala Leu Phe Pro Thr Ser Pro Met
        355                 360                 365

Lys Ala Ala Leu Glu Gln Val Val Ala Phe Cys Leu Ala Arg Ser His
    370                 375                 380


<210> SEQ ID NO 43
<211> LENGTH: 11
<212> TYPE: PRT
<213> ORGANISM: Artificial Sequence
<220> FEATURE:
<223> OTHER INFORMATION: Decaprenyl diphosphate synthase signature motif
<220> FEATURE:
<221> NAME/KEY: MISC_FEATURE
<222> LOCATION: (4)..(4)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is any amino acid

<400> SEQUENCE: 43

Gly Lys Arg Xaa Arg Pro Xaa Leu Xaa Leu Ala
1               5                   10


<210> SEQ ID NO 44
<211> LENGTH: 25
<212> TYPE: PRT
<213> ORGANISM: Artificial Sequence
<220> FEATURE:
<223> OTHER INFORMATION: Decaprenyl diphosphate synthase signature motif
<220> FEATURE:
<221> NAME/KEY: MISC_FEATURE
<222> LOCATION: (3)..(3)
<223> OTHER INFORMATION: Xaa is any amino acid
<220> FEATURE:
<221> NAME/KEY: MISC_FEATURE
<222> LOCATION: (18)..(19)
<223> OTHER INFORMATION: Xaa is any amino acid
<220> FEATURE:
<221> NAME/KEY: MISC_FEATURE
<222> LOCATION: (23)..(25)
<223> OTHER INFORMATION: Xaa is any amino acid

<400> SEQUENCE: 44

Glu Phe Xaa His Thr Ala Thr Leu Leu His Asp Asp Val Val Asp Glu
1               5                   10                  15

Ser Xaa Xaa Arg Arg Gly Xaa Xaa Xaa
            20                  25


<210> SEQ ID NO 45
<211> LENGTH: 5
```

<212> TYPE: PRT
<213> ORGANISM: Artificial Sequence
<220> FEATURE:
<223> OTHER INFORMATION: Decaprenyl diphosphate synthase signature motif
<220> FEATURE:
<221> NAME/KEY: MISC_FEATURE
<222> LOCATION: (4)..(4)
<223> OTHER INFORMATION: Xaa is any amino acid

<400> SEQUENCE: 45

Val Gly Asp Xaa Leu
1               5

<210> SEQ ID NO 46
<211> LENGTH: 7
<212> TYPE: PRT
<213> ORGANISM: Artificial Sequence
<220> FEATURE:
<223> OTHER INFORMATION: Decaprenyl diphosphate synthase signature motif
<220> FEATURE:
<221> NAME/KEY: MISC_FEATURE
<222> LOCATION: (5)..(5)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa is any amino acid

<400> SEQUENCE: 46

Glu Gly Glu Val Xaa Gln Xaa
1               5

<210> SEQ ID NO 47
<211> LENGTH: 37
<212> TYPE: PRT
<213> ORGANISM: Artificial Sequence
<220> FEATURE:
<223> OTHER INFORMATION: Decaprenyl diphosphate synthase signature motif
<220> FEATURE:
<221> NAME/KEY: MISC_FEATURE
<222> LOCATION: (3)..(4)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa is any amino acid
<220> FEATURE:
<221> NAME/KEY: MISC_FEATURE
<222> LOCATION: (10)..(17)
<223> OTHER INFORMATION: Xaa is any amino acid
<220> FEATURE:
<221> NAME/KEY: MISC_FEATURE
<222> LOCATION: (20)..(21)
<223> OTHER INFORMATION: Xaa is any amino acid
<220> FEATURE:
<221> NAME/KEY: MISC_FEATURE
<222> LOCATION: (25)..(25)
<223> OTHER INFORMATION: Xaa is any amino acid
<220> FEATURE:
<221> NAME/KEY: MISC_FEATURE
<222> LOCATION: (28)..(28)
<223> OTHER INFORMATION: Xaa is any amino acid
<220> FEATURE:
<221> NAME/KEY: MISC_FEATURE
<222> LOCATION: (30)..(30)
<223> OTHER INFORMATION: Xaa is any amino acid
<220> FEATURE:
<221> NAME/KEY: MISC_FEATURE
<222> LOCATION: (34)..(37)
<223> OTHER INFORMATION: Xaa is any amino acid

<400> SEQUENCE: 47

Phe Gln Xaa Xaa Asp Asp Xaa Leu Asp Xaa Xaa Xaa Xaa Xaa Xaa Xaa
1               5                   10                  15

```
Xaa Gly Lys Xaa Xaa Gly Asp Asp Xaa Arg Glu Xaa Lys Xaa Thr Leu
            20                  25                  30

Pro Xaa Xaa Xaa Xaa
        35


<210> SEQ ID NO 48
<211> LENGTH: 22
<212> TYPE: PRT
<213> ORGANISM: Artificial Sequence
<220> FEATURE:
<223> OTHER INFORMATION: Decaprenyl diphosphate synthase signature motif
<220> FEATURE:
<221> NAME/KEY: MISC_FEATURE
<222> LOCATION: (1)..(9)
<223> OTHER INFORMATION: Xaa is any amino acid
<220> FEATURE:
<221> NAME/KEY: MISC_FEATURE
<222> LOCATION: (11)..(19)
<223> OTHER INFORMATION: Xaa is any amino acid
<220> FEATURE:
<221> NAME/KEY: MISC_FEATURE
<222> LOCATION: (21)..(22)
<223> OTHER INFORMATION: Xaa is any amino acid

<400> SEQUENCE: 48

Xaa Xaa Xaa Xaa Xaa Xaa Xaa Xaa Xaa Leu Xaa Xaa Xaa Xaa Xaa Xaa
1               5                   10                  15

Xaa Xaa Xaa Arg Xaa Xaa
            20


<210> SEQ ID NO 49
<211> LENGTH: 11
<212> TYPE: PRT
<213> ORGANISM: Artificial Sequence
<220> FEATURE:
<223> OTHER INFORMATION: Decaprenyl diphosphate synthase signature motif
<220> FEATURE:
<221> NAME/KEY: MISC_FEATURE
<222> LOCATION: (4)..(4)
<223> OTHER INFORMATION: Xaa is Leu or Ile
<220> FEATURE:
<221> NAME/KEY: MISC_FEATURE
<222> LOCATION: (7)..(7)
<223> OTHER INFORMATION: Xaa is Leu, Asn, or Met
<220> FEATURE:
<221> NAME/KEY: MISC_FEATURE
<222> LOCATION: (9)..(9)
<223> OTHER INFORMATION: Xaa is Thr or Val

<400> SEQUENCE: 49

Gly Lys Arg Xaa Arg Pro Xaa Leu Xaa Leu Ala
1               5                   10


<210> SEQ ID NO 50
<211> LENGTH: 25
<212> TYPE: PRT
<213> ORGANISM: Artificial Sequence
<220> FEATURE:
<223> OTHER INFORMATION: Decaprenyl diphosphate synthase signature motif
<220> FEATURE:
<221> NAME/KEY: MISC_FEATURE
<222> LOCATION: (3)..(3)
<223> OTHER INFORMATION: Xaa is Ile or Met
<220> FEATURE:
<221> NAME/KEY: MISC_FEATURE
<222> LOCATION: (18)..(18)
<223> OTHER INFORMATION: Xaa is Thr, Glu, Asp, Gly, or Ala
<220> FEATURE:
<221> NAME/KEY: MISC_FEATURE
<222> LOCATION: (19)..(19)
<223> OTHER INFORMATION: Xaa is Leu, Met, or Gln
```

<220> FEATURE:
<221> NAME/KEY: MISC_FEATURE
<222> LOCATION: (23)..(23)
<223> OTHER INFORMATION: Xaa is Leu, Lys, or Arg
<220> FEATURE:
<221> NAME/KEY: MISC_FEATURE
<222> LOCATION: (24)..(24)
<223> OTHER INFORMATION: Xaa is Ala, Lys, Ser, or Pro
<220> FEATURE:
<221> NAME/KEY: MISC_FEATURE
<222> LOCATION: (25)..(25)
<223> OTHER INFORMATION: Xaa is Ser or Thr

<400> SEQUENCE: 50

```
Glu Phe Xaa His Thr Ala Thr Leu Leu His Asp Asp Val Val Asp Glu
1               5                   10                  15

Ser Xaa Xaa Arg Arg Gly Xaa Xaa Xaa
            20                  25
```

<210> SEQ ID NO 51
<211> LENGTH: 5
<212> TYPE: PRT
<213> ORGANISM: Artificial Sequence
<220> FEATURE:
<223> OTHER INFORMATION: Decaprenyl diphosphate synthase signature motif
<220> FEATURE:
<221> NAME/KEY: MISC_FEATURE
<222> LOCATION: (4)..(4)
<223> OTHER INFORMATION: Xaa is Phe or Tyr

<400> SEQUENCE: 51

```
Val Gly Asp Xaa Leu
1               5
```

<210> SEQ ID NO 52
<211> LENGTH: 7
<212> TYPE: PRT
<213> ORGANISM: Artificial Sequence
<220> FEATURE:
<223> OTHER INFORMATION: Decaprenyl diphosphate synthase signature motif
<220> FEATURE:
<221> NAME/KEY: MISC_FEATURE
<222> LOCATION: (5)..(5)
<223> OTHER INFORMATION: Xaa is Leu or Met
<220> FEATURE:
<221> NAME/KEY: MISC_FEATURE
<222> LOCATION: (7)..(7)
<223> OTHER INFORMATION: Xaa is Met or Leu

<400> SEQUENCE: 52

```
Glu Gly Glu Val Xaa Gln Xaa
1               5
```

<210> SEQ ID NO 53
<211> LENGTH: 37
<212> TYPE: PRT
<213> ORGANISM: Artificial Sequence
<220> FEATURE:
<223> OTHER INFORMATION: Decaprenyl diphosphate synthase signature motif
<220> FEATURE:
<221> NAME/KEY: MISC_FEATURE
<222> LOCATION: (3)..(3)
<223> OTHER INFORMATION: Xaa is Leu, Ile, or Met
<220> FEATURE:
<221> NAME/KEY: MISC_FEATURE
<222> LOCATION: (4)..(4)
<223> OTHER INFORMATION: Xaa is Val, Ile, or Ala
<220> FEATURE:
<221> NAME/KEY: MISC_FEATURE
<222> LOCATION: (7)..(7)
<223> OTHER INFORMATION: Xaa is Ala, Val, or Leu
<220> FEATURE:

<221> NAME/KEY: MISC_FEATURE
<222> LOCATION: (10)..(10)
<223> OTHER INFORMATION: Xaa is Tyr or Trp
<220> FEATURE:
<221> NAME/KEY: MISC_FEATURE
<222> LOCATION: (11)..(11)
<223> OTHER INFORMATION: Xaa is Ala, Gly, Gln, or Thr
<220> FEATURE:
<221> NAME/KEY: MISC_FEATURE
<222> LOCATION: (12)..(12)
<223> OTHER INFORMATION: Xaa is Ala or Gly
<220> FEATURE:
<221> NAME/KEY: MISC_FEATURE
<222> LOCATION: (13)..(13)
<223> OTHER INFORMATION: Xaa is Asp, Lys, or Thr
<220> FEATURE:
<221> NAME/KEY: MISC_FEATURE
<222> LOCATION: (14)..(14)
<223> OTHER INFORMATION: Xaa is Gln, Ala, Ser, Pro, Thr, or Val
<220> FEATURE:
<221> NAME/KEY: MISC_FEATURE
<222> LOCATION: (15)..(15)
<223> OTHER INFORMATION: Xaa is Gln, Ala, Lys, Asn, or Asp
<220> FEATURE:
<221> NAME/KEY: MISC_FEATURE
<222> LOCATION: (16)..(16)
<223> OTHER INFORMATION: Xaa is Val, Lys, Asp, Ala, or Ser
<220> FEATURE:
<221> NAME/KEY: MISC_FEATURE
<222> LOCATION: (17)..(17)
<223> OTHER INFORMATION: Xaa is Leu or Thr
<220> FEATURE:
<221> NAME/KEY: MISC_FEATURE
<222> LOCATION: (20)..(20)
<223> OTHER INFORMATION: Xaa is Thr or Asn
<220> FEATURE:
<221> NAME/KEY: MISC_FEATURE
<222> LOCATION: (21)..(21)
<223> OTHER INFORMATION: Xaa is Val, Thr, or Ile
<220> FEATURE:
<221> NAME/KEY: MISC_FEATURE
<222> LOCATION: (25)..(25)
<223> OTHER INFORMATION: Xaa is Met or Phe
<220> FEATURE:
<221> NAME/KEY: MISC_FEATURE
<222> LOCATION: (28)..(28)
<223> OTHER INFORMATION: Xaa is Gly or Arg
<220> FEATURE:
<221> NAME/KEY: MISC_FEATURE
<222> LOCATION: (30)..(30)
<223> OTHER INFORMATION: Xaa is Ile, Val, or Leu
<220> FEATURE:
<221> NAME/KEY: MISC_FEATURE
<222> LOCATION: (34)..(34)
<223> OTHER INFORMATION: Xaa is Val or Leu
<220> FEATURE:
<221> NAME/KEY: MISC_FEATURE
<222> LOCATION: (35)..(35)
<223> OTHER INFORMATION: Xaa is Leu, Val, or Ile
<220> FEATURE:
<221> NAME/KEY: MISC_FEATURE
<222> LOCATION: (36)..(36)
<223> OTHER INFORMATION: Xaa is Ala, Leu, Lys, or Arg
<220> FEATURE:
<221> NAME/KEY: MISC_FEATURE
<222> LOCATION: (37)..(37)
<223> OTHER INFORMATION: Xaa is Ala or Ser

<400> SEQUENCE: 53

```
Phe Gln Xaa Xaa Asp Asp Xaa Leu Asp Xaa Xaa Xaa Xaa Xaa Xaa Xaa
1               5                   10                  15

Xaa Gly Lys Xaa Xaa Gly Asp Asp Xaa Arg Glu Xaa Lys Xaa Thr Leu
            20                  25                  30

Pro Xaa Xaa Xaa Xaa
        35
```

<210> SEQ ID NO 54
<211> LENGTH: 22
<212> TYPE: PRT
<213> ORGANISM: Artificial Sequence
<220> FEATURE:
<223> OTHER INFORMATION: Decaprenyl diphosphate synthase signature motif
<220> FEATURE:
<221> NAME/KEY: MISC_FEATURE
<222> LOCATION: (1)..(1)
<223> OTHER INFORMATION: Xaa is Phe or Leu
<220> FEATURE:
<221> NAME/KEY: MISC_FEATURE
<222> LOCATION: (2)..(2)
<223> OTHER INFORMATION: Xaa is Pro or Glu
<220> FEATURE:
<221> NAME/KEY: MISC_FEATURE
<222> LOCATION: (3)..(3)
<223> OTHER INFORMATION: Xaa is Asp, Thr, Gln, Glu, or Asn
<220> FEATURE:
<221> NAME/KEY: MISC_FEATURE
<222> LOCATION: (4)..(4)
<223> OTHER INFORMATION: Xaa is Ser, Thr, or His
<220> FEATURE:
<221> NAME/KEY: MISC_FEATURE
<222> LOCATION: (5)..(5)
<223> OTHER INFORMATION: Xaa is Glu, Pro, Val, Arg, or Asp
<220> FEATURE:
<221> NAME/KEY: MISC_FEATURE
<222> LOCATION: (6)..(6)
<223> OTHER INFORMATION: Xaa is Leu, Met, Trp, Gln, Ile, or Val
<220> FEATURE:
<221> NAME/KEY: MISC_FEATURE
<222> LOCATION: (7)..(7)
<223> OTHER INFORMATION: Xaa is Arg, Lys, Thr, or Gln
<220> FEATURE:
<221> NAME/KEY: MISC_FEATURE
<222> LOCATION: (8)..(8)
<223> OTHER INFORMATION: Xaa is Arg, Ala, Asn, Ser, Thr, or Gln
<220> FEATURE:
<221> NAME/KEY: MISC_FEATURE
<222> LOCATION: (9)..(9)
<223> OTHER INFORMATION: Xaa is Leu, Ala, Met, or His
<220> FEATURE:
<221> NAME/KEY: MISC_FEATURE
<222> LOCATION: (11)..(11)
<223> OTHER INFORMATION: Xaa is Ile, Glu, Leu, Met, Ser, Arg, or Asp
<220> FEATURE:
<221> NAME/KEY: MISC_FEATURE
<222> LOCATION: (12)..(12)
<223> OTHER INFORMATION: Xaa is Glu, Gln, Asp, or Asn
<220> FEATURE:
<221> NAME/KEY: MISC_FEATURE
<222> LOCATION: (13)..(13)
<223> OTHER INFORMATION: Xaa is Thr, Val, or Leu
<220> FEATURE:
<221> NAME/KEY: MISC_FEATURE
<222> LOCATION: (14)..(14)
<223> OTHER INFORMATION: Xaa is Val, Ile, or Ala
<220> FEATURE:
<221> NAME/KEY: MISC_FEATURE
<222> LOCATION: (15)..(15)
<223> OTHER INFORMATION: Xaa is Gln, Ala, Asp, or Gly
<220> FEATURE:
<221> NAME/KEY: MISC_FEATURE
<222> LOCATION: (16)..(16)
<223> OTHER INFORMATION: Xaa is Phe or Tyr
<220> FEATURE:
<221> NAME/KEY: MISC_FEATURE
<222> LOCATION: (17)..(17)
<223> OTHER INFORMATION: Xaa is Thr, Cys, or Val
<220> FEATURE:
<221> NAME/KEY: MISC_FEATURE
<222> LOCATION: (18)..(18)
<223> OTHER INFORMATION: Xaa is Val, Leu, or Ile
<220> FEATURE:
<221> NAME/KEY: MISC_FEATURE
<222> LOCATION: (19)..(19)
<223> OTHER INFORMATION: Xaa is Asn, Ala, Glu, or Ser -continued

```
<220> FEATURE:
<221> NAME/KEY: MISC_FEATURE
<222> LOCATION: (21)..(21)
<223> OTHER INFORMATION: Xaa is Ala, Ser, Leu, Val, or Ile
<220> FEATURE:
<221> NAME/KEY: MISC_FEATURE
<222> LOCATION: (22)..(22)
<223> OTHER INFORMATION: Xaa is Arg, His, Asn, or Ser

<400> SEQUENCE: 54

Xaa Xaa Xaa Xaa Xaa Xaa Xaa Xaa Xaa Leu Xaa Xaa Xaa Xaa Xaa Xaa
1               5                   10                  15

Xaa Xaa Xaa Arg Xaa Xaa
            20
```

COENZYME $Q_{10}$ PRODUCTION IN A RECOMBINANT OLEAGINOUS YEAST

This application claims the benefit of U.S. Provisional Pat. App. No. 60/991,266, filed Nov. 30, 2007 and hereby incorporated herein by reference in its entirety.

FIELD OF THE INVENTION

This invention is in the field of biotechnology. More specifically, this invention pertains to a process of producing the antioxidant coenzyme $Q_{10}$ and at least one ω-3/ω-6 polyunsaturated fatty acids in oleaginous yeast, yeast biomass produced by the process, and oils obtained from the yeast biomass.

BACKGROUND OF THE INVENTION

Antioxidants can be described as compounds (e.g., enzymes, organic molecules) that slow the rate of oxidation reactions or that can counteract the damaging effects of oxygen. Although the term technically applies to molecules reacting with oxygen, it is often applied to molecules that protect from any free radical (i.e., a molecule with an unpaired electron, such as hydroxyl radicals, lipid oxyl or peroxyl radicals, singlet oxygen, and peroxinitrite formed from nitrogen oxide). Free radicals are natural by-products of cellular processes in an organism or are created by exposure to environmental factors. Within cellular organisms, free radicals can cause cellular and tissue damage, which can ultimately lead to disease. Antioxidants neutralize free radicals by donating one of their own electrons to the free radical, since the radicalized antioxidant molecule is more stable as a free-radical than the original free-radical.

A variety of nutrients or dietary components have antioxidant properties and thus can function to decrease the tissue content of reactive oxygen. Common antioxidants include vitamins C and E, β-carotene, proanthocyanidin, the minerals selenium and zinc, and coenzyme Q. Coenzyme Q, also known as ubiquinone and referred to herein as "CoQ", refers to a series of related 2-3-dimethoxy-5-methyl-benzoquinones with a polyisoprenoid side chain in the 6-position that are widely distributed in animals, plants and microorganisms.

In structure, the CoQ group closely resembles the members of the vitamin K group and the tocopherylquinones (derived from tocopherols, e.g., vitamin E) in that they all possess: 1) a quinonoid ring derived from tyrosine or phenylalanine that functions as an electron-carrier; and, 2) a long hydrocarbon tail comprised of 5-carbon isoprene units. The quinones of the CoQ series, that is $Q_6$, $Q_7$, $Q_8$, $Q_9$ and $Q_{10}$, found in various biological species differ only slightly in chemical structure based on the length of the hydrocarbon tail, which ranges from 30 to 50 carbon atoms (corresponding to 6, 7, 8, 9 or 10 isoprenoid units in the side chain) and which facilitates CoQ's localization in mitochondrial or cytoplasmic membranes. Differences in properties are due to the differences in length of the side chain.

The antioxidant properties of $CoQ_{10}$ are directly related to the coenzyme's bioenergetic functions. Specifically, $CoQ_{10}$ is involved in the terminal electron transport system by transporting electrons from organic substrates to oxygen in the respiratory chain of mitochondria, which is essential in the production of biochemical energy (e.g., ATP) in all cells of aerobic organisms. As an energy carrier, $CoQ_{10}$ is continually going through an oxidation-reduction cycle. Specifically, $CoQ_{10}$ is reduced to a free radical semiquinone by the uptake of a single electron; reduction of this enzyme-bound intermediate by a second electron yields ubiquinol. As ubiquinol, the molecule holds electrons loosely and can easily donate one or two electrons to neutralize free radicals, which can be created in part by the energy-generating process.

The antioxidant properties of $CoQ_{10}$ are significant. In addition to quenching free radicals that threaten cellular components, such as nucleic acids and proteins in the mitochondria, ubiquinol also inhibits lipid peroxidation (i.e., degradation of lipids) in biological membranes and in low-density lipoprotein ["LDL"]. Furthermore, functionality of $CoQ_{10}$ may be enhanced in the presence of carotenoid compounds (see Int'l. App. Pub. No. WO 2005/097091 A1).

Based on the physiological role that $CoQ_{10}$ plays within living organisms, the coenzyme has become widely used as a nutritional supplement and as a pharmacological active agent. It has wide use and acceptance in the treatment of: mitochondrial disorders, cardiovascular disease processes, atherosclerosis, slow muscle degeneration (dystrophy or atrophy), neurodegenerative diseases (e.g., Parkinson's disease, Huntington's disease, Alzheimer's, amyotrophic lateral sclerosis ["ALS"]), periodontal disease, diabetes and $CoQ_{10}$ deficiency. $CoQ_{10}$ is also believed to strengthen the immune system, act as an anticancer agent and help counteract the aging processes.

$CoQ_{10}$ is currently available via chemical synthesis, semi-chemical synthesis and microbial conversion (Choi, Jin-Ho et al., *Appl. Microbiol. Biotechnol.,* 68:9-15 (2005)). In the biotechnological arena, several strains of *Agrobacterium tumefaciens, A. radiobacter, Rhodobacter sphaeroides* and *Paracoccus denitrificans* have been identified that produce $CoQ_{10}$ in significant quantities (Yoshida et al., *J. Gen. Appl. Microbiol.,* 44:19-26 (1998)), and marine bacteria of the genus *Erythrobacter, Sphingomonas, Exiguobacterium, Lutibacterium* and *Bacillus* have also been found to naturally produce $CoQ_{10}$ (Int'l. App. Pub. No. WO 2008023264). Genetic engineering of microbes, such as *Escherichia coli, Rhodobacter sphaeroides*, and plants such as brown rice for $CoQ_{10}$ biosynthesis has also been demonstrated with the expression of heterologous genes encoding decaprenyl diphosphate synthase (e.g., Zahiri et al., *Metabol. Engineering,* 8:406-416 (2006); JP 10057072; JP 2005211020; JP 2006 204215; Int'l. App. Pub. No. WO 00/047746; Int'l. App. Pub. No. WO 02/026933; U.S. Pat. No. 6,461,842; U.S. Pat. App. Pub. No. 2006/010519; Int'l. App. Pub. No. WO 07/120423). An oleaginous microbial host cell having the ability to co-produce $CoQ_{10}$ and at least 25% of its dry cell weight ["DCW"] as oil, wherein the $CoQ_{10}$ can advantageously help protect against autoxidation of the oil is expected to be advantageous. Both $CoQ_{10}$ and oil can be extracted with hexane or other solvents, thus reducing production cost. The offering of a final product containing both ingredients, that is, a stabilized microbial oil, may command a higher premium or competitive advantage.

An oleaginous microbial host cell that can co-produce $CoQ_{10}$ and polyunsaturated fatty acids ["PUFAs"] has not been reported. This deficiency exists despite previous descriptions of the utility of co-administration of $CoQ_{10}$ with PUFAs (see e.g., U.S. Pat. App. Pub. No. 2002/0198177 A1) and despite previous recognition that identification of such a microbe would be advantageous (e.g., see screening studies of various Thraustochytrids (marine fungoid protists) by Ocean Nutrition Canada, Ltd., as described in Burja et al., *Appl. Microbiol. Biotechnol.,* 72:1161-1169 (2006) and Armenta et al., *J. Agric, Food Chem.,* 54:9752-9758 (2006)). A means to recombinantly produce both $CoQ_{10}$ and PUFAs in a single microbial host cell would create a single product comprising both ingredients. This is particularly attractive when the recombinant cell biomass is used directly in the formulation, such as an animal feed.

Additionally, there are no reports of a microbial host cell that can co-produce $CoQ_{10}$, PUFAs and carotenoids, wherein said host cell comprises at least 25% of its DCW as oil, although it is recognized that the functionality of $CoQ_{10}$ may be enhanced in the presence of carotenoid compounds (see Int'l. App. Pub. No. WO 2005/097091 A1).

Carotenoids are themselves generally classified as antioxidants and may help to protect one another from oxidation during production and/or storage. As such, some carotenoids may alternatively be viewed as natural antioxidants in certain product applications where the carotenoid is not used as a pigment; for example, use of lycopene as an antioxidant in food products and/or animal feeds.

Many commercial products are formulated to contain a mixture of natural antioxidants, such as $CoQ_{10}$, and fats/lipids and/or pigments. For example, animal feeds, dietary supplements, and personal care products are formulated to contain antioxidants, PUFAs and carotenoids. Typically, for example, a commercial product formulator will obtain these compounds from a variety of sources and formulate them into a final product that contains an effective amount of each ingredient. The composition, purity and source of each ingredient may vary, resulting in a final product formulation that may require significant monitoring and/or processing to obtain the desired product specifications.

Engineering an oleaginous microorganism to simultaneously produce both $CoQ_{10}$ and at least one ω-3/ω-6 PUFA (and optionally at least one $C_{40}$ carotenoid) would create a higher value product or reduce production costs. Since carotenoids and PUFAs may undergo oxidation during storage, materials comprising these compounds are typically supplemented with one or more antioxidants. However, many of the synthetic antioxidants currently used in the market are undesirable due to their cost and/or possible safety concerns. If a microbial host produces both carotenoids and PUFAs in conjunction with a reduced form of $CoQ_{10}$, the $CoQ_{10}$ may aid in protecting compositions comprising carotenoids, PUFAs, and mixtures thereof from oxidation.

The problem to be solved therefore, is to provide a recombinant oleaginous yeast capable of producing the antioxidant $CoQ_{10}$ in combination with at least one ω-3/ω-6 PUFA (and optionally at least one $C_{40}$ carotenoid).

SUMMARY OF THE INVENTION

The stated problem has been solved by providing a recombinant oleaginous yeast capable of producing the antioxidant, coenzyme $Q_{10}$, and polyunsaturated fatty acids.

Provided herein are methods of co-producing coenzyme $Q_{10}$ with polyunsaturated fatty acids (and optionally, $C_{40}$ carotenoids) from the same oleaginous yeast.

The importance of PUFAs is well understood. For example, certain PUFAs are important biological components of healthy cells and are recognized as: "essential" fatty acids that cannot be synthesized de novo in mammals and instead must be obtained either in the diet or derived by further desaturation and elongation of linoleic acid (LA; 18:2 ω-6) or α-linolenic acid (ALA; 18:3 ω-3); constituents of plasma membranes of cells, where they may be found in such forms as phospholipids or triacylglycerols; necessary for proper development (particularly in the developing infant brain) and for tissue formation and repair; and, precursors to several biologically active eicosanoids of importance in mammals (e.g., prostacyclins, eicosanoids, leukotrienes, prostaglandins). Additionally, a high intake of long-chain ω-3 PUFAs has cardiovascular protective effects (Dyerberg, J. et al., *Amer. J. Clin. Nutr.,* 28:958-966 (1975); Dyerberg, J. et al., *Lancet,* 2(8081):117-119 (1978); Shimokawa, H., *World Rev. Nutr. Diet,* 88:100-108 (2001); von Schacky, C. and Dyerberg, J., *World Rev. Nutr. Diet,* 88:90-99 (2001)). Numerous other studies document wide-ranging health benefits conferred by administration of ω-3/ω-6 PUFAs against a variety of symptoms and diseases, such as asthma, psoriasis, eczema, diabetes, cancer.

Carotenoids are required elements of aquaculture. Salmon and shrimp aquaculture are particularly useful applications for this invention as carotenoid pigmentation is critically important for the value of these organisms (F. Shahidi, J. A. Brown, Carotenoid pigments in seafood and aquaculture: Critical reviews in food *Science* 38(1):1-67 (1998)). Additionally, carotenoids have utility as intermediates in the synthesis of steroids, flavors and fragrances and compounds with potential electro-optic applications.

Accordingly provided herein is a method for the production of $CoQ_{10}$ in a recombinant oleaginous yeast, comprising:

a) providing an oleaginous yeast, the oleaginous yeast
   1.) producing a quinone of the coenzyme Q series selected from the group consisting of: $CoQ_6$, $CoQ_7$, $CoQ_8$ and $CoQ_9$,
   2.) comprising genetic constructs encoding a functional ω-3/ω-6 polyunsaturated fatty acid biosynthetic pathway whereby the transformed yeast cells produce at least one polyunsaturated fatty acid; and,
   3.) optionally comprising genetic constructs encoding a functional carotenoid biosynthetic pathway whereby the transformed yeast cells produce at least one carotenoid;
b) transforming the oleaginous yeast host cell with at least one copy of a genetic construct encoding decaprenyl diphosphate synthase; and,
c) culturing the transformed yeast cells of step (b) under suitable conditions, whereby the decaprenyl diphosphate synthase is expressed and whereby $CoQ_{10}$ is produced.

Also described herein is an oil comprising coenzyme $Q_{10}$ and at least one compound selected from the group consisting of: a ω-6 PUFA and a ω-3 PUFA.

A recombinant oleaginous yeast is provided comprising at least one copy of a genetic construct encoding decaprenyl diphosphate synthase.

Described herein is also a food or feed product comprising an effective amount of a microbial oil comprising coenzyme $Q_{10}$ and PUFAs (and optionally $C_{40}$ carotenoids).

BIOLOGICAL DEPOSITS

The following biological materials were made under the terms of the Budapest Treaty on the International Recognition of the Deposit of Microorganisms for the Purposes of Patent Procedure:

| Biological Material | Accession Number | Date of Deposit |
|---|---|---|
| *Yarrowia lipolytica* Y2047 | ATCC PTA-7186 | Oct. 26, 2005 |
| *Yarrowia lipolytica* Y2201 | ATCC PTA-7185 | Oct. 26, 2005 |
| *Yarrowia lipolytica* Y2096 | ATCC PTA-7184 | Oct. 26, 2005 |
| *Yarrowia lipolytica* Y3000 | ATCC PTA-7187 | Oct. 26, 2005 |
| *Yarrowia lipolytica* Y4128 | ATCC PTA-8614 | Aug. 23, 2007 |
| *Yarrowia lipolytica* Y4127 | ATCC PTA-8802 | Nov. 29, 2007 |

As used herein, "ATCC" refers to the American Type Culture Collection International Depository Authority located at ATCC, 10801 University Blvd., Manassas, Va. 20110-2209, U.S.A. The listed deposit will be maintained in the indicated international depository for at least 30 years and will be made available to the public upon the grant of a patent disclosing it. The availability of a deposit does not constitute a license to practice the subject invention in derogation of patent rights granted by government action.

BRIEF DESCRIPTION OF THE FIGURES AND SEQUENCE DESCRIPTIONS

FIG. 4 provides plasmid maps for the following: (A) pZUF17; and, (B) pDMW359.

Figure 5:
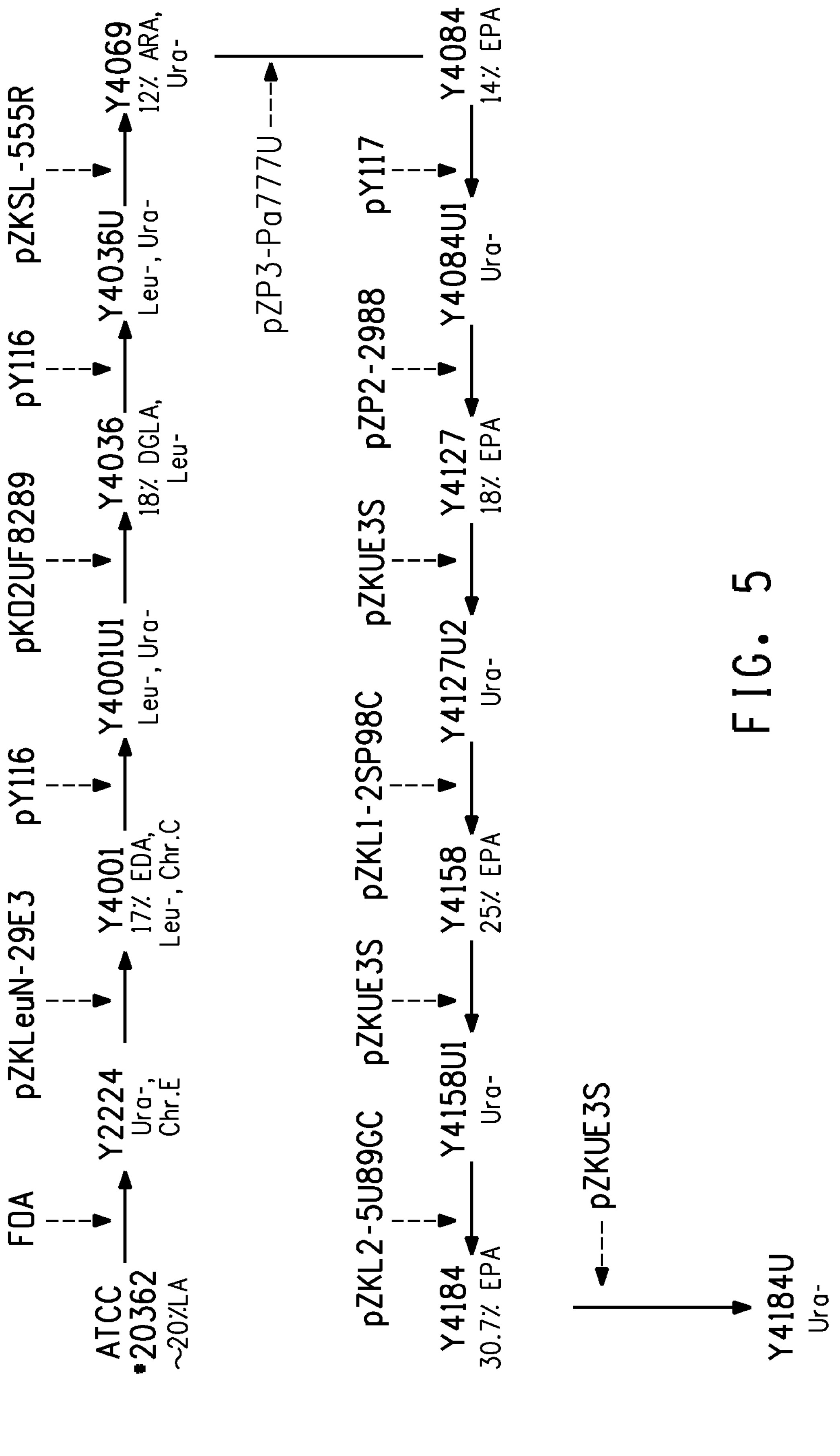

FIG. 5 diagrams the development of *Yarrowia lipolytica* strain Y4184U, producing EPA in the total lipid fraction.

The invention can be more fully understood from the following detailed description and the accompanying drawings and Sequence Listing, which form a part of this application.

The following sequences comply with 37 C.F.R. §1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs:1-42 are ORFs encoding genes or proteins (or portions thereof), or plasmids, as identified in Table 1.

TABLE 1

Summary Of Nucleic Acid And Protein SEQ ID Numbers

| Description and Abbreviation | Nucleic acid SEQ ID NO. | Protein SEQ ID NO. |
|---|---|---|
| *Yarrowia lipolytica* gene encoding a mutant acetohydroxyacid synthase (AHAS) comprising a W497L mutation (CDS corresponds to bases 146-2556, with a 461 bp intron between bases 268-732) | 1 (2987 bp) | — |
| *Euglena gracilis* Δ9 elongase ("EgD9e") | 3 (777 bp) | 4 (258 AA) |
| Plasmid pZUF17 | 5 (8165 bp) | — |
| Plasmid pDMW359 | 6 (7865 bp) | — |
| *Gluconobacter oxydans* ddsA (GenBank ® Accession No. BAA32241) | — | 7 (315 AA) |
| *Sulfitobacter* sp. ddsA (GenBank ® Accession No. EAP81866) | — | 8 (332 AA) |
| *Silicibacter pomeroyi* ddsA (GenBank ® Accession No. AAV93637) | — | 9 (332 AA) |
| *Oceanicola batsensis* ddsA (GenBank ® Accession No. EAQ04419) | — | 10 (331 AA) |
| *Rhizobium leguminosarum* ddsA (GenBank ® Accession No. CAK06434) | — | 11 (338 AA) |
| *Mesorhizobium loti* ddsA (GenBank ® Accession No. BAB53531) | — | 12 (338 AA) |
| *Agrobacterium tumefaciens* str. C58 ddsA (GenBank ® Accession No. AAL41650) | — | 13 (338 AA) |
| *Roseovarius* sp. ddsA (GenBank ® Accession No. EAQ24568) | — | 14 (333 AA) |
| *Rhodopseudomonas palustris* ddsA (GenBank ® Accession No. ABD89877) | — | 15 (336 AA) |
| *Yarrowia lipolytica* ppt1 (GenBank Accession No. XP_505040) | — | 16 (397 AA) |
| Fusion of GenBank Accession No. XP_505040 (N-terminus of *Yarrowia lipolytica* ppt1) and GenBank ® Accession No. BAA32241 (*Gluconobacter oxydans* ddsA) | 17 (1168 bp) | 18 (385 AA) |
| Plasmid pDMW359-Ss_ddsA | 19 (8231 bp) | — |
| Fusion of GenBank Accession No. XP_505040 (N-terminus of *Yarrowia lipolytica* ppt1) and GenBank ® Accession No. EAP81866 (*Sulfitobacter* sp. ddsA), codon-optimized for expression in *Y. lipolytica* | 20 (1153 bp) | 21 (380 AA) |
| Plasmid pDMW359-Sp_ddsA | 22 (8231 bp) | — |
| Fusion of GenBank Accession No. XP_505040 (N-terminus of *Yarrowia lipolytica* ppt1) and GenBank ® Accession No. AAV93637 (*Silicibacter pomeroyi* ddsA), codon-optimized for expression in *Y. lipolytica* | 23 (1153 bp) | 24 (380 AA) |
| Plasmid pDMW359-Ob_ddsA | 25 (8228 bp) | — |
| Fusion of GenBank Accession No. XP_505040 (N-terminus of *Yarrowia lipolytica* ppt1) and GenBank ® Accession No. EAQ04419 (*Oceanicola batsensis* ddsA), codon-optimized for expression in *Y. lipolytica* | 26 (1150 bp) | 27 (379 AA) |
| Plasmid pDMW359-Rl_ddsA | 28 (8249 bp) | — |
| Fusion of GenBank Accession No. XP_505040 (N-terminus of *Yarrowia lipolytica* ppt1) and GenBank ® Accession No. CAK06434 (*Rhizobium leguminosarum* ddsA), codon-optimized for expression in *Y. lipolytica* | 29 (1171 bp) | 30 (386 AA) |
| Plasmid pDMW359-Ml_ddsA | 31 (8249 bp) | — |
| Fusion of GenBank Accession No. XP_505040 (N-terminus of *Yarrowia lipolytica* ppt1) and GenBank ® Accession No. BAB53531 (*Mesorhizobium loti* ddsA), codon-optimized for expression in *Y. lipolytica* | 32 (1171 bp) | 33 (386 AA) |
| Plasmid pDMW359-At_ddsA | 34 (8248 bp) | — |
| Fusion of GenBank Accession No. XP_505040 (N-terminus of *Yarrowia lipolytica* ppt1) and GenBank ® Accession No. AAL41650 (*Agrobacterium tumefaciens* str. C58 ddsA), codon-optimized for expression in *Y. lipolytica* | 35 (1170 bp) | 36 (386 AA) |
| Plasmid pDMW359-Rs_ddsA | 37 (8234 bp) | — |
| Fusion of GenBank Accession No. XP_505040 (N-terminus of *Yarrowia lipolytica* ppt1) and GenBank ® Accession No. EAQ24568 (*Roseovarius* sp. ddsA), codon-optimized for expression in *Y. lipolytica* | 38 (1156 bp) | 39 (381 AA) |
| Plasmid pDMW359-Rp_ddsA | 40 (8243 bp) | — |
| Fusion of GenBank Accession No. XP_505040 (N-terminus of *Yarrowia lipolytica* ppt1) and GenBank ® Accession No. ABD89877 (*Rhodopseudomonas palustris* ddsA), codon-optimized for expression in *Y. lipolytica* | 41 (1165 bp) | 42 (384 AA) |

DETAILED DESCRIPTION OF THE INVENTION

Described herein is a recombinant oleaginous yeast production host for the production of coenzyme $Q_{10}$ ["$CoQ_{10}$"] and at least one polyunsaturated fatty acid, wherein said host comprises at least one copy of a ddsA gene encoding a decaprenyl diphosphate synthase, wherein expression of said decaprenyl diphosphate synthase enzyme results in the production of $CoQ_{10}$. The recombinant oleaginous yeast production host can optionally also produce at least one $C_{40}$ carotenoid.

In all of the above aspects, a recombinant oleaginous yeast is used as the production platform. In a preferred aspect, the oleaginous yeast host cell is *Yarrowia lipolytica.*

DEFINITIONS

In this disclosure, a number of terms and abbreviations are used. The following definitions are provided.

"Coenzyme Q" is abbreviated "CoQ".

"Open reading frame" is abbreviated "ORF".

"Polymerase chain reaction" is abbreviated "PCR".

"American Type Culture Collection" is abbreviated "ATCC".

"Polyunsaturated fatty acid(s)" is abbreviated "PUFA(s)".

"Triacylglycerols" are abbreviated "TAGs".

The term "invention" or "present invention" as used herein is not meant to be limiting but applies generally to any of the inventions defined in the claims or described herein.

As used herein, the term "comprising" means the presence of the stated features, integers, steps, or components as referred to in the claims, but it does not preclude the presence or addition of one or more other features, integers, steps, components or groups thereof.

As used herein, the term "about" modifying the quantity of an ingredient or reactant of the invention employed refers to variation in the numerical quantity that can occur, for example, through: typical measuring and liquid handling procedures used for making concentrates or use solutions in the real world; inadvertent error in these procedures; differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. In one aspect, the term "about" means within 20% of the recited numerical value, preferably within 10%, and most preferably within 5%.

As used herein, "coenzyme Q", "CoQ" and "ubiquinone" will be used interchangeably and will refer to lipophillic redox-active molecules comprised of a redox-active quinone structure (CAS Registry No. 1339-63-5). In its reduced state, CoQ acts as an antioxidant; in its oxidized state, it can undergo a redox cycle in the presence of an electron donor and oxygen such that the electron donor is oxidized, the oxygen is reduced and the CoQ is available to undergo another redox cycle. The compound occurs in the majority of aerobic organisms, from bacteria to higher plants and animals.

The term coenzyme $Q_{10}$ ["$CoQ_{10}$"] refers to 2,3-dimethoxy-dimethyl-6-decaprenyl-1,4-benzoquinone, also known as ubiquinone-10 (CAS Registry No. 303-98-0). This coenzyme has a hydrocarbon tail that is 50 carbon atoms in length, comprised of ten 5-carbon isoprene units. Synthesis of $CoQ_{10}$ requires a prenyl diphosphate synthase, known as decaprenyl diphosphate ["DPP" or "DecPP"] synthase.

The terms, "prenyl diphosphate synthase", "prenyl diphosphate synthetase" and "prenyltransferase" are used interchangeably herein. Each is a general term for those enzymes which catalyze a condensation reaction that polymerizes prenyl diphosphate (an allylic primer) and 3-isopentenyl diphosphate ["IPP"] to produce polyprenyl diphosphate. This class of genes is divided into 2 types, based on whether the condensation reaction of IPP is cis- [or (Z)-chain] elongation or trans- [or (E)-chain] elongation. Further, the maximum length of the isoprene chain which each prenyl diphosphate synthase can produce is fixed. Since the hydrophobic property of a product varies depending on the isoprene chain length of the product, there is great difference in the mode of requirement for the activity of enzymes. When bacterial enzymes are compared in terms of the mode of requirement, prenyl diphosphate synthases are classified into the following four groups: 1) Prenyl diphosphate synthase I comprising E type, short chain prenyl diphosphate synthases such as geranyl diphosphate synthase ("GPP"; catalyzing a $C_5 \rightarrow C_{10}$ reaction), farnesyl diphosphate synthase ("FPP"; catalyzing a $C_5 \rightarrow C_{15}$ reaction) and geranylgeranyl diphosphate synthase ("GGPP"; catalyzing a $C_5 \rightarrow C_{20}$ reaction); 2) Prenyl diphosphate synthase II comprising E type, medium chain prenyl diphosphate synthases such as hexaprenyl diphosphate synthase ("HexPP"; catalyzing a $C_{15} \rightarrow C_{30}$ reaction) and heptaprenyl diphosphate synthase ("HepPP"; catalyzing a $C_{15} \rightarrow C_{35}$ reaction); 3) Prenyl diphosphate synthase III comprising E type, long chain prenyl diphosphate synthases such as octaprenyl diphosphate synthase ("OctPP"; catalyzing a $C_{15} \rightarrow C_{40}$ reaction), solanesyl [or nonaprenyl] diphosphate synthase ("SPP" or "NonPP"; catalyzing a $C_{15} \rightarrow C_{45}$ reaction) and decaprenyl diphosphate synthase ("DecPP"; catalyzing a $C_{15} \rightarrow C_{50}$ reaction); and 4) Prenyl diphosphate synthase IV comprising Z type, long chain prenyl diphosphate synthases such as Z-nonaprenyl diphosphate synthase (catalyzing a $C_{15} \rightarrow C_{45}$ reaction), undecaprenyl diphosphate synthase ("UPP"; catalyzing a $C_{15} \rightarrow C_{55}$ reaction) and dehydrodolichyl diphosphate synthase ("deDoIPP"; catalyzing a $C_{15} \rightarrow C_{85-105}$ reaction) (reviewed in Szkopińska, A., *Acta Biochimica Polonica,* 47(2):469-480 (2000)). Of particular interest in the application herein are Group III long chain prenyl diphosphate synthases, particularly solanesyl and decaprenyl diphosphate synthases.

"Lipid bodies" refer to lipid droplets that are bound by a monolayer of phospholipid and, usually, by specific proteins. These organelles are sites where most organisms transport/store neutral lipids. Lipid bodies are thought to arise from microdomains of the endoplasmic reticulum that contain triacylglycerol ["TAG"] biosynthesis enzymes. Their synthesis and size appear to be controlled by specific protein components.

"Neutral lipids" refer to those lipids commonly found in cells in lipid bodies as storage fats and oils and are so called because at cellular pH, the lipids bear no charged groups. Generally, they are completely non-polar with no affinity for water. Neutral lipids generally refer to mono-, di-, and/or triesters of glycerol with fatty acids, also called monoacylglycerol, diacylglycerol or triacylglycerol, respectively, or collectively, acylglycerols. A hydrolysis reaction must occur to release free fatty acids from acylglycerols.

The terms "triacylglycerols" ["TAGs"] and "oil" are interchangeable and refer to neutral lipids composed of three fatty acyl residues esterified to a glycerol molecule. TAGs can contain long chain PUFAs, as well as shorter saturated and unsaturated fatty acids and longer chain saturated fatty acids. The TAG fraction of cells is also referred to as the "oil fraction", and "oil biosynthesis" generically refers to the synthesis of TAGs in the cell. The oil or TAG fraction is a subfraction of the total lipid fraction, although also it constitutes a major part of the total lipid content, measured as the weight of total fatty acids in the cell as a percent of the DCW, in oleaginous organisms. The fatty acid composition in the oil ["TAG"] fraction and the fatty acid composition of the total lipid fraction are generally similar. Thus, an increase or decrease in the concentration of PUFAs in the total lipid fraction will correspond with an increase or decrease in the concentration of PUFAs in the oil ["TAG"] fraction, and vice versa.

As used herein, the term "biomass" refers specifically to recombinant yeast cellular material from the fermentation of an oleaginous yeast. The biomass may be in the form of whole cells, whole cell lysates, homogenized cells, partially hydrolyzed cellular material, and/or partially purified cellular material (e.g., microbially produced oil). Preferably, the fermentation utilizes a recombinant oleaginous yeast producing $CoQ_{10}$ and at least one PUFA (and optionally at least one one $C_{40}$ carotenoid).

The term "oleaginous" refers to those organisms that tend to store their energy source in the form of lipid (Weete, In: Fungal Lipid Biochemistry, 2$^{nd}$ Ed., Plenum, 1980). Generally, the cellular oil content of these microorganisms follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.,* 57:419-25 (1991)).

The term "oleaginous yeast" refers to those microorganisms classified as yeasts that can make oil, in excess of about 25% of their DCW as oil. Examples of oleaginous yeast include, but are no means limited to, the following genera: *Yarrowia, Candida, Rhodotorula, Rhodosporidium, Cryptococcus, Trichosporon* and *Lipomyces.*

The term "fermentable carbon source" means a carbon source that a microorganism will metabolize to derive energy. Typical carbon sources include, but are not limited to: monosaccharides, oligosaccharides, polysaccharides, alkanes, fatty acids, esters of fatty acids, monoglycerides, diglycerides, triglycerides, carbon dioxide, methanol, formaldehyde, formate and carbon-containing amines.

As used herein, an "isolated nucleic acid fragment" or "genetic construct" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

The term "complementary" is used to describe the relationship between nucleotide bases that are capable of hybridizing to one another. For example, with respect to DNA, adenosine is complementary to thymine and cytosine is complementary to guanine.

"Codon degeneracy" refers to the nature in the genetic code permitting variation of the nucleotide sequence without effecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments that are then enzymatically assembled to construct the entire gene. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell, where sequence information is available. For example, the codon usage profile for *Yarrowia lipolytica* is provided in U.S. Pat. No. 7,125,672.

"Gene" refers to a nucleic acid fragment that expresses a specific protein, and that may refer to the coding region alone or may include regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene that is introduced into the host organism by gene transfer. Foreign genes can comprise native genes inserted into a non-native organism, native genes introduced into a new location within the native host, or chimeric genes. A "transgene" is a gene that has been introduced into the genome by a transformation procedure. A "codon-optimized gene" is a gene having its frequency of codon usage designed to mimic the frequency of preferred codon usage of the host cell.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing sites, effector binding sites and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The terms "3' non-coding sequences" and "transcription terminator" refer to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" or "mRNA" refers to the RNA that is without introns and that can be translated into protein by the cell. "cDNA" refers to a double-stranded DNA that is complementary to, and derived from, mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; Int'l. App. Pub. No. WO 99/28508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated and yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from nucleic acid fragments. Expression may also refer to translation of mRNA into a polypeptide.

"Mature" protein refers to a post-translationally processed polypeptide, i.e., one from which any pre- or propeptides present in the primary translation product have been removed. "Precursor" protein refers to the primary product of translation of mRNA, i.e., with pre- and propeptides still present. Pre- and propeptides may be (but are not limited to) intracellular localization signals.

The term "recombinase" refers to an enzyme(s) that carries out site-specific recombination to alter the DNA structure and includes transposases, lambda integration/excision enzymes, as well as site-specific recombinases.

"Recombinase site" or "site-specific recombinase sequence" means a DNA sequence that a recombinase will recognize and bind to. It will be appreciated that this may be a wild type or mutant recombinase site, as long as functionality is maintained and the recombinase enzyme may still recognize the site, bind to the DNA sequence, and catalyze recombination between two adjacent recombinase sites.

"Transformation" refers to the transfer of a nucleic acid molecule into a host organism, resulting in genetically stable inheritance. The nucleic acid molecule may be a plasmid that replicates autonomously, for example, or, it may integrate into the genome of the host organism. Host organisms containing the transformed nucleic acid fragments are referred to as "transgenic" or "recombinant" or "transformed" organisms.

The terms "plasmid" and "vector" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing an expression cassette(s) into a cell.

The term "expression cassette" refers to a fragment of DNA comprising the coding sequence of a selected gene and regulatory sequences preceding (5' non-coding sequences) and following (3' non-coding sequences) the coding sequence that are required for expression of the selected gene product. Thus, an expression cassette is typically composed of: 1) a promoter sequence; 2) a coding sequence (i.e., ORF); and, 3) a 3' untranslated region (i.e., a terminator) that, in eukaryotes, usually contains a polyadenylation site. The expression cassette(s) is usually included within a vector, to facilitate cloning and transformation. Different expression cassettes can be transformed into different organisms including bacteria, yeast, plants and mammalian cells, as long as the correct regulatory sequences are used for each host.

The term "homologous recombination" refers to the exchange of DNA fragments between two DNA molecules (during cross over). The fragments that are exchanged are flanked by sites of identical nucleotide sequences between the two DNA molecules (i.e., "regions of homology"). The term "regions of homology" refer to stretches of nucleotide sequence on nucleic acid fragments that participate in homologous recombination that have homology to each other. Effective homologous recombination will generally take place where these regions of homology are at least about 10 bp in length, where at least about 50 bp in length is preferred. Typically fragments that are intended for recombination contain at least two regions of homology where targeted gene disruption or replacement is desired.

As used herein, the term "chromosomal integration" means that a chromosomal integration vector becomes congruent with the chromosome of a microorganism through recombination between homologous DNA regions on the chromosomal integration vector and within the chromosome. Many of the modifications to the oleaginous yeast *Yarrowia lipolytica* were introduced by chromosomal integration.

As used herein, the term "chromosomal integration vector" means an extra-chromosomal vector that is capable of integrating into the host's genome through homologous recombination.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.,* 215: 403-410 (1993)). In general, a sequence of ten or more contiguous amino acids or thirty or more nucleotides is necessary in order to identify putatively a polypeptide or nucleic acid sequence as homologous to a known protein or gene. Moreover, with respect to nucleotide sequences, gene-specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence.

As used herein, "substantially similar" enzymes will refer to enzymes belonging to a family of proteins in the art known to share similar structures and function. It is well within the skill of one in the art to identify substantially similar proteins given a known structure. Typical methods to identify substantially similar structures will rely upon known sequence information (nucleotide sequence and/or amino acid sequences) and may include PCR amplification, nucleic acid hybridization, and/or sequence identity/similarity analysis (e.g., sequence alignments between partial and/or complete sequences and/or known functional motifs associated with the desired activity).

A nucleic acid molecule is "hybridizable" to another nucleic acid molecule, such as a cDNA, genomic DNA, or RNA molecule, when a single-stranded form of the nucleic acid molecule can anneal to the other nucleic acid molecule under the appropriate conditions of temperature and solution ionic strength. Given the nucleic acid sequences described herein, one of skill in the art can identify substantially similar nucleic acid fragments that may encode proteins having similar activity. Hybridization and washing conditions are well known and exemplified in Sambrook, J., Fritsch, E. F. and Maniatis, T. *Molecular Cloning: A Laboratory Manual,* $3^{rd}$ ed., Cold Spring Harbor Laboratory: Cold Spring Harbor, N.Y. (2001), particularly Chapter 11 and Table 11.1 therein. The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washes with 2×SSC, 0.1% SDS at 65° C. followed by 0.1×SSC, 0.1% SDS at 65° C., for example.

In one aspect, suitable nucleic acid fragments encode polypeptides that are at least about 70% identical to the amino acid sequences reported herein. In another aspect, the nucleic acid fragments encode amino acid sequences that are about 85-90% identical to the amino acid sequences reported herein. In a further aspect, the nucleic acid fragments encode amino acid sequences that are at least about 90-100% identical to the amino acid sequences reported herein. Suitable nucleic acid fragments not only have the above homologies but typically encode a polypeptide having at least about 50 amino acids, preferably at least about 100 amino acids, more preferably at least about 150 amino acids, still more preferably at least about 200 amino acids, and most preferably at least about 250 amino acids.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1) the GCG suite of programs (Wisconsin Package Version 9.0, Genetics Computer Group (GCG), Madison, Wis.); 2) BLASTP, BLASTN, BLASTX (Altschul et al., *J Mol. Biol.,* 215:403-410 (1990)); 3) DNASTAR (DNASTAR, Inc. Madison, Wis.); 4) Sequencher (Gene Codes Corporation, Ann Arbor, Mich.); and, 5) the FASTA program incorporating the Smith-Waterman algorithm (W. R. Pearson, *Comput. Methods Genome Res*., [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein, "default values" will mean any set of values or parameters (as set by the software manufacturer) which originally load with the software when first initialized.

Standard recombinant DNA and molecular cloning techniques used herein are well known in the art and are described by Sambrook, J., Fritsch, E. F. and Maniatis, T., *Molecular Cloning: A Laboratory Manual,* $3^{rd}$ ed., Cold Spring Harbor Laboratory: Cold Spring Harbor, N.Y. (2001) (hereinafter "Maniatis"); by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience, Hoboken, N.J. (1987).

Microbial Hosts for $CoQ_{10}$ and PUFA Production: Oleaginous Yeasts

Oleaginous organisms are those organisms that tend to store their energy source in the form of lipid (Weete, In: Fungal Lipid Biochemistry, $2^{nd}$ Ed., Plenum, 1980). Oleaginous yeast can accumulate in excess of about 25% of their DCW as oil, more preferably greater than about 30% of the cellular dry weight, and most preferably greater than about 40% of the cellular dry weight under oleaginous conditions. Examples of oleaginous yeast include, but are no means limited to, the following genera: *Yarrowia, Candida, Rhodotorula, Rhodosporidium, Cryptococcus, Trichosporon* and *Lipomyces*. More specifically, illustrative oil-synthesizing yeasts include: *Rhodosporidium toruloides, Liopmyces starkeyii, L. lipoferus, Candida revkaufi, C. pulcherrima, C. tropicalis, C. utilis, Trichosporon pullans, T. cutaneum, Rhodotorula glutinus, R. graminis* and *Yarrowia lipolytica* (formerly classified as *Candida lipolytica*). The technology for growing oleaginous yeast with high oil content is well developed (for example, see EP 0 005 277B1; Ratledge, C., *Prog. Ind. Microbiol.,* 16:119-206 (1982)). These organisms have been commercially used for a variety of purposes in the past.

Of those organisms classified as oleaginous yeast, *Yarrowia lipolytica* was selected as a preferred microbial host for the purposes herein. This selection was based on: 1) confirmation that the organism naturally produces high levels (at least about 2000 ppm) of the natural antioxidant $CoQ_9$; and, 2) previous genetic engineering by the Applicants' Assignee resulting in significant production of various ω-3/ω-6 PUFAs and proof-of-concept production of various carotenoids (details infra). The *Y. lipolytica* strains designated as ATCC #20362, ATCC #8862, ATCC #18944, ATCC #76982 and/or LGAM S(7)1 (Papanikolaou S., and Aggelis G., *Bioresour. Technol.* 82(1):43-9 (2002)) are preferred wildtype hosts, due to preliminary studies targeted toward identification of wildtype strains having high lipid content (measured as a percent dry weight) and high volumetric productivity (measured as g/L $h^{-1}$).

The CoQ Biosynthetic Pathway

A metabolic pathway, or biosynthetic pathway, in a biochemical sense, can be regarded as a series of chemical reactions occurring in order within a cell, catalyzed by enzymes, to achieve either the formation of a metabolic product to be used or stored by the cell, or the initiation of another metabolic pathway (then called a flux generating step). Many of these pathways are elaborate, and involve a step by step modification of the initial substance to shape it into a product having the exact chemical structure desired.

Figure 1A:
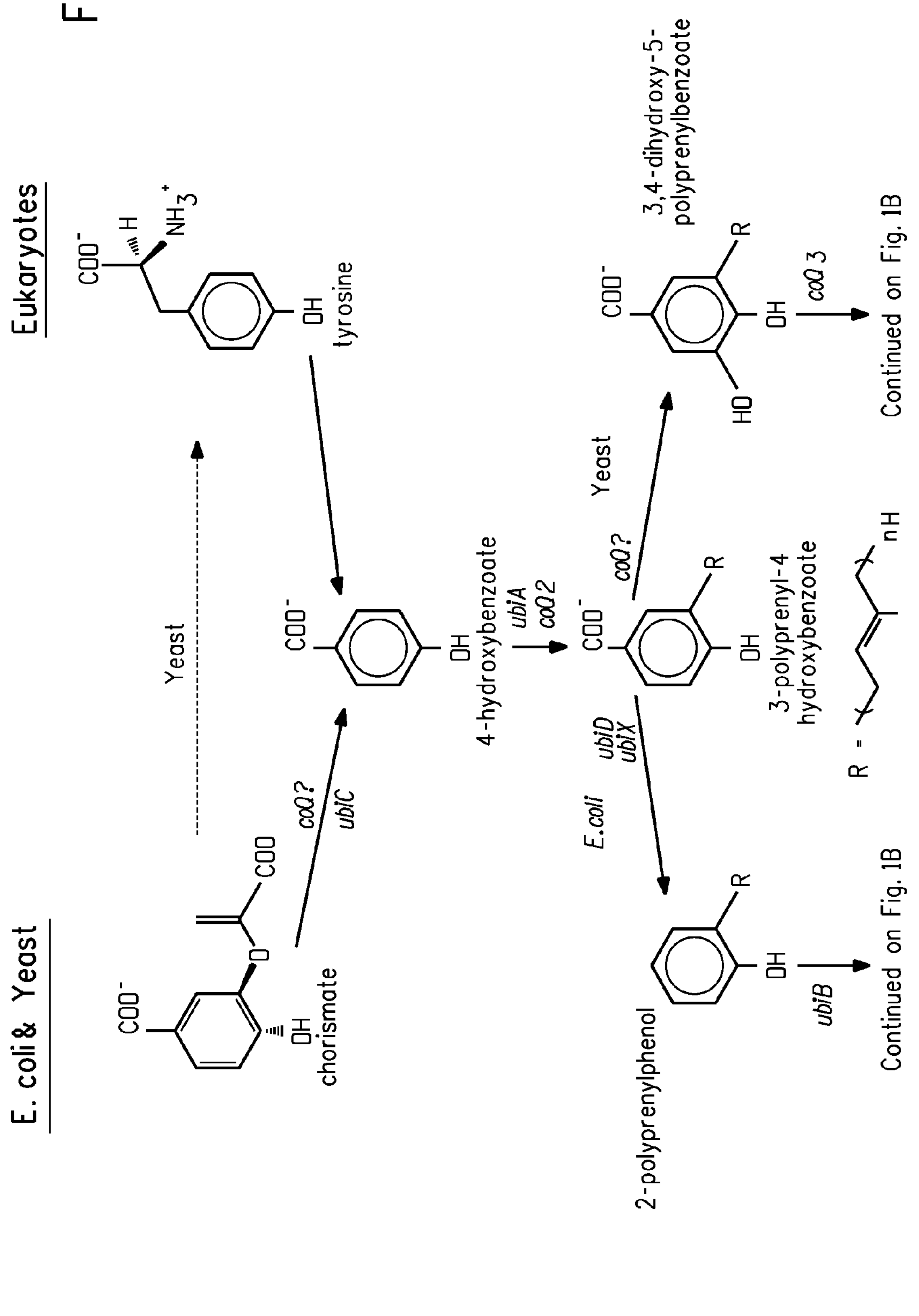
FIGS. 1A and 1B illustrate the CoQ biosynthetic pathway.
Figure 1B:
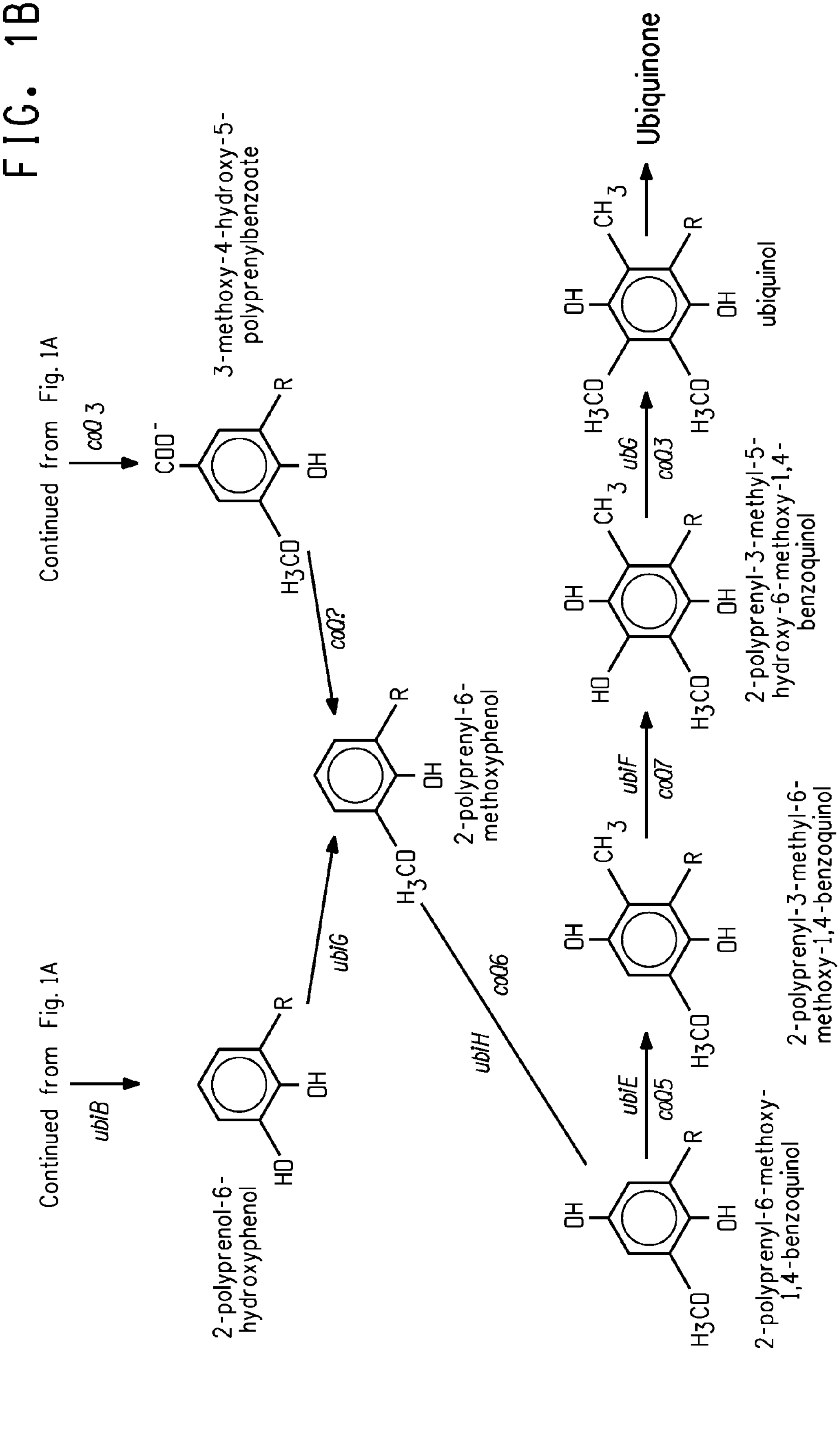

The biochemical reactions that lead to production of the quinones of the coenzyme Q series (i.e., $Q_6$, $Q_7$, $Q_8$, $Q_9$ and $Q_{10}$) are well-described in the minireview of R. Meganathan (*FEMS Microbiol. Lett.,* 203:131-139 (2001)) for *Escherichia coli* and *Saccharomyces cerevisiae* and are summarized in FIGS. 1A and 1B herein. In brief, the quinonoid nucleus is derived from the shikimate pathway via chorismate or tyrosine. Formation of 4-hydroxybenzoate is the first committed step in the biosynthesis of CoQ. This molecule then undergoes prenylation, wherein the polyprenyl side chain of the final CoQ enzyme is added.

Prenylation:

The polyprenyl side chain itself is formed via the mevalonate pathway, which results in the formation of the $C_5$ isoprene subunit, isopentenyl pyrophosphate ["IPP"] from the starting precursor, acetyl-CoA. More specifically, two molecules of acetyl-CoA are condensed by thiolase to yield acetoacetyl-CoA, which is subsequently converted to 3-hydroxy-3-methylglutaryl-CoA ["HMG-CoA"] by the action of 3-hydroxymethyl-3-glutaryl-CoA synthase ["HMG-CoA synthase"]. Next, 3-hydroxy-3-methylglutaryl-CoA reductase ["HMG-CoA reductase"), the rate controlling step in the mevalonate pathway, converts HMG-CoA to mevalonate, to which two molecules of phosphate residues are then added by the action of two kinases (i.e., mevalonate kinase and phosphomevalonate kinase, respectively). Mevalonate pyrophosphate is then decarboxylated by the action of mevalonate pyrophosphate decarboxylase to yield IPP, which becomes the building unit for a wide variety of isoprene molecules necessary in living organisms.

IPP is isomerized to dimethylaryl pyrophosphate ["DMAPP"] by the action of isopentenyl pyrophosphate isomerase ["IPP isomerase"]. IPP and DMAPP are then converted to the $C_{10}$ unit geranyl pyrophosphate ["GPP"] by a head-to-tail condensation. In a similar condensation reaction between GPP and IPP, GPP is converted to the $C_{15}$ unit farnesyl pyrophosphate ["FPP"]. The biosynthesis of GPP and FPP from IPP and DMAPP is catalyzed by the enzyme FPP synthase. The product then reacts with a polyprenyl phosphate synthase, to produce the final polyprenyl side chain having from 30-50 carbon atoms, corresponding to 6, 7, 8, 9 or 10 isoprenoid units in the side chain. The precise length of the polyprenyl side chain present in a particular organism is constant and is determined by the nature of the polyprenyl phosphate synthase. For example, a hexaprenyl diphosphate synthase leads to synthesis of $CoQ_6$, while an octaprenyl diphosphate synthase leads to synthesis of $CoQ_8$, a solanesyl diphosphate synthase leads to synthesis of $CoQ_9$, and a decaprenyl diphosphate synthase leads to synthesis of $CoQ_{10}$. Studies summarized in Meganathan (supra) have demonstrated that mutant bacteria and yeast expressing a non-native polyprenyl phosphate synthase that results in a side chain of different length than in the parent do not affect the mutant strain.

Subsequent Ring Modifications:

Prenylation results in the formation of 3-polyprenyl-4-hydroxybenzoate. This molecule then undergoes multiple ring modifications, including hydroxylation, methylation, decarboxylation, to result in formation of ubiquinol, which is non-enzymatically converted to ubiquinone ["CoQ"].

The genes required for CoQ biosynthesis in *Yarrowia lipolytica* have not been extensively characterized, since the wildtype oleaginous yeast contains all of the genes required for $CoQ_9$ production and thus only requires a single additional gene to enable biosynthesis of $CoQ_{10}$. However, based on the complete sequencing of the entire genome (Dujon, B. et al., *Nature,* 430 (6995):35-44 (2004)) and the public *Y. lipolytica* protein database of the "Yeast project Genolevures" (Center for Bioinformatics, LaBRI, Talence Cedex, France), one skilled in the art would readily be able to identify homologous genes corresponding to the ubiC, ubiA, ubiD, ubiX, ubiB, ubiG, ubiH, ubiE and ubiF genes of *Escherichia coli* and/or the coq2, coq3, coq6, coq5 and coq7 genes of *Saccharomyces cerevisiae*, which are known to catalyze the reactions diagrammed in FIGS. 1A and 1B. Similarly, the initial and intermediate genes of the mevalonate pathway responsible for the biosynthesis of the polyprenyl side chain of $CoQ_9$ should also easily be identified, up to and including FPP synthase. The last gene required for synthesis of the polyprenyl side chain of *Yarrowia lipolytica*'s $CoQ_9$ is a solanesyl diphosphate synthase, which has not yet been identified or characterized.

One of skill in the art would recognize, for example, that any previously identified genes of the CoQ biosynthetic pathway, e.g., those from *E. coli* and/or *S. cerevisiae*, or portions thereof may be used to search for homologs in *Yarrowia lipolytica* using sequence analysis software. In general, such computer software matches similar sequences by assigning degrees of homology to various substitutions, deletions and other modifications. Alternatively, any of the previously identified sequences or portions thereof may also be employed as hybridization reagents for the identification of *Y. lipolytica* CoQ homologs. Hybridization methods are well defined and will not be reiterated herein. Alternately, isolation of homologous genes using sequence-dependent protocols is well known in the art. Examples of sequence-dependent protocols include, but are not limited to: 1) methods of nucleic acid hybridization; 2) methods of DNA and RNA amplification, as exemplified by various uses of nucleic acid amplification technologies [e.g., polymerase chain reaction ["PCR"], Mullis et al., U.S. Pat. No. 4,683,202; ligase chain reaction ["LCR"], Tabor, S. et al., *Proc. Acad. Sci. U.S.A.,* 82:1074 (1985); or strand displacement amplification ["SDA"], Walker, et al., *Proc. Natl. Acad. Sci. U.S.A.,* 89:392 (1992)]; and 3) methods of library construction and screening by complementation. This would enable direct isolation of any of the genes from *Yarrowia lipolytica* that are involved in the organism's native CoQ biosynthetic pathway, based on previously identified genes of the CoQ biosynthetic pathway from related organisms, such as those from *E. coli* and/or *S. cerevisiae.*

Genetic engineering of a strain of *Yarrowia lipolytica* that is capable of $CoQ_{10}$ production requires the expression of a heterologous decaprenyl diphosphate synthase, encoded by a ddsA gene. Although the decaprenyl diphosphate synthase of *Gluconobacter oxydans* is most well-characterized (Okada, K., et al., *Eur. J. Biochem.,* 255(1):52-59 (1998); see also GenBank® Accession No. BAA32241), several ddsA genes have been identified from other organisms that have the putative ability to synthesize $CoQ_{10}$ based on homology searches. These genes have been identified in *Sulfitobacter* sp. NAS-14.1 (GenBank® Accession No. EAP81866), *Silicibacter pomeroyi* DSS-3 (GenBank® Accession No. AAV93637), *Paracoccus denitrificans* (U.S. Pat. No. 6,225,097), *Paracoccus zeaxanthinifaciens* (GenBank® Accession No. AJ431695), *Rhodobacter capsulatus* (GenBank® Accession No. DQ1 91802; U.S. Pat. No. 6,103,488), *Oceanicola batsensis* HTCC2597 (GenBank® Accession No. EAQ04419), *Schizosaccharomyces pombe* (Suzuki et al., *J. Biochem.,* 121 (3):496-505 (1997)), *Agrobacterium tumerifaciens* (GenBank® Accession No. DQ865262) and *Sinorhizobium*

*meliloti* (GenBank® Accession No. DQ241792), for example. This, of course, is not intended to be limiting, as numerous other ddsA genes could be identified, isolated and expressed in an oleaginous yeast, such as *Yarrowia lipolytica*, according to the methods provided herein.

Amino acid sequence comparisons of various E-polyprenyl diphosphate synthases have revealed the presence of seven highly conserved regions, including 2 aspartate-rich domains (i.e., Domain II and Domain VI), which are thought to be the binding sites for the diphosphate moieties for IPP and allylic substrates (Koyama, T., *J. Biochem* (Tokyo), 113 (3):355-363 (1993); Chen, A. et al., *Protein Science,* 3:600-607 (1994)). One skilled in the art would readily be able to use these conserved regions or portions thereof to search for homologs having decaprenyl diphosphate synthase activity in any organism having the ability to produce $CoQ_{10}$. As described previously, means for the identification of these homologs could include sequence analysis software, hybridization methods, nucleic acid amplification technologies and/or methods of library construction and screening by complementation.

Upon identification of an appropriate heterologous decaprenyl diphosphate synthase, construction of a suitable expression vector, and transformation into an oleaginous yeast, it is expected that the transformant host organism expressing the ddsA gene will produce $CoQ_{10}$. It is well known that CoQ compounds are insoluble in water and therefore, within the cell, they partition into the cell membrane, simplifying purification. As such, the $CoQ_{10}$ would be expected to remain in the hydrophobic/lipophillic portions of the biomass during processing (i.e., in the microbially produced oil).

Production of PUFAs in Oleaginous Yeast

Figure 2A:
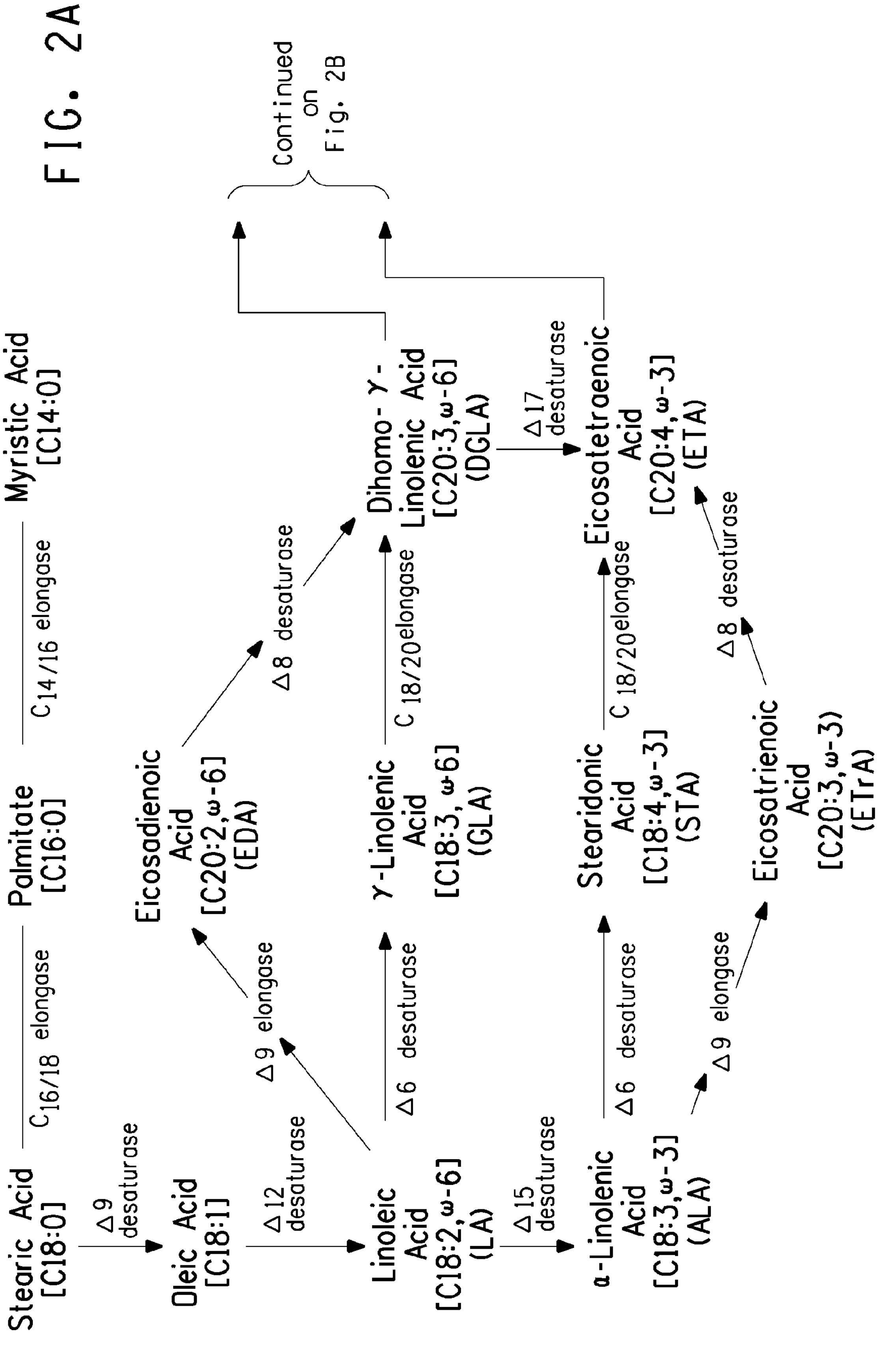
FIGS. 2A and 2B illustrates the ω-3/ω-6 fatty acid biosynthetic pathway.
Figure 2B:
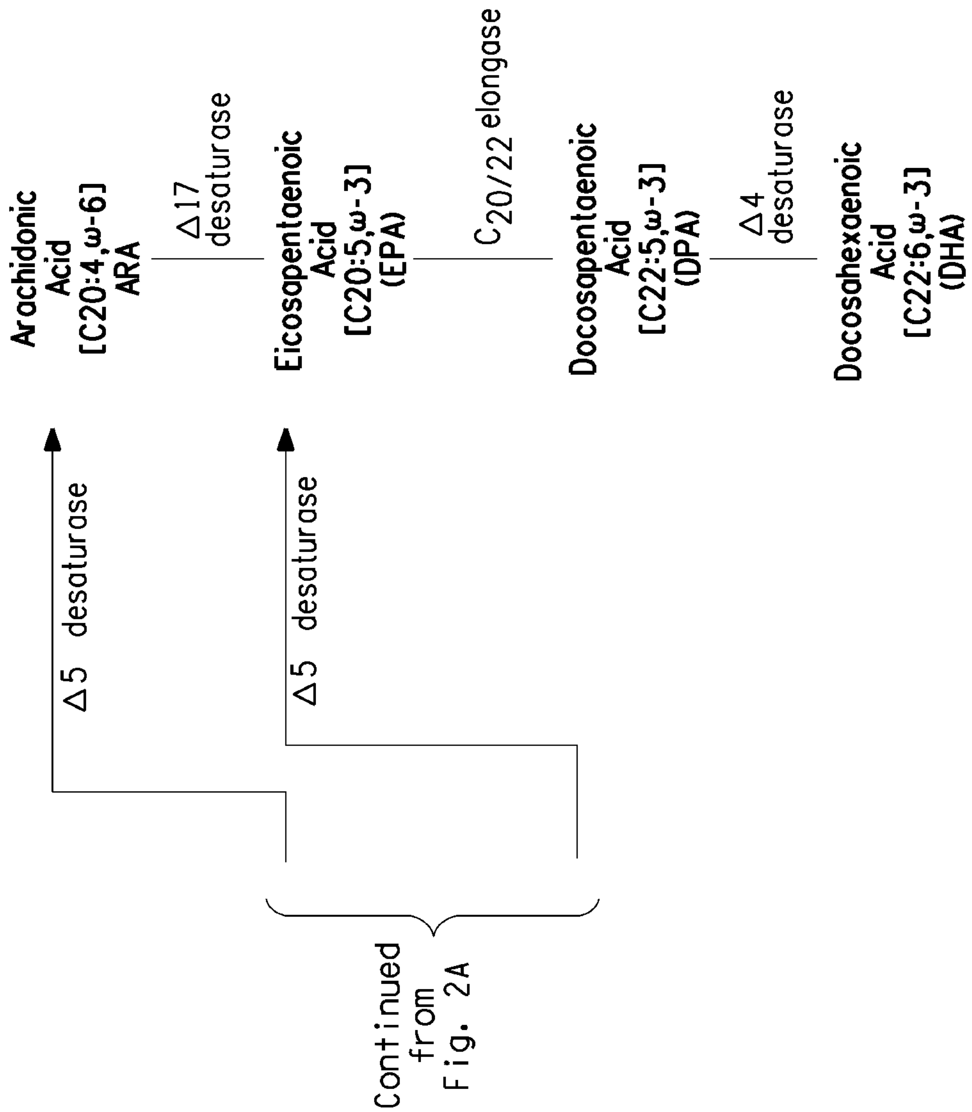

A variety of different hosts including plants, algae, fungi and yeast are being investigated as means for commercial PUFA production. Genetic engineering has demonstrated that the natural abilities of some hosts, even those natively limited to LA and ALA fatty acid production, can be substantially altered to result in high-level production of various long-chain ω-3/ω-6 PUFAs (FIGS. 2A and 2B). Particularly relevant herein, the Applicants' Assignee has recently explored the utility of oleaginous yeast, and specifically, *Yarrowia lipolytica* (formerly classified as *Candida lipolytica*), as a preferred class of microorganisms for production of PUFAs. Despite a natural deficiency in the production of ω-6/ω-3 fatty acids in these organisms (since naturally produced PUFAs are limited to 18:2 fatty acids (and less commonly, 18:3 fatty acids)), high production of GLA, ARA, EPA and DHA relative to the total fatty acids in *Y. lipolytica* has been reported (U.S. patent application Ser. No. 11/198,975, Ser. No. 11/265,761, Ser. No. 11/264,784 and Ser. No. 11/264,737, corresponding to Int'l. App. Pub. No. WO 2006/033723, WO 2006/052870, WO 2006/055322 and WO 2006/052871).

Polyunsaturated Fatty Acid Definitions and Biosynthetic Pathway

The term "fatty acids" refers to long chain aliphatic acids (alkanoic acids) of varying chain lengths, from about $C_{12}$ to $C_{22}$ (although both longer and shorter chain-length acids are known). The predominant chain lengths are between $C_{16}$ and $C_{22}$. The structure of a fatty acid is represented by a simple notation system of "X:Y", where X is the total number of carbon ["C"] atoms in the particular fatty acid and Y is the number of double bonds. Additional details concerning the differentiation between "saturated fatty acids" versus "unsaturated fatty acids", "monounsaturated fatty acids" versus "polyunsaturated fatty acids" ["PUFAs"], and "omega-6 fatty acids" ["ω-6" or "n-6"] versus "omega-3 fatty acids" ["ω-3" or "n-3"] are provided in U.S. Pat. No. 7,238,482, which is hereby incorporated herein by reference.

Nomenclature used to describe PUFAs is shown below in Table 2. In the column titled "Shorthand Notation", the omega-reference system is used to indicate the number of carbons, the number of double bonds and the position of the double bond closest to the omega carbon, counting from the omega carbon (which is numbered 1 for this purpose). The remainder of the Table summarizes the common names of ω-3 and ω-6 fatty acids and their precursors, the abbreviations that will be used throughout the specification and the chemical name of each compound.

TABLE 2

Nomenclature of Various PUFAs And Precursors

| Common Name | Abbreviation | Chemical Name | Shorthand Notation |
|---|---|---|---|
| Myristic | — | tetradecanoic | 14:0 |
| Palmitic | Palmitate | hexadecanoic | 16:0 |
| Palmitoleic | — | 9-hexadecenoic | 16:1 |
| Stearic | — | octadecanoic | 18:0 |
| Oleic | — | cis-9-octadecenoic | 18:1 |
| Linoleic | LA | cis-9,12-octadecadienoic | 18:2 □-6 |
| γ-Linolenic | GLA | cis-6,9,12-octadecatrienoic | 18:3 □-6 |
| Eicosadienoic | EDA | cis-11,14-eicosadienoic | 20:2 □-6 |
| Dihomo-γ Linolenic | DGLA | cis-8,11,14-eicosatrienoic | 20:3-□6 |
| Arachidonic | ARA | cis-5,8,11,14-eicosatetraenoic | 20:4 □6 |
| α-Linolenic | ALA | cis-9,12,15-octadecatrienoic | 18:3 □-3 |
| Stearidonic | STA | cis-6,9,12,15-octadecatetraenoic | 18:4 □-3 |
| Eicosatrienoic | ETrA | cis-11,14,17-eicosatrienoic | 20:3 □-3 |
| Eicosa-tetraenoic | ETA | cis-8,11,14,17-eicosatetraenoic | 20:4 □-3 |
| Eicosa-pentaenoic | EPA | cis-5,8,11,14,17-eicosapentaenoic | 20:5 □-3 |
| Docosatrienoic | DRA | cis-10,13,16-docosatrienoic | 22:3 □-3 |
| Docosa-tetraenoic | DTA | cis-7,10,13,16-docosatetraenoic | 22:4 □-6 |
| Docosa-pentaenoic | DPAn-6 | cis-4,7,10,13,16-docosapentaenoic | 22:5 □-6 |
| Docosa-pentaenoic | DPA | cis-7,10,13,16,19-docosapentaenoic | 22:5 □-3 |
| Docosa-hexaenoic | DHA | cis-4,7,10,13,16,19-docosahexaenoic | 22:6 □-3 |

The term "total fatty acids" ["TFAs"] herein refer to the sum of all cellular fatty acids that can be derivitized to fatty acid methyl esters ["FAMEs"] by the base transesterification method (as known in the art) in a given sample, which may be the total lipid fraction or the oil fraction, for example. Thus, total fatty acids include fatty acids from neutral and polar lipid fractions, including the phosphatidylcholine fraction, the phosphatidyletanolamine fraction and the diacylglycerol, monoacylglycerol and triacylglycerol ["TAG or oil"] fractions but not free fatty acids.

The term "total lipid content" of cells is a measure of TFAs as a percent of the dry cell weight ["DCW"]. Thus, total lipid content ["TFAs % DCW"] is equivalent to, e.g., milligrams of total fatty acids per 100 milligrams of DCW.

Generally, the concentration of a fatty acid is expressed herein as a weight percent of TFAs ["% TFAs"], e.g., milligrams of the given fatty acid per 100 milligrams of TFAs. Unless otherwise specifically stated in the disclosure herein, reference to the percent of a given fatty acid with respect to total lipids is equivalent to concentration of the fatty acid as % TFAs (e.g., % EPA of total lipids is equivalent to EPA % TFAs).

The terms "lipid profile" and "lipid composition" are interchangeable and refer to the amount of an individual fatty acid contained in a particular lipid fraction, such as in the total lipid fraction or the oil ["TAG"] fraction, wherein the amount is expressed as a percent of TFAs. The sum of each individual fatty acid present in the mixture should be 100.

The term "PUFA biosynthetic pathway" refers to a metabolic process that converts oleic acid to ω-6 fatty acids such as LA, EDA, GLA, DGLA, ARA, DRA, DTA and DPAn-6 and ω-3 fatty acids such as ALA, STA, ETrA, ETA, EPA, DPA and DHA. This process is well described in the literature. See e.g., Int'. App. Pub. No. WO 2006/052870. Briefly, this process involves elongation of the carbon chain through the addition of carbon atoms and desaturation of the molecule through the addition of double bonds, via a series of special elongation and desaturation enzymes, respectively, (i.e., "PUFA biosynthetic pathway enzymes") present in the endoplasmic reticulim membrane. More specifically, "PUFA biosynthetic pathway enzyme" refers to any of the following enzymes (and genes which encode said enzymes) associated with the biosynthesis of a PUFA, including: a Δ9 elongase, a $C_{14/16}$ elongase, a $C_{16/18}$ elongase, a $C_{18/20}$ elongase, a $C_{20/22}$ elongase. a Δ4 desaturase, a Δ5 desaturase, a Δ6 desaturase, a Δ8 desaturase, Δ9 desaturase, a Δ12 desaturase, a Δ15 desaturase, and/or Δ17 desaturase.

The term "ω-3/ω-6 fatty acid biosynthetic pathway" refers to a set of genes which, when expressed under the appropriate conditions, encode enzymes that catalyze the production of either or both ω-3 and ω-6 fatty acids. Typically the genes involved in the ω-3/ω-6 fatty acid biosynthetic pathway encode PUFA biosynthetic pathway enzymes. A representative pathway is illustrated in FIGS. 2A and 2B, providing for the conversion of myristic acid through various intermediates to DHA, which demonstrates how both ω-3 and ω-6 fatty acids may be produced from a common source. The pathway is naturally divided into two portions, such that one portion generates only ω-3 fatty acids and the other portion, only ω-6 fatty acids. That portion that generates only ω-3 fatty acids is referred to herein as the ω-3 fatty acid biosynthetic pathway, whereas that portion that generates only ω-6 fatty acids is referred to herein as the ω-6 fatty acid biosynthetic pathway. However, as seen in FIGS. 2A and 2B and as described below, there are often multiple alternate pathways for production of a specific PUFA.

All pathways require the initial conversion of oleic acid to linoleic acid ["LA"], the first of the ω-6 fatty acids, by a Δ12 desaturase. Then, using the "Δ9 elongase/Δ8 desaturase pathway" and LA as substrate, long-chain ω-6 fatty acids are formed as follows: 1) LA is converted to eicosadienoic acid ["EDA"] by a Δ9 elongase; 2) EDA is converted to dihomo-γ-linolenic acid ["DGLA"] by a Δ8 desaturase; 3) DGLA is converted to arachidonic acid ["ARA"] by a Δ5 desaturase; 4) ARA is converted to docosatetraenoic acid ["DTA"] by a $C_{20/22}$ elongase; and, 5) DTA is converted to docosapentaenoic acid ["DPAn-6"] by a Δ4 desaturase. Alternatively, the "Δ9 elongase/Δ8 desaturase pathway" can use α-linolenic acid ["ALA"] as substrate to produce long-chain ω-3 fatty acids as follows: 1) LA is converted to ALA, the first of the ω-3 fatty acids, by a Δ15 desaturase; 2) ALA is converted to eicosatrienoic acid ["ETrA"] by a Δ9 elongase; 3) ETrA is converted to eicosatetraenoic acid ["ETA"] by a Δ8 desaturase; 4) ETA is converted to eicosapentaenoic acid ["EPA"] by a Δ5 desaturase; 5) EPA is converted to docosapentaenoic acid ["DPA"] by a $C_{20/22}$ elongase; and, 6) DPA is converted to docosahexaenoic acid ["DHA"] by a Δ4 desaturase. Optionally, ω-6 fatty acids may be converted to ω-3 fatty acids; for example, ETA and EPA are produced from DGLA and ARA, respectively, by Δ17 desaturase activity.

Alternate pathways for the biosynthesis of ω-3/ω-6 fatty acids utilize a Δ6 desaturase and $C_{18/20}$ elongase (i.e., the "Δ6 desaturase/Δ6 elongase pathway"). More specifically, LA and ALA may be converted to γ-linolenic acid ["GLA"] and stearidonic acid ["STA"], respectively, by a Δ6 desaturase; then, a $C_{18/20}$ elongase converts GLA to DGLA and/or STA to ETA. Downstream PUFAs are subsequently formed as described above.

As used herein, the term "functional" as used herein relating to the (ω-3/ω-6 fatty acid biosynthetic pathway, means that some (or all) of the genes in the pathway express active enzymes, resulting in in vivo catalysis or substrate conversion. It should be understood that "ω-3/ω-6 fatty acid biosynthetic pathway" or "functional ω-3/ω-6 fatty acid biosynthetic pathway" does not imply that all the genes listed in the above paragraph are required, as a number of fatty acid products will only require the expression of a subset of the genes of this pathway.

As used herein, the term "desaturase" refers to a polypeptide that can desaturate adjoining carbons in a fatty acid by removing a hydrogen from one of the adjoining carbons and thereby introducing a double bond between them. Desaturation produces a fatty acid or precursor of interest. Despite use of the omega-reference system throughout the specification to refer to specific fatty acids, it is more convenient to indicate the activity of a desaturase by counting from the carboxyl end of the substrate using the delta-system. Of particular interest herein are: 1) Δ5 desaturases that catalyze the conversion of the substrate fatty acid, DGLA, to ARA and/or of the substrate fatty acid, ETA, to EPA; 2) Δ17 desaturases that desaturate a fatty acid between the $17^{th}$ and $18^{th}$ carbon atom numbered from the carboxyl-terminal end of the molecule and which, for example, catalyze the conversion of the substrate fatty acid, ARA, to EPA and/or the conversion of the substrate fatty acid, DGLA, to ETA; 3) Δ6 desaturases that catalyze the conversion of the substrate fatty acid, LA, to GLA and/or the conversion of the substrate fatty acid, ALA, to STA; 4) Δ12 desaturases that catalyze the conversion of the substrate fatty acid, oleic acid, to LA; 5) Δ15 desaturases that catalyze the conversion of the substrate fatty acid, LA, to ALA and/or the conversion of the substrate fatty acid, GLA, to STA; 6) Δ4 desaturases that catalyze the conversion of the substrate fatty acid, DPA, to DHA and/or the conversion of the substrate fatty acid, DTA, to DPAn-6; 7) Δ8 desaturases that catalyze the conversion of the substrate fatty acid, EDA, to DGLA and/or the conversion of the substrate fatty acid, ETrA, to ETA; and, 8) Δ9 desaturases that catalyze the conversion of the substrate fatty acid, palmitate, to palmitoleic acid (16:1) and/or the conversion of the substrate fatty acid, stearic acid, to oleic acid. Δ15 and Δ17 desaturases are also occasionally referred to as "omega-3 desaturases", "ω-3 desaturases", and/or "Δ-3 desaturases", based on their ability to convert ω-6 fatty acids into their ω-3 counterparts (e.g., conversion of LA into ALA and ARA into EPA, respectively). It may be desirable to desirable to empirically determine the specificity of a particular fatty acid desaturase by transforming a suitable host with the gene for the fatty acid desaturase and determining its effect on the fatty acid profile of the host.

As used herein, the term "elongase" refers to a polypeptide that can elongate a fatty acid carbon chain to produce an acid 2 carbons longer than the fatty acid substrate that the elongase acts upon. This process of elongation occurs in a multi-step mechanism in association with fatty acid synthase, as described in U.S. Pat. App. Pub. No. 2005/0132442 and Int'l App. Pub. No. WO 2005/047480. Examples of reactions catalyzed by elongase systems are the conversion of GLA to DGLA, STA to ETA and EPA to DPA. In general, the substrate selectivity of elongases is somewhat broad but segregated by both chain length and the degree and type of unsaturation. For example, a $C_{14/16}$ elongase will utilize a $C_{14}$ substrate (e.g., myristic acid), a $C_{16/18}$ elongase will utilize a $C_{16}$ substrate (e.g., palmitate), a $C_{18/20}$ elongase will utilize a $C_{18}$ substrate (e.g., GLA, STA) and a $C_{20/22}$ elongase will utilize a $C_{20}$ substrate (e.g., EPA). In like manner, a Δ9 elongase is able to catalyze the conversion of LA and ALA to EDA and ETrA, respectively. It is important to note that some elongases have broad specificity and thus a single enzyme may be capable of catalyzing several elongase reactions. For example, a single enzyme may thus act as both a $C_{16/18}$ elongase and a $C_{18/20}$ elongase.

Genetically Engineered Oleaginous Yeast for PUFA Production

As described above, oleaginous yeast can be engineered to produce ω-3/ω-6 PUFAs by integration of appropriate heterologous genes encoding desaturases and elongases of the Δ6 desaturase/Δ6 elongase pathway or the Δ9 elongase/Δ8 desaturase pathway into the host organism for production of any particular PUFA of interest. Preferred genes and considerations for choosing a specific polypeptide having desaturase or elongase activity are detailed in U.S. patent application Ser. No. 11/198,975, Ser. No. 11/265,761, Ser. No. 11/264,784, Ser. No. 11/264,737 and Ser. No. 12/244,822, as are details concerning additional modifications that may be required to enable high level production of a particular PUFA, including: 1) manipulation of the activity of acyltransferases that allow for the transfer of omega fatty acids into storage lipid pools (i.e., the TAG fraction); 2) over-expression of desaturases, elongases, diacylglycerol cholinephosphotransferases and acyltransferases by use of strong promoters, expression in multicopy, and/or codon-optimization; 3) down-regulation of the expression of specific genes within the PUFA biosynthetic pathway that diminish overall accumulation of the desired PUFA; and, 4) manipulation of pathways and global regulators that affect production of the desired PUFA. The term "high-level production" refers to production of at least about 5% of the desired PUFA (i.e., LA, ALA, EDA, GLA, STA, ETrA, DGLA, ETA, ARA, EPA, DTA, DPAn-6, DPA and/or DHA) in the total lipids of the microbial host, preferably at least about 10% of the desired PUFA in the total lipids, more preferably at least about 15-25% of the desired PUFA in the total lipids, more preferably at least about 25-35% of the desired PUFA in the total lipids, and most preferably at least about 35-45% of the desired PUFA in the total lipids. The structural form of the PUFA is not limiting; thus, for example, the EPA may exist in the total lipids as free fatty acids or in esterified forms such as acylglycerols, phospholipids, sulfolipids or glycolipids Although numerous oleaginous yeast could be engineered for production of preferred ω-3/ω-6 PUFAs based on the teachings herein and in co-pending and commonly owned U.S. patent application Ser. No. 11/198,975 [Int'l. App. Pub. No. WO 2006/033723], Ser. No. 11/265,761 [Int'l. App. Pub. No. WO 2006/052870], Ser. No. 11/264,784 [Int'l. App. Pub. No. WO 2006/055322], Ser. No. 11/264,737 [Int'l. App. Pub. No. WO 2006/052871] and Ser. No. 12/244,822 (filed Oct. 3, 2008), representative strains of the oleaginous yeast *Yarrowia lipolytica* are described in Table 11 of Example 5. These include the following strains that have been deposited with the American Type Culture Collection (ATCC): *Y. lipolytica* strain Y2047 (producing ARA via the Δ6 desaturase/Δ6 elongase pathway; ATCC Accession No. PTA-7186); *Y. lipolytica* strain Y2096 (producing EPA via the Δ6 desaturase/Δ6 elongase pathway; ATCC Accession No. PTA-7184); *Y. lipolytica* strain Y2201 (producing EPA via the Δ9 elongase/Δ8 desaturase pathway; ATCC Accession No. PTA-7185); and *Y. lipolytica* strain Y3000 (producing DHA via the Δ6 desaturase/Δ6 elongase pathway; ATCC Accession No. PTA-7187); *Y. lipolytica* strain Y4128 (producing EPA via the Δ9 elongase/Δ8 desaturase pathway; ATCC Accession No. PTA-8614); and *Y. lipolytica* strain Y4127 (producing EPA via the Δ9 elongase/Δ8 desaturase pathway; ATCC Accession No. PTA-8802).

Oleaginous Yeast for PUFA Production and $CoQ_{10}$ Production

In living organisms, lipids serve as structural components of cell membranes, are important hormones or contain essential fatty acids, and are used for energy storage. TAGs are the primary storage unit for fatty acids; and, a wide spectrum of fatty acids can be incorporated into TAGs, including saturated and unsaturated fatty acids and short-chain and long-chain fatty acids. Some non-limiting examples of fatty acids that can be incorporated into TAGs by acyltransferases include: capric (10:0), lauric (12:0), myristic (14:0), palmitic (16:0), palmitoleic (16:1), stearic (18:0), oleic (18:1), vaccenic (18:1), LA, eleostearic (18:3), ALA, GLA, arachidic (20:0), EDA, ETrA, DGLA, ETA, ARA, EPA, behenic (22:0), DPA, DHA, lignoceric (24:0), nervonic (24:1), cerotic (26:0) and montanic (28:0) fatty acids.

Lipid peroxidation, which leads to rancidity in oils, most often affects PUFAs, because they contain multiple double bonds in between which lie methylene (i.e., $—CH_2$) groups that are especially reactive to hydrogen. The oxygen-dependent deterioration can occur non-enzymatically via a free radical chain reaction mechanism (i.e., autoxidation) or via photo-oxygenation; additionally, fatty acids may also be peroxidized via enzymatic peroxidation (i.e., via lipoxygenase enzymes). Furthermore, fatty acids may be autoxidized either in free form or combined into glycerolipids or glycolipids. Thus, oxidized triacylglycerol monomers include molecules containing different oxygenated groups, mainly hydroxyl-, keto- and epoxy-, as well as short-chain fatty acyl and short-chain n-oxo fatty acyl groups as the main products (Chang, S. S. et al., *JOACS,* 55:718 (1978); Velasco, J. et al., *Eur. J. Lipid Sci. Technol.,* 106:728 (2004)). Autoxidation of fatty acids with more than 3 double bonds leads to even more complex mixtures of product (e.g., see Porter, N. A. et al., *J. Am. Chem. Soc.,* 103:6447 (1981) and Bruna, E. et al., *Lipids,* 24:970 (1990) concerning autoxidation of arachidonic, pentaenoic and hexaenoic acids).

Based on the above, a recombinant oleaginous yeast engineered to co-produce both $CoQ_{10}$ and PUFAs should prove advantageous. It is expected that the presence of $CoQ_{10}$ should minimize overall lipid peroxidation and thus stabilize the PUFAs. Thus, described herein is a recombinant oleaginous yeast production host for the production of antioxidants and PUFAs comprising:

a) at least one copy of a ddsA gene encoding a decaprenyl diphosphate synthase, wherein expression of said decaprenyl diphosphate synthase enzyme results in the production of $COQ_{10}$; and, b) a functional ω-3/ω-6 PUFA biosynthetic pathway, wherein expression of said ω-3/ω-6 PUFA biosynthetic pathway results in the production of at least one PUFA selected from the group consisting of: an ω-6 PUFA and an ω-3 PUFA;

wherein said oleaginous yeast produces at least about 25 weight percent (%) of its DCW as oil.

Similarly, described herein is a method for the production of $CoQ_{10}$ and PUFAs in a recombinant oleaginous yeast, comprising:

a) providing an oleaginous yeast, the oleaginous yeast
   1.) producing a quinone of the coenzyme Q series selected from the group consisting of: $CoQ_6$, $CoQ_7$, $CoQ_8$ and $CoQ_9$,; and,
   2.) comprising genetic constructs encoding a functional ω-3/ω-6 polyunsaturated fatty acid biosynthetic pathway whereby the transformed yeast cells produce at least one polyunsaturated fatty acid;

b) transforming the oleaginous yeast host cell with at least one copy of a genetic construct encoding decaprenyl diphosphate synthase; and, c) culturing the transformed yeast cells of step (b) under suitable conditions, whereby
   i.) the decaprenyl diphosphate synthase is expressed and whereby $CoQ_{10}$ is produced; and,
   ii.) the functional ω-3/ω-6 PUFA biosynthetic pathway is expressed and at least one PUFA is produced selected from the group consisting of LA, ALA, EDA, GLA, STA, ETrA, DGLA, ETA, ARA, DTA, DPAn-6, EPA, DPA and DHA.

The oleaginous yeast preferably is a recombinant strain of *Yarrowia lipolytica* that has been previously engineered for high-level production of a preferred ω-3/ω-6 PUFA. Upon transformation with at least one ddsA gene using the methodology described previously, the resultant recombinant yeast will co-produce $CoQ_{10}$ and PUFAs.

A variety of means are available to increase the total amount of $CoQ_{10}$ that is produced in the above recombinant oleaginous yeast. For example, previous work in *Yarrowia lipolytica* has demonstrated that use of strong promoters, expression in multicopy, and/or codon-optimization of heterologous genes can very successfully be used as a means to increase expression. These tools should be equally applicable with respect to expression of decaprenyl diphosphate synthase (encoded by ddsA).

Manipulation of pathways and global regulators that affect production of $CoQ_{10}$ and/or down-regulation of the expression of specific genes within the $CoQ_{10}$ biosynthetic pathway that diminish overall accumulation of $CoQ_{10}$ are also contemplated by the Applicants herein as a means to increase $CoQ_{10}$ production. For example, it may be useful to disrupt the recombinant host organism's native E-polyprenyl diphosphate synthases that do not have decaprenyl diphosphate synthase activity, to thereby enable all CoQ production in the engineered recombinant host to be in the form of $CoQ_{10}$. Thus, when engineering *Yarrowia lipolytica* for $CoQ_{10}$ production, for example, it may prove useful to diminish or inactivate the organism's native solanesyl diphosphate synthase. Furthermore, rate limiting steps in the pathway can be identified and overcome by increasing the expression level of the genes involved.

Preferably, the $CoQ_{10}$ produced is at least about 0.0001% of the total DCW, more preferably at least about 0.001%, more preferably at least about 0.01%, even more preferably at least about 0.1% and most preferably at least about 1% of the total DCW.

The naturally produced CoQg and recombinantly produced $CoQ_{10}$ by *Yarrowia lipolytica* during fermentation is typically in a substantially reduced state. As used herein, "substantially reduced form of CoQ" or "substantially reduced" refers to a condition where the majority of the CoQ present in a composition is in the reduced form. In one aspect, substantially reduced refers to a condition whereby at least about 50% of the CoQ (percentage based on total CoQ present) in a composition is in the reduced state, preferably at least about 70% is in the reduced form, more preferably at least about 80% is in the reduced form, even more preferably at least about 90% is in the reduced form, yet even more preferably at least about 95% is in the reduced form, and most preferably at least about 98% of the CoQ in a composition is in the reduced form.

Production of $CoQ_{10}$ PUFAs, and Carotenoids in Oleaginous Yeast Carotenoid Definitions and Biosynthetic Pathway As used herein, the term "isoprenoid compound" refers to compounds formally derived from isoprene (2-methylbuta-1,3-diene; $CH_2{=}C(CH_3)CH{=}CH_2$), the skeleton of which can generally be discerned in repeated occurrence in the molecule. These compounds are produced biosynthetically via the isoprenoid pathway beginning with isopentenyl pyrophosphate (IPP) and formed by the head-to-tail condensation of isoprene units, leading to molecules which may be, for example, of 5, 10, 15, 20, 30, or 40 carbons in length.

As used herein, the term "carotenoid" refers to a class of hydrocarbons having a conjugated polyene carbon skeleton formally derived from isoprene. Although carotenoids can be of various lengths and can be acyclic or terminated with one (monocyclic) or two (bicyclic) cyclic end groups, for the purposes of the present application the term carotenoids will generally refer to $C_{40}$ carotenoids that consist of eight isoprenoid units joined in such a manner that the arrangement of isoprenoid units is reversed at the center of the molecule so that the two central methyl groups are in a 1,6-positional relationship and the remaining nonterminal methyl groups are in a 1,5-positional relationship. All $C_{40}$ carotenoids may be formally derived from the acyclic $C_{40}H_{56}$ structure. These molecules typically have strong light absorbing properties. Also, these compounds react destructively with oxygen and hence may require other antioxidant compounds that act as preservatives.

$C_{40}$ carotenoids may include both carotenes and xanthophylls. A "carotene" refers to a hydrocarbon carotenoid. The term "xanthophyll" refers to a $C_{40}$ carotenoid that contains one or more oxygen atoms in the form of hydroxy-, methoxy-, oxo-, epoxy-, carboxy- or aldehydic functional groups. Examples of xanthophylls include, but are not limited to: antheraxanthin, adonixanthin, astaxanthin, canthaxanthin, β-cryptoxanthin, keto-γ-carotene, echinenone, 3-hydroxyechinenone, 3'-hydroxyechinenone, zeaxanthin, adonirubin, tetrahydroxy-β,β'-caroten-4,4'-dione, tetrahydroxy-β,β'-caroten-4-one, caloxanthin, erythroxanthin, nostoxanthin, flexixanthin, 3-hydroxy-γ-carotene, 3-hydroxy-4-keto-γ-carotene, bacteriorubixanthin, bacteriorubixanthinal and lutein. In one aspect, preferred xanthophylls are selected from the group consisting of: lycopene, β-carotene, canthaxanthin, astaxanthin and zeaxanthin.

As used herein, the terms "carotenoid biosynthetic pathway" and "carotenoid pathway" will be used interchangeably and refer to those enzymes which convert farnesyl pyrophosphate (FPP) to a $C_{40}$ carotenoid. The enzymes within this pathway are encoded by the "crt" genes including, but not limited to: crtE, crtY, crtI, crtB, crtZ, crtO, and crtW. Finally, the term "carotenoid biosynthetic enzyme" is an inclusive term referring to any and all of the enzymes in the pathway involved in the biosynthesis of astaxanthin including, but not limited to: CrtE, CrtY, CrtI, CrtB, CrtZ, CrtO and CrtW.

The genetics of carotenoid biosynthesis are well known (Armstrong, G., in *Comprehensive Natural Products Chemistry*, Elsevier, v. 2, pp 321-352 (1999)); Lee, P. and Schmidt-Dannert, C., *Appl. Microbiol. Biotechnol.,* 60:1-11 (2002); Lee et al., *Chem. Biol.,* 10:453-462 (2003), and Fraser, P. and Bramley, P. (*Progress in Lipid Research,* 43:228-265 (2004)).

This pathway is extremely well studied in the Gram-negative, pigmented bacteria of the genera *Pantoea*, formerly known as *Erwinia*. Of particular interest are the genes responsible for the production of $C_{40}$ carotenoids used as pigments in animal feed (e.g., zeaxanthin, lutein, canthaxanthin and astaxanthin).

Figure 3A:
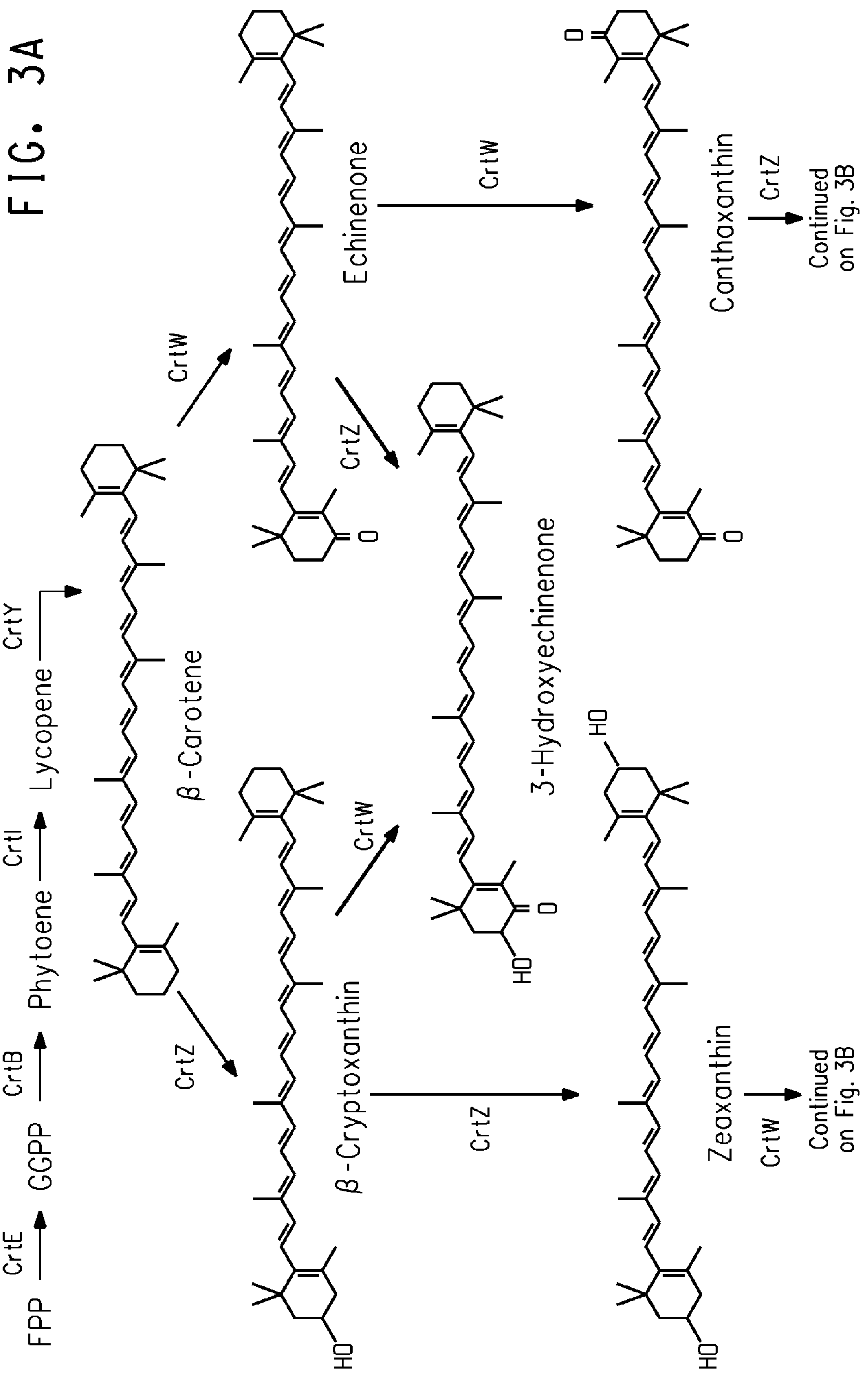
FIGS. 3A and 3B illustrates the carotenoid biosynthetic pathway from farnesyl pyrophosphate to astaxanthin.
Figure 3B:
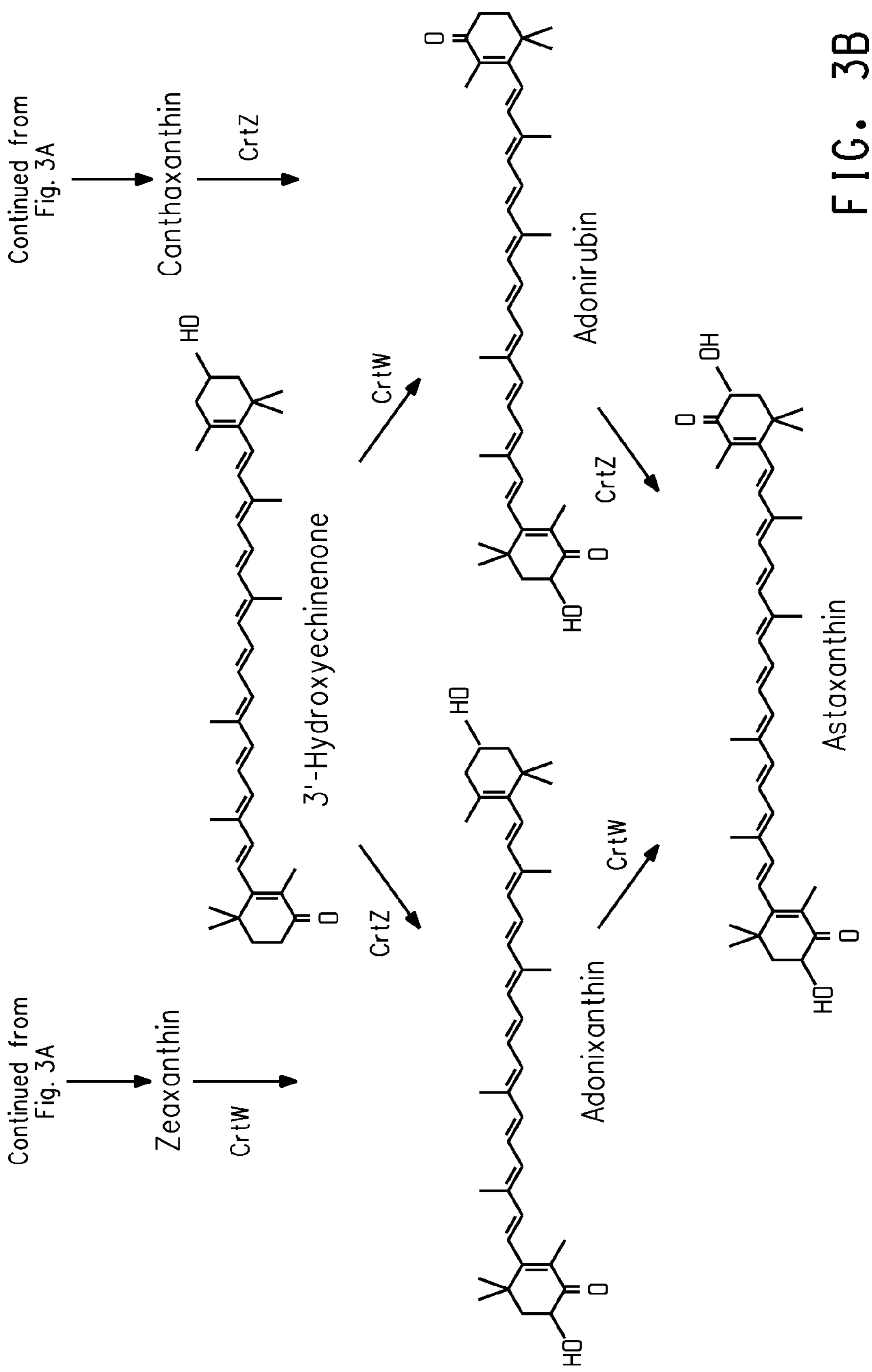

Although the enzymatic pathway involved in the biosynthesis of carotenoid compounds converts FPP to $C_{40}$ carotenoids, the pathway can be subdivided into two parts comprising: 1) the $C_{40}$ backbone genes (i.e., crtE, crtB, crtI, and crtY) encoding enzymes responsible for converting FPP to β-carotene; and, 2) subsequent functionalization genes (e.g., crtW, crtO, crtR, crtX and crtZ) responsible for adding various functional groups to the β-ionone rings of β-carotene (FIGS. 3A and 3B).

More specifically, the carotenoid biosynthetic pathway begins with the conversion of FPP to geranylgeranyl pyrophosphate (GGPP). In this first step, the enzyme geranylgeranyl pyrophosphate synthase (encoded by the crtE gene) condenses the $C_{15}$ FPP with a $C_5$ isopentenyl diphosphate (IPP), creating the $C_{20}$ compound GGPP. Thus, the term "CrtE" refers to a geranylgeranyl pyrophosphate synthase enzyme encoded by the crtE gene and which converts trans-trans-farnesyl diphosphate and IPP to pyrophosphate and GGPP. Next, a phytoene synthase (encoded by the gene crtB) condenses two GGPP molecules to form phytoene, the first $C_{40}$ carotenoid compound in the pathway. The term "CrtB" refers to a phytoene synthase enzyme encoded by the crtB gene which catalyzes the reaction from prephytoene diphosphate to phytoene. Subsequently, a series of sequential desaturations (i.e., producing the intermediaries of phytofluene, ζ-carotene and neurosporene) occur catalyzed by the enzyme phytoene desaturase (encoded by the gene crtI), resulting in the production of lycopene. As used herein, the term "CrtI" refers to a phytoene desaturase enzyme encoded by the crtI gene which converts phytoene into lycopene by the introduction of 4 double bonds. Finally, the enzyme lycopene cyclase (encoded by the gene crtY) forms β-ionone rings on each end of lycopene, forming the bicyclic carotenoid β-carotene. The term "CrtY" refers to a lycopene cyclase enzyme encoded by the crtY gene that converts lycopene to β-carotene.

The rings of β-carotene can subsequently be functionalized by a carotenoid ketolase (encoded by the genes crtW, crtO or bkt) and/or carotenoid hydroxylase (encoded by the genes crtZ or crtR) forming commercially important xanthophyll pigments such as canthaxanthin, astaxanthin and zeaxanthin. In terms of the ketolation and hydroxylation reactions, the CrtW-type ketolases and the CrtZ-type hydroxylases are preferred. The pathway from β-carotene to astaxanthin is somewhat non-linear in nature as a variety of intermediates can be formed (FIGS. 3A and 3B).

As used herein, the term "CrtW" refers to a β-carotene ketolase (also referred to as a carotenoid ketolase) enzyme encoded by the crtW gene that catalyzes an oxidation reaction where a keto group is introduced on the β-ionone type ring of cyclic carotenoids. This reaction converts cyclic carotenoids (i.e., β-carotene or zeaxanthin) into ketocarotenoids (i.e., canthaxanthin or astaxanthin, respectively). Intermediates in the process typically include echinenone and adonixanthin.

As used herein, the term "CrtO" refers to a β-carotene ketolase (also referred to as a carotenoid ketolase) enzyme encoded by the crtO gene that catalyzes an oxidation reaction where a keto group is introduced on the β-ionone type ring of cyclic carotenoids. The CrtO-type carotenoid ketolases are structurally unrelated to the CrtW-type ketolases. This reaction converts cyclic carotenoids (i.e., β-carotene or zeaxanthin) into ketocarotenoids (i.e., canthaxanthin or astaxanthin, respectively). Intermediates in the process typically include echinenone and adonixanthin. In one aspect, a mixture of CrtW-type and CrtO-type carotenoid ketolases are used to produce the desired ketocarotenoids.

As used herein, the term "CrtZ" refers to a carotenoid hydroxylase enzyme (also referred to herein as a "β-carotene hydroxylase") encoded by the crtZ gene that catalyzes a hydroxylation reaction. The oxidation reaction adds a hydroxyl group to cyclic carotenoids having a β-ionone type ring.

It is known that CrtW ketolases, CrtO ketolases and CrtZ hydroxylases typically exhibit substrate flexibility, enabling production of a variety of ketocarotenoids or hydroxylated carotenoids, respectively, depending upon available substrates.

Genetically Engineered Oleaginous Yeast for Carotenoid Production

It has recently been demonstrated that oleaginous yeast can be engineered to produce $C_{40}$ carotenoids by integration of appropriate heterologous genes encoding cdE, crtY, crtI, crtB, crtZ, crtO and crtW into the host organism for production of any particular $C_{40}$ carotenoid of interest (see U.S. patent application Ser. No. 11/952,243 [Int'l. App. Pub. No. WO 2008/073367]).

The source of the carotenoid biosynthesis gene(s) to be heterologously expressed in an oleaginous yeast, such as *Yarrowia lipolytica*, may vary as carotenoid biosynthesis has been reported in a variety of organisms. Depending upon the source of carotenoid biosynthesis gene(s), it may be necessary to codon-optimize at least a portion (up to the entire length) of the gene targeted for heterologous expression using the preferred codon usage within the host cell. The preferred codon usage for *Yarrowia lipolytica* has previously been reported (see U.S. Pat. No. 7,125,672).

The genes required for carotenoid production are well-known in the art and can be selected based on the carotenoid targeted for production, as summarized in the Table below.

TABLE 3

| Genes Required For Synthesis Of Various Carotenoids | crtE | crtB | crtI | crtY | crtW or crtO | crtZ or crtR |
|---|---|---|---|---|---|---|
| Lycopene | 1 (+) | 1 (+) | 1 (+) | — | — | — |
| β-Carotene | 1 (+) | 1 (+) | 1 (+) | 1 (+) | — | — |
| Canthaxanthin | 1 (+) | 1 (+) | 1 (+) | 1 (+) | 1 (+) | — |
| Zeaxanthin | 1 (+) | 1 (+) | 1 (+) | 1 (+) | — | 1 (+) |
| Astaxanthin | 1 (+) | 1 (+) | 1 (+) | 1 (+) | 1 (+) | 1 (+) |

Note:
The designation 1 (+) represents "one or more".

Thus, for example, production of a ketocarotenoid, such as canthaxanthin, will require expression of the $C_{40}$ backbone genes (i.e., crtE, crtB, crtI and crtY) and at least one carotenoid ketolase gene (i.e., crtW and/or crtO). Production of hydroxylated carotenoids, such as zeaxanthin and astaxanthin, require the expression of the $C_{40}$ backbone genes (i.e., crtE, crtB, crtI and crtY) and at least one carotenoid hydroxylating gene (i.e., crtZ).

Examples of suitable carotenoid biosynthesis genes include, but are not limited to those provided in Table 4.

TABLE 4

Sources of Genes Encoding the Carotenoid Biosynthetic Pathway

| Gene | GenBank ® Accession Number |
|---|---|
| crtE (GGPP Synthase) | AB000835, AB016043, AB019036, AB016044, AB027705, AB027706, AB034249, AB034250, AF020041, AF049658, AF049659, AF139916, AF279807, AF279808, AJ010302, AJ133724, AJ276129, D85029, L25813, L37405, U15778, U44876, X92893, X95596, X98795 and Y15112 |
| crtX (Zeaxanthin glucosylase) | D90087, M87280 and M90698 |
| crtY (Lycopene-β-cyclase) | AF139916, AF152246, AF218415, AF272737, AJ133724, AJ250827, AJ276965, D58420, D83513, L40176, M87280, U50738, U50739, U62808, X74599, X81787, X86221, X86452, X95596 and X98796 |
| crtI (Phytoene desaturase) | AB046992, AF039585, AF049356, AF139916, AF218415, AF251014, AF364515, D58420, D83514, L16237, L37405, L39266, M64704, M88683, S71770, U37285, U46919, U62808, X55289, X59948, X62574, X68058, X71023, X78271, X78434, X78815, X86783, Y14807, Y15007, Y15112, Y15114 and Z11165 |
| crtB (Phytoene synthase) | AB001284, AB032797, AB034704, AB037975, AF009954, AF139916, AF152892, AF218415, AF220218, AJ010302, AJ133724, AJ278287, AJ304825 and AJ308385, D58420, L23424, L25812, L37405, M38424, M87280, S71770, U32636, U62808, U87626, U91900, X52291, X60441, X63873, X68017, X69172 and X78814 |
| crtZ (β-carotene hydro-xyllase) | D58420, D58422, D90087, M87280, U62808 and Y15112 |
| crtW (β-carotene ketolase) | AF218415, D45881, D58420, D58422, X86782 and Y15112 |

Preferred sources of carotenoid biosynthesis genes are from *Pantoea stewartii* (ATCC #8199; Int'l. App. Pub. No. WO 2002/079395), *Pantoea stewartii* DC413 (U.S. Pat. No. 7,288,387), *Pantoea agglomerans* DC404 (U.S. Pat. No. 6,929,928), Enterobacteriaceae DC260 (U.S. Pat. No. 7,064,196), *Brevundimonas vesicularis* DC263 (U.S. Pat. No. 7,252,985 and U.S. Pat. No. 7,091,031), *Sphingomonas melonis* DC18 (U.S. Pat. No. 7,252,985), *Novosphingobium aromaticivorans* ATCC #700278 (U.S. Pat. No. 7,091,031) and *Agrobacterium aurantiacum* (U.S. Pat. No. 5,811,273, U.S. Pat. No. 5,972,690 and U.S. Pat. No. 6,150,130).

By using various combinations of the genes presented in Table 4, a variety of $C_{40}$ carotenoids can be made from FPP. Furthermore, one of skill in the art recognizes that the copy number and/or the expression level of each gene can be altered for optimal carotenoid production. The recombinant oleaginous yeast may comprise at least one copy of each gene required to produce the desired carotenoid. More preferred, the recombinant oleaginous yeast comprises a plurality of each gene required to produce the desired carotenoid. To clarify, for example, if 2 copies of a crtY are required, this can refer to: 1) two copies of an identical coding sequence for a particular crtY isolated from a single species; or, 2) one coding sequence for crtY isolated from a species "A" and one coding sequence for a crtY isolated from a species "B", thus collectively resulting in two crtY genes.

It is also understood that one or more genes in the mevalonate pathway may be overexpressed to increase carotenoid production. This is especially true when the concentration of FPP appears to be limited.

It is also understood that one or more genes encoding enzymes that direct carbon flow away from carotenoid biosynthesis may be downregulated and/or disrupted (assuming it is not an essential gene) to increase carotenoid and/or isoprenoid production. Means to down-regulate and/or disrupt genes are well known in the art (Maniatis, supra).

Numerous oleaginous yeast could be engineered for production of preferred $C_{40}$ carotenoids based on the teachings in co-pending U.S. patent application Ser. No. 11/952,243 [Int'l. App. Pub. No. WO 2008/073367]. Representative carotenoid-producing strains of the oleaginous yeast *Yarrowia lipolytica* described therein include the following: *Y. lipolytica* strain LY5 (producing lycopene), the *Y. lipolytica* YCS1001-YCS1010 series and YCS1011-YCS1020 series (producing lycopene), the *Y. lipolytica* YCS1200 series and YCS1300 series (producing primarily β-carotene), the *Y. lipolytica* YCS3700 series and YCS4100 series (producing zeaxanthin), and the *Y. lipolytica* YCS4100 series (producing canthaxanthin). Although these strains are not high-producing, they are suitable to demonstrate proof of concept. Following the teachings provided to enable high-level production of various PUFAs (e.g., use of strong promoters, expression of genes in high copy number), similar strategies could readily be applied to enable one skilled in the art to genetically engineer a strain of *Y. lipolytica* having the ability to produce high titers of preferred $C_{40}$ carotenoids, wherein the total $C_{40}$ carotenoid in the microbial host is preferably at least about 100 ppm, more preferably at least about 500 ppm and most preferably at least about 1000 ppm.

It should be noted that, for those recombinant oleaginous yeast hosts that produce more than one carotenoid, it will sometimes be possible to adjust the relative amounts of individual carotenoids produced by adjusting growth conditions. For example, it has been reported that controlling the concentration of dissolved oxygen in a culture during cultivation can regulate relative production levels of certain carotenoids such as β-carotene, echinenone, β-cryptoxanthin, 3-hydroxyechinenone, asteroidenone, canthaxanthin, zeaxanthin, adonirubin, adonixanthin and astaxanthin (see, for example, U.S. Pat. No. 6,825,002).

Genetically Engineered Oleaginous Yeast for $CoQ_{10}$ PUFA and Carotenoid Production Also provided herein are recombinant oleaginous yeast producing $CoQ_{10}$, PUFAs and $C_{40}$ carotenoids. A PUFA-producing yeast is effectively transformed with the genetic elements of the $C_{40}$ pathway as described herein and a gene (ddsA) responsible for the condensation reaction that polymerizes prenyl diphosphate (an allylic primer) and 3-isopentenyl diphosphate (IPP) to produce polyprenyl diphosphate. Enzymes of particular usefulness in the expression of $C_{40}$ carotenoids include, but are not limited to phytoene synthase (crtB), phytoene desaturase (crtI), lycopene cyclase (crtY), carotenoid hydroxylase (crtZ), and a carotenoid ketolase (crtW). Carotenoids of particular relevance herein include but are not limited to: lycopene, β-carotene, zeaxanthin, lutein, canthaxanthin and astaxanthin. ω-3 PUFAs including ALA, STA, ETA, ETrA, EPA, DPA and DHA and ω-6 PUFAs including LA, GLA, EDA, DGLA, ARA, DTA and DPAn-6 are of particular interest. PUFA synthesis may take many paths but generally utilizes enzymes selected from the group consisting of desaturases (e.g., Δ4, Δ5, Δ6, Δ8, Δ9, Δ12, Δ15, Δ17 desaturases) and elongases (e.g., Δ9 elongases and $C_{14/16}$, $C_{16/18}$, $C_{18/20}$ and $C_{20/22}$ elongases).

These host may be genetically engineered using methods well known in the art.

Microbial Expression Systems, Cassettes & Vectors, and Transformation

Microbial expression systems and expression vectors containing regulatory sequences that direct high level expression of foreign proteins are well known to those skilled in the art. Any of these could be used to construct chimeric genes for production of the desired compounds, that is, $CoQ_{10}$ and PUFAs (and optionally, $C_{40}$ carotenoids). These chimeric genes could then be introduced into appropriate microorganisms via transformation to allow for high level expression of the enzymes.

Vectors (e.g., constructs, plasmids) and DNA expression cassettes are well known in the art. The specific choice of sequences present in the construct is dependent upon the desired expression products (supra), the nature of the host cell and the proposed means of separating transformed cells versus non-transformed cells. Typically, however, the vector contains at least one expression cassette, a selectable marker and sequences allowing autonomous replication or chromosomal integration. Suitable expression cassettes comprise a region 5' of the gene that controls transcriptional initiation (e.g., a promoter), the gene coding sequence, and a region 3' of the DNA fragment that controls transcriptional termination (i.e., a terminator). It is most preferred when both control regions are derived from genes homologous to the transformed host cell, although it is to be understood that such control regions need not be derived from the genes native to the specific species chosen as a production host.

Initiation control regions or promoters, which are useful to drive expression of the relevant genes in the desired yeast host cell are numerous and familiar to those skilled in the art. Virtually any promoter capable of directing expression of these genes in the selected host cell is suitable. Expression in a host cell can be accomplished in a transient or stable fashion. Transient expression can be accomplished by inducing the activity of a regulatable promoter operably linked to the gene of interest. Stable expression can be achieved by the use of a constitutive promoter operably linked to the gene of interest. As an example, when the host cell is yeast, transcriptional and translational regions functional in yeast cells are provided, particularly from the host species (e.g., see U.S. Pat. No. 7,238,482 and Int'l.

App. Pub. No. WO 2006/052870 [U.S. Publication 2006-0115881-A1] for preferred transcriptional initiation regulatory regions for use in *Yarrowia lipolytica*). Any one of a number of regulatory sequences can be used, depending upon whether constitutive or induced transcription is desired, the efficiency of the promoter in expressing the ORF of interest, the ease of construction and the like.

Nucleotide sequences surrounding the translational initiation codon 'ATG' have been found to affect expression in yeast cells. If the desired polypeptide is poorly expressed in yeast, the nucleotide sequences of exogenous genes can be modified to include an efficient yeast translation initiation sequence to obtain optimal gene expression. For expression in yeast, this can be done by site-directed mutagenesis of an inefficiently expressed gene by fusing it in-frame to an endogenous yeast gene, preferably a highly expressed gene. Alternatively, as demonstrated in *Yarrowia lipolytica*, one can determine the consensus translation initiation sequence in the host and engineer this sequence into heterologous genes for their optimal expression in the host of interest.

Termination control regions may be derived from various genes native to the preferred hosts. Optionally, a termination site may be unnecessary; however, it is most preferred if included. As used herein, the termination region can be derived from the 3' region of the gene from which the initiation region was obtained or from a different gene. A large number of termination regions are known and function satisfactorily in a variety of hosts (when utilized both in the same and different genera and species from where they were derived). Typically, the termination region usually is selected more as a matter of convenience rather than because of any particular property. For the purposes herein, wherein the host cell is an oleaginous yeast, the termination region is preferably derived from a yeast gene, particularly *Saccharomyces, Schizosaccharomyces, Candida, Yarrowia* or *Kluyveromyces*. The 3'-regions of mammalian genes encoding γ-interferon and α-2 interferon are also known to function in yeast. Although not intended to be limiting, preferred termination regions useful in the disclosure herein include: ~100 bp of the 3' region of the *Yarrowia lipolytica* extracellular protease (Xpr; GenBank® Accession No. M17741); the acyl-CoA oxidase (Aco3: GenBank® Accession No. AJ001301 and No. CAA04661; Pox3: GenBank® Accession No. XP_503244) terminators; the Pex20 (GenBank® Accession No. AF054613) terminator; the Pex16 (GenBank® Accession No. U75433) terminator; the Lip1 (GenBank® Accession No. Z50020) terminator; the Lip2 (GenBank® Accession No. AJ012632) terminator; and the 3-oxoacyl-coA thiolase (Oct; GenBank® Accession No. X69988) terminator.

As one of skill in the art is aware, merely inserting a gene into a cloning vector does not ensure that it will be successfully expressed at the level needed. In response to the need for a high expression rate, many specialized expression vectors have been created by manipulating a number of different genetic elements that control aspects of transcription, translation, protein stability, oxygen limitation and secretion from the microbial host cell. More specifically, some of the molecular features that have been manipulated to control gene expression include: 1) the nature of the relevant transcriptional promoter and terminator sequences; 2) the number of copies of the cloned gene and whether the gene is plasmid-borne or integrated into the genome of the host cell; 3) the final cellular location of the synthesized foreign protein; 4) the efficiency of translation and correct folding of the protein in the host organism; 5) the intrinsic stability of the mRNA and protein of the cloned gene within the host cell; and, 6) the codon usage within the cloned gene, such that its frequency approaches the frequency of preferred codon usage of the host cell. Each of these types of modifications are encompassed herein, as means to further optimize expression of the required ddsA genes and PUFA biosynthetic genes (and optionally carotenoid biosynthetic genes). Methods of codon-optimizing foreign genes for optimal expression in *Yarrowia lipolytica* are set forth in U.S. Pat. No. 7,125,672.

Once the DNA encoding a polypeptide suitable for expression in an appropriate microbial host cell (e.g., oleaginous yeast) has been obtained (e.g., a chimeric gene comprising a promoter, ORF and terminator), it is placed in a plasmid vector capable of autonomous replication in a host cell, or it is directly integrated into the genome of the host cell. Integration of expression cassettes can occur randomly within the host genome or can be targeted through the use of constructs containing regions of homology with the host genome sufficient to target recombination within the host locus. Where constructs are targeted to an endogenous locus, all or some of the transcriptional and translational regulatory regions can be provided by the endogenous locus.

Constructs comprising a coding region of interest may be introduced into a host cell by any standard technique. These techniques include transformation (e.g., lithium acetate transformation [Guthrie, C., *Methods in Enzymology,* 194:186-187 (1991)]), protoplast fusion, biolistic impact, electroporation, microinjection, or any other method that introduces the gene of interest into the host cell. More specific teachings applicable for oleaginous yeast (i.e., *Yarrowia lipolytica*)

include U.S. Pat. No. 4,880,741 and No. 5,071,764 and Chen, D. C. et al. (*Appl. Microbiol. Biotechnol.,* 48(2):232-235 (1997)).

The preferred method of expressing genes in *Yarrowia lipolytica* is by integration of linear DNA into the genome of the host; and, integration into multiple locations within the genome can be particularly useful when high level expression of genes are desired. For example, preferred loci for integration include: the Ura3 locus (GenBank® Accession No. AJ306421), the Leu2 gene locus (GenBank® Accession No. AF260230), the Lys5 gene (GenBank® Accession No. M34929), the Aco2 gene locus (GenBank® Accession No. AJ001300), the Pox3 gene locus (Pox3: GenBank® Accession No. XP_503244; or, Aco3: GenBank® Accession No. AJ001301), the Δ12 desaturase gene locus (U.S. Pat. No. 7,214,491), the Lip1 gene locus (GenBank® Accession No. Z50020), the Lip2 gene locus (GenBank® Accession No. AJ012632), the SCP2 gene locus (GenBank® Accession No. AJ431362), the Pex3 gene locus (GenBank® Accession No. CAG78565), the Pex16 gene locus (GenBank® Accession No. CAG79622) and/or the Pex10 gene locus (GenBank® Accession No. CAG81606).

Where two or more genes are expressed from separate replicating vectors, it is desirable that each vector has a different means of selection and should lack homology to the other construct(s) to maintain stable expression and prevent reassortment of elements among constructs. Judicious choice of regulatory regions, selection means and method of propagation of the introduced construct(s) can be experimentally determined so that all introduced genes are expressed at the necessary levels to provide for synthesis of the desired products.

For convenience, a host cell that has been manipulated by any method to take up a DNA sequence (e.g., an expression cassette) will be referred to as "transformed" or "recombinant" herein. The transformed host will have at least one copy of the expression construct and may have two or more, depending upon whether the gene is integrated into the genome, amplified, or is present on an extrachromosomal element having multiple copy numbers.

The transformed host cell can be identified by various selection techniques, as described in U.S. Pat. No. 7,238,482 and Int'l. App. Pub. No. WO 2006/052870 [U.S. Publication 2006-0115881-A1]. Preferred selection methods for use herein are resistance to kanamycin, hygromycin and the amino glycoside G418, as well as ability to grow on media lacking uracil, leucine, lysine, tryptophan or histidine. Alternately, 5-fluoroorotic acid (5-fluorouracil-6-carboxylic acid monohydrate; "5-FOA") is used for selection of yeast $Ura^-$ mutants. The compound is toxic to yeast cells that possess a functioning URA3 gene encoding orotidine 5'-monophosphate decarboxylase (OMP decarboxylase); thus, based on this toxicity, 5-FOA is especially useful for the selection and identification of $Ura^-$ mutant yeast strains (Bartel, P. L. and Fields, S., Yeast 2-Hybrid System, Oxford University: New York, v. 7, pp 109-147, 1997). More specifically, one can first knockout the native Ura3 gene to produce a strain having a Ura– phenotype, wherein selection occurs based on 5-FOA resistance. Then, a cluster of multiple chimeric genes and a new Ura3 gene can be integrated into a different locus of the *Yarrowia* genome to thereby produce a new strain having a Ura+ phenotype. Subsequent integration produces a new Ura3– strain (again identified using 5-FOA selection), when the introduced Ura3 gene is knocked out. Thus, the Ura3 gene (in combination with 5-FOA selection) can be used as a selection marker in multiple rounds of transformation.

An alternate preferred selection method utilized herein relies on a dominant, non antibiotic marker for *Yarrowia lipolytica* based on sulfonylurea resistance (see Int'l. App. Pub. No. WO 2006/052870 for additional details). The technique is also generally applicable to other industrial yeast strains that may be haploid, diploid, aneuploid or heterozygous. Specifically, the sulfonylurea resistance selection marker utilized herein for transforming *Yarrowia lipolytica* does not rely on a foreign gene but on a mutant native gene. Thus, it neither requires auxotrophy nor results in auxotrophy and allows transformation of wild type strains. More specifically, the marker gene (SEQ ID NO:1) is a native acetohydroxyacid synthase (AHAS or acetolactate synthase; E.C. 4.1.3.18) that has a single amino acid change (W497L) that confers sulfonyl urea herbicide resistance. AHAS is the first common enzyme in the pathway for the biosynthesis of branched-chain amino acids and it is the target of the sulfonylurea and imidazolinone herbicides. The W497L mutation has been reported in *Saccharomyces cerevisiae* (Falco, S. C., et al., *Dev. Ind. Microbiol.,* 30:187-194 (1989); Duggleby, R. G., et. al., *Eur. J. Biochem.,* 270:2895 (2003)).

An additional method for recycling a selection marker relies on site-specific recombinase systems. Briefly, the site-specific recombination system consists of two elements: 1) a recombination site having a characteristic DNA sequence [e.g., LoxP]; and, 2) a recombinase enzyme that binds to the DNA sequence specifically and catalyzes recombination (i.e., excision) between DNA sequences when two or more of the recombination sites are oriented in the same direction at a given interval on the same DNA molecule [e.g., Cre]. This methodology has utility as a means of selection, since it is possible to "recycle" a pair of preferred selection markers for their use in multiple sequential transformations.

Specifically, an integration construct is created comprising a target gene that is desirable to insert into the host genome (e.g., a ddsA gene), as well as a first selection marker (e.g., ura) that is flanked by recombination sites. Following transformation and selection of the transformants, the first selection marker is excised from the chromosome by the introduction of a replicating plasmid carrying a second selection marker (e.g., sulfonylurea resistance [AHAS]) and a recombinase suitable to recognize the site-specific recombination sites introduced into the genome. Upon selection of those transformants carrying the second marker and confirmation of excision of the first selection marker from the host genome, the replicating plasmid is then cured from the host in the absence of selection. This produces a transformant that possesses neither the first nor second selection marker, and thus the cured strain is available for another round of transformation. One skilled in the art will recognize that the methodology is not limited to the particular selection markers or site-specific recombination system used in the present description.

Metabolic Engineering in Microbes

Methods for manipulating biochemical pathways are well known to those skilled in the art; and, it is expected that numerous manipulations will be possible to maximize $CoQ_{10}$ and PUFA production (and optionally $C_{40}$ carotenoid biosynthesis) in oleaginous yeasts, and particularly, in *Yarrowia lipolytica*. This may require metabolic engineering directly within the $CoQ_{10}$, PUFA and/or $C_{40}$ carotenoid biosynthetic pathway or additional coordinated manipulation of various other metabolic pathways.

In the case of manipulations within the $CoQ_{10}$ biosynthetic pathway, it may be desirable to increase the production of FPP to enable increased production of $CoQ_{10}$. Introducing and/or amplifying the idi gene (responsible for isomerization of IPP to dimethyl allyl diphosphate, a rate limiting step in the biosynthesis of carotenoids genes [Wang et al., *Biotechnol. Bioeng.,* 62:235-241 (1999)]) may accomplish this. Similarly, to maximize production of $CoQ_{10}$, it is well known to one skilled in the art that production is favored in a host microorganism whose native E-polyprenyl diphosphate synthase is removed or inhibited, thereby minimizing production of other quinones of the coenzyme Q series, that is $Q_6$, $Q_7$, $Q_8$ and $Q_9$. The endogenous desaturase activity can be reduced or eliminated by, for example: 1) providing a cassette for transcription of antisense sequences to the native E-polyprenyl diphosphate synthase transcription product; 2) disrupting the native E-polyprenyl diphosphate synthase gene through insertion, substitution and/or deletion of all or part of the target gene; or, 3) using a host cell which naturally has [or has been mutated to have] low native E-polyprenyl diphosphate synthase activity.

Microbial Fermentation Processes

The transformed microbial host cell is grown under conditions that optimize expression of chimeric genes and produce the greatest and the most economical yield of desired $CoQ_{10}$ and PUFAs (and optionally, $C_{40}$ carotenoids). In general, media conditions that may be optimized include the type and amount of carbon source, the type and amount of nitrogen source, the carbon-to-nitrogen ratio, the oxygen level, growth temperature, pH, length of the biomass production phase, length of the oil accumulation phase and the time and method of cell harvest. Microorganisms of interest, such as oleaginous yeast (e.g., *Yarrowia lipolytica*) are generally grown in complex media (e.g., yeast extract-peptone-dextrose broth (YPD)) or a defined minimal media that lacks a component necessary for growth and thereby forces selection of the desired expression cassettes (e.g., Yeast Nitrogen Base (DIFCO Laboratories, Detroit, Mich.)).

Fermentation media for the methods and host cells described herein must contain a suitable carbon source such as are taught in U.S. Pat. No. 7,238,482. Suitable sources of carbon encompass a wide variety of sources, with sugars, glycerol and/or fatty acids being preferred. Most preferred is glucose and/or fatty acids containing between 10-22 carbons.

Nitrogen may be supplied from an inorganic (e.g., $(NH_4)_2SO_4$) or organic (e.g., urea or glutamate) source. In addition to appropriate carbon and nitrogen sources, the fermentation media must also contain suitable minerals, salts, cofactors, buffers, vitamins and other components known to those skilled in the art suitable for the growth of the oleaginous host and promotion of the enzymatic pathways necessary for $CoQ_{10}$ and PUFA production (and optionally, $C_{40}$ carotenoid production). Particular attention is given to several metal ions (e.g., $Fe^{+2}$, $Cu^{+2}$, $Mn^{+2}$, $Co^{+2}$, $Zn^{+2}$, $Mg^{+2}$) that promote synthesis of lipids and PUFAs (Nakahara, T. et al., *Ind. Appl. Single Cell Oils*, D. J. Kyle and R. Colin, eds. pp 61-97 (1992)).

Preferred growth media in the present invention are common commercially prepared media, such as Yeast Nitrogen Base (DIFCO Laboratories, Detroit, Mich.). Other defined or synthetic growth media may also be used and the appropriate medium for growth of the transformant host cells will be known by one skilled in the art of microbiology or fermentation science. A suitable pH range for the fermentation is typically between about pH 4.0 to pH 8.0, wherein pH 5.5 to pH 7.5 is preferred as the range for the initial growth conditions. The fermentation may be conducted under aerobic or anaerobic conditions, wherein microaerobic conditions are preferred.

Typically, accumulation of high levels of $CoQ_{10}$ and PUFAs (and optionally $C_{40}$ carotenoids) in oleaginous yeast cells requires a two-stage process, since the metabolic state must be "balanced" between growth and synthesis/storage of fats. Thus, most preferably, a two-stage fermentation process is necessary for production in oleaginous yeast (e.g., *Yarrowia lipolytica*). This approach is described in U.S. Pat. No. 7,238,482, as are various suitable fermentation process designs (i.e., batch, fed-batch and continuous) and considerations during growth.

Purification and Processing of $CoQ_{10}$ and PUFAs

The primary product is oleaginous yeast biomass. As such, isolation and purification of the $CoQ_{10}$- and PUFA-containing oils (optionally including carotenoids) from the biomass may not be necessary (i.e., wherein the biomass is the product).

However, certain end uses may require partial and/or complete isolation/purification of the $CoQ_{10}$- and PUFA-containing oils (optionally including carotenoids) from the biomass. Given the lipophilic/hydrophobic nature of carotenoids, many techniques applied to isolate/purify microbially produced oils/PUFAs should work to isolate carotenoids as well, especially when the desired product is a pigmented oil. As such, any number of well known techniques can be used to isolate the lipophilic/hydrophobic compounds from the biomass including, but not limited to extraction (e.g., U.S. Pat. No. 6,797,303 and No. 5,648,564) with organic solvents, sonication, supercritical fluid extraction (e.g., using carbon dioxide), saponification and physical means such as presses, or combinations thereof. One is referred to the teachings of U.S. Pat. No. 7,238,482 for additional details.

One review of PUFA extraction techniques, quality analysis and acceptability standards for yeast lipids is that of Z. Jacobs (*Critical Reviews in Biotechnology,* 12(5/6):463-491 (1992)). A brief review of downstream processing is also available by A. Singh and O. Ward (*Adv. Appl. Microbiol.,* 45:271-312 (1997)).

Use of Compositions Comprising $CoQ_{10}$

Given the desire for natural antioxidants in the e.g., food/feed industry and the proven ability to recombinantly produce $CoQ_{10}$ and ω-3/ω-6 PUFAs in an oleaginous yeast, it is expected that the $CoQ_{10}$ may function as a useful antioxidant to stabilize ω-3/ω-6 PUFAs and ω-3/ω-6 PUFA/$C_{40}$ carotenoid mixtures. As such, a method to stabilize microbially produced PUFAs and PUFA/carotenoid mixtures using $CoQ_{10}$ is provided. Similarly, "stabilized microbial oils" are provided herein, wherein one of skill in the art of processing and formulation will understand how the amount and composition of the stabilized microbial oil may be added to the product. Such an amount will be referred to herein as an "effective" amount and will depend on the food or feed product, the diet that the product is intended to supplement or the medical condition that the medical food or medical nutritional is intended to correct or treat.

The term "stabilized microbial oils" refers herein to a microbial oil comprising $CoQ_{10}$ as an antioxidant and at least one ω-3/ω-6 PUFA (and optionally comprising at least one $C_{40}$ carotenoid). Preferably, the $CoQ_{10}$ is present in an "effective" amount, wherein the term "effective amount of microbially-produced antioxidant" refers to the amount of a microbially-produced antioxidant that is effective in decreasing the rate of oxidation of a $C_{40}$ carotenoid pigment, an ω-3/ω-6 PUFA, or mixtures thereof (or any other compound that is subject to oxidation). One of skill in the art recognizes that the antioxidant will typically be used in a substantially reduced form and that an effective amount of microbially-produced antioxidant varies according to the product and/or product formulation according to target species and/or end use. Typically, the amount of antioxidant incorporated into the product takes into account losses associated with processing conditions, typical handling and storage conditions and the stability of the antioxidant in the product, to name a few. Preferably, the amount of antioxidant produced by the oleaginous yeast biomass is at least about 0.0001 wt %, preferably at least about 0.001 wt %, even more preferably at least about 0.01 wt %, and most preferably at least about 0.1 wt % (based on DCW).

The amount of PUFA present in the "stabilized microbial oils" described herein is an "effective" amount wherein the term "effective amount of a PUFA" refers to the amount of a microbially produced ω-3/ω-6 PUFA incorporated into a product formulation that is sufficient to provide the desirable health characteristics associated with ω-3/ω-6 PUFA consumption. One of skill in the art can vary the amount and type of PUFA incorporated into the product formulation according to target species and/or end use. Typically, the amount of PUFA incorporated into the product takes into account losses associated with processing conditions, typical handling and storage conditions, the stability of the PUFA in the product, and the bioavailability/bioabsorption efficiency with the target species, to name a few.

The amount of $C_{40}$ carotenoid (or "pigment") present in the "stabilized microbial oils" described herein is an "effective" amount, wherein the term "effective amount of pigment" refers to the amount of pigment incorporated into an animal feed product that effectively pigments at least one animal tissue (e.g., chicken products such as egg yolks; crustacean muscle tissue and/or shell tissue; fish muscle tissue and/or skin tissue, etc.) under feeding conditions considered suitable for growth of the target animal species. The amount of pigment incorporated into the animal feed may vary according to target species. Typically, the amount of pigment product incorporated into the feed product takes into account pigmentation losses associated with feed processing conditions, typical handling and storage conditions, the stability of the pigment in the feed, the bioavailability/bioabsorption efficiency of the particular species, the pigmentation rate of the animal tissue targeted for pigmentation, and the overall profile of pigment isomers (wherein some are preferentially absorbed over others), to name a few. In one aspect, the effective amount of pigment in the pigmented feed is at least about 10 mg/kg feed, preferably at least about 10 mg/kg to about 250 mg/kg, more preferably about 20 mg/kg to about 100 mg/kg, and most preferably about 30 mg/kg to about 100 mg/kg feed. Alternately, the "effective amount of pigment" may also refer to an amount of carotenoid pigment added to effectively function as an additional antioxidant in the target application.

The present oleaginous yeast biomass comprising $CoQ_{10}$ and at least one ω-3/ω-6 PUFA (and optionally at least one $C_{40}$ carotenoid) can be prepared and sold in a variety of product forms including, but not limited to whole cell biomass, partially purified biomass, purified oil, and purified $CoQ_{10}$. The product form will depend upon the targeted end use.

An animal feed, food product, dietary supplement, pharmaceutical composition, infant formula, or personal care product comprising oleaginous yeast biomass comprising the antioxidant $CoQ_{10}$ and at least one ω-3/ω-6 PUFA (and optionally at least one $C_{40}$ carotenoid) is also provided herein. It is contemplated that the stabilized microbial oils comprising $CoQ_{10}$ and ω-3/ω-6 PUFAs will function in each of these applications to impart the health benefits of current formulations using more traditional sources of ω-3/ω-6 PUFAs. Similarly, an animal feed, food product, dietary supplement, pharmaceutical composition, infant formula, or personal care product comprising a stabilized microbial oil isolated from the recombinant oleaginous yeast biomass is also provided. Preferably, the yeast biomass comprises at least about 25 wt % oil, more preferably at least about 30-40 wt %, and most preferably at least about 40-50 wt % microbially-produced oil.

Food Products and Infant Formulas

Stabilized microbial oils containing ω-3/ω-6 PUFAs and optionally at least one $C_{40}$ carotenoid will be suitable for use in a variety of food and feed products including, but not limited to food analogs, meat products, cereal products, baked foods, snack foods and dairy products. Alternatively, the stabilized PUFAs (or derivatives thereof) may be incorporated into cooking oils, fats or margarines formulated so that in normal use the recipient would receive the desired amount for dietary supplementation. The stabilized PUFAs may also be incorporated into infant formulas, nutritional supplements or other food products and may find use as anti-inflammatory or cholesterol lowering agents.

The term "food product" refers to any food generally suitable for human consumption. This definition encompasses a "food analog", i.e., a food-like product manufactured to resemble its food counterpart, whether meat, cheese, milk or the like, and that is intended to have the appearance, taste, and texture of its counterpart. Typical food products include but are not limited to meat products, cereal products, baked foods, snack foods, fried foods, beverages, dairy products, infant formulas and the like. Description of each of these product classes is provided in Int'l. App. Pub. No. WO 2006/052870 [U.S. Publication 2006-0115881-A1].

Additional food products into which the stabilized microbial oils could be included are, for example: chewing gums, confections and frostings, gelatins and puddings, hard and soft candies, jams and jellies, white granulated sugar, sugar substitutes, sweet sauces, toppings and syrups, and dry-blended powder mixes.

Health Food Products and Pharmaceuticals

A health food product is any food product that imparts a health benefit and include "functional foods", "medical foods", "medical nutritionals" and "dietary supplements". Description of each of these product classes is provided in Int'l. App. Pub. No. WO 2006/052870 [U.S. Publication 2006-0115881-A1].

Stabilized microbial oils of the invention may also be used in standard pharmaceutical compositions. The term "pharmaceutical" means a compound or substance which if sold in the United States would be controlled by e.g., Section 505 of the Federal Food, Drug and Cosmetic Act.

Engineered strains of oleaginous yeast (engineered to produce $CoQ_{10}$ and at least one ω-3/ω-6 PUFA [and optionally at least one $C_{40}$ carotenoid]) or the stabilized microbial oils produced therefrom could readily be incorporated into the any of the above mentioned health food products, to thereby produce e.g., a functional or medical food. For example more concentrated formulations comprising $CoQ_{10}$ and ω-3/ω-6 PUFAs (e.g., ARA or EPA) include capsules, powders, tablets, softgels, gelcaps, liquid concentrates and emulsions which can be used as a dietary supplement in humans or animals other than humans. Similarly, compositions comprising $CoQ_{10}$ and at least one ω-3/ω-6 PUFA (and optionally at least one $C_{40}$ carotenoid) can be used as dietary substitutes, or supplements, particularly infant formulas, for patients undergoing intravenous feeding or for preventing or treating malnutrition. Optionally, the compositions may be used for pharmaceutical use (human or veterinary). In this case, the stabilized PUFAs are generally administered orally but can be administered by any route by which they may be successfully absorbed, e.g., parenterally (e.g., subcutaneously, intramuscularly or intravenously), rectally, vaginally or topically (e.g., as a skin ointment or lotion).

Animal Feed Products

Animal feeds are generically defined herein as products intended for use as feed or for mixing in feed for animals other than humans. More specifically, the term "animal feed" refers to feeds intended exclusively for consumption by animals, including domestic animals (e.g., pets, farm animals, home aquarium fish, etc.) or for animals raised for the production of food (e.g., poultry, eggs, fish, crustacea, etc.).

More specifically, although not limited therein, it is expected that the recombinant oleaginous yeast described herein or stabilized microbial oils thereof can be used within pet food products, ruminant and poultry food products and aquacultural food products. Pet food products are those products intended to be fed to a pet (e.g., a dog, cat, bird, reptile, rodent); these products can include the cereal and health food products above, as well as meat and meat byproducts, soy protein products, grass and hay products (e.g., alfalfa, timothy, oat or brome grass, vegetables). Ruminant and poultry food products are those wherein the product is intended to be fed to e.g., turkeys, chickens, cattle and swine. As with the pet foods above, these products can include cereal and health food products, soy protein products, meat and meat byproducts, and grass and hay products as listed above. Aquacultural food products (or "aquafeeds") are those products intended to be used in aquafarming which concerns the propagation, cultivation or farming of aquatic organisms and/or animals in fresh or marine waters. More specifically, the term "aquaculture" refers to the production and sale of farm raised aquatic plants and animals. Typical examples of animals produced through aquaculture include, but are not limited to: lobsters, shrimp, prawns, and fish (i.e., ornamental and/or food fish).

The biomass and/or stabilized microbial oils (comprising $CoQ_{10}$ and (ω-3/ω-6 PUFAs [and optionally $C_{40}$ carotenoids]) can be used as an ingredient in any of the animal feeds described above. In addition to providing necessary ω-3/ω-6 PUFAs in a stabilized form (and optionally, carotenoid pigment), the oleaginous yeast itself is a useful source of protein and other nutrients (e.g., vitamins, minerals, nucleic acids, complex carbohydrates, etc.) that can contribute to overall animal health and nutrition, as well as increase a formulation's palatability. Accordingly it is contemplated that the addition of yeast biomass comprising the recombinant production hosts described herein will be an excellent additional source of feed nutrients in animal feed formulations, wherein the term "feed nutrient" means nutrients such as proteins, lipids, carbohydrates, vitamins, minerals and nucleic acids that may be derived from the yeast biomass comprising the recombinant production hosts.

More specifically, for example, *Yarrowia lipolytica* (ATCC #20362) has the following approximate chemical composition, as a percent relative to the DCW: 35% protein, 40% lipid, 10% carbohydrate, 5% nucleic acids, 5% ash and 5% moisture. Furthermore, within the carbohydrate fraction, β-glucans comprise approximately 45.6 mg/g, mannans comprise approximately 11.4 mg/g, and chitin comprises approximately 52.6 mg/g (while trehalose is a minor component [approximately 0.7 mg/g]).

A considerable body of literature has examined the immuno-modulating effects of yeast β-glucans, mannans and chitin in both traditional animal husbandry and within the aquacultural sector. The means by which β-glucans, the primary constituents of bacterial and fungal cell walls, stimulate non-specific immunity (i.e., "immunostimulant effects") to thereby improve health of aquaculture species, pets and farm animals and humans are best studied, although both chitin and mannans are similarly recognized as useful immunostimulants (see Int'l. App. Pub. No. WO 2006/052870 for additional details).

Based on the unique protein:lipid:carbohydrate composition of *Yarrowia lipolytica*, as well as the unique complex carbohydrate profile (comprising an approximate 1:4:4.6 ratio of mannan:β-glucans:chitin), it is contemplated that the genetically engineered yeast cells of the present invention (or portions thereof) would be useful additives to animal feed formulations (e.g., as whole [lyophilized] yeast cells, as purified cells walls, as purified yeast carbohydrates or within various other fractionated forms).

When the biomass and/or stabilized microbial oils of the recombinant production hosts herein comprise an effective amount of $C_{40}$ carotenoids (preferably lutein, lycopene, β-carotene, canthaxanthin, astaxanthin, and/or zeaxanthin), the biomass and/or oil is suitable as an ingredient in a "pigmented feed product" or "pigmented animal feed". As used herein, "pigmented" or "pigment" will refer to a material having coloration provided by at least one $C_{40}$ carotenoid pigment produced from a recombinant oleaginous yeast. Many animals have been reported to acquire tissue pigmentation by absorbing xanthophylls in their feed. The pigmented animal feed may be an animal feed selected from the group consisting of fish feed, crustacea feed, shrimp feed, crab feed, lobster feed, and chicken feed. The nutritional requirements and feed forms for each animal feed are well known in the art (for example, see *Nutrient Requirements of Fish*, published by the Board of Agriculture's Committee on Animal Nutrition, National Research Council, National Academy: Washington, D.C. 1993; and *Nutrient Requirements of Poultry*, published by the Board of Agriculture's Committee on Animal Nutrition, National Research Council, National Academy: Washington, D.C. 1994).

The pigmented feed product is typically a feed pellet formed using one of many techniques known in the art such cold pressed pellets, extruded pellets, and feed pellets wherein the pigmented product is suspended in oil and applied to the feed pellet after the extrusion process ("post-extrusion applied" or PE). In preferred aspects, the pigmentation product is oleaginous yeast biomass comprising stabilized and pigmented microbially-produced oil (additionally comprising ω-3/ω-6 PUFAs), or purified oil isolated from the recombinant oleaginous yeast biomass. The size and shape of the feed pellets may vary according to the target species and developmental stage. The incorporation of the pigmented product post-extrusion can be accomplished using a variety of techniques. Typically, the pigmentation product is mixed with a suitable oil (e.g., vegetable oil, corn oil, sunflower, soybean oil, fish oil) and prior to applying the pigment to the extruded feed pellet. The amount of pigmented biomass product formulated into feed pellets can be adjusted and/or optimized for the particular application. Factors to consider include, but are not limited to: the concentration of the pigment in the biomass, the concentration of the pigment in the pigmentation product, the target species, the age and/or growth rate of the selected species, the type of carotenoid used, the bioabsorption characteristics of the chosen pigment in the context of the species to be pigmented, the feeding schedule, the cost of the pigment, and the palatability of the resulting feed. One of skill in the art can adjust the amount of pigmented biomass incorporated into the feed so that adequate levels of carotenoid are present while balancing the nutritional requirements of the species. Typical concentrations of the carotenoid pigment incorporated into, for example, fish feed range from about 10 to about 200 mg/kg of fish feed, wherein a preferred range is from about 10 mg/kg to about 100 mg/kg, a more preferred range is from about 10 mg/kg to about 80 mg/kg and a most preferred range is from about 20 mg/kg to about 60 mg/kg, depending on the specific product.

Although numerous commercial products comprising the oleaginous yeasts, the stabilized microbially produced oil thereof, or isolated $CoQ_{10}$ are contemplated by the Applicants herein, applications of the products are described below in additional detail in reference to various specific animal feeds. Generally, the recombinant oleaginous yeast biomass comprises about 0.1 weight percent (wt %) to about 50 wt % of the animal feed, preferably about 0.5 wt % to about 20 wt %, more preferably about 1 wt % to about 10 wt %, most preferably about 1 wt % to about 5 wt %. These examples are not intended to be limiting.

Chicken Feed—Nutritional Requirements: The dietary requirements of poultry are well known (see Nutrient Requirements of Poultry, published by the Board of Agriculture's Committee on Animal Nutrition, National Research Council, National Academy: Washington, D.C. 1994). Typical feeds are comprised of crude protein (including essentially amino acids), carbohydrates, fats/lipids (e.g., ω-3/ω-6 PUFAs), vitamins (i.e., fat and water soluble), minerals (i.e., both macrominerals and trace minerals) and water. Additional feed ingredients may include antioxidants (e.g., $CoQ_{10}$; typically included to prevent oxidation of lipids and/or pigments), hormones, antibiotics and pigments (i.e., carotenoids), to name of few. The source of the various components is typically chosen based on cost, availability and quality of the nutrients they contain. Typically, components include, but are not limited to: cereal grains (primarily carbohydrates and protein), animal protein meal, animal or vegetable fats/lipids, and isolates from various plants including corn, rice, alfalfa and soybean, to name a few.

When producing a "poultry pigmentation product", referring to pigmented feed additives used to color poultry via commercial farming techniques, preferred carotenoids are lutein, canthaxanthin, astaxanthin and/or zeaxanthin. Typically, the poultry is a chicken and the pigmentation product is used to pigment chicken tissue (e.g., skin) and/or egg yolks.

Crustacea Feed—Nutritional Requirements: The dietary requirements of crustacea are well-known (see "Training Manual on Shrimp and Fish Nutrition and Feed Management", CIBA Special Bulletin No. 15; Oct. 22-31, 2002; Ali, Amanad, editor; published by the Central Institute of Brackishwater Aquaculture (CIBA), Chennai, India, hereinafter referred to as "Amanad"). Typical feeds are comprised of crude protein (including essentially amino acids), carbohydrates, fats/lipids (e.g., ω-3/ω-6 PUFAs), vitamins (i.e., fat and water soluble), minerals (i.e., both macrominerals and trace minerals) and water. Additional feed ingredients may include antioxidants (e.g., $CoQ_{10}$; typically included to prevent oxidation of lipids and/or pigments), hormones, antibiotics and pigments (i.e., carotenoids), to name of few. The source of the various components is typically chosen based on cost, availability and quality of the nutrients they contain. Typically, components include, but are not limited to: cereal grains (primarily carbohydrates and protein), animal protein meal (e.g., fish, prawn, squid, and clam meat meal), animal or vegetable fats/lipids, and isolates from various plants including corn, rice, alfalfa, soybean, groundnut cake (i.e., peanuts), sunflower cake, and gingelly (sesame) cake, to name a few. Examples of the moisture, protein, fat, fiber, carbohydrate, and ash content of various raw feed materials typically used in feed is shown in Tables 5 and 6 (see Amanad).

TABLE 5

Composition Of Various Raw Feed Materials Used In Preparing Shrimp Feed

| Ingredient | Moisture | Protein | Fat | Fiber | Carbohydrate | Ash |
|---|---|---|---|---|---|---|
| Fish Meal | 10.8 | 55.0 | 5.4 | 1.73 | 3.27 | 23.78 |
| Prawn Head | 9.91 | 39.8 | 9.6 | 16.3 | 4.0 | 20.18 |
| Squid Meal | 8.4 | 66.5 | 4.4 | 3.98 | 5.9 | 10.8 |
| Clam meat meal | 10.1 | 49.9 | 8.66 | — | 28.3 | 7.75 |
| Soybean Meal | 10.45 | 51.5 | 1.00 | 8.85 | 19.7 | 8.5 |
| Groundnut Cake | 13.05 | 46.93 | 5.0 | 8.9 | 18.03 | 8.9 |
| Sunflower Cake | 7.0 | 26.69 | 2.04 | 30.13 | 26.37 | 7.7 |
| Gingelly Cake | 9.76 | 38.71 | 6.00 | 10.96 | 15.8 | 19.02 |

*Note:
All values reported as weight percent (wt %) of ingredient.

TABLE 6

Typical Composition Of Feed Formulation For Shrimp

| Ingredient | Starter Feed | Grower Feed | Finishing Feed |
|---|---|---|---|
| Crude protein | 40-45 | 38-40 | 35-38 |
| Lipid | 6-8 | 8-10 | 8-10 |
| Carbohydrate | 10-16 | 15-20 | 20-25 |
| Crude fiber | 1-2 | 1-3 | 2-4 |
| Ash | 10-12 | 10-15 | 12-18 |
| Mineral mix | 2-5 | 2-5 | 2-5 |

*Note:
All values reported as weight percent (wt %) of ingredient.

Mixtures comprising these compositions are blended and then pelleted and dried with 16-17% moisture.

When producing a "crustacean pigmentation product", referring to pigmented feed additives used to color crustaceans via commercial aquacultural techniques, preferred carotenoids are canthaxanthin and/or astaxanthin. Typically, the crustaceans are shrimp or lobsters and the pigmentation product is used to pigment tissue and shells.

Fish Feed—Nutritional Requirements: An increased understanding of the nutritional requirements for various fish species and technological advances in feed manufacturing have allowed the development and use of manufactured or artificial diets (formulated feeds) to supplement or to replace natural feeds in the aquaculture industry. The dietary requirements of fish are well known (see Nutrient Requirements of Fish, published by the Board of Agriculture's Committee on Animal Nutrition, National Research Council, National Academy: Washington, D.C. 1993). The dietary requirements of fish feed may vary according to species, aquatic environment, temperature and age. However, the general nutrition requirements for most aquatic species produced via aquaculture are known and are generally comprised of about 25 wt % to about 55 wt % crude protein (including essentially amino acids), up to about 30 wt % lipids (e.g., ω-3/ω-6 PUFAs), vitamins (i.e., fat and water soluble), minerals (i.e., including essential minerals), carbohydrates (sometimes included as an economical energy source although not required) and water (typically about 6-40 wt % depending upon the desired product form). Additional feed ingredients may include: 1) antioxidants (i.e., $CoQ_{10}$), to prevent oxidation of lipids and/or pigments and to extend product shelf-life; 2) carotenoids, particularly for salmonid and ornamental "aquarium" fishes, to enhance tissue coloration of e.g., muscle, skin, shell, etc.; 3) binding agents, to provide stability to the pellet and reduce leaching of nutrients into the water (e.g., beef heart, starch, cellulose, pectin, gelatin, gum arabic, locust bean, agar, carageenin and other alginates); 4) chemoattractants and flavorings, to enhance feed palatability and its intake; and, 5) other feedstuffs. These other feedstuffs can include such materials as hormones, antibiotics, fiber and ash (for use as a filler and as a source of calcium and phosphorus, respectively), vegetable matter and/or fish or squid meal (e.g., live, frozen or dried algae, brine shrimp, rotifers or other zooplankton) to enhance the nutritional value of the diet and increase its acceptance by the fish.

When producing a “fish pigmentation product”, referring to pigmented feed additives used to color fish via commercial aqucultural techniques, preferred carotenoids are canthaxanthin and/or astaxanthin. Fish pigmented by absorbing carotenoids include, but are not limited to salmonids, carp (*Cyprinus* sp.), red sea bream, tilapia, goldfish, Cichlidae, and yellowtail (Serola lalandi). In one aspect, fish pigmented using the present materials are members of the family Salmonidae, whose typical members include salmon, trout and chars.

The source of the various components is typically chosen based on cost relative to growth performance. Typically, components include but are not limited to: fish meal, fish oil (typically marine fish oil), meat meal, shrimp meal, and isolates from various plants including corn, rice, and soybean, to name a few. In one aspect, the majority of the crude protein and crude lipids in the fish feed is preferably provided by fish meal and fish oil.

The manufacture of aquafeed formulations requires consideration of a variety of factors, since a complete diet must be nutritionally balanced, palatable, water stable and have the proper size and texture. With regard to nutrient composition of aquafeeds, one is referred to: *Handbook on Ingredients for Aquaculture Feeds* (Hertrampf, J. W. and F. Piedad-Pascual. Kluwer Academic: Dordrecht, The Netherlands, 2000) and *Standard Methods for the Nutrition and Feeding of Farmed Fish and Shrimp* (Tacon, A. G. J. Argent Laboratories: Redmond, 1990). In general, feeds are formulated to be dry (i.e., final moisture content of 6-10%), semi-moist (i.e., 35-40% water content) or wet (i.e., 50-70% water content). Dry feeds include the following: simple loose mixtures of dry ingredients (i.e., “mash” or “meals”); compressed pellets, crumbles or granules; and flakes. Depending on the feeding requirements of the fish, pellets can be made to sink or float. Semimoist and wet feeds are made from single or mixed ingredients (e.g., trash fish or cooked legumes) and can be shaped into cakes or balls.

EXAMPLES

The present invention is further described in the following Examples, which illustrate reductions to practice of the invention but do not completely define all of its possible variations.

General Methods

Standard recombinant DNA and molecular cloning techniques used in the Examples are well known in the art and are described by: 1) Sambrook, J. and Russell, D. *Molecular Cloning: A Laboratory Manual;* $3^{rd}$ Ed. Cold Spring Harbor Laboratory: Cold Spring Harbor, N.Y. (2001); 2) T. J. Silhavy, M. L. Bennan, and L. W. Enquist, *Experiments with Gene Fusions*; Cold Spring Harbor Laboratory: Cold Spring Harbor, N.Y. (1984); and 3) Ausubel, F. M. et al., *Current Protocols in Molecular Biology*, published by Greene Publishing Assoc. and Wiley-Interscience, Hoboken, N.J. (1987).

Materials and methods suitable for the maintenance and growth of microbial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994)); or by Thomas D. Brock in *Biotechnoloyy: A Textbook of Industrial Microbiology,* $2^{nd}$ ed., Sinauer Associates: Sunderland, Mass. (1989). All reagents, restriction enzymes and materials used for the growth and maintenance of microbial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.), unless otherwise specified.

*E. coli* (XL1-Blue or XL2-Blue) competent cells were purchased from the Stratagene Company (San Diego, Calif.). *E. coli* strains were typically grown at 37° C. on Luria Bertani (LB) plates.

General molecular cloning was performed according to standard methods (Sambrook et al., supra). Oligonucleotides were synthesized by Sigma-Genosys (Spring, Tex.). Individual PCR amplification reactions were carried out in a 50 µl total volume, comprising: PCR buffer (containing 10 mM KCl, 10 mM $(NH_4)_2SO_4$, 20 mM Tris-HCl (pH 8.75), 2 mM $MgSO_4$, 0.1% Triton X-100), 100 µg/mL BSA (final concentration), 200 µM each deoxyribonucleotide triphosphate, 10 pmole of each primer and 1 µl of Pfu DNA polymerase (Stratagene, San Diego, Calif.), unless otherwise specified.

The meaning of abbreviations is as follows: “sec” means second(s), “min” means minute(s), “h” means hour(s), “d” means day(s), “µL” means microliter(s), “mL” means milliliter(s), “L” means liter(s), “µM” means micromolar, “mM” means millimolar, “M” means molar, “mmol” means millimole(s), “µmol” mean micromole(s), “g” means gram(s), “µg” means microgram(s), “ng” means nanogram(s), “U” means unit(s), “bp” means base pair(s), “kB” means kilobase(s), “DCW” means dry cell weight, and “TFAs” means total fatty acids.

The structure of an expression cassette will be represented by a simple notation system of “X::Y::Z”, wherein X describes the promoter fragment, Y describes the gene fragment, and Z describes the terminator fragment, which are all operably linked to one another.

Cultivation of *Yarrowia lipolytica*

*Yarrowia lipolytica* strain ATCC #20362 was purchased from the American Type Culture Collection (Rockville, Md.). *Yarrowia lipolytica* strains were routinely grown at 30° C. in several media: minimal media (MM), fermentation media, YPD media and Oil Induction media. Agar plates were prepared as required by addition of 20 g/L agar to each liquid media, according to standard methodology.

Basic Minimal Media (MM) Recipe (per liter): 20 g glucose; 1.7 g yeast nitrogen base without amino acids; 1.0 g proline; and pH 6.1 (not adjusted).

Fermentation medium: 6.70 g/L Yeast nitrogen base; 5.00 g/L Yeast extract (BBL); 6.00 g/L $KH_2PO_4$; 2.00 g/L $K_2HPO_4$; 1.50 g/L $MgSO_4*7H_2O$; and 20 g/L Glucose.

YPD agar medium (per liter): 10 g of yeast extract [Difco], 20 g of Bacto peptone [Difco]; and 20 g of glucose.

Oil induction (OI) medium: 100 mM Glucose and 50 mM (pH 6.5) Potassium phosphate.

High Glucose Media (HGM) (per liter): 80 glucose, 2.58 g $KH_2PO_4$ and 5.36 g $K_2HPO_4$, pH 7.5 (do not need to adjust).

Example 1

DNA Transformation in *Yarrowia lipolytica*

The following general procedure was used to make *Yarrowia lipolytica* chemically competent for DNA transformation (Chen, D. C. et al., *Appl. Microbiol. Biotechnol.,* 48(2): 232-235-(1997)).

*Yarrowia* cells were streaked onto YPD media plates 1 day prior to transformation. The cells were incubated at 30° C.

Several large loopfuls (~3) of cells from the YPD plate were resuspended in 1 mL of transformation media [comprising 2.25 mL 50% PEG (average MW 3350); 0.125 mL 2 M lithium acetate pH 6.0; 0.125 mL 2 M dithiothreitol (DTT; prepared fresh prior to each use); and 50 μL salmon sperm DNA (10 mg/mL)].

The *Yarrowia* cells suspended in transformation solution were transferred as 100 μL aliquots into microfuge tubes using a large-bore pipette tip. Approximately 100 to 500 ng (5 μL) of the desired plasmid (in linearized form when transforming integration plasmids) was added and the mixture was incubated at 39° C. for 1 hr with vortexing of the mixture every 15 min. After incubation, approximately 50 μL of the cell mixture were plated on MM agar plates with appropriate selection and incubated at 30° C. for a defined period of time (typically up to 4 days) depending upon the specific plasmid.

Alternatively, transformants were selected on 5-fluoroorotic acid ("FOA"; also 5-fluorouracil-6-carboxylic acid monohydrate) selection media, comprising: 0.17% yeast nitrogen base (DIFCO Laboratories) without ammonium sulfate or amino acids, 2% glucose, 0.1% proline, 75 mg/L uracil, 75 mg/L uridine, 900 mg/L FOA (Zymo Research Corp., Orange, Calif.) and 20 g/L agar.

Transformants containing self-replicating plasmid were visible within about 2-6 days depending upon the strain. Transformants containing integrative plasmid were typically visible within 3-4 days.

Example 2

Coenzyme Q Pathway and Profile in Wildtype *Yarrowia lipolytica*

The present Example describes the quantification of $CoQ_9$ in wildtype *Yarrowia lipolytica*. Specifically, determination of the amount of $CoQ_9$ in *Yarrowia lipolytica* strain ATCC #20362 was made using an Agilent series 1100 HPLC equipped with a DAD detector. The sample was generated by extracting the oil in 3:1 hexane:methanol overnight, partitioning the solvents using a 1 N NaCl solution and stripping the hexane with a Büchi® Rotavapor® (New Castle, Del.).

Three samples of approximately 15, 38, and 86 mg were added to a 4 mL amber vial. Then, 100 μL of glass beads and 1.0 mL of a previously sparged 1:1 tetrahydrofuran(THF)/methanol (MeOH) solution were added and shaken for 15 min at 200 rpm. The sample was then transferred to a Whatman uni-prep vial and analyzed.

A 1 mg standard sample of $CoQ_9$ received from Fluka Chemical Corp. (Milwaukee, Wis.; Catalog #27597, lot #378472) was diluted to 0.1 mg using 1:1 THF/MeOH and analyzed. The standard received was assumed to be exactly 1 mg.

The HPLC conditions used were as follows: Zorbax SB-C18 4.6×250 mm column, 5 micron; 1.0 mL/min flow rate; 35° C. column temperature; 5 μL injection volume; UV detection at 270 and 450 nm wavelengths.

TABLE 7

HPLC Solvents/Gradients For $CoQ_9$ Extraction

| Time (min) | Solvent A: Acetonitrile | Solvent B: Isopropanol |
|---|---|---|
| 0.0 | 95% | 5% |
| 30.0 | 0% | 100% |
| 35.0 | 0% | 100% |
| 36.0 | 95% | 5% |
| 45.0 | 95% | 5% |

Calculations were performed as follows. Specifically, the standard reference factor was equivalent to the milligrams (mg) of standard/area. The percent (%) sample amount was determined according to the following formula:

standard reference factor*(sample peak area/sample concentration)*100.

The ratio of the sample against the standard was calculated and the sample weight taken into account. The sample used was 26.64 mg and diluted with 1 mL of MeOH/THF that had been sparged of air. This was run against the existing standard of 0.1 mg/mL of $CoQ_9$. The area counts for the standard were 18.9 at 450 nm and 711 at 270 nm, while for the sample, the area counts were 13 at 450 nm and 569 at 270 nm. Based on these results, the $CoQ_9$ calculated in the oil was in the range of 0.2 to 0.3%.

Example 3

Construction of *Yarrowia* Expression Plasmid pDMW359

The present Example describes the generation of pDMW359, comprising a chimeric FBAIN::EgD9e::Pex20-3' gene, wherein EgD9e refers to a Δ9 elongase enzyme (SEQ ID NO:4) isolated from *Euglena gracilis*, encoded by SEQ ID NO:3. EgD9e is described in Int'l. App. Pub. No. WO 2007/061742.

Figure 4A:
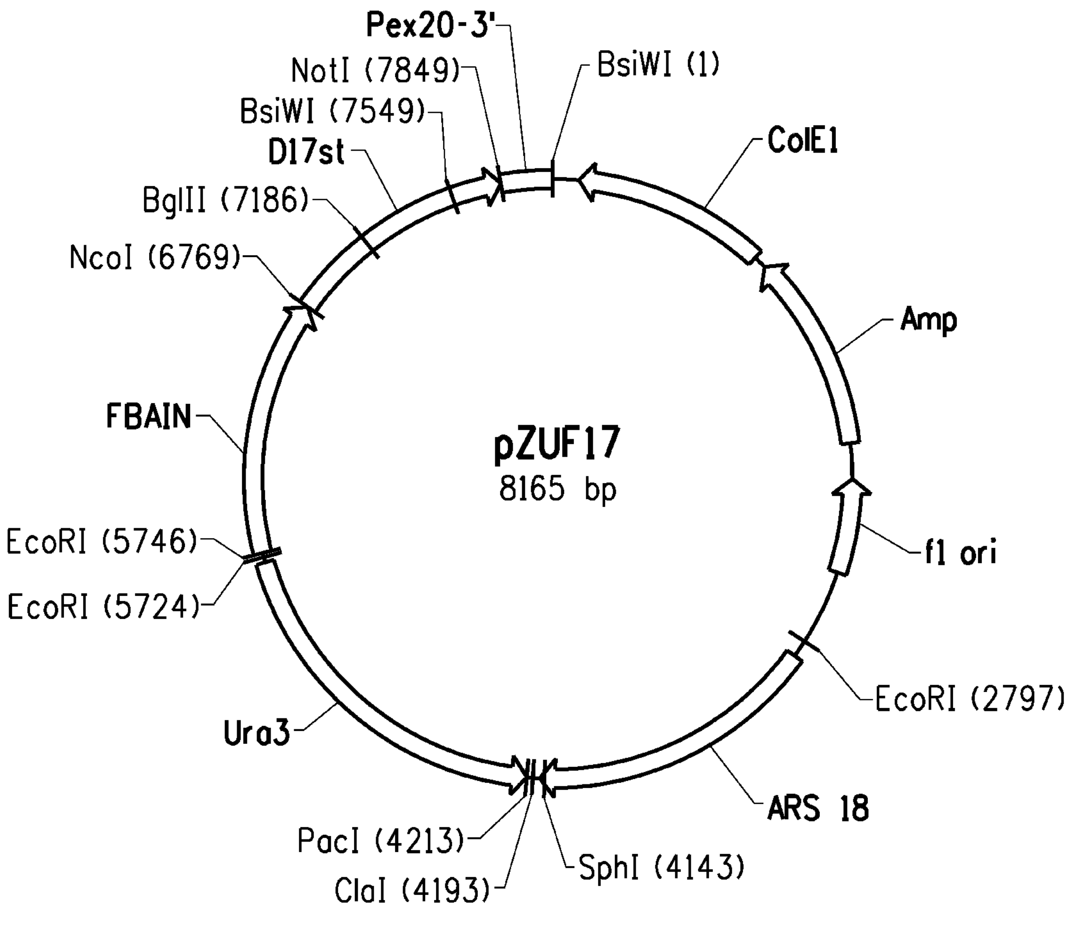
Figure 4B:
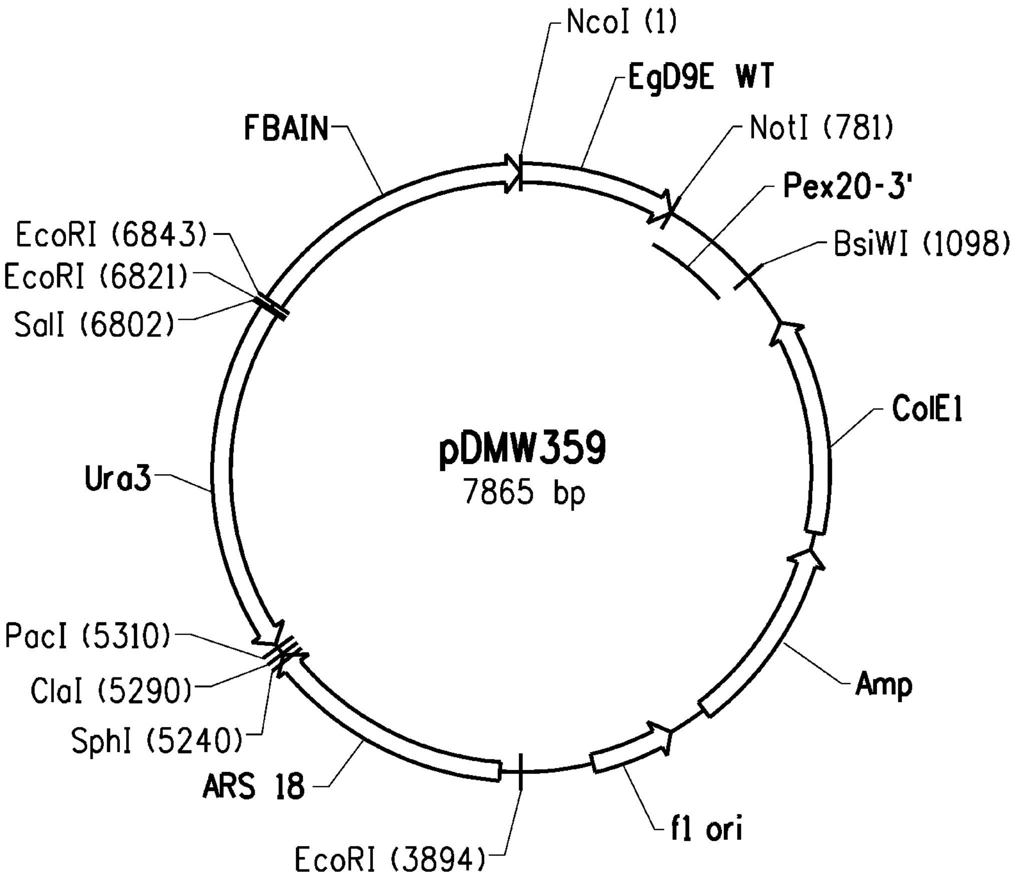

Plasmid pDMW359 was derived from plasmid pZUF17 (FIG. 4A; SEQ ID NO:5; comprising a synthetic Δ17 desaturase gene ["D17st"] derived from *Saprolegnia diclina* (U.S. Pat. App. Pub. No. 2003/0196217 A1), codon-optimized for expression in *Yarrowia lipolytica* (U.S. Pat. No. 7,238,482)). Specifically, a NcoI/NotI fragment containing the coding region of the wild type *Euglena gracilis* Δ9 elongase (EgD9e) was used to replace the NcoI/NotI fragment containing the Δ17 desaturase coding region of pZUF17. The product of this ligation was pDMW359 (FIG. 4B; SEQ ID NO:6), which thereby contained the following components:

TABLE 8

Components of Plasmid pDMW359 (SEQ ID NO: 6)

| RE Sites And Nucleotides Within SEQ ID NO: 6 | Description Of Fragment And Chimeric Gene Components |
|---|---|
| 2134-1254 | ColE1 plasmid origin of replication |
| 3064-2204 | Ampicillin-resistance gene ($Amp^R$) |
| 3963-5267 | *Yarrowia* autonomous replication sequence (ARS18; GenBank Accession No. A17608) |
| SalI/PacI 6802-5301 | *Yarrowia* Ura3 gene (GenBank Accession No. AJ306421) |

TABLE 8-continued

| Components of Plasmid pDMW359 (SEQ ID NO: 6) | |
|---|---|
| RE Sites And Nucleotides Within SEQ ID NO: 6 | Description Of Fragment And Chimeric Gene Components |
| EcoRI/BsiWI 6843-1098 | FBAIN::EgD9e::Pex20, comprising:<br>FBAIN: *Yarrowia lipolytica* FBAIN promoter (U.S. Pat. No. 7,202,356);<br>EgD9e: *Euglena gracilis* Δ9 elongase (labeled as "EgD9E WT" in Figure) (SEQ ID NO: 3; Int'l. App. Pub. No. WO 2007/061742);<br>Pex20: Pex20 terminator sequence from *Yarrowia* Pex20 gene (GenBank Accession No. AF054613) |

Example 4

Construction of Codon-Optimized ddsA Genes for Expression in *Yarrowia lipolytica*

Decaprenyl diphosphate synthase, encoded by the ddsA gene, is required for $CoQ_{10}$ biosynthesis. Various prenyl diphosphate synthases have been identified in publicly available literature, based on homology to the well characterized *Gluconobacter oxydans* ddsA gene described by Okada, K., et al. (GenBank® Accession No. BAA32241; *Eur. J. Biochem.,* 255(1):52-59 (1998)) and typical signature sequences of prenyl diphosphate synthases (Okada, K., et al., *J. Bacteriol.,* 179:5992-5998 (1997)). Despite sharing at least 47% sequence identity with the *Gluconobacter oxydans* ddsA, few of the proteins summarized below in Table 9 have been heterologously expressed to confirm their putative annotation.

TABLE 9

| Publicly Described Prenyl Diphosphate Synthases | | |
|---|---|---|
| GenBank ® Accession Number | GenBank ® Description | SEQ ID NO |
| BAA32241 | *Gluconobacter oxydans* decaprenyl diphosphate synthase | 7 |
| EAP81866 | *Sulfitobacter* sp. NAS-14.1 decaprenyl diphosphate synthase | 8 |
| AAV93637 | *Silicibacter pomeroyi* DSS-3 decaprenyl diphosphate synthase | 9 |
| EAQ04419 | *Oceanicola batsensis* HTCC2597 decaprenyl diphosphate synthase | 10 |
| CAK06434 | *Rhizobium leguminosarum* bv. *viciae* 3841 putative octaprenyl-diphosphate synthase | 11 |
| BAB53531 | *Mesorhizobium loti* MAFF303099 octaprenyl-diphosphate synthase | 12 |
| AAL41650 | *Agrobacterium tumefaciens* str. C58 octaprenyl-diphosphate synthase | 13 |
| EAQ24568 | *Roseovarius* sp. 217 Geranylgeranyl pyrophosphate synthase/Polyprenyl synthetase | 14 |
| ABD89877 | *Rhodopseudomonas palustris* BisB18 Farnesyltranstransferase | 15 |

Any of the proteins listed above in Table 9 could be used for expression in *Yarrowia lipolytica*, to enable synthesis of $CoQ_{10}$. More specifically, in order to express the heterologous ddsA gene in *Yarrowia* in the most efficient manner, each gene was synthesized according to the codon usage preference of *Yarrowia lipolytica* (U.S. Pat. No. 7,125,672). Thus, according to the *Yarrowia* codon usage pattern, the consensus sequence around the ATG translation initiation codon, and the general rules of RNA stability (Guhaniyogi, G. and J. Brewer, *Gene,* 265(1-2):11-23 (2001)), codon-optimized ddsA genes were designed, based on each of the sequences presented above as SEQ ID NOs:7-15 and their corresponding nucleotide sequence. In addition, a mitichondria target sequence (e.g., the first 47 to 50 amino acids from the *Yarrowia* ppt1 gene encoding p-hydroxybenzoate:polyprenyl transferase [GenBank Accession No. XP_505040; SEQ ID NO:16) was placed in the front of these bacterial genes to create a fusion protein. The synthetic ddsA fusion gene was designed to contain a NcoI site at the 5' end and a NotI site at the 3' end. These DNA fragments were then cloned into the corresponding sites in self-replicating plasmid pDMW359 with a FBAIN promoter and the Pex20-3' terminator (from Example 3).

Based on the above methodology, the following plasmids (Table 10) were constructed, each comprising a chimeric FBAIN::synthetic fusion ppt1-ddsA::Pex20 gene construct, wherein the synthetic ddsA was codon-optimized for expression in *Yarrowia lipolytica*. None of the modifications in the codon-optimized gene changed the amino acid sequence of the encoded protein (i.e., as set forth in SEQ ID NOs:7-15, respectively). The designed fusion ppt1-ddsA genes were synthesized by GenScript Corporation (Piscataway, N.J.) and individually cloned into intermediary vector pUC57 (GenBank Accession No. Y14837), prior to cloning into pDMW359 using standard methodology.

TABLE 10

| Plasmids Comprising Codon-Optimized Prenyl Diphosphate Synthase Genes For Expression In Yarrowia lipolytica | | | |
|---|---|---|---|
| Plasmid Name | Plasmid SEQ ID NO | Synthetic Fusion | Fusion SEQ ID NOs |
| — | — | Fusion of GenBank Accession No. XP_505040 (N-terminus of *Yarrowia lipolytica* ppt1) and GenBank ® Accession No. BAA32241 (*Gluconobacter oxydans* ddsA), codon-optimized for expression in *Yarrowia lipolytica* | 17, 18 |
| pDMW359-Ss_ddsA | 19 | Fusion of GenBank Accession No. XP_505040 (N-terminus of *Yarrowia lipolytica* ppt1) and GenBank ® Accession No. EAP81866 (*Sulfitobacter* sp. ddsA), codon-optimized for expression in *Yarrowia lipolytica* | 20, 21 |
| pDMW359-Sp_ddsA | 22 | Fusion of GenBank Accession No. XP_505040 (N-terminus of *Yarrowia lipolytica* ppt1) and GenBank ® Accession No. AAV93637 (*Silicibacter pomeroyi* ddsA), codon-optimized for expression in *Yarrowia lipolytica* | 23, 24 |
| pDMW359-Ob_ddsA | 25 | Fusion of GenBank Accession No. XP_505040 (N-terminus of *Yarrowia lipolytica* ppt1) and GenBank ® Accession No. EAQ04419 (*Oceanicola batsensis* ddsA), codon-optimized for expression in *Yarrowia lipolytica* | 26, 27 |
| pDMW359-Rl_ddsA | 28 | Fusion of GenBank Accession No. XP_505040 (N-terminus of *Yarrowia lipolytica* ppt1) and GenBank ® Accession No. CAK06434 (*Rhizobium leguminosarum* ddsA), codon-optimized for expression in *Yarrowia lipolytica* | 29, 30 |
| pDMW359-Ml_ddsA | 31 | Fusion of GenBank Accession No. XP_505040 (N-terminus of *Yarrowia lipolytica* ppt1) and GenBank ® Accession No. BAB53531 (*Mesorhizobium loti* ddsA), codon-optimized for expression in *Yarrowia lipolytica* | 32, 33 |

TABLE 10-continued

| Plasmid Name | Plasmid SEQ ID NO | Synthetic Fusion | Fusion SEQ ID NOs |
|---|---|---|---|
| Plasmids Comprising Codon-Optimized Prenyl Diphosphate Synthase Genes For Expression In Yarrowia lipolytica | | | |
| pDMW359-At_ddsA | 34 | Fusion of GenBank Accession No. XP_505040 (N-terminus of *Yarrowia lipolytica* ppt1) and GenBank ® Accession No. AAL41650 (*Agrobacterium tumefaciens* str. C58 ddsA), codon-optimized for expression in *Yarrowia lipolytica* | 35, 36 |
| pDMW359-Rs_ddsA | 37 | Fusion of GenBank Accession No. XP_505040 (N-terminus of *Yarrowia lipolytica* ppt1) and GenBank ® Accession No. EAQ24568 (*Roseovarius* sp. ddsA), codon-optimized for expression in *Yarrowia lipolytica* | 38, 39 |
| pDMW359-Rp_ddsA | 40 | Fusion of GenBank Accession No. XP_505040 (N-terminus of *Yarrowia lipolytica* ppt1) and GenBank ® Accession No. ABD89877 (*Rhodopseudomonas palustris* ddsA), codon-optimized for expression in *Yarrowia lipolytica* | 41, 42 |

Example 5

Construction of Various *Yarrowia lipolytica* Strains Producing ω-3/ω-6 PUFAs The present Example describes various strains of *Yarrowia lipolytica* that have been engineered to produce ω-3/ω-6 polyunsaturated fatty acids ["PUFAs"]. It is contemplated that any of these *Y. lipolytica* host strains could be engineered to co-produce $CoQ_{10}$ and ω-3/ω-6 PUFAs, if a ddsA gene was simultaneously expressed (as described in Example 6, infra).

More specifically, a variety of *Yarrowia lipolytica* strains have been engineered by the Applicant's Assignee to produce high concentrations of various ω-3/ω-6 PUFAs. Since naturally produced PUFAs are limited to 18:2 fatty acids in this organism, all of the genetically engineered strains have been transformed to express various PUFA biosynthetic pathway genes (i.e., desaturases and elongases) of the Δ6 desaturase/Δ6 elongase PUFA pathway or the Δ9 elongase/Δ8 desaturase PUFA pathway.

Summary of Representative *Yarrowia lipolytica* Strains Producing ω-3/ω-6 PUFAs

Although some representative strains are summarized in the Table below, the disclosure of *Yarrowia lipolytica* strains producing ω-3/ω-6 PUFAs is not limited in any way to the strains therein. Instead, all of the teachings provided in the following commonly owned and co-pending applications, are useful for development of a suitable *Yarrowia lipolytica* strain engineered to produce ω-3/ω-6 PUFAs. These specifically include the following Applicants' Assignee's co-pending patents and applications: U.S. Pat. No. 7,125,672, U.S. Pat. No. 7,189,559, U.S. Pat. No. 7,192,762, U.S. Pat. No. 7,198,937, U.S. Pat. No. 7,202,356, U.S. Pat. No. 7,214,491, U.S. Pat. No. 7,238,482, U.S. Pat. No. 7,256,033, U.S. Pat. No. 7,259,255, U.S. Pat. No. 7,264,949, U.S. Pat. No. 7,267,976, U.S. Pat. No. 7,273,746, U.S. patent application Ser. No. 10/985,254 and Ser. No. 10/985,691 (filed Nov. 10, 2004), U.S. patent application Ser. No. 11/183,664 (filed Jul. 18, 2005), U.S. patent application Ser. No. 11/185,301 (filed Jul. 20, 2005), U.S. patent application Ser. No. 11/190,750 (filed Jul. 27, 2005), U.S. patent application Ser. No. 11/198,975 (filed Aug. 8, 2005), U.S. patent application Ser. No. 11/253,882 (filed Oct. 19, 2005), U.S. patent application Ser. No. 11/264,784 and Ser. No. 11/264,737 (filed Nov. 1, 2005), U.S. patent application Ser. No. 11/265,761 (filed Nov. 2, 2005), U.S. patent application Ser. No. 11/601,563 and Ser. No. 11/601,564 (filed Nov. 16, 2006), U.S. patent application Ser. No. 11/635,258 (filed Dec. 7, 2006), U.S. patent application Ser. No. 11/613,420 (filed Dec. 20, 2006), U.S. patent application Ser. No. 11/787,772 (filed Apr. 18, 2007), U.S. patent application Ser. No. 11/737,772 (filed Apr. 20, 2007), U.S. patent application Ser. No. 11/740,298 (filed Apr. 26, 2007), U.S. patent application Ser. No. 12/111,237 (filed Apr. 29, 2008), U.S. patent application Ser. No. 11/748,629 and Ser. No. 11/748,637 (filed May 15, 2007), U.S. patent application Ser. No. 11/779,915 (filed Jul. 19, 2007), U.S. Pat. App. No. 60/991,266 (filed Nov. 30, 2007), U.S. patent application Ser. No. 11/952,243 (filed Dec. 7, 2007), U.S. Pat. App. No. 61/041,716 (filed Apr. 2, 2008), U.S. patent application Ser. No. 12/061,738 (filed Apr. 3, 2008), U.S. patent application Ser. No. 12/099,811 (filed Apr. 9, 2008), U.S. patent application Ser. No. 12/102,879 (filed Apr. 15, 2008), U.S. patent application Ser. No. 12/111,237 (filed Apr. 29, 2008), U.S. Pat. App. No. 61/055,511 (filed May 23, 2008), U.S. Pat. App. No. 61/085,482 (filed Aug. 1, 2008), U.S. Pat. App. No. 61/093,007 (filed Aug. 29, 2008), U.S. Pat. App. No. 61/098,333 (filed Sep. 19, 2008), U.S. patent application Ser. No. 12/244,822 (filed Oct. 3, 2008) and U.S. patent application Ser. No. 12/244,950 (filed Oct. 3, 2008).

TABLE 11

Lipid Profile Of Representative Yarrowia lipolytica Strains Engineered To Produce ω-3/ω-6 PUFAs

| Strain | Reference | ATCC Deposit No. | Fatty Acid Content (As A Percent [%] of Total Fatty Acids) 16:0 | 16:1 | 18:0 | 18:1 | 18:2 | (ALA) |
|---|---|---|---|---|---|---|---|---|
| Wildtype | US 2006-0035351- | #76982 | 14 | 11 | 3.5 | 34.8 | 31 | — |
| pDMW208 | A1; WO2006/033723 | — | 11.9 | 8.6 | 1.5 | 24.4 | 17.8 | — |
| pDMW208D62 | | — | 16.2 | 1.5 | 0.1 | 17.8 | 22.2 | — |
| M4 | US 2006-0115881-A1; WO2006/052870 | — | 15 | 4 | 2 | 5 | 27 | — |
| Y2034 | US 2006-0094092- | — | 13.1 | 8.1 | 1.7 | 7.4 | 14.8 | — |
| Y2047 | A1; WO2006/055322 | PTA-7186 | 15.9 | 6.6 | 0.7 | 8.9 | 16.6 | — |
| Y2214 | | — | 7.9 | 15.3 | 0 | 13.7 | 37.5 | — |
| EU | US 2006-0115881- | — | 19 | 10.3 | 2.3 | 15.8 | 12 | — |
| Y2072 | A1; WO2006/052870 | — | 7.6 | 4.1 | 2.2 | 16.8 | 13.9 | — |
| Y2102 | | — | 9 | 3 | 3.5 | 5.6 | 18.6 | — |

TABLE 11-continued

Lipid Profile Of Representative Yarrowia lipolytica Strains Engineered To Produce ω-3/ω-6 PUFAs

| | | | | | | | | |
|---|---|---|---|---|---|---|---|---|
| Y2088 | | — | 17 | 4.5 | 3 | 2.5 | 10 | — |
| Y2089 | | — | 7.9 | 3.4 | 2.5 | 9.9 | 14.3 | — |
| Y2095 | | — | 13 | 0 | 2.6 | 5.1 | 16 | — |
| Y2090 | | — | 6 | 1 | 6.1 | 7.7 | 12.6 | — |
| Y2096 | | PTA-7184 | 8.1 | 1 | 6.3 | 8.5 | 11.5 | — |
| Y2201 | | PTA-7185 | 11 | 16.1 | 0.7 | 18.4 | 27 | — |
| Y3000 | US 2006-0110806-A1; WO2006/052871 | PTA-7187 | 5.9 | 1.2 | 5.5 | 7.7 | 11.7 | — |
| Y4001 | WO2008/073367 | — | 4.3 | 4.4 | 3.9 | 35.9 | 23 | 0 |
| Y4036 | | — | 7.7 | 3.6 | 1.1 | 14.2 | 32.6 | 0 |
| Y4070 | | — | 8 | 5.3 | 3.5 | 14.6 | 42.1 | 0 |
| Y4158 | | — | 3.2 | 1.2 | 2.7 | 14.5 | 30.4 | 5.3 |
| Y4184 | | — | 3.1 | 1.5 | 1.8 | 8.7 | 31.5 | 4.9 |

| | Fatty Acid Content (As A Percent [%] of Total Fatty Acids) | | | | | | | | Lipid % |
|---|---|---|---|---|---|---|---|---|---|
| Strain | GLA | 20:2 | DGLA | ARA | ETA | EPA | DPA | DHA | dcw |
| Wildtype | 0 | — | — | — | — | — | — | — | — |
| pDMW208 | 25.9 | — | — | — | — | — | — | — | — |
| pDMW208D62 | 34 | — | — | — | — | — | — | — | — |
| M4 | 35 | — | 8 | 0 | 0 | 0 | — | — | — |
| Y2034 | 25.2 | — | 8.3 | 11.2 | — | — | — | — | — |
| Y2047 | 29.7 | — | 0 | 10.9 | — | — | — | — | — |
| Y2214 | 0 | — | 7.9 | 14 | — | — | — | — | — |
| EU | 18.7 | — | 5.7 | 0.2 | 3 | 10.3 | — | — | 36 |
| Y2072 | 27.8 | — | 3.7 | 1.7 | 2.2 | 15 | — | — | — |
| Y2102 | 29.6 | — | 3.8 | 2.8 | 2.3 | 18.4 | — | — | — |
| Y2088 | 20 | — | 3 | 2.8 | 1.7 | 20 | — | — | — |
| Y2089 | 37.5 | — | 2.5 | 1.8 | 1.6 | 17.6 | — | — | — |
| Y2095 | 29.1 | — | 3.1 | 1.9 | 2.7 | 19.3 | — | — | — |
| Y2090 | 26.4 | — | 6.7 | 2.4 | 3.6 | 26.6 | — | — | 22.9 |
| Y2096 | 25 | — | 5.8 | 2.1 | 2.5 | 28.1 | — | — | 20.8 |
| Y2201 | — | 3.3 | 3.3 | 1 | 3.8 | 9 | — | — | — |
| Y3000 | 30.1 | — | 2.6 | 1.2 | 1.2 | 4.7 | 18.3 | 5.6 | — |
| Y4001 | — | 23.8 | 0 | 0 | 0 | — | — | — | |
| Y4036 | — | 15.6 | 18.2 | 0 | 0 | — | — | — | |
| Y4070 | — | 6.7 | 2.4 | 11.9 | — | — | — | — | |
| Y4158 | — | 6.2 | 3.1 | 0.3 | 3.4 | 20.5 | — | — | 27.3 |
| Y4184 | — | 5.6 | 2.9 | 0.6 | 2.4 | 28.9 | — | — | 23.9 |

For fatty acid analysis, *Yarrowia lipolytica* cells were collected by centrifugation and lipids are extracted as described in Bligh, E. G. & Dyer, W. J. (*Can. J. Biochem. Physiol.,* 37:911-917 (1959)). Fatty acid methyl esters ["FAMES"] were prepared by transesterification of the lipid extract with sodium methoxide (Roughan, G., and Nishida I., *Arch. Biochem. Biophys.,* 276(1):38-46 (1990)) and subsequently analyzed with a Hewlett-Packard 6890 GC fitted with a 30-m× 0.25 mm (i.d.) HP-INNOWAX (Hewlett-Packard) column. The oven temperature was from 170° C. (25 min hold) to 185° C. at 3.5° C./min.

For direct base transesterification, *Yarrowia* culture (3 mL) was harvested, washed once in distilled water, and dried under vacuum in a Speed-Vac for 5-10 min. Sodium methoxide (100 μl of 1%) was added to the sample, and then the sample was vortexed and rocked for 20 min. After adding 3 drops of 1 M NaCl and 400 μl hexane, the sample was vortexed and spun. The upper layer was removed and analyzed by GC as described above.

Generation of Y4184U4 Strain to Produce EPA

*Y. lipolytica* strain Y4184U4 was used as the host in Example 6, infra, and its construction is diagrammed in FIG. 5.

Strain Y4184U4 was derived from *Y. lipolytica* ATCC #20362, and is capable of producing EPA via expression of a Δ9 elongase/Δ8 desaturase pathway. The strain has a Ura-phenotype and its construction is described in Example 7 of Int'l. App. Pub. No. WO 2008/073367, hereby incorporated herein by reference.

The final genotype of strain Y4184 (producing 31% EPA of total lipids) with respect to wildtype *Yarrowia lipolytica* ATCC #20362 was unknown 1-, unknown 2-, unknown 4-, unknown 5-, unknown 6-, unknown 7-, YAT1::ME3S::Pex16, EXP1::ME3S::Pex20 (2 copies), GPAT::EgD9e::Lip2, FBAINm::EgD9eS::Lip2, EXP1::EgD9eS::Lip1, FBA::EgD9eS::Pex20, YAT1::EgD9eS::Lip2, GPD::EgD9eS::Lip2, GPDIN::EgD8M::Lip1, YAT1::EgD8M::Aco, EXP1::EgD8M::Pex16, FBAINm::EgD8M::Pex20, FBAIN::EgD8M::Lip1 (2 copies), GPM/FBAIN::FmD12S::Oct, EXP1::FmD12S::Aco, YAT1::FmD12::Oct, GPD::FmD12::Pex20, EXP1::EgD5S::Pex20, YAT1::EgD5S::Aco, YAT1::Rd5S::Oct, FBAIN::EgD5::Aco, FBAINm::PaD17::Aco, EXP1::PaD17::Pex16, YAT1::PaD17S::Lip1, YAT1::YICPT1::Aco, GPD::YICPT1::Aco (wherein FmD12 is a *Fusarium moniliforme* Δ12 desaturase gene [Int'l. App. Pub. No. WO 2005/047485]; FmD12S is a codon-optimized Δ12 desaturase gene, derived from *Fusarium moniliforme* [Int'l. App. Pub. No. WO 2005/047485]; ME3S is a codon-optimized $C_{16/18}$ elongase gene, derived from *Mortierella alpina* [Int'l. App. Pub. No. WO 2007/046817]; EgD9e is a *Euglena gracilis* Δ9 elongase gene [Int'l. App. Pub. No. WO 2007/061742]; EgD9eS is a codon-optimized Δ9 elongase gene, derived from *Euglena gracilis* [Int'l. App. Pub. No. WO 2007/061742]; EgD8M is a synthetic mutant Δ8 desaturase [Int'l. App. Pub. No. WO 2008/073271], derived from *Euglena gracilis* [U.S. Pat. No. 7,256,033]; EgD5 is a *Euglena gracilis* Δ5 desaturase [U.S. Pat. App. Pub. US 2007-0292924-A1];

EgD5S is a codon-optimized Δ5 desaturase gene, derived from *Euglena gracilis* [U.S. Pat. App. Pub. No. 2007-0292924]; RD5S is a codon-optimized Δ5 desaturase, derived from *Peridinium* sp. CCMP626 [U.S. Pat. App. Pub. No. 2007-0271632]; PaD17 is a *Pythium aphanidermatum* Δ17 desaturase [Int'l. App. Pub. No. WO 2008/054565]; PaD17S is a codon-optimized Δ17 desaturase, derived from *Pythium aphanidermatum* [Int'l. App. Pub. No. WO 2008/054565]; and, YICPT1 is a *Yarrowia lipolytica* diacylglycerol choline-phosphotransferase gene [Int'l. App. Pub. No. WO 2006/052870]).

In order to disrupt the Ura3 gene in strain Y4184, construct pZKUE3S (described in Table 22 of Int'l. App. Pub. No. WO 2008/073367 and set forth therein as SEQ ID NO:78, hereby incorporated herein by reference) was used to integrate an EXP1::ME3S::Pex20 chimeric gene into the Ura3 gene of strain Y4184 to result in strains Y4184U1 (11.2% EPA of total lipids), Y4184U2 (10.6% EPA of total lipids) and Y4184U4 (15.5% EPA of total lipids), respectively (collectively, Y4184U).

Example 6

Production of $CoQ_{10}$ in *Yarrowia lipolytica* Strains Co-Producing ω-3/ω-6 PUFAs The present Example describes co-production of $CoQ_{10}$ and ω-3/ω-6 polyunsaturated fatty acids ["PUFAs"]. This was accomplished via expression of various ddsA genes in *Yarrowia lipolytica* strain Y4184U4 (Example 5).

Although the present Example is useful for purposes of demonstration, one skilled in the art will realize that any of the *Yarrowia lipolytica* strains listed in Example 5 (or constructed using the teachings of the cited commonly owned and co-pending applications) could be used as the host cell for transformation with an integration or expression vector comprising a chimeric ddsA gene, as described above in Example 5, and using the methodology for transformation described in Example 1. $CoQ_{10}$ would be extracted and quantified.

Transformation of Plasmids Comprising Synthetic ddsA Constructs Into Y4184U4

Plasmids pDMW359-Ss_ddsA, pDMW359-Sp_ddsA, pDMW359-Ob_ddsA, pDMW359-RI_ddsA, pDMW359-MI_ddsA, pDMW359-At_ddsA and pDMW359-Rs_ddsA (Example 4) were each individually transformed into strain Y4184U4 (Example 5), as described in Example 1. After transformation, the cells were plated onto MM plates without uracil supplementation.

Characterization of $CoQ_{10}$ and ω-3/ω-6 PUFA Production in Transformants

Strains containing expression plasmids pDMW359-Ss-_ddsA, pDMW359-Sp_ddsA, pDMW359-Ob_ddsA, pDMW359-RI_ddsA, pDMW359-MI_ddsA, pDMW359-At_ddsA and pDMW359-Rs_ddsA were re-streaked onto MM plates, and then inoculated into liquid MM at 30° C. and shaken at 250 rpm/min for 2 days. The cells were collected by centrifugation, resuspended in HGM and then shaken at 250 rpm/min for 5 days. The cells were collected by centrifugation, lipids were extracted, and FAMEs were prepared by trans-esterification, and subsequently analyzed with a Hewlett-Packard 6890 GC, as described in Example 5.

As shown in Table 12, ω-3/ω-6 PUFAs were produced in the transformant strains. Total lipid content ["TFAs % DCW"] and concentration of a given fatty acid(s) expressed as a weight percent (wt. %) of total fatty acids ["% TFAs"] are provided; fatty acids are identified as 16:0 (palmitate), 16:1 (palmitoleic acid), 18:0 (stearic acid), 18:1 (oleic acid), 18:2 (LA), ALA, EDA, DGLA, ARA, ETrA, ETA, EPA and "other". ω-3/ω-6 PUFAs include LA, ALA, EDA, DGLA, ARA, ETrA, ETA and EPA and account for at least 69% of the TFAs.

TABLE 12

Lipid Composition In Yarrowia lipolytica Strain Y4184U4 Transformed With Various ddsA Plasmids

| | | % TFAs | | | | | | | | | | | | |
|---|---|---|---|---|---|---|---|---|---|---|---|---|---|---|
| Plasmid | TFAs % DCW | 16:0 | 16:1 | 18:0 | 18:1 | 18:2 | 18:3 (n-3) ALA | 20:2 EDA | 20:3 (n-6) DGLA | 20:4 ARA | EtrA | 20:4 (n-3) ETA | 20:5 EPA | other |
| pDMW359-Ss_ddsA | 23 | 3.5 | 1.6 | 2.0 | 8.1 | 30.8 | 4.2 | 5.1 | 1.2 | 0.6 | 1.5 | 1.3 | 24.6 | 15.4 |
| pDMW359-Sp_ddsA | 25 | 4.0 | 1.7 | 2.1 | 7.7 | 32.2 | 3.8 | 5.0 | 1.3 | 0.7 | 1.4 | 1.4 | 27.4 | 11.2 |
| pDMW359-Ob_ddsA | 16 | 4.4 | 1.9 | 2.1 | 8.2 | 33.0 | 4.0 | 5.2 | 1.3 | 0.8 | 1.4 | 1.3 | 26.6 | 9.7 |
| pDMW359-Rl_ddsA | 26 | 3.9 | 1.6 | 2.1 | 7.7 | 32.8 | 3.8 | 4.9 | 1.3 | 0.7 | 1.4 | 1.4 | 26.6 | 11.9 |
| pDMW359-Ml_ddsA | 19 | 4.4 | 1.9 | 2.1 | 7.8 | 32.4 | 3.6 | 5.2 | 1.3 | 0.8 | 1.5 | 1.5 | 26.8 | 10.8 |
| pDMW359-At_ddsA | 23 | 4.2 | 1.9 | 2.1 | 8.1 | 32.0 | 3.8 | 5.2 | 1.3 | 0.7 | 1.5 | 1.5 | 26.5 | 11.0 |
| pDMW359-Rs_ddsA | 21 | 4.4 | 2.0 | 2.1 | 8.2 | 31.9 | 3.8 | 5.3 | 1.3 | 0.8 | 1.5 | 1.5 | 26.1 | 11.2 |

To analyze the presence of $CoQ_{10}$, colonies were inoculated into flasks containing fermentation medium supplemented with 5% glucose. After 2 days of growth, the $CoQ_{10}$ was extracted and quantified via HPLC. The extraction protocol was based on the previously described procedure of Zahiri, H. S. et al. (*Metab. Eng.,* 8(5):406-16 (2006)). Specifically, a 1 mL sample of each culture was centrifuged at 14,000 rpm for 15 sec using a bench-top centrifuge. The cell pellets were re-suspended in 400 μl of Solution I (Zymoprep II Yeast Plasmid Mini-prep Kit, Zymo Research, Orange, Calif.; Catalog #D2004) and incubated at 37° C. After 60 min, about 40 μl of 0.5 mm glass beads was added to the suspensions. The tubes were shaken with a bead beater for 5 min at the highest setting. $CoQ_{10}$ was extracted from the cell lysate with 900 μl of a hexane/propanol (5:3) mixture and then with 500 μl of hexane. Following each extraction, the hexane organic phase containing $CoQ_{10}$ was separated from the aqueous phase by centrifugation at 14,000 rpm and collected into a new tube. The hexane extract was evaporated to dryness under a stream of $N_2$ at room temperature. The pellets were first dissolved in 200 μl of chloroform (Sigma), then with 1800 μl of ethanol:methanol (7:3).

An aliquot of 10 μl was injected into a HPLC (Shimadzu 10A system) equipped with a Symmetry® C18 column (Waters Corp., Milford, Mass.). The chromatography was operated at room temperature using an isocratic solvent mixture of ethanol and methanol (70:30 v/v, Fisher Scientific, HPLC grade) as a mobile phase at a flow rate of 1 mL/min. A UV detector was used at 275 nm for the detection and quantification of $CoQ_{10}$. Authentic standards, $CoQ_9$ and $CoQ_{10}$ (Sigma), were used to distinguish the corresponding peaks in the HPLC chromatograms of the experimental samples. All the samples showed the presence of the $CoQ_{10}$ peak. In addition, the mass of these peaks were confirmed to be that of $CoQ_{10}$ by mass spectrometry.

The above results demonstrated that ω-3/ω-6 PUFAs and $CoQ_{10}$ were co-produced in *Yarrowia lipolytica* strain Y4184U4.

Example 7

Construction of Various *Yarrowia lipolytica* Strains Producing $C_{40}$ Carotenoids The present Example describes various strains of *Yarrowia lipolytica* that have been engineered to produce $C_{40}$ carotenoids. More specifically, a variety of *Y. lipolytica* strains have been engineered by the Applicant's Assignee to produce various $C_{40}$ carotenoids. Since the organism does not natively produce $C_{40}$ carotenoids, all of the genetically engineered strains have been transformed to express various $C_{40}$ carotenoid biosynthetic pathway genes (i.e., crtE, crtB, crtI, crtY, crtW and crtZ).

Summary of Representative *Yarrowia lipolytica* Strains Producing $C_{40}$ Carotenoids Although some representative strains are summarized in the Table below, the disclosure of *Y. lipolytica* strains producing $C_{40}$ carotenoids is not limited to the strains therein. Instead, the teachings provided in the present Application, in addition to commonly owned and co-pending U.S. patent application Ser. No. 11/952,243, are useful for development of a suitable *Y. lipolytica* strain engineered to produce $C_{40}$ carotenoids.

TABLE 13

Carotenoid Profile Of Representative Yarrowia lipolytica Strains Engineered To Produce $C_{40}$ Carotenoids

| Strain(s) | Reference | Carotenoid Produced | Quantification |
|---|---|---|---|
| *Yarrowia lipolytica* strain YL5 | Example 2 of Int'l. App. Pub. No. WO 2008/073367 | lycopene | — |
| *Yarrowia lipolytica* strains YCS1001-YSC1026 | Example 3 of Int'l. App. Pub. No. WO 2008/073367 | lycopene | — |
| YCS1200 series of carotenoid-producing *Y. lipolytica* transformants | Example 5 of Int'l. App. Pub. No. WO 2008/073367 | β-carotene | e.g., strain YCS1201 produced 15% lycopene, 72% β-carotene, 5% zeaxanthin |
| YCS1300 series of carotenoid-producing *Y. lipolytica* transformants | Example 5 of Int'l. App. Pub. No. WO 2008/073367 | β-carotene | e.g., strain YCS1302 produced 40% lycopene, 53% β-carotene |
| YCS3700 series of carotenoid-producing *Y. lipolytica* transformants | Example 6 of Int'l. App. Pub. No. WO 2008/073367 | zeaxanthin | e.g., strain YCS3701 produced 6% zeaxanthin; YCS3702 produced 4% zeaxanthin |
| YCS4000 series of carotenoid-producing *Y. lipolytica* transformants | Example 6 of Int'l. App. Pub. No. WO 2008/073367 | canthaxanthin | e.g., strain YCS4002 produced 5% canthaxanthin |
| YCS4100 series of carotenoid-producing *Y. lipolytica* transformants | Example 6 of Int'l. App. Pub. No. WO 2008/073367 | zeaxanthin | e.g., strain YCS4101 produced 6% zeaxanthin |

Example 8 (Prophetic)

Production of $CoQ_{10}$ in *Yarrowia lipolytica* Strains Co-Producing $C_{40}$ Carotenoids and ω-3/ω-6 PUFAs Any *Y. lipolytica* strains producing ω-3/ω-6 PUFAs, as described in Example 5, maybe engineered to also co-produce $CoQ_{10}$ and $C_{40}$ carotenoids.

Specifically, *Yarrowia lipolytica* strains engineered to produce high concentrations of various ω-3/ω-6 PUFAs could be transformed with e.g., integration vector pYCRTEBI (described in Example 2 of Int'l. App. Pub. No. WO 2008/073367, and set forth therein as SEQ ID NO:12) and optionally integration vector pYPS108 (described in Example 5 of Int'l. App. Pub. No. WO 2008/073367, and set forth therein as SEQ ID NO:36) and optionally integration vector pYPS127 (described in Example 6 of Int'l. App. Pub. No. WO 2008/073367, and set forth therein as SEQ ID NO:43) and/or pYPS128 (described in Example 6 of Int'l. App. Pub. No. WO 2008/073367, and set forth therein as SEQ ID NO:44) to produce a strain co-producing ω-3/ω-6 PUFAs and $C_{40}$ carotenoids. Subsequently, the resulting transformant cells could be used as host for transformation with an integration or expression vector comprising a chimeric ddsA gene, as described herein, to thereby enable co-production of $CoQ_{10}$, ω-3/ω-6 PUFAs, and $C_{40}$ carotenoids.

What is claimed is:

1. A recombinant oleaginous yeast *Yarrowia lipolytica* comprising:

(a) at least one copy of a genetic construct encoding decaprenyl diphosphate synthase, wherein said decaprenyl diphosphate synthase comprises a signature motif that aligns with a reference sequence SEQ ID NO: 7, said signature motif comprising:

1) SEQ ID NO:43 at positions corresponding to positions 31-41 of SEQ ID NO: 7;

2) SEQ ID NO:44 at positions corresponding to positions 65-89 of SEQ ID NO: 7;

3) SEQ ID NO:45 at positions corresponding to positions 102-106 of SEQ ID NO:7;

4) SEQ ID NO:46 at positions corresponding to positions 135-141 of SEQ ID NO: 7;

5) a XKT motif at positions corresponding to positions 160-162 of SEQ ID NO: 7;

6) SEQ ID NO:47 at positions corresponding to positions 198-234 of SEQ ID NO: 7; and, 7) SEQ ID NO:48 at positions corresponding to positions 294-315 of SEQ ID NO:7; and, (b) at least one genetic construct encoding at least one omega-3/omega-6 polyunsaturated fatty acid biosynthetic pathway protein for expression of a functional omega-3/omega-6 polyunsaturated fatty acid biosynthetic pathway;

wherein said yeast produces at least one polyunsaturated fatty acid that is at least 18 carbon atoms in length and has at least three double bonds.

2. The recombinant oleaginous yeast of claim 1, wherein the at least one genetic construct encoding at least one omega-3/omega-6 polyunsaturated fatty acid biosynthetic pathway protein comprises at least one protein selected from the group consisting of Δ9 elongase, Δ8 desaturase, Δ5 desaturase and Δ17 desaturase.

3. The recombinant oleaginous yeast of claim 1, further comprising at least one genetic construct encoding at least one carotenoid biosynthetic pathway protein for expression of a functional carotenoid biosynthetic pathway.

4. The recombinant oleaginous yeast of claim 1, wherein said signature motif that aligns with a reference sequence SEQ ID NO: 7 comprises:

(a) SEQ ID NO:49 at positions corresponding to positions 31-41 of SEQ ID NO: 7;

(b) SEQ ID NO:50 at positions corresponding to positions 65-89 of SEQ ID NO: 7;

(c) SEQ ID NO:51 at positions corresponding to positions 102-106 of SEQ ID NO:7;

(d) SEQ ID NO:52 at positions corresponding to positions 135-141 of SEQ ID NO: 7;

(e) a (G/A)KT motif at positions corresponding to positions 160-162 of SEQ ID NO: 7;

(f) SEQ ID NO:53 at positions corresponding to positions 198-234 of SEQ ID NO: 7; and, (g) SEQ ID NO:54 at positions corresponding to positions 294-315 of SEQ ID NO:7.

5. A method for the production of $CoQ_{10}$ in a recombinant oleaginous yeast, comprising:

a) Providing the recombinant oleaginous yeast *Yarrowia lipolytica* of claim 1, the recombinant oleaginous yeast *Yarrowia lipolytica*

1) producing a quinone of the coenzyme Q series selected from the group consisting of: $CoQ_6$, $CoQ_7$, $CoQ_8$, and $CoQ_9$, 2) comprising genetic constructs encoding a functional ω-3/ω-6 polyunsaturated fatty acid biosynthetic pathway whereby the transformed yeast cells produce at least one polyunsaturated fatty acid; and 3) optionally comprising genetic constructs encoding a functional carotenoid biosynthetic pathway whereby the transformed yeast cells produce at least one carotenoid;

b) transforming the recombinant oleaginous yeast *Yarrowia lipolytica* with at least one copy of a genetic construct encoding decaprenyl diphosphate synthase; and, c) culturing the transformed recombinant oleaginous yeast *Yarrowia lipolytica* of step (b) under suitable conditions, whereby the decaprenyl diphosphate synthase is expressed and whereby $CoQ_{10}$ is produced.

6. The method of claim 1, wherein the at least one polyunsaturated fatty acid is an ω-3 polyunsaturated fatty acid selected from the group consisting of α-linolenic acid, stearidonic acid, eicosatrienoic acid, eicosatetraenoic acid, eicosapentaenoic acid, docosapentaenoic acid and docosahexaenoic acid or an ω-6 polyunsaturated fatty acid selected from the group consisting of linoleic acid, γ-linolenic acid, eicosadienoic acid, dihomo-γ-linolenic acid, arachidonic acid, docosatetraenoic acid and docosapentaenoic acid.

7. The method of claim 1, wherein the ω-3/ω-6 polyunsaturated fatty acid biosynthetic pathway comprises at least one set of genes selected from the group consisting of:

a) at least one genetic construct encoding a Δ6 desaturase, a $C_{18/20}$ elongase and a Δ5 desaturase;

b) at least one genetic construct encoding a Δ9 elongase, a Δ8 desaturase and a Δ5 desaturase;

c) at least one genetic construct encoding a Δ6 desaturase, a $C_{18/20}$ elongase, a Δ5 desaturase and a Δ17 desaturase;

d) at least one genetic construct encoding a Δ9 elongase, a Δ8 desaturase, a Δ5 desaturase and a Δ17 desaturase;

e) at least one genetic construct encoding a Δ15 desaturase, a Δ6 desaturase, a $C_{18/20}$ elongase and a Δ5 desaturase;

f) at least one genetic construct encoding a Δ15 desaturase, a Δ9 elongase, a Δ8 desaturase and a Δ5 desaturase;

g) at least one genetic construct encoding a Δ6 desaturase, a $C_{18/20}$ elongase, a Δ5 desaturase, a Δ17 desaturase and a $C_{20/22}$ elongase;

h) at least one genetic construct encoding a Δ6 desaturase, a $C_{18/20}$ elongase, a Δ5 desaturase, a Δ17 desaturase, a $C_{20/22}$ elongase and a Δ4 desaturase;

i) at least one genetic construct encoding a Δ9 elongase, a Δ8 desaturase, a Δ5 desaturase, a Δ17 desaturase and a $C_{20/22}$ elongase;

j) at least one genetic construct encoding a Δ9 elongase, a Δ8 desaturase, a Δ5 desaturase, a Δ17 desaturase, a $C_{20/22}$ elongase and a Δ4 desaturase;

k) at least one genetic construct encoding a Δ15 desaturase, a Δ6 desaturase, a $C_{18/20}$ elongase, a Δ5 desaturase, a $C_{20/22}$ elongase and a Δ4 desaturase; and, l) at least one genetic construct encoding a Δ15 desaturase, a Δ9 elongase, a Δ8 desaturase, a Δ5 desaturase, a $C_{20/22}$ elongase and a Δ4 desaturase.

8. The method of claim 1, wherein the carotenoid is a $C_{40}$ carotenoid selected from the group consisting of: lycopene, β-carotene, zeaxanthin, lutein, canthaxanthin and astaxanthin.

9. The method of claim 1, wherein the carotenoid biosynthetic pathway comprises at least one genetic construct encoding an enzyme selected from the group consisting of phytoene synthase (crtB), phyotene desaturase (crtI), lycopene cyclase (crtY), carotenoid hydroxylase (crtZ) and a caroetnoid ketolase (crtW).

10. The method of claim 1, wherein the coenzyme $Q_{10}$ produced is from about 0.0001% to less than 1% of the total dry weight of the recombinant oleaginous yeast.

* * * * *

UNITED STATES PATENT AND TRADEMARK OFFICE

CERTIFICATE OF CORRECTION

PATENT NO. : 8,815,567 B2
APPLICATION NO. : 12/277856
DATED : August 26, 2014
INVENTOR(S) : Rick W Ye It is certified that error appears in the above-identified patent and that said Letters Patent is hereby corrected as shown below:

In the Claims

In Column 208, Line 29, Claim 5, please change “Providing” to -- providing --

In Column 208, Line 30, Claim 5, please change “claim 1” to -- claim 5 --

In Column 208, Line 59, Claim 7, please change “claim 1” to -- claim 5 --

In Column 210, Line 7, Claim 8, please change “claim 1” to -- claim 5 --

In Column 210, Line 11, Claim 9, please change “claim 1” to -- claim 5 --

In Column 210, Line 16, Claim 10, please change “claim 1” to -- claim 5 --

Signed and Sealed this
Fifth Day of May, 2015

Michelle K. Lee
*Director of the United States Patent and Trademark Office*